United States Patent [19]

Nagase et al.

[11] Patent Number: 5,776,945
[45] Date of Patent: Jul. 7, 1998

[54] 4A-ARYLDECAHYDROISOQUINOLINE COMPOUND AND MEDICINAL USE OF THE SAME

[75] Inventors: Hiroshi Nagase; Yoshifumi Imamura; Hiroshi Ohno, all of Kamakura; Takashi Endo, Kanagawa, all of Japan

[73] Assignee: Toray Industries, Inc., Tokyo, Japan

[21] Appl. No.: 809,226

[22] PCT Filed: Jul. 19, 1996

[86] PCT No.: PCT/JP96/02030

§ 371 Date: May 8, 1997

§ 102(e) Date: May 8, 1997

[87] PCT Pub. No.: WO97/03968

PCT Pub. Date: Feb. 6, 1997

[30] Foreign Application Priority Data

Jul. 20, 1995 [JP] Japan .................................. 7-183811

[51] Int. Cl.$^6$ .......................... C07D 217/04; A61K 31/46
[52] U.S. Cl. ............................................. 514/307; 546/144
[58] Field of Search ..................................... 546/144, 367

[56] References Cited

U.S. PATENT DOCUMENTS 4,301,290 11/1981 Pfaffli et al. ............................ 546/143

*Primary Examiner*—Zinna Northington Davis
*Attorney, Agent, or Firm*—Birch, Stewart, Kolasch & Birch, LLP

[57] ABSTRACT

The present invention relates to a 4a-aryldecahydroisoquinoline compound, which is represented by a compound 1, or a pharmacologically acceptable salt thereof.

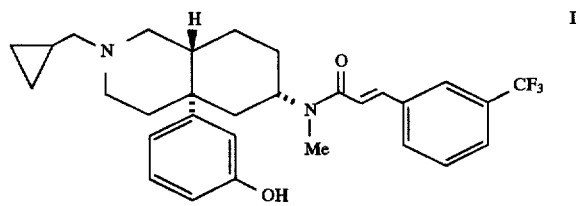

As the results of in vitro and in vivo pharmacological evaluations, it was found that the compounds of the present invention had excellent preventive effects on ischemic death of cerebral neurocytes, suppressive effects on development of cerebral infarction, and strong analgesic and antitussive effects; therefore the compounds of the present invention can be utilized in the medicinal field as a useful cerebral cytoprotective agent, which is aimed at preventing and treating cerebrovascular disorder, ischemic cerebral disorder, cerebral neurocyte disorder, and dementia, an analgesic, and an antitussive.

13 Claims, No Drawings

4A-ARYLDECAHYDROISOQUINOLINE COMPOUND AND MEDICINAL USE OF THE SAME

This is a 371 Application of PCT/JP96/02030, filed Mar. 18, 1997.

TECHNICAL FIELD

The present invention relates to a 4a-aryldecahydroisoquinoline compound and a pharmacologically acceptable salt thereof, and also relates to a medicine, a cerebral cytoprotective agent, an analgesic, and an antitussive, each of which contains the foregoing compound or salt as an active ingredient.

BACKGROUND ART

Recently, cases of various cerebrovascular diseases have increased with the arrival of an aging society. Cerebrovascular diseases are considered to be caused by aging, hypertension, arterial sclerosis, hyper lipidemia, and the like, and are generally called as stroke. However, cerebral functional damage due to head trauma and the like are occasionally included in the cerebrovascular diseases in a broad sense.

Stroke is roughly divided into infarctional diseases and hemorrhagic diseases such that the former includes cerebral infarction (cerebral thrombosis and cerebral embolus) and the latter includes cerebral hemorrhage and subarachnoid hemorrhage. These diseases cause supply shortages of glucose, oxygen, and the like, which are the energy source of cerebral neurocytes; thus cerebral edema or infarction consequently occurs, resulting in death of the cerebral neurocytes positioned in and around the ischemic areas. As a result, various aftereffects such as cerebrovascular dementia occur, and together with Alzheimer-type senile dementia and the like, they appear as medically and socially serious problems at present.

Conventionally, medicines developed to be applied for improvement in psychoneurotic symptoms associated with the above cerebrovascular diseases and senile dementia mainly take effect through promoting supply of glucose, oxygen, etc. to ischemic areas by increasing the blood flow to the brain, and based on these functional mechanisms, they are called by ambiguous names such as agents for improving cerebral circulation, activators for cerebral metabolism, and agents for improving cerebral functions. However, almost all of these medicines are aimed at improving the above aftereffects and are regarded to be effective for improving peripheral symptoms such as volition disorder, emotional disorder, and abnormal behavior; meanwhile their effectiveness on core symptoms of dementia such as memory disorder(s) is considered to be doubtful by many people. Anyway, these medicines are almost ineffective for cerebral neurocytes damaged by cerebrovascular disorder and, up to the present, almost no medicine has been found which is effective for this damage. In particular, treatment of the acute stage which is within 24 hours from the onset of cerebrovascular diseases is regarded to be important, and development of a cerebral cytoprotective agent which has reliable protective effects and which can be used in a safe and easy way is in demand under present conditions.

Meanwhile, analgesics which exhibit their effect by affecting the central nervous system and which are represented by morphines and the like are frequently used at present because of their strong analgesic action, however strict management is required in using these medicines since they have severe adverse effect including dependence, respiratory supression and smooth muscle deppressomotor (constipation). Therefore, central analgesics have been in demand which are highly effective and which can be used with relief. In addition, codeine and dextromethorphan which are known as strong central antitussives are generally used for not only prescription medicines but also a component of commercially available cold medicines, and these medicines fundamentally have similar severe adverse effect. In particular, abuse of antitussives containing codeine and psychogenesis of dextromethorphan are serious, and development of safer and stronger central antitussives has been expected.

DISCLOSURE OF THE INVENTION

As a result of in depth study conducted for solving the above problems, inventors of the present invention have found that a 4a-aryldecahydroisoquinoline compound of general formula (I) and a pharmacologically acceptable acid addition salt thereof exhibit cerebral cytoprotective effect analgesic action, and an antitussive effect with the above excellent properties, and the inventors have completed the present invention.

In other words, the present invention relates to a 4a-aryldecahydroisoquinoline compound and a pharmacologically acceptable acid addition salt thereof. In addition, the present invention provides: a cerebral cytoprotective agent which has the 4a-aryldecahydroisoquinoline compound or the pharmacologically acceptable acid addition salt thereof as an active ingredient and which is used for prevention and treatment of cerebrovascular diseases such as stroke and head trauma, cerebral neurocyte disorder caused by cerebral ischemia, and cerebrovascular-disease aftereffects, such as dementia; and a strong central analgetic and a strong central antitussive which have the 4a-aryldecahydroisoquinoline compound or the pharmacologically acceptable acid addition salt thereof as an active ingredient and do not have morphine-like adverse effects.

In other words, the present invention relates to a 4a-aryldecahydroisoquinoline compound of general formula (I), a pharmacologically acceptable acid addition salt thereof, and the medicinal uses thereof:

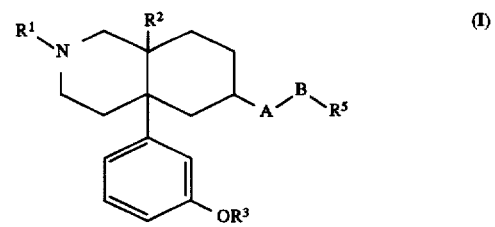

(I)

[wherein $R^1$ is either hydrogen, alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 2 to 7 carbon atoms, furan-2-ylalkyl having 1 to 5 carbon atoms, or thiophene-2-ylalkyl having 1 to 5 carbon atoms; $R^2$ is either hydrogen, hydroxy, alkanoyloxy having 1 to 5 carbon atoms, or alkoxy having 1 to 5 carbon atoms; $R^3$ is either hydrogen, alkyl having 1 to 5 carbon atoms, alkanoyl having 1 to 5 carbon atoms, or aralkyl having 7 to 13 carbon atoms; A is either —XC(=Y)—, —XC(=Y)Z—, —X—, —XSO$_2$—, or —OC(OR$^4$)R$^4$—(wherein X, Y, and Z are independently NR$^4$, S, or O); $R^4$ is either hydrogen, straight or branched alkyl having 1 to 14 carbon atoms (may be substituted by at least one substituent selected from the group consisting of alkoxy having 1 to 5 carbon atoms, alkanoyloxy having 1 to 5 carbon atoms, fluoro, chloro, bromo, iodo, nitro, and cyano), cycloalkylalkyl having 4 to 15 carbon atoms (may be substituted by at least one substituent selected from the group consisting of alkyl having 1 to 5 carbon atoms, aryl having 6 to 12 carbon atoms, alkoxy having 1 to 5 carbon atoms, alkanoyloxy having 1 to 5 carbon atoms, fluoro, chloro, bromo, iodo, nitro, cyano, and trifluoromethyl), aralkyl having 7 to 15 carbon atoms (may be substituted by at least one substituent selected from the group consisting of alkyl having 1 to 5 carbon atoms, aryl having 6 to 12 carbon atoms, alkoxy having 1 to 5 carbon atoms, alkanoyloxy having 1 to 5 carbon atoms, fluoro, chloro, bromo, iodo, nitro, cyano, trifluoromethyl, and trifluoromethoxy), or aryl having 6 to 12 carbon atoms (may be substituted by at least one substituent selected from the group consisting of alkyl having 1 to 5 carbon atoms, aryl having 6 to 12 carbon atoms, alkoxy having 1 to 5 carbon atoms, alkanoyloxy having 1 to 5 carbon atoms, fluoro, chloro, bromo, iodo, nitro, cyano, trifluoromethyl, and trifluoromethoxy); and $R^4$ may be the same or different; B is a valence bond, a straight acyclic hydrocarbon chain having 1 to 14 carbon atoms, or a branched acyclic hydrocarbon chain having 3 to 14 carbon atoms (the hydrocarbon chains may have 1 to 3 unsaturated bonds; 1 to 3 methylene groups which are not positioned adjacent to each other and which are not directly linked with A may be replaced by —(C=O)—, —S—, —O—, and/or —NH—; and the hydrocarbon chains may be substituted by at least one substituent selected from the group consisting of alkoxy having 1 to 5 carbon atoms, alkanoyloxy having 1 to 5 carbon atoms, hydroxy, fluoro, chloro, bromo, iodo, amino, nitro, cyano, and phenoxy); $R^5$ is hydrogen or an organic group including saturated or unsaturated monocyclic hydrocarbon having 3 to 8 carbon atoms, saturated or unsaturated fused polycyclic hydrocarbon having 8 to 18 carbon atoms, aromatic hydrocarbon having 6 to 18 carbon atoms, a saturated or unsaturated hetero monocyclic hydrocarbon compound having 3 to 7 carbon atoms, a saturated or unsaturated hetero fused polycyclic hydrocarbon compound having 5 to 17 carbon atoms, or an aromatic hetero hydrocarbon compound having 3 to 17 carbon atoms, (wherein the hetero atoms used herein independently mean nitrogen, oxygen, or sulfur atoms; and the above organic group may be substituted by at least one substituent selected from the group consisting of alkyl having 1 to 5 carbon atoms, alkoxy having 1 to 5 carbon atoms, alkanoyloxy having 1 to 5 carbon atoms, hydroxy, fluoro, chloro, bromo, iodo, amino, nitro, cyano, isothiocyanato, trifluoromethyl, trifluoromethoxy, and methylenedioxy); and the general formula (I) includes (+), (−), and (±) isomers].

BEST MODE FOR CARRYING OUT THE INVENTION

In the general formula (I), $R^1$ is preferably hydrogen, alkyl having 1 to 5 carbon atoms, cycloalkylmethyl having 4 to 7 carbon atoms, cycloalkenylmethyl having 5 to 7 carbon atoms, phenyl, naphthyl, phenylalkyl having 7 to 13 carbon atoms, alkenyl having 3 to 7 carbon atoms, or furan-2-yl-alkyl having 1 to 5 carbon atoms (wherein the number of carbon atoms indicated here means the number of carbon atoms of the alkyl moiety of the furan-2-yl-alkyl), thiophene-2-ylalkyl having 1 to 5 carbon atoms (wherein the number of carbon atoms indicated here means the number of the alkyl moiety of thiophene-2-ylalkyl), and in particular, methyl, ethyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl, allyl, furan-2-yl-methyl, and thiophene-2-yl-methyl.

As $R^2$, hydrogen, hydroxy, acetoxy, propionoxy, methoxy, and ethoxy are preferable, and in particular, hydrogen, hydroxy, acetoxy, and methoxy are preferable.

As $R^3$, hydrogen, methyl, ethyl, acetyl, propionyl and benzyl, are preferable.

Preferably, A is —NR$^4$C(=O)—, —NR$^4$C(=O)O—, —NR$^4$C(=O)NR$^4$—, —NR$^4$C(=S)NR$^4$—, —NR$^4$CSO$_2$—, —NR$^4$—, —OC(=O)—, —OSO$_2$—, —O—, and —SC(=O)—. In particular, those in which X is —NR$^4$— are preferably used, and practically, —NR$^4$C(=O)—, —NR$^4$C(=O)O—, —NR$^4$C(=O)NR$^4$—, —NR$^4$C(=S)NR$^4$—, —NR$^4$SO$_2$—, and —NR$^4$— are preferable. Moreover, —NR$^4$C(=O)— and —NR$^4$C(=O)O— are particularly preferable among these and —NR$^4$C(=O)— is further preferable.

$R^4$ is either preferably hydrogen, straight or branched alkyl having 1 to 14 carbon atoms, cycloalkylalkyl having 4 to 15 carbon atoms, aralkyl having 7 to 15 carbon atoms or phenyl; and each of which may be substituted by at least one substituent selected from the group consisting of methyl, ethyl, propyl, butyl, pentyl, phenyl, methoxy, ethoxy, acetoxy, fluoro, chloro, bromo, iodo, nitro, cyano, trifluoromethyl, and trifluoromethoxy. Among the above mentioned groups for $R^4$, methyl, ethyl, propyl, isopropyl, butyl, isobutyl, pentyl, benzyl, phenethyl, phenylpropyl, phenylbutyl, diphenylethyl, and cyclohexylmethyl are particularly preferable.

B is preferably —(CH$_2$)n— (n=0 to 14), —(CH$_2$)n—C(=O)— (n=0 to 14), —CH=CH—(CH$_2$)n— (n=0 to 10), —C C—(CH$_2$)n—(n=0 to 10), —CH$_2$—O—, —CH$_2$—S—, —CH$_2$—O—(CH$_2$)$_2$—O—(CH$_2$)$_2$—, CH$_2$—O—CH$_2$—NH—CH$_2$—O—CH$_2$—, and —CH$_2$—O—CH$_2$—S—CH$_2$—O—CH$_2$—; and in particular, —(CH$_2$)n— (n=0 to 10), —CH=CH—(CH$_2$)n— (n=0 to 10), —C C—(CH$_2$)n—(n=0 to 10), —CH$_2$—O—, and —CH$_2$—S— are preferable.

$R^5$ is hydrogen, or an organic group including cycloalkyl having 3 to 8 carbon atoms, cycloalkenyl having 3 to 8 carbon atoms, fused bicycloalkyl having 8 to 14 carbon atoms, fused bicycloalkenyl having 8 to 14 carbon atoms and 1 to 3 unsaturated bonds, aryl having 6 to 18 carbon atoms, hetero cycloalkyl having 3 to 7 carbon atoms and 1 or 2 hetero atoms, hetero cycloalkenyl having 3 to 7 carbon atoms, 1 or 2 hetero atoms, and 1 unsaturated bond, hetero fused bicycloalkyl having 6 to 13 carbon atoms and 1 or 2 hetero atoms, hetero fused bicycloalkenyl having 6 to 13 carbon atoms, 1 or 2 hetero atoms, and 1 to 3 unsaturated bonds, and hetero aryl having 3 to 13 carbon atoms and 1 to 3 hetero atoms. Practical examples of the organic group are: hydrogen; cycloalkyl such as cyclopentyl, cyclohexyl, and cycloheptyl; cycloalkenyl such as cyclopentenyl, cyclohexenyl, cycloheptenyl; aryl such as phenyl, naphthyl, indacenyl, acenaphthenyl, phenanthrenyl, anthracenyl, and fluoranthenyl; organic rings such as dihydronaphthyl, tetrahydronaphthyl, perhydronaphthyl, and indanyl, in which one or all of the unsaturated bonds of the above aryl are saturated; heteroaryl such as furyl, thienyl, pyrrolyl, imidazolyl, pyrazolyl, oxazolyl, pyridyl, pyrazinyl, pyrimidyl, pyridazinyl, benzofuranyl, benzothienyl, indolyl, indazolyl, quinolyl, carbazolyl, and acrydinyl; and organic hetero rings such as dihydrofuranyl, tetrahydrofuranyl, dihydrothienyl, tetrahydrothienyl, pyrrolnyl, pyrrolydinyl, dihydropyridyl, piperidyl, piperazinyl, indolinyl, dihydropyranyl, perhydroindolyl, and tetrahydropyranyl, in which one or all of the unsaturated bonds of the above heteroaryl are saturated; however, the organic group is not restricted to the above mentioned groups. Each of the organic groups may be substituted by at least one substituent selected from the group consisting of methyl, ethyl, methoxy, ethoxy, acetoxy, propionoxy, hydroxy, fluoro, chloro, bromo, iodo, amino, nitro, cyano, isothiocyanato, trifluoromethyl, trifluoromethoxy, and methylenedioxy. Among the above groups for $R^5$, hydrogen, cyclopentyl, cyclohexyl, cyclopentenyl, cyclohexenyl, indanyl, decalinyl, phenyl, naphthyl, pyrrolyl, furyl, thienyl, imidazolyl, pyrazolyl, pyridyl, benzofuranyl, benzothienyl, indolyl, quinolyl, dichlorophenyl, chlorophenyl, difluorophenyl, fluorophenyl, bromophenyl, nitrophenyl, trifluoromethylphenyl, methylphenyl, and methoxyphenyl are preferable; and furyl, phenyl, naphthyl, dichlorophenyl, and trifluoromethylphenyl are particularly preferable; however $R^5$ is not restricted to the above groups.

Pharmacologically acceptable acid addition salts preferably include: those with inorganic acids, such as hydrochlorides, sulfates, nitrates, hydrobromides, hydroiodides, and phosphates; those with organic carboxylic acids, such as acetates, lactates, citrates, oxalates, glutarates, malates, tartrates, fumarates, mandelates, maleates, benzoates, and phthalates; and those with organic sulfonic acids such as methanesulfonates, ethanesulfonates, benzenesulfonates, p-toluenesulfonates, and camphorsulfonates; and hydrochlorides, hydrobromides, phosphates, tartrates, and methanesulfonates are preferably used among these, however the acid addition salts are not limited to these salts.

The 4a-aryldecahydroisoquinoline compounds having the general formula (I) incorporated in the present invention include a trans isomer in which the ring juncture positions of the decahydroisoquinoline skeleton are fused in a trans form (i.e., the side of the decahydroisoquinoline ring face on which $R^2$ is positioned differs from that on which the 4a-aryl group is positioned) and a cis isomer in which the ring juncture positions of the decahydroisoquinoline skeleton are fused in a cis form (i. e., $R^2$ and the 4a-aryl group are positioned at the same side of the decahydroisoquinoline ring face).

Among the compounds of general formula (I) incorporated in the present invention, a compound 1, in which $R^1$ is cyclopropylmethyl, $R^2$ and $R^3$ are hydrogen, A is a—$NR^4C$ (=O)—, $R^4$ is methyl, B is —CH=CH—, $R^5$ is trifluoromethylphenyl, and the ring juncture positions of the decahydroisoquinoline skeleton are fused in a trans form, is named trans-2-cyclopropylmethyl-4a-(3-hydroxyphenyl) -6α-[N-methyl- (3trifluoromethylcinnamamido)] decahydroisoquinoline.

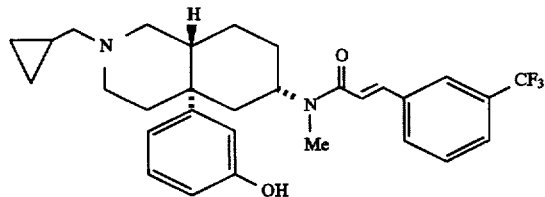

I

According to the above-mentioned nomenclature, concrete examples of the compound incorporated in the present invention are as follows:

trans-2-cyclopropylmethyl-4a-(3-hydroxyphenyl)-6α-(3-trifluoromethylcinnamamido)decahydroisoquinoline,
trans-2-cyclopropylmethyl-4a-(3-hydroxyphenyl)-6α-(6-phenylhexanamido)decahydroisoquinoline, trans-2-cyclopropylmethyl-4a-(3-hydroxyphenyl)-6α-(3,4-dichlorophenylacetamido)decahydroisoquinoline, trans-2-cyclopropylmethyl-4a-(3-hydroxyphenyl)-6α-benzamidodecahydroisoquinoline, trans-2-cyclopropylmethyl-4a-(3-hydroxyphenyl)-6α-(2-naphthamido)decahydroisoquinoline, trans-2-cyclopropylmethyl-4a-(3-hydroxyphenyl)-6α-[N-methyl-3-trifluoromethylcinnamamido)] decahydroisoquinoline, trans-2-cyclopropylmethyl-4a-(3-hydroxyphenyl)-6α-[N-methyl-(6-phenylhexanamido)] decahydroisoquinoline, trans-2-cyclopropylmethyl-4a-(3-hydroxyphenyl)-6α-[N-methyl-(3,4-dichlorophenylacetamido)]decahydroisoquinoline, trans-2-cyclopropylmethyl-4a-(3-hydroxyphenyl)-6α-(N-methylbenzamido)decahydroisoquinoline, trans-2-cyclopropylmethyl-4a-(3-hydroxyphenyl)-6α-[N-methyl-(2-naphthamido)]decahydroisoquinoline, trans-2-cyclopropylmethyl-4a-(3-hydroxyphenyl)-6α-[N-isobutyl-3-trifluoromethylcinnamamido)] decahydroisoquinoline, trans-2-cyclopropylmethyl-4a-(3-hydroxyphenyl)-6α-[N-isobutyl-(6-phenylhexanamido)] decahydroisoquinoline, trans-2-cyclopropylmethyl-4a-(3-hydroxyphenyl)-6α-[N-isobutyl-(3,4-dichlorophenylacetamido)]decahydroisoquinoline, trans-2-cyclopropylmethyl-4a-(3-hydroxyphenyl)-6α-(N-isobutylbenzamido)decahydroisoquinoline, trans-2-cyclopropylmethyl-4a-(3-hydroxyphenyl)-6α-[N-isobutyl-(2-naphthamido)]decahydroisoquinoline, trans-2-cyclopropylmethyl-8a-hydroxy-4a-(3-hydroxyphenyl)-6a-(3-trifluoromethylcinnamamido) decahydroisoquinoline, trans-2-cyclopropylmethyl-8a-hydroxy-4a-(3-hydroxyphenyl)-6α-(6-phenylhexanamido)decahydroisoquinoline, trans-2-cyclopropylmethyl-8a-hydroxy-4a-(3-hydroxyphenyl)-6α-(3,4-dichlorophenylacetamido) decahydroisoquinoline, trans-2-cyclopropylmethyl-8a-hydroxy-4a-(3-hydroxyphenyl)-6α-benzamidodecahydroisoquinoline, trans-2-cyclopropylmethyl-8a-hydroxy-4a-(3-hydroxyphenyl)-6α-(2-naphthamido)decahydroisoquinoline, trans-2-cyclopropylmethyl-8a- hydroxy-4a-(3-hydroxyphenyl)-6α-[N-methyl-3- trifluoromethylcinnamamido)] decahydroisoquinoline, trans-2- cyclopropylmethyl-8a-hydroxy-4a-(3-hydroxyphenyl)-6α-[N-methyl-(6-phenylhexanamido)]decahydroisoquinoline, trans-2-cyclopropylmethyl-8a-hydroxy-4a-(3-hydroxyphenyl)-6α-[N-methyl- (3,4-dichlorophenylacetamido)] decahydroisoquinoline, trans-2- cyclopropylmethyl-8a-hydroxy-4a-(3-hydroxyphenyl)-6α-(N-methylbenzamido)decahydroisoquinoline, trans-2-cyclopropylmethyl-8a-hydroxy-4a-(3-hydroxyphenyl)-6α-[N-methyl- (2-naphthamido)]decahydroisoquinoline, trans-2- cyclopropylmethyl-8a-hydroxy-4a-(3-hydroxyphenyl)-6α-[N-isobutyl-3-trifluoromethylcinnamamido)]decahydroisoquinoline, trans-2- cyclopropylmethyl-8a-hydroxy-4a-(3-hydroxyphenyl)-6α-[N-isobutyl- (6-phenylhexanamido)] decahydroisoquinoline, trans-2- cyclopropylmethyl-8a-hydroxy-4a-(3-hydroxyphenyl)-6α-[N-isobutyl- (3,4-dichlorophenylacetamido)]decahydroisoquinoline, trans-2- cyclopropylmethyl-8a-hydroxy-4a-(3-hydroxyphenyl) -6α-(N- isobutylbenzamido)decahydroisoquinoline, trans-2- cyclopropylmethyl-8a-hydroxy-4a-(3-hydroxyphenyl)-6α-[N-isobutyl- (2-naphthamido)] decahydroisoquinoline, trans-2-cyclopropylmethyl-8a-acetoxy-4a-(3-hydroxyphenyl)-6α-(3-trifluoromethylcinnamamido)decahydroisoquinoline, trans-2- cyclopropylmethyl-8a-acetoxy-4a-(3-hydroxyphenyl)-6α-(6- phenylhexanamido)decahydroisoquinoline, trans-2- cyclopropylmethyl-8a-acetoxy-4a-(3-hydroxyphenyl)-6α-(3,4-dichlorophenylacetamido)decahydroisoquinoline, trans-2- cyclopropylmethyl-8a-acetoxy-4a-(3-hydroxyphenyl)-6α- benzamidodecahydroisoquinoline, trans-2-cyclopropylmethyl-8- acetoxy-4a-(3-hydroxyphenyl)-6α-(2- naphthamido)decahydroisoquinoline, trans-2-cyclopropylmethyl-8- acetoxy-4a-(3-hydroxyphenyl)-6α-[N-methyl-3- trifluoromethylcinnamamido)]decahydroisoquinoline, trans-2- cyclopropylmethyl-8a-acetoxy-4a-(3-hydroxyphenyl)-6α-[N-methyl-(6-phenylhexanamido)]decahydroisoquinoline, trans-2-cyclopropylmethyl-8a-acetoxy-4a-(3-hydroxyphenyl)-6α-[N-methyl- (3,4-dichlorophenylacetamido)]decahydroisoquinoline, trans-2- cyclopropylmethyl-8a-acetoxy-4a-(3-hydroxyphenyl)-6α-(N-methylbenzamido)decahydroisoquinoline, trans-2-cyclopropylmethyl-8a-acetoxy-4a-(3-hydroxyphenyl)-6α-[N-methyl- (2-naphthamido)]decahydroisoquinoline, trans-2- cyclopropylmethyl-8a-acetoxy-4a-(3-hydroxyphenyl)-6α-[N-isobutyl-3-trifluoromethylcinnamamido)]decahydroisoquinoline, trans-2- cyclopropylmethyl-8a-acetoxy-4a-(3-hydroxyphenyl)-6α-[N-isobutyl- (6-phenylhexanamido)]decahydroisoquinoline, trans-2- cyclopropylmethyl-8a-acetoxy-4a-(3-hydroxyphenyl)-6α-[N-isobutyl- (3,4-dichlorophenylacetamido)]decahydroisoquinoline, trans-2- cyclopropylmethyl-8a-acetoxy-4a-(3-hydroxyphenyl)-6α-(N- isobutylbenzamido)decahydroisoquinoline, trans-2- cyclopropylmethyl-8a-acetoxy-4a-(3-hydroxyphenyl)-6α-[N-isobutyl- (2-naphthamido)]decahydroisoquinoline, trans-2-cyclopropylmethyl-8a-methoxy-4a-(3-hydroxyphenyl)-6α-(3- trifluoromethylcinnamamido)decahydroisoquinoline, trans-2- cyclopropylmethyl-8a-methoxy-4a-(3-hydroxyphenyl)-6α-(6- phenylhexanamido)decahydroisoquinoline, trans-2- cyclopropylmethyl-8a-methoxy-4a-(3-hydroxyphenyl)-6α-(3,4-dichlorophenylacetamido)decahydroisoquinoline, trans-2- cyclopropylmethyl-8a-methoxy-4a-(3-hydroxyphenyl)-6α- benzamidodecahydroisoquinoline, trans-2-cyclopropylmethyl-8- methoxy-4a-(3-hydroxyphenyl)-6α-(2- naphthamido)decahydroisoquinoline, trans-2- cyclopropylmethyl-8- methoxy-4a-(3-hydroxyphenyl)-6α-[N-methyl-3- trifluoromethylcinnamamido)]decahydroisoquinoline, trans-2- cyclopropylmethyl-8a-methoxy-4a-(3-hydroxyphenyl)-6α-[N-methyl-(6-phenylhexanamido)]decahydroisoquinoline, trans-2- cyclopropylmethyl-8a-methoxy-4a-(3-hydroxyphenyl)-6α-[N-methyl- (3,4-dichlorophenylacetamido)]decahydroisoquinoline, trans-2- cyclopropylmethyl-8a-methoxy-4a-(3-hydroxyphenyl)-6α-(N-methylbenzamido)decahydroisoquinoline, trans-2- cyclopropylmethyl-8a-methoxy-4a-(3-hydroxyphenyl)-6α-[N-methyl- (2-naphthamido)]decahydroisoquinoline, trans-2- cyclopropylmethyl-8a-methoxy-4a-(3-hydroxyphenyl)-6α-[N-isobutyl-3-trifluoromethylcinnamamido)]decahydroisoquinoline, trans-2- cyclopropylmethyl-8a-methoxy-4a-(3-hydroxyphenyl)-6α-[N-isobutyl- (6-phenylhexanamido)]decahydroisoquinoline, trans-2- cyclopropylmethyl-8a-methoxy-4a-(3-hydroxyphenyl)-6α-[N-isobutyl- (3,4-dichlorophenylacetamido)]decahydroisoquinoline, trans-2- cyclopropylmethyl-8a-methoxy-4a-(3-hydroxyphenyl)-6α-(N- isobutylbenzamido)decahydroisoquinoline, trans-2- cyclopropylmethyl-8a-methoxy-4a-(3-hydroxyphenyl)-6α-[N-isobutyl- (2-naphthamido)]decahydroisoquinoline, trans-2-cyclopropylmethyl-4a-(3-methoxyphenyl)-6α-(3- trifluoromethylcinnamamido)decahydroisoquinoline, trans-2- cyclopropylmethyl-4a-(3-methoxyphenyl)-6α-(6- phenylhexanamido)decahydroisoquinoline, trans-2- cyclopropylmethyl-4a-(3-methoxyphenyl)-6α-(3,4- dichlorophenylacetamido)decahydroisoquinoline, trans-2- cyclopropylmethyl-4a-(3-methoxyphenyl)-6α- benzamidodecahydroisoquinoline, trans-2-cyclopropylmethyl-4a-(3- methoxyphenyl)-6α-(2-naphthamido)decahydroisoquinoline, trans-2- cyclopropylmethyl-4a-(3-methoxyphenyl) -6α-[N-methyl-3- trifluoromethylcinnamamido)]decahydroisoquinoline, trans-2- cyclopropylmethyl-4a-(3-methoxyphenyl) -6αa-[N-methyl-(6-phenylhexanamido)]decahydroisoquinoline, trans-2- cyclopropylmethyl-4a-(3-methoxyphenyl)-6α-[N-methyl-(3,4- dichlorophenylacetamido)]decahydroisoquinoline, trans-2- cyclopropylmethyl-4a-(3-methoxyphenyl)-6α-((N- methylbenzamido)decahydroisoquinoline, trans-2- cyclopropylmethyl-4a-(3-methoxyphenyl)-6α-[N-methyl-(2- naphthamido)]decahydroisoquinoline, trans-2-cyclopropylmethyl- 4a-(3-methoxyphenyl)-6α-[N-isobutyl-3-trifluoromethylcinnamamido)]decahydroisoquinoline, trans-2- cyclopropylmethyl-4a-(3-methoxyphenyl)-6α-[N-isobutyl-(6- phenylhexanamido)]decahydroisoquinoline, trans-2- cyclopropylmethyl-4a-(3-methoxyphenyl)-6α-[N-isobutyl-(3,4-dichlorophenylacetamido)]decahydroisoquinoline, trans-2- cyclopropylmethyl-4a-(3-methoxyphenyl)-6α-(N-isobutylbenzamido)decahydroisoquinoline, trans-2-cyclopropylmethyl-4a-(3-methoxyphenyl)-6α-[N-isobutyl-(2- naphthamido)]decahydroisoquinoline, trans-2-cyclopropylmethyl-8a-hydroxy-4a-(3-methoxyphenyl)-6α-(3- trifluoromethylcinnamamido)decahydroisoquinoline, trans-2- cyclopropylmethyl-8a-hydroxy-4a-(3-methoxyphenyl)-6α-(6- phenylhexanamido)decahydroisoquinoline, trans-2- cyclopropylmethyl-8a-hydroxy-4a-(3-methoxyphenyl)-6α-(3,4- dichlorophenylacetamido)decahydroisoquinoline, trans-2- cyclopropylmethyl-8a-hydroxy-4a-(3-methoxyphenyl)-6α- benzamidodecahydroisoquinoline, trans-2- cyclopropylmethyl-8a- hydroxy-4a-(3-methoxyphenyl)-6α-(2- naphthamido)decahydroisoquinoline, trans-2- cyclopropylmethyl-8a- hydroxy-4a-(3-methoxyphenyl)-6α-[N-methyl-3- trifluoromethylcinnamamido)]decahydroisoquinoline, trans-2- cyclopropylmethyl-8a-hydroxy-4a-(3-methoxyphenyl)-6α-[N-methyl-(6-phenylhexanamido)]decahydroisoquinoline, trans-2- cyclopropylmethyl-8a-hydroxy-4a-(3-methoxyphenyl)-6α-[N-methyl- (3,4-dichlorophenylacetamido)]decahydroisoquinoline, trans-2- cyclopropylmethyl-8a-hydroxy-4a-(3-methoxyphenyl)-6α-(N-methylbenzamido)decahydroisoquinoline, trans-2- cyclopropylmethyl-8a-hydroxy-4a-(3-methoxyphenyl)-6α-[N-methyl- (2-naphthamido)]decahydroisoquinoline, trans-2- cyclopropylmethyl-8a-hydroxy-4a-(3-methoxyphenyl)-6α-[N-isobutyl-3-trifluoromethylcinnamamido)]decahydroisoquinoline, trans-2- cyclopropylmethyl-8a-hydroxy-4a-(3-methoxyphenyl)-6α-[N-isobutyl-(6-phenylhexanamido)]decahydroisoquinoline, trans-2- cyclopropylmethyl-8a-hydroxy-4a-(3-methoxyphenyl)-6α-[N-isobutyl- (3,4- dichlorophenylacetamido)]decahydroisoquinoline, trans-2- cyclopropylmethyl-8a-hydroxy-4a-(3-methoxyphenyl)-6α-(N- isobutylbenzamido)decahydroisoquinoline, trans-2- cyclopropylmethyl-8a-hydroxy-4a-(3-methoxyphenyl)-6α-[N-isobutyl- (2-naphthamido)]decahydroisoquinoline, trans-2-cyclopropylmethyl-8-acetoxy-4a-(3-methoxyphenyl)-6α-(3-trifluoromethylcinnamamido)decahydroisoquinoline, trans-2- cyclopropylmethyl-8a-acetoxy-4a-(3-methoxyphenyl)-6α-(6- phenylhexanamido)decahydroisoquinoline, trans-2- cyclopropylmethyl-8a-acetoxy-4a-(3-methoxyphenyl)-6α-(3,4-dichlorophenylacetamido)decahydroisoquinoline, trans-2- cyclopropylmethyl-8a-acetoxy-4a-(3-methoxyphenyl)-6α- benzamidodecahydroisoquinoline, trans-2- cyclopropylmethyl-8a- acetoxy-4a-(3-methoxyphenyl)-6α-(2- naphthamido)decahydroisoquinoline, trans-2- cyclopropylmethyl-8a- acetoxy-4a-(3-methoxyphenyl)-6α-[N-methyl-3- trifluoromethylcinnamamido)]decahydroisoquinoline, trans-2- cyclopropylmethyl-8a-acetoxy-4a-(3-methoxyphenyl)-6α-[N-methyl-(6-phenylhexanamido)]decahydroisoquinoline, trans-2- cyclopropylmethyl-8a-acetoxy-4a-(3-methoxyphenyl)-6α-[N-methyl- (3,4-dichlorophenylacetamido)]decahydroisoquinoline, trans-2- cyclopropylmethyl-8a-acetoxy-4a-(3-methoxyphenyl)-6α-(N-methylbenzamido)decahydroisoquinoline, trans-2- cyclopropylmethyl-8a-acetoxy-4a-(3-methoxyphenyl)-6α-[N-methyl- (2-naphthamido)]decahydroisoquinoline, trans-2- cyclopropylmethyl-8a-acetoxy-4a-(3-methoxyphenyl)-6α-[N-isobutyl-3-trifluoromethylcinnamamido)]decahydroisoquinoline, trans-2- cyclopropylmethyl-8a-acetoxy-4a-(3-methoxyphenyl)-6α-[N-isobutyl- (6-phenylhexanamido)]decahydroisoquinoline, trans-2- cyclopropylmethyl-8a-acetoxy-4a-(3-methoxyphenyl)-6α-[N-isobutyl- (3,4-dichlorophenylacetamido)]decahydroisoquinoline, trans-2- cyclopropylmethyl-8a-acetoxy-4a-(3-methoxyphenyl)-6α-(N- isobutylbenzamido)decahydroisoquinoline, trans-2- cyclopropylmethyl-8a-acetoxy-4a-(3-methoxyphenyl)-6α-[N-isobutyl- (2-naphthamido)]decahydroisoquinoline, trans-2-cyclopropylmethyl-8a-methoxy-4a-(3-methoxyphenyl)-6α-(3-trifluoromethylcinnamamido)decahydroisoquinoline, trans-2- cyclopropylmethyl-8a-methoxy-4a-(3-methoxyphenyl)-6α-(6- phenylhexanamido)decahydroisoquinoline, trans-2- cyclopropylmethyl-8a-methoxy-4a-(3-methoxyphenyl)-6α-(3,4-dichlorophenylacetamido)decahydroisoquinoline, trans-2- cyclopropylmethyl-8a-methoxy-4a-(3-methoxyphenyl)-6α- benzamidodecahydroisoquinoline, trans-2-cyclopropylmethyl-8a- methoxy-4a-(3-methoxyphenyl)-6α-(2- naphthamido)decahydroisoquinoline, trans-2-cyclopropylmethyl-8a-methoxy-4a-(3-methoxyphenyl)-6α-[N-methyl-3- trifluoromethylcinnamamido)]decahydroisoquinoline, trans-2- cyclopropylmethyl-8a-methoxy-4a-(3-methoxyphenyl)-6α-[N-methyl- (6-phenylhexanamido)]decahydroisoquinoline, trans-2- cyclopropylmethyl-8a-methoxy-4a-(3-methoxyphenyl)-6α-[N-methyl- (3,4-dichlorophenylacetamido)]decahydroisoquinoline, trans-2- cyclopropylmethyl-8a-methoxy-4a-(3-methoxyphenyl)-6α-(N- methylbenzamido)decahydroisoquinoline, trans-2-cyclopropylmethyl-8a-methoxy-4a-(3-methoxyphenyl)-6α-[N-methyl- (2-naphthamido)]decahydroisoquinoline, trans-2-cyclopropylmethyl-8a-methoxy-4a-(3-methoxyphenyl)-6α-[N-isobutyl- 3-trifluoromethylcinnamamido)]decahydroisoquinoline, trans-2- cyclopropylmethyl-8a-methoxy-4a-(3-methoxyphenyl)-6α-[N-isobutyl- (6-phenylhexanamido)]decahydroisoquinoline, trans-2-cyclopropylmethyl-8a-methoxy-4a-(3-methoxyphenyl)-6α-[N-isobutyl- (3,4-dichlorophenylacetamido)]decahydroisoquinoline, trans-2- cyclopropylmethyl-8a-methoxy-4a-(3-methoxyphenyl)-6α-(N-isobutylbenzamido)decahydroisoquinoline, trans-2- cyclopropylmethyl-8a-methoxy-4a-(3-methoxyphenyl)-6α-[(N-isobutyl- (2-naphthamido)]decahydroisoquinoline, trans-2-cyclopropylmethyl-4a-(3-acetoxyphenyl)-6α-(3- trifluoromethylcinnamamido)decahydroisoquinoline, trans-2- cyclopropylmethyl-4a-(3-acetoxyphenyl)-6α-(6- phenylhexanamido)decahydroisoquinoline, trans-2- cyclopropylmethyl-4a-(3-acetoxyphenyl)-6α-(3,4- dichlorophenylacetamido)decahydroisoquinoline, trans-2- cyclopropylmethyl-4a-(3-acetoxyphenyl)-6α- benzamidodecahydroisoquinoline, trans-2-cyclopropylmethyl-4a-(3- acetoxyphenyl)-6α-(2-naphthamido)decahydroisoquinoline, trans-2- cyclopropylmethyl-4a-(3-acetoxyphenyl)-6α-[N-methyl-3- trifluoromethylcinnamamido)]decahydroisoquinoline, trans-2- cyclopropylmethyl-4a-(3-acetoxyphenyl)-6α-[N-methyl-(6- phenylhexanamido)]decahydroisoquinoline, trans-2- cyclopropylmethyl-4a-(3-acetoxyphenyl)-6α-[N-methyl-(3,4-dichlorophenylacetamido)]decahydroisoquinoline, trans-2- cyclopropylmethyl-4a-(3-acetoxyphenyl)-6α-(N-methylbenzamido)decahydroisoquinoline, trans-2-cyclopropylmethyl-4a-(3-acetoxyphenyl)-6α-[N-methyl-(2- naphthamido)]decahydroisoquinoline, trans-2-cyclopropylmethyl- 4a-(3-acetoxyphenyl)-6α-[N-isobutyl-3-trifluoromethylcinnamamido)]decahydroisoquinoline, trans-2- cyclopropylmethyl-4a-(3-acetoxyphenyl)-6α-[N-isobutyl-(6-phenylhexanamido)]decahydroisoquinoline, trans-2- cyclopropylmethyl-4a-(3-acetoxyphenyl)-6α-[N-isobutyl-(3,4- dichlorophenylacetamido)]decahydroisoquinoline, trans-2- cyclopropylmethyl-4a-(3-acetoxyphenyl)-6α-(N- isobutylbenzamido)decahydroisoquinoline, trans-2- cyclopropylmethyl-4a-(3-acetoxyphenyl)-6α-[N-isobutyl-(2- naphthamido)]decahydroisoquinoline, trans-2-cyclopropylmethyl-8a-hydroxy-4a-(3-acetoxyphenyl)-6α-(3-trifluoromethylcinnamamido)decahydroisoquinoline, trans-2- cyclopropylmethyl-8a-hydroxy-4a-(3-acetoxyphenyl)-6α-(6- phenylhexanamido)decahydroisoquinoline, trans-2- cyclopropylmethyl-8a-hydroxy-4a-(3-acetoxyphenyl)-6α-(3,4-dichlorophenylacetamido)decahydroisoquinoline, trans-2- cyclopropylmethyl-8a-hydroxy-4a-(3-acetoxyphenyl)-6α- benzamidodecahydroisoquinoline, trans-2-cyclopropylmethyl-8- hydroxy-4a-(3-acetoxyphenyl)-6α-(2- naphthamido)decahydroisoquinoline, trans-2- cyclopropylmethyl-8- hydroxy-4a-(3-acetoxyphenyl)-6α-[N-methyl-3- trifluoromethylcinnamamido)]decahydroisoquinoline, trans-2- cyclopropylmethyl-8a-hydroxy-4a-(3-acetoxyphenyl)-6α-[N-methyl- (6-phenylhexanamido)]decahydroisoquinoline, trans-2- cyclopropylmethyl-8a-hydroxy-4a-(3-acetoxyphenyl)-6α-[N-methyl- (3,4-dichlorophenylacetamido)]decahydroisoquinoline, trans-2- cyclopropylmethyl-8a-hydroxy-4a-(3-acetoxyphenyl)-6α-(N-methylbenzamido)decahydroisoquinoline, trans-2- cyclopropylmethyl-8a-hydroxy-4a-(3-acetoxyphenyl)-

6α-[N-methyl- (2-naphthamido)]decahydroisoquinoline, trans-2- cyclopropylmethyl-8a-hydroxy-4a-(3-acetoxyphenyl)-6α-[N-isobutyl-3-trifluoromethylcinnamamido)]decahydroisoquinoline, trans-2- cyclopropylmethyl-8a-hydroxy-4a-(3-acetoxyphenyl)-6α-[N-isobutyl- (6-phenylhexanamido)]decahydroisoquinoline, trans-2- cyclopropylmethyl-8a-hydroxy-4a-(3-acetoxyphenyl)-6α-[N-isobutyl- (3,4-dichlorophenylacetamido)]decahydroisoquinoline, trans-2- cyclopropylmethyl-8a-hydroxy-4a-(3-acetoxyphenyl)-6α-(N- isobutylbenzamido)decahydroisoquinoline, trans-2- cyclopropylmethyl-8a-hydroxy-4a-(3-acetoxyphenyl)-6α-[N-isobutyl- (2-naphthamido)]decahydroisoquinoline, trans-2-cyclopropylmethyl-8a-acetoxy-4a-(3-acetoxyphenyl)-6α-(3-trifluoromethylcinnamamido)decahydroisoquinoline, trans-2- cyclopropylmethyl-8a-acetoxy-4a-(3-acetoxyphenyl)-6α-(6- phenylhexanamido)decahydroisoquinoline, trans-2- cyclopropylmethyl-8a-acetoxy-4a-(3-acetoxyphenyl)-6α-(3,4-dichlorophenylacetamido)decahydroisoquinoline, trans-2- cyclopropylmethyl-8a-acetoxy-4a-(3-acetoxyphenyl)-6α- benzamidodecahydroisoquinoline, trans-2- cyclopropylmethyl-8- acetoxy-4a-(3-acetoxyphenyl)-6α-(2- naphthamido)decahydroisoquinoline, trans-2- cyclopropylmethyl-8- acetoxy-4a-(3-acetoxyphenyl)-6α-[N-methyl-3- trifluoromethylcinnamamido)]decahydroisoquinoline, trans-2- cyclopropylmethyl-8a-acetoxy-4a-(3-acetoxyphenyl)-6α-[N-methyl-(6-phenylhexanamido)]decahydroisoquinoline, trans-2- cyclopropylmethyl-8a-acetoxy-4a-(3-acetoxyphenyl)-6α-[N-methyl- (3,4-dichlorophenylacetamido)]decahydroisoquinoline, trans-2- cyclopropylmethyl-8a-acetoxy-4a-(3-acetoxyphenyl)-6α-(N- methylbenzamido)decahydroisoquinoline, trans-2- cyclopropylmethyl-8a-acetoxy-4a-(3-acetoxyphenyl)-6α-[N-methyl-(2-naphthamido)]decahydroisoquinoline, trans-2- cyclopropylmethyl-8a-acetoxy-4a-(3-acetoxyphenyl)-6α-[N-isobutyl- 3-trifluoromethylcinnamamido)]decahydroisoquinoline, trans-2- cyclopropylmethyl-8a-acetoxy-4a-(3-acetoxyphenyl)-6α-[N-isobutyl-(6-phenylhexanamido)]decahydroisoquinoline, trans-2- cyclopropylmethyl-8a-acetoxy-4a-(3-acetoxyphenyl)-6α-[N-isobutyl- (3,4-dichlorophenylacetamido)]decahydroisoquinoline, trans-2- cyclopropylmethyl-8a-acetoxy-4a-(3-acetoxyphenyl)-6α-(N-isobutylbenzamido)decahydroisoquinoline, trans-2- cyclopropylmethyl-8a-acetoxy-4a-(3-acetoxyphenyl)-6α-[N-isobutyl- (2-naphthamido)]decahydroisoquinoline, trans-2-cyclopropylmethyl-8a-methoxy-4a-(3-acetoxyphenyl)-6α-(3-trifluoromethylcinnamamido)decahydroisoquinoline, trans-2- cyclopropylmethyl-8a-methoxy-4a-(3-acetoxyphenyl)-6α-(6- phenylhexanamido)decahydroisoquinoline, trans-2- cyclopropylmethyl-8a-methoxy-4a-(3-acetoxyphenyl)-6α-(3,4-dichlorophenylacetamido)decahydroisoquinoline, trans-2- cyclopropylmethyl-8a-methoxy-4a-(3-acetoxyphenyl)-6α- benzamidodecahydroisoquinoline, trans-2- cyclopropylmethyl-8- methoxy-4a-(3-acetoxyphenyl)-6α-(2- naphthamido)decahydroisoquinoline, trans-2- cyclopropylmethyl-8- methoxy-4a-(3-acetoxyphenyl)-6α-[N-methyl-3- trifluoromethylcinnamamido)]decahydroisoquinoline, trans-2- cyclopropylmethyl-8a-methoxy-4a-(3-acetoxyphenyl)-6α-[N-methyl-(6-phenylhexanamido)]decahydroisoquinoline, trans-2- cyclopropylmethyl-8a-methoxy-4a-(3-acetoxyphenyl)-6α-[N-methyl-(3,4-dichlorophenylacetamido)]decahydroisoquinoline, trans-2- cyclopropylmethyl-8a-methoxy-4a-(3-acetoxyphenyl)-6α-(N-methylbenzamido)decahydroisoquinoline, trans-2- cyclopropylmethyl-8a-methoxy-4a-(3-acetoxyphenyl)-6α-[N-methyl- (2-naphthamido)]decahydroisoquinoline, trans-2- cyclopropylmethyl-8a-methoxy-4a-(3-acetoxyphenyl)-6α-[N-isobutyl-3-trifluoromethylcinnamamido)]decahydroisoquinoline, trans-2- cyclopropylmethyl-8a-methoxy-4a-(3-acetoxyphenyl)-6α-[N-isobutyl- (6-phenylhexanamido)]decahydroisoquinoline, trans-2- cyclopropylmethyl-8a-methoxy-4a-(3-acetoxyphenyl)-6α-[N-isobutyl- (3,4-dichlorophenylacetamido)]decahydroisoquinoline, trans-2- cyclopropylmethyl-8a-methoxy-4a-(3-acetoxyphenyl)-6α-(N- isobutylbenzamido)decahydroisoquinoline, trans-2- cyclopropylmethyl-8α-methoxy-4a-(3-acetoxyphenyl)-6α-[N-isobutyl- (2-naphthamido)]decahydroisoquinoline, trans-2-allyl-4a-(3-hydroxyphenyl)-6α-(3- trifluoromethylcinnamamido)decahydroisoquinoline, trans-2-allyl- 4a-(3-hydroxyphenyl)-6α-(6- phenylhexanamido)decahydroisoquinoline, trans-2-allyl-4a-(3-hydroxyphenyl)-6α-(3,4- dichlorophenylacetamido)decahydroisoquinoline, trans-2-allyl-4a-(3-hydroxyphenyl)-6α-benzamidodecahydroisoquinoline, trans-2- allyl-4a-(3-hydroxyphenyl)-6a-(2- naphthamido)decahydroisoquinoline, trans-2-allyl-4a-(3-hydroxyphenyl)-6α-[N-methyl-3-trifluoromethylcinnamamido)]decahydroisoquinoline, trans-2- allyl-4a-(3-hydroxyphenyl)-6α-[N-methyl-(6-phenylhexanamido)]decahydroisoquinoline, trans-2-allyl-4a-(3- hydroxyphenyl)-6α-[N-methyl-(3,4-dichlorophenylacetamido)]decahydroisoquinoline, trans-2-allyl- 4a-(3-hydroxyphenyl)-6α-(N- methylbenzamido)decahydroisoquinoline, trans-2-allyl-4a-(3-hydroxyphenyl)-6α-[N-methyl-(2- naphthamido)]decahydroisoquinoline, trans-2-allyl-4a-(3-hydroxyphenyl)-6α-[N-isobutyl-3-trifluoromethylcinnamamido)]decahydroisoquinoline, trans-2- allyl-4a-(3-hydroxyphenyl)-6α-[N-isobutyl-(6-phenylhexanamido)]decahydroisoquinoline, trans-2-allyl-4a-(3- hydroxyphenyl)-6α-[N-isobutyl-(3,4-dichlorophenylacetamido)]decahydroisoquinoline, trans-2-allyl- 4a-(3-hydroxyphenyl)-6α-(N-isobutylbenzamido)decahydroisoquinoline, trans-2-allyl-4a-(3- hydroxyphenyl)-6α-[N-isobutyl-(2- naphthamido)]decahydroisoquinoline, trans-2-allyl-8a-hydroxy-4a-(3-hydroxyphenyl)-6α-(3- trifluoromethylcinnamamido)decahydroisoquinoline, trans-2-allyl- 8a-hydroxy-4a-(3-hydroxyphenyl)-6α-(6- phenylhexanamido)decahydroisoquinoline, trans-2-allyl-8a-hydroxy- 4a-(3-hydroxyphenyl)-6α-(3,4- dichlorophenylacetamido)decahydroisoquinoline, trans-2-allyl-8a- hydroxy-4a-(3-hydroxyphenyl)-6α-benzamidodecahydroisoquinoline, trans-2-allyl-8a-hydroxy-4a-(3-hydroxyphenyl)-6α-(2-naphthamido)decahydroisoquinoline, trans-2-allyl-8a-hydroxy-4a- (3-hydroxyphenyl)-6α-[N-methyl-3-trifluoromethylcinnamamido)]decahydroisoquinoline, trans-2- allyl-8a-hydroxy-4a-(3-hydroxyphenyl)-6α-[N-methyl-(6-phenylhexanamido)]decahydroisoquinoline, trans-2-allyl-8a- hydroxy-4a-(3-hydroxyphenyl)-6α-[N-methyl-(3,4- dichlorophenylacetamido)]decahydroisoquinoline, trans-2-allyl-8a- hydroxy-4a-(3-hydroxyphenyl)-6α-(N- methylbenzamido)decahydroisoquinoline, trans-2-allyl-8a-hydroxy- 4a-(3- hydroxyphenyl)-6α-[N-methyl-(2- naphthamido)] decahydroisoquinoline, trans-2-allyl-8a-hydroxy-4a-(3-hydroxyphenyl)-6α-[N-isobutyl-3-trifluoromethylcinnamamido)]decahydroisoquinoline, trans-2- allyl-8a-hydroxy-4a-(3-hydroxyphenyl)-6α-[N-isobutyl-(6- phenylhexanamido)]decahydroisoquinoline, trans-2-allyl-8a- hydroxy-4a-(3-hydroxyphenyl)-6α-[N-isobutyl-(3,4- dichlorophenylacetamido)] decahydroisoquinoline, trans-2-allyl-8a- hydroxy-4a-(3-hydroxyphenyl)-6α-(N- isobutylbenzamido) decahydroisoquinoline, trans-2-allyl-8a- hydroxy-4a-(3-hydroxyphenyl)-6α-[N-isobutyl-(2- naphthamido)] decahydroisoquinoline, trans-2-allyl-8a-acetoxy-4a-(3-hydroxyphenyl)-6α-(3- trifluoromethylcinnamamido) decahydroisoquinoline, trans-2-allyl- 8-acetoxy-4a-(3- hydroxyphenyl)-6α-(6- phenylhexanamido) decahydroisoquinoline, trans-2-allyl-8a-acetoxy- 4a-(3-hydroxyphenyl)-6α-(3,4- dichlorophenylacetamido) decahydroisoquinoline, trans-2-allyl-8a- acetoxy-4a-(3-hydroxyphenyl)-6α-benzamidodecahydroisoquinoline, trans-2-allyl-8a-acetoxy-4a-(3-hydroxyphenyl)-6α-(2-naphthamido)decahydroisoquinoline, trans-2-allyl-8a-acetoxy-4a- (3-hydroxyphenyl)-6α-[N-methyl-3-trifluoromethylcinnamamido)]decahydroisoquinoline, trans-2- allyl-8a-acetoxy-4a-(3-hydroxyphenyl)-6α-[N-methyl-(6- phenylhexanamido)]decahydroisoquinoline, trans-2-allyl-8a- acetoxy-4a-(3-hydroxyphenyl)-6α-[N-methyl-(3,4- dichlorophenylacetamido)] decahydroisoquinoline, trans-2-allyl-8a- acetoxy-4a-(3-hydroxyphenyl)-6α-(N- methylbenzamido) decahydroisoquinoline, trans-2-allyl-8a-acetoxy- 4a-(3-hydroxyphenyl)-6α-[N-methyl-(2- naphthamido)] decahydroisoquinoline, trans-2-allyl-8a-acetoxy-4a-(3-hydroxyphenyl)-6α-[N-isobutyl-3-trifluoromethylcinnamamido)]decahydroisoquinoline, trans-2- allyl-8a-acetoxy-4a-(3-hydroxyphenyl)-6α-[N-isobutyl-(6- phenylhexanamido)]decahydroisoquinoline, trans-2-allyl-8a- acetoxy-4a-(3-hydroxyphenyl)-6α-[N-isobutyl-(3,4- dichlorophenylacetamido)] decahydroisoquinoline, trans-2-allyl-8a- acetoxy-4a-(3- hydroxyphenyl)-6α-(N- isobutylbenzamido) decahydroisoquinoline, trans-2-allyl-8a- acetoxy-4a-(3-hydroxyphenyl)-6α-[N-isobutyl-(2- naphthamido)] decahydroisoquinoline, trans-2-allyl-8a-methoxy-4a-(3-hydroxyphenyl)-6α-(3- trifluoromethylcinnamamido) decahydroisoquinoline, trans-2-allyl- 8a-methoxy-4a-(3-hydroxyphenyl)-6α-(6- phenylhexanamido) decahydroisoquinoline, trans-2-allyl-8a-methoxy- 4a-(3-hydroxyphenyl)-6α-(3,4- dichlorophenylacetamido) decahydroisoquinoline, trans-2-allyl-8a- methoxy-4a-(3-hydroxyphenyl)-6α-benzamidodecahydroisoquinoline, trans-2-allyl-8a-methoxy-4a-(3-hydroxyphenyl)-6α-(2-naphthamido)decahydroisoquinoline, trans-2-allyl-8a-methoxy-4a- (3-hydroxyphenyl)-6α-[N-methyl-3-trifluoromethylcinnamamido)]decahydroisoquinoline, trans-2- allyl-8a-methoxy-4a-(3-hydroxyphenyl) -6α-[N-methyl-(6- phenylhexanamido)]decahydroisoquinoline, trans-2-allyl-8a- methoxy-4a-(3-hydroxyphenyl)-6α-[N-methyl-(3,4- dichlorophenylacetamido)] decahydroisoquinoline, trans-2-allyl-8a- methoxy-4a-(3-hydroxyphenyl)-6α-(N- methylbenzamido) decahydroisoquinoline, trans-2-allyl-8a-methoxy- 4a-(3-hydroxyphenyl)-6α-[N-methyl-(2- naphthamido)] decahydroisoquinoline, trans-2-allyl-8a-methoxy-4a- (3-hydroxyphenyl)-6α-[N-isobutyl-3-trifluoromethylcinnamamido)]decahydroisoquinoline, trans-2- allyl-8a-methoxy-4a-(3-hydroxyphenyl)-6α-[N-isobutyl-(6- phenylhexanamido)]decahydroisoquinoline, trans-2-allyl-8a- methoxy-4a-(3-hydroxyphenyl)-6α-[N-isobutyl-(3,4- dichlorophenylacetamido)] decahydroisoquinoline, trans-2-allyl-8a- methoxy-4a-(3-hydroxyphenyl)-6α-(N- isobutylbenzamido) decahydroisoquinoline, trans-2-allyl-8a- methoxy-4a-(3-hydroxyphenyl)-6α-[N-isobutyl-(2- naphthamido)] decahydroisoquinoline, trans-2-allyl-4a-(3-methoxyphenyl)-6α-(3- trifluoromethylcinnamamido) decahydroisoquinoline, trans-2-allyl- 4a-(3-methoxyphenyl)-6α-(6- phenylhexanamido) decahydroisoquinoline, trans-2-allyl-4a-(3-methoxyphenyl)-6α-(3,4- dichlorophenylacetamido) decahydroisoquinoline, trans-2-allyl-4a- (3-methoxyphenyl)-6α-benzamidodecahydroisoquinoline, trans-2- allyl-4a-(3-methoxyphenyl)-6a-(2- naphthamido) decahydroisoquinoline, trans-2-allyl-4a-(3-methoxyphenyl)-6α-[N-methyl-3-trifluoromethylcinnamamido)]decahydroisoquinoline, trans-2- allyl-4a-(3-methoxyphenyl)-6α-[N-methyl-(6-phenylhexanamido)]decahydroisoquinoline, trans-2-allyl-4a-(3- methoxyphenyl)-6α-[N-methyl-(3,4-dichlorophenylacetamido)]decahydroisoquinoline, trans-2-allyl- 4a-(3-methoxyphenyl)-6α-(N-methylbenzamido)decahydroisoquinoline, trans-2-allyl-4a-(3- methoxyphenyl)-6α-[N-methyl-(2- naphthamido)] decahydroisoquinoline, trans-2-allyl-4a-(3-methoxyphenyl)-6α-[N-isobutyl-3-trifluoromethylcinnamamido)]decahydroisoquinoline, trans-2- allyl-4a-(3-methoxyphenyl)-6α-[N-isobutyl-(6-phenylhexanamido)]decahydroisoquinoline, trans-2-allyl-4a-(3- methoxyphenyl)-6α-[N-isobutyl-(3,4-dichlorophenylacetamido)]decahydroisoquinoline, trans-2-allyl- 4a-(3-methoxyphenyl)-6α-(N-isobutylbenzamido)decahydroisoquinoline, trans-2-allyl-4a-(3- methoxyphenyl)-6α-[N-isobutyl-(2- naphthamido)]decahydroisoquinoline, trans-2-allyl-8a-hydroxy-4a-(3-methoxyphenyl)-6α-(3- trifluoromethylcinnamamido) decahydroisoquinoline, trans-2-allyl- 8a-hydroxy-4a-(3-methoxyphenyl)-6α-(6- phenylhexanamido) decahydroisoquinoline, trans-2-allyl-8a-hydroxy- 4a-(3-methoxyphenyl)-6α-6(3,4- dichlorophenylacetamido) decahydroisoquinoline, trans-2-allyl-8a- hydroxy-4a-(3-methoxyphenyl)-6α-benzamidodecahydroisoquinoline, trans-2-allyl-8a-hydroxy-4a-(3-methoxyphenyl)-6α-(2-naphthamido)decahydroisoquinoline, trans-2-allyl-8a-hydroxy-4a- (3-methoxyphenyl)-6α-[N-methyl-3-trifluoromethylcinnamamido)]decahydroisoquinoline, trans-2- allyl-8a-hydroxy-4a-(3-methoxyphenyl)-6α-[N-methyl-(6- phenylhexanamido)]decahydroisoquinoline, trans-2-allyl-8a- hydroxy-4a-(3-methoxyphenyl)-6α-[N-methyl-(3,4- dichlorophenylacetamido)] decahydroisoquinoline, trans-2-allyl-8a- hydroxy-4a-(3-methoxyphenyl)-6α-(N- methylbenzamido) decahydroisoquinoline, trans-2-allyl-8a-hydroxy- 4a-(3-methoxyphenyl)-6α-[N-methyl-(2- naphthamido)] decahydroisoquinoline, trans-2-allyl-8a-hydroxy-4a- (3-methoxyphenyl)-6α-[N-isobutyl-3-trifluoromethylcinnamamido)]decahydroisoquinoline, trans-2- allyl-8a-hydroxy-4a-(3-methoxyphenyl)-6α-[N-isobutyl-(6- phenylhexanamido)]decahydroisoquinoline, trans-2-allyl-8a- hydroxy-4a-(3-methoxyphenyl)-6α-[N-isobutyl-(3,4- dichlorophenylacetamido)] decahydroisoquinoline, trans-2-allyl-8a- hydroxy-4a-(3-methoxyphenyl)-6α-(N- isobutylbenzamido) decahydroisoquinoline, trans-2-allyl-8a- hydroxy-4a-(3- methoxyphenyl)-6α-[N-isobutyl-(2- naphthamido)] decahydroisoquinoline, trans-2-allyl-8a-acetoxy-4a-(3-methoxyphenyl)-6α-(3- trifluoromethylcinnamamido) decahydroisoquinoline, trans-2-allyl- 8a-acetoxy-4a-(3-methoxyphenyl)-6α-(6- phenylhexanamido) decahydroisoquinoline, trans-2-allyl-8a-acetoxy- 4a-(3-methoxyphenyl)-6α-(3,4- dichlorophenylacetamido) decahydroisoquinoline, trans-2-allyl-8a- acetoxy-4a-(3-methoxyphenyl)-6α-benzamidodecahydroisoquinoline, trans-2-allyl-8a-acetoxy-4a-(3-methoxyphenyl)-6α-(2- naphthamido)decahydroisoquinoline, trans-2-allyl-8a-acetoxy-4a- (3-methoxyphenyl)-6α-[N-methyl-3-trifluoromethylcinnamamido)]decahydroisoquinoline, trans-2- allyl-8a-acetoxy-4a-(3-methoxyphenyl)-6α-[N-methyl-(6- phenylhexanamido)]decahydroisoquinoline, trans-2-allyl-8a- acetoxy-4a-(3-methoxyphenyl)-6α-[N-methyl-(3,4- dichlorophenylacetamido)] decahydroisoquinoline, trans-2-allyl-8a- acetoxy-4a-(3-methoxyphenyl)-6α-(N- methylbenzamido) decahydroisoquinoline, trans-2-allyl-8a-acetoxy- 4a-(3-methoxyphenyl)-6α-[N-methyl-(2- naphthamido)] decahydroisoquinoline, trans-2-allyl-8a-acetoxy-4a-(3-methoxyphenyl)-6α-[N-isobutyl-3-trifluoromethylcinnamamido)]decahydroisoquinoline, trans-2- allyl-8a-acetoxy-4a-(3-methoxyphenyl)-6α-[N-isobutyl-(6- phenylhexanamido)]decahydroisoquinoline, trans-2-allyl-8a- acetoxy-4a-(3-methoxyphenyl)-6α-[N-isobutyl-(3,4- dichlorophenylacetamido)] decahydroisoquinoline, trans-2-allyl-8a- acetoxy-4a-(3-methoxyphenyl)-6α-(N- isobutylbenzamido) decahydroisoquinoline, trans-2-allyl-8a- acetoxy-4a-(3-methoxyphenyl)-6α-[N-isobutyl-(2- naphthamido)] decahydroisoquinoline, trans-2-allyl-8a-methoxy-4a-(3-methoxyphenyl)-6α-(3- trifluoromethylcinnamamido) decahydroisoquinoline, trans-2-allyl- 8a-methoxy-4a-(3-methoxyphenyl)-6α-(6- phenylhexanamido) decahydroisoquinoline, trans-2-allyl-8a-methoxy- 4a-(3-methoxyphenyl)-6α-(3,4- dichlorophenylacetamido) decahydroisoquinoline, trans-2-allyl-8a- methoxy-4a-(3-methoxyphenyl)-6a-benzamidodecahydroisoquinoline, trans-2-allyl-8a-methoxy-4a-(3-methoxyphenyl)-6α-(2- naphthamido)decahydroisoquinoline, trans-2-allyl-8a-methoxy-4a- (3-methoxyphenyl)-6α-[N-methyl-3-trifluoromethylcinnamamido)]decahydroisoquinoline, trans-2- allyl-8a-methoxy-4a-(3-methoxyphenyl)-6α-[N-methyl-(6- phenylhexanamido)]decahydroisoquinoline, trans-2-allyl-8a- methoxy-4a-(3-methoxyphenyl)-6α-[N-methyl-(3,4- dichlorophenylacetamido)] decahydroisoquinoline, trans-2-allyl-8a- methoxy-4a-(3-methoxyphenyl)-6α-(N- methylbenzamido) decahydroisoquinoline, trans-2-allyl-8a-methoxy- 4a-(3-methoxyphenyl)-6α-[N-methyl-(2- naphthamido)] decahydroisoquinoline, trans-2-allyl-8a-methoxy-4a- (3-methoxyphenyl)-6α-[N-isobutyl-3-trifluoromethylcinnamamido)]decahydroisoquinoline, trans-2- allyl-8a-methoxy-4a-(3-methoxyphenyl)-6α-[N-isobutyl-(6- phenylhexanamido)]decahydroisoquinoline, trans-2-allyl-8a- methoxy-4a-(3-methoxyphenyl)-6α-[N-isobutyl-(3,4- dichlorophenylacetamido)] decahydroisoquinoline, trans-2-allyl-8a- methoxy-4a-(3-methoxyphenyl)-6α-(N- isobutylbenzamido) decahydroisoquinoline, trans-2-allyl-8a- methoxy-4a-(3-methoxyphenyl)-6α-[N-isobutyl-(2- naphthamido)] decahydroisoquinoline, trans-2-allyl-4a-(3-acetoxyphenyl)-6α-(3- trifluoromethylcinnamamido) decahydroisoquinoline, trans-2-allyl- 4a-(3-acetoxyphenyl)-6α-(6- phenylhexanamido) decahydroisoquinoline, trans-2-allyl-4a-(3-acetoxyphenyl)-6α-(3,4- dichlorophenylacetamido) decahydroisoquinoline, trans-2-allyl-4a- (3-acetoxyphenyl)-6α-benzamidodecahydroisoquinoline, trans-2- allyl-4a-(3-acetoxyphenyl)-6α-(2- naphthamido) decahydroisoquinoline, trans-2-allyl-4a-(3-acetoxyphenyl)-6α-[N-methyl-3-trifluoromethylcinnamamido)]decahydroisoquinoline, trans-2- allyl-4a-(3-acetoxyphenyl)-6α-[N-methyl-(6- phenylhexanamido)]decahydroisoquinoline, trans-2-allyl-4a-(3- acetoxyphenyl)-6α-[N-methyl-(3,4-dichlorophenylacetamido)]decahydroisoquinoline, trans-2-allyl- 4a-(3-acetoxyphenyl)-6α-(N- methylbenzamido) decahydroisoquinoline, trans-2-allyl-4a-(3-acetoxyphenyl)-6α-[N-methyl-(2- naphthamido)] decahydroisoquinoline, trans-2-allyl-4a-(3-acetoxyphenyl)-6α-[N-isobutyl-3-trifluoromethylcinnamamido)]decahydroisoquinoline, trans-2- allyl-4a-(3-acetoxyphenyl)-6α-[N-isobutyl-(6- phenylhexanamido)]decahydroisoquinoline, trans-2-allyl-4a-(3- acetoxyphenyl)-6α-[N-isobutyl-(3,4-dichlorophenylacetamido)]decahydroisoquinoline, trans-2-allyl- 4a-(3-acetoxyphenyl)-6α-(N- isobutylbenzamido)decahydroisoquinoline, trans-2-allyl-4a-(3- acetoxyphenyl)-6α-(N-isobutyl-(2- naphthamido)] decahydroisoquinoline, trans-2-allyl-8a-hydroxy-4a-(3-acetoxyphenyl)-6α-(3- trifluoromethylcinnamamido) decahydroisoquinoline, trans-2-allyl- 8a-hydroxy-4a-(3-acetoxyphenyl)-6α-(6- phenylhexanamido) decahydroisoquinoline, trans-2-allyl-8a-hydroxy- 4a-(3-acetoxyphenyl)-6α-(3,4- dichlorophenylacetamido) decahydroisoquinoline, trans-2-allyl-8a- hydroxy-4a-(3-acetoxyphenyl)-6α-benzamidodecahydroisoquinoline, trans-2-allyl-8a-hydroxy-4a-(3-acetoxyphenyl)-6α-(2- naphthamido)decahydroisoquinoline, trans-2-allyl-8a-hydroxy-4a- (3-acetoxyphenyl)-6α-[N-methyl-3-trifluoromethylcinnamamido)]decahydroisoquinoline, trans-2- allyl-8a-hydroxy-4a-(3-acetoxyphenyl)-6α-[N-methyl-(6- phenylhexanamido)]decahydroisoquinoline, trans-2-allyl-8a- hydroxy-4a-(3-acetoxyphenyl)-6α-[N-methyl-(3,4- dichlorophenylacetamido)] decahydroisoquinoline, trans-2-allyl-8a- hydroxy-4a-(3-acetoxyphenyl)-6α-(N- methylbenzamido) decahydroisoquinoline, trans-2-allyl-8a-hydroxy- 4a-(3-acetoxyphenyl)-6α-[N-methyl-(2- naphthamido)] decahydroisoquinoline, trans-2-allyl-8a-hydroxy-4a- (3-acetoxyphenyl)-6α-[N-isobutyl-3-trifluoromethylcinnamamido)]decahydroisoquinoline, trans-2- allyl-8a-hydroxy-4a-(3-acetoxyphenyl)-6α-[N-isobutyl-(6- phenylhexanamido)]decahydroisoquinoline, trans-2-allyl-8a- hydroxy-4a-(3-acetoxyphenyl)-6α-[N-isobutyl-(3,4- dichlorophenylacetamido)] decahydroisoquinoline, trans-2-allyl-8a- hydroxy-4a-(3-acetoxyphenyl)-6α-(N- isobutylbenzamido) decahydroisoquinoline, trans-2-allyl-8a- hydroxy-4a-(3-acetoxyphenyl)-6α-[N-isobutyl-(2- naphthamido)] decahydroisoquinoline, trans-2-allyl-8a-acetoxy-4a-(3-acetoxyphenyl)-6α-(3- trifluoromethylcinnamamido) decahydroisoquinoline, trans-2-allyl- 8a-acetoxy-4a-(3-acetoxyphenyl)-6α-(6- phenylhexanamido) decahydroisoquinoline, trans-2-allyl-8a-acetoxy- 4a-(3-acetoxyphenyl)-6α-(3,4- dichlorophenylacetamido) decahydroisoquinoline, trans-2-allyl-8a- acetoxy-4a-(3-acetoxyphenyl)-6α-benzamidodecahydroisoquinoline, trans-2-allyl-8a-acetoxy-4a-(3-acetoxyphenyl)-6α-(2- naphthamido)decahydroisoquinoline, trans-2-allyl-8a- acetoxy-4a- (3-acetoxyphenyl)-6α-[N-methyl-3- trifluoromethylcinnamamido)]decahydroisoquinoline, trans-2- allyl-8a-acetoxy-4a-(3-acetoxyphenyl)-6α-[N-methyl-(6- phenylhexanamido)]decahydroisoquinoline, trans-2-allyl-8a- acetoxy-4a-(3-acetoxyphenyl)-6α-[N-methyl-(3,4- dichlorophenylacetamido)] decahydroisoquinoline, trans-2-allyl-8- acetoxy-4a-(3-acetoxyphenyl)-6α-(N- methylbenzamido) decahydroisoquinoline, trans-2-allyl-8-acetoxy- 4a-(3-acetoxyphenyl)-6α-[N-methyl-(2- naphthamido)] decahydroisoquinoline, trans-2-allyl-8-acetoxy-4a- (3-acetoxyphenyl)-6α-[N-isobutyl-3- trifluoromethylcinnamamido)]decahydroisoquinoline, trans-2- allyl-8a-acetoxy-4a-(3-acetoxyphenyl)-6α-[N-isobutyl-(6- phenylhexanamido)]decahydroisoquinoline, trans-2-allyl-8a- acetoxy-4a-(3-acetoxyphenyl)-6α-[N-isobutyl-(3,4- dichlorophenylacetamido)] decahydroisoquinoline, trans-2-allyl-8a- acetoxy-4a-(3-acetoxyphenyl)-6α-(N- isobutylbenzamido) decahydroisoquinoline, trans-2-allyl-8a- acetoxy-4a-(3-acetoxyphenyl)-6α-[N-isobutyl-(2- naphthamido)] decahydroisoquinoline, trans-2-allyl-8a-methoxy-4a-(3-acetoxyphenyl)-6α-(3- trifluoromethylcinnamamido) decahydroisoquinoline, trans-2-allyl- 8a-methoxy-4a-(3-acetoxyphenyl)-6α-(6- phenylhexanamido) decahydroisoquinoline, trans-2-allyl-8a-methoxy- 4a-(3-acetoxyphenyl)-6α-(3,4- dichlorophenylacetamido) decahydroisoquinoline, trans-2-allyl-8a- methoxy-4a-(3-acetoxyphenyl)-6α-benzamidodecahydroisoquinoline, trans-2-allyl-8a-methoxy-4a-(3-acetoxyphenyl)-6α-(2- naphthamido)decahydroisoquinoline, trans-2-allyl-8a- methoxy-4a- (3-acetoxyphenyl)-6α-[N-methyl-3- trifluoromethylcinnamamido)]decahydroisoquinoline, trans-2- allyl-8a-methoxy-4a-(3-acetoxyphenyl)-6α-[N-methyl-(6- phenylhexanamido)]decahydroisoquinoline, trans-2-allyl-8a- methoxy-4a-(3-acetoxyphenyl)-6α-[N-methyl-(3,4- dichlorophenylacetamido)] decahydroisoquinoline, trans-2-allyl-8-a methoxy-4a-(3-acetoxyphenyl)-6α-(N- methylbenzamido) decahydroisoquinoline, trans-2-allyl-8a-methoxy- 4a-(3-acetoxyphenyl)-6α-(N-methyl-(2- naphthamido)] decahydroisoquinoline, trans-2-allyl-8a-methoxy-4a- (3-acetoxyphenyl)-6α-[N-isobutyl-3- trifluoromethylcinnamamido)]decahydroisoquinoline, trans-2- allyl-8a-methoxy-4a-(3-acetoxyphenyl)-6α-[N-isobutyl-(6- phenylhexanamido)]decahydroisoquinoline, trans-2-allyl-8a- methoxy-4a-(3-acetoxyphenyl)-6α-[N-isobutyl-(3,4- dichlorophenylacetamido)] decahydroisoquinoline, trans-2-allyl-8a- methoxy-4a-(3-acetoxyphenyl)-6α-(N- isobutylbenzamido) decahydroisoquinoline, trans-2-allyl-8a- methoxy-4a-(3-acetoxyphenyl)-6α-[N-isobutyl-(2- naphthamido)] decahydroisoquinoline, trans-2-methyl-4a-(3- hydroxyphenyl)-6α-(3- trifluoromethylcinnamamido) decahydroisoquinoline, trans-2- methyl-4a-(3- hydroxyphenyl)-6α-(6- phenylhexanamido) decahydroisoquinoline, trans-2-methyl-4a-(3- hydroxyphenyl)-6α-(3,4- dichlorophenylacetamido) decahydroisoquinoline, trans-2-methyl- 4a-(3- hydroxyphenyl)-6α-benzamidodecahydroisoquinoline, trans-2- methyl-4a-(3-hydroxyphenyl)-6α-(2- naphthamido)decahydroisoquinoline, trans-2-methyl-4a- (3- hydroxyphenyl)-6α-[N-methyl-3- trifluoromethylcinnamamido)]decahydroisoquinoline, trans-2- methyl-4a-(3-hydroxyphenyl)-6α-[N-methyl-(6- phenylhexanamido)]decahydroisoquinoline, trans-2- methyl-4a-(3- hydroxyphenyl)-6α-[N-methyl-(3,4- dichlorophenylacetamido)]decahydroisoquinoline, trans- 2-methyl- 4a-(3-hydroxyphenyl)-6α-(N- methylbenzamido)decahydroisoquinoline, trans-2-methyl-4a-(3- hydroxyphenyl)-6α-[N-methyl-(2- naphthamido)]decahydroisoquinoline, trans-2-methyl-4a- (3- hydroxyphenyl)-6α-[N-isobutyl-3- trifluoromethylcinnamamido)]decahydroisoquinoline, trans-2- methyl-4a-(3-hydroxyphenyl)-6α-[N-isobutyl-(6- phenylhexanamido)]decahydroisoquinoline, trans-2- methyl-4a-(3- hydroxyphenyl)-6α-[N-isobutyl-(3,4- dichlorophenylacetamido)]decahydroisoquinoline, trans-2-methyl- 4a-(3-hydroxyphenyl)-6α-(N- isobutylbenzamido)decahydroisoquinoline, trans-2-methyl-4a-(3- hydroxyphenyl)-6α-[N-isobutyl-(2- naphthamido)]decahydroisoquinoline, trans-2-methyl-8a- hydroxy-4a-(3-hydroxyphenyl)-6α-(3- trifluoromethylcinnamamido)decahydroisoquinoline, trans-2- methyl-8a-hydroxy-4a-(3-hydroxyphenyl)-6α- (6- phenylhexanamido)decahydroisoquinoline, trans-2- methyl-8a- hydroxy-4a-(3-hydroxyphenyl)-6α-(3,4- dichlorophenylacetamido)decahydroisoquinoline, trans- 2-methyl-8a- hydroxy-4a-(3-hydroxyphenyl)-6α- benzamidodecahydroisoquinoline, trans-2-methyl-8a- hydroxy-4a-(3-hydroxyphenyl)-6α-(2- naphthamido) decahydroisoquinoline, trans-2-methyl-8-hydroxy-4a- (3-hydroxyphenyl)-6α-[N-methyl-3- trifluoromethylcinnamamido)]decahydroisoquinoline, trans-2- methyl-8a-hydroxy-4a-(3-hydroxyphenyl)-6α- [N-methyl-(6- phenylhexanamido)] decahydroisoquinoline, trans-2-methyl-8a- hydroxy-4a-(3-hydroxyphenyl)-6α-[N-methyl-(3,4- dichlorophenylacetamido)]decahydroisoquinoline, trans-2-methyl- 8a-hydroxy-4a-(3-hydroxyphenyl)-6α-(N- methylbenzamido)decahydroisoquinoline, trans-2- methyl-8a-hydroxy- 4a-(3-hydroxyphenyl)-6α-[N- methyl-(2- naphthamido)]decahydroisoquinoline, trans- 2-methyl-8a-hydroxy-4a- (3-hydroxyphenyl)-6α-[N- isobutyl-3- trifluoromethylcinnamamido)] decahydroisoquinoline, trans-2- methyl-8a-hydroxy-4a- (3-hydroxyphenyl)-6α-[N-isobutyl-(6- phenylhexanamido)]decahydroisoquinoline, trans-2- methyl-8a- hydroxy-4a-(3-hydroxyphenyl)-6α-[N- isobutyl-(3,4- dichlorophenylacetamido)] decahydroisoquinoline, trans-2-methyl- 8a-hydroxy-4a- (3-hydroxyphenyl)-6α-(N- isobutylbenzamido) decahydroisoquinoline, trans-2-methyl-8a- hydroxy-4a- (3-hydroxyphenyl)-6α-[N-isobutyl-(2- naphthamido)] decahydroisoquinoline, trans-2-methyl-8a-acetoxy-4a-(3- hydroxyphenyl)-6α-(3- trifluoromethylcinnamamido) decahydroisoquinoline, trans-2- methyl-8a-acetoxy-4a- (3-hydroxyphenyl)-6α-(6- phenylhexanamido) decahydroisoquinoline, trans-2-methyl-8a- acetoxy-4a- (3-hydroxyphenyl)-6α-(3,4- dichlorophenylacetamido) decahydroisoquinoline, trans-2-methyl-8a- acetoxy-4a- (3-hydroxyphenyl)-6α- benzamidodecahydroisoquinoline, trans-2-methyl-8a- acetoxy-4a-(3-hydroxyphenyl)-6α-(2- naphthamido) decahydroisoquinoline, trans-2-methyl-8a-acetoxy-4a- (3-hydroxyphenyl)-6α-[N-methyl-3- trifluoromethylcinnamamido)]decahydroisoquinoline, trans-2- methyl-8a-acetoxy-4a-(3-hydroxyphenyl)-6α- [N-methyl-(6- phenylhexanamido)] decahydroisoquinoline, trans-2-methyl-8a- acetoxy-4a- (3-hydroxyphenyl)-6α-[N-methyl-(3,4- dichlorophenylacetamido)]decahydroisoquinoline, trans- 2-methyl- 8-acetoxy-4a-(3-hydroxyphenyl)-6α-(N- methylbenzamido)decahydroisoquinoline, trans-2- methyl-8a-acetoxy- 4a-(3-hydroxyphenyl)-6α-[N- methyl-(2- naphthamido)]decahydroisoquinoline, trans-2-methyl-8a-acetoxy-4a- (3-hydroxyphenyl)-6α-[N-isobutyl-3- trifluoromethylcinnamamido)] decahydroisoquinoline, trans-2- methyl-8a-acetoxy-4a-(3-hydroxyphenyl)-6α-[N-isobutyl-(6- phenylhexanamido)]decahydroisoquinoline, trans-2-methyl-8a- acetoxy-4a-(3-hydroxyphenyl)-6α-[N-isobutyl-(3,4- dichlorophenylacetamido)] decahydroisoquinoline, trans-2-methyl- 8a-acetoxy-4a-(3-hydroxyphenyl)-6α-(N- isobutylbenzamido) decahydroisoquinoline, trans-2-methyl-8a- acetoxy-4a-(3-hydroxyphenyl)-6α-[N-isobutyl-(2- naphthamido)] decahydroisoquinoline, trans-2-methyl-8a-methoxy-4a-(3-hydroxyphenyl)-6α-(3- trifluoromethylcinnamamido) decahydroisoquinoline, trans-2- methyl-8a-methoxy-4a-(3-hydroxyphenyl)-6α-(6- phenylhexanamido) decahydroisoquinoline, trans-2-methyl-8a- methoxy-4a-(3-hydroxyphenyl)-6α-(3,4- dichlorophenylacetamido) decahydroisoquinoline, trans-2-methyl-8a- methoxy-4a-(3-hydroxyphenyl)-6α-benzamidodecahydroisoquinoline, trans-2-methyl-8-methoxy-4a-(3-hydroxyphenyl)-6α-(2- naphthamido) decahydroisoquinoline, trans-2-methyl-8a-methoxy-4a-(3-hydroxyphenyl)-6α-[N-methyl-3- trifluoromethylcinnamamido)]decahydroisoquinoline, trans-2- methyl-8a-methoxy-4a-(3-hydroxyphenyl)-6α-[N-methyl-(6- phenylhexanamido)] decahydroisoquinoline, trans-2-methyl-8a- methoxy-4a-(3-hydroxyphenyl)-6α-[N-methyl-(3,4- dichlorophenylacetamido)]decahydroisoquinoline, trans-2-methyl- 8a-methoxy-4a-(3-hydroxyphenyl)-6α-(N-methylbenzamido)decahydroisoquinoline, trans-2-methyl-8a-methoxy- 4a-(3-hydroxyphenyl)-6α-[N-methyl-(2- naphthamido)]decahydroisoquinoline, trans-2-methyl-8a-methoxy-4a- (3-hydroxyphenyl)-6α-[N-isobutyl-3- trifluoromethylcinnamamido)] decahydroisoquinoline, trans-2- methyl-8a-methoxy-4a-(3-hydroxyphenyl)-6α-[N-isobutyl-(6-phenylhexanamido)]decahydroisoquinoline, trans-2-methyl-8-a methoxy-4a-(3-hydroxyphenyl)-6α-[N,- isobutyl-(3,4- dichlorophenylacetamido)] decahydroisoquinoline, trans-2-methyl- 8a-methoxy-4a-(3-hydroxyphenyl)-6α-(N- isobutylbenzamido) decahydroisoquinoline, trans-2-methyl-8a- methoxy-4a-(3-hydroxyphenyl)-6α-[N-isobutyl-(2- naphthamido)] decahydroisoquinoline, trans-2-methyl-4a-(3-methoxyphenyl)-6α-(3- trifluoromethylcinnamamido) decahydroisoquinoline, trans-2- methyl-4a-(3-methoxyphenyl)-6α-(6- phenylhexanamido) decahydroisoquinoline, trans-2-methyl-4a-(3-methoxyphenyl)-6α-(3,4- dichlorophenylacetamido) decahydroisoquinoline, trans-2-methyl- 4a-(3-methoxyphenyl)-6α-benzamidodecahydroisoquinoline, trans-2- methyl-4a-(3-methoxyphenyl)-6α-(2-naphthamido)decahydroisoquinoline, trans-2-methyl-4a-(3- methoxyphenyl)-6α-[N-methyl-3- trifluoromethylcinnamamido)]decahydroisoquinoline, trans-2- methyl-4a-(3-methoxyphenyl)-6α-[N-methyl-(6-phenylhexanamido)]decahydroisoquinoline, trans-2-methyl-4a-(3- methoxyphenyl)-6α-[N-methyl-(3,4-dichlorophenylacetamido)]decahydroisoquinoline, trans-2-methyl- 4a-(3-methoxyphenyl)-6α-(N-methylbenzamido)decahydroisoquinoline, trans-2-methyl-4a-(3- methoxyphenyl)-6α-[N-methyl-(2-naphthamido)]decahydroisoquinoline, trans-2-methyl-4a-(3- methoxyphenyl)-6α-[N-isobutyl-3-trifluoromethylcinnamamido)]decahydroisoquinoline, trans-2- methyl-4a-(3-methoxyphenyl)-6α-[N-isobutyl-(6- phenylhexanamido)]decahydroisoquinoline, trans-2-methyl-4a-(3- methoxyphenyl)-6α-[N-isobutyl-(3,4-dichlorophenylacetamido)]decahydroisoquinoline, trans-2-methyl- 4a-(3-methoxyphenyl)-6α-(N-isobutylbenzamido)decahydroisoquinoline, trans-2-methyl-4a-(3- methoxyphenyl)-6α-[N-isobutyl-(2- naphthamido)]decahydroisoquinoline, trans-2-methyl-8a-hydroxy-4a-(3-methoxyphenyl)-6α-(3- trifluoromethylcinnamamido)decahydroisoquinoline, trans-2- methyl-8a-hydroxy-4a-(3-methoxyphenyl)-6α-(6- phenylhexanamido)decahydroisoquinoline, trans-2-methyl-8a- hydroxy-4a-(3-methoxyphenyl)-6α-(3,4-dichlorophenylacetamido)decahydroisoquinoline, trans-2-methyl-8a- hydroxy-4a-(3-methoxyphenyl)-6α-benzamidodecahydroisoquinoline, trans-2-methyl-8a-hydroxy-4a-(3-methoxyphenyl)-6α-(2- naphthamido) decahydroisoquinoline, trans-2-methyl-8a-hydroxy-4a-(3-methoxyphenyl)-6α-[N-methyl-3- trifluoromethylcinnamamido)]decahydroisoquinoline, trans-2- methyl-8a-hydroxy-4a-(3-methoxyphenyl)-6α-[N-methyl-(6- phenylhexanamido)] decahydroisoquinoline, trans-2-methyl-8a- hydroxy-4a-(3-methoxyphenyl)-6α-[N-methyl-(3,4-dichlorophenylacetamido)]decahydroisoquinoline, trans-2-methyl- 8a-hydroxy-4a-(3-methoxyphenyl)-6α-(N-methylbenzamido)decahydroisoquinoline, trans-2-methyl-8a-hydroxy- 4a-(3-methoxyphenyl)-6α-[N-methyl-(2- naphthamido)]decahydroisoquinoline, trans-2-methyl-8a-hydroxy-4a- (3-methoxyphenyl)-6α-[N-isobutyl-3- trifluoromethylcinnamamido)] decahydroisoquinoline, trans-2- methyl-8a-hydroxy-4a-(3-methoxyphenyl)-6α-[N-isobutyl-(6-phenylhexanamido)]decahydroisoquinoline, trans-2-methyl-8a- hydroxy-4a-(3-methoxyphenyl)-6α-[N-isobutyl-(3,4- dichlorophenylacetamido)] decahydroisoquinoline, trans-2-methyl- 8a-hydroxy-4a-(3-methoxyphenyl)-6α-(N- isobutylbenzamido) decahydroisoquinoline, trans-2-methyl-8a- hydroxy-4a-(3-methoxyphenyl)-6α-[N-isobutyl-(2- naphthamido)] decahydroisoquinoline, trans-2-methyl-8a-acetoxy-4a-(3-methoxyphenyl)-6α-(3- trifluoromethylcinnamamido) decahydroisoquinoline, trans-2- methyl-8a-acetoxy-4a-(3-methoxyphenyl)-6α-(6- phenylhexanamido) decahydroisoquinoline, trans-2-methyl-8a- acetoxy-4a-(3-methoxyphenyl)-6α-(3,4- dichlorophenylacetamido) decahydroisoquinoline, trans-2-methyl-8a- acetoxy-4a-(3-methoxyphenyl)-6α-benzamidodecahydroisoquinoline, trans-2-methyl-8a-acetoxy-4a-(3-methoxyphenyl)-6α-(2- naphthamido) decahydroisoquinoline, trans-2-methyl-8-acetoxy-4a-(3-methoxyphenyl)-6α-[N-methyl-3- trifluoromethylcinnamamido)]decahydroisoquinoline, trans-2- methyl-8a-acetoxy-4a-(3-methoxyphenyl)-6α-[N-methyl-(6- phenylhexanamido)] decahydroisoquinoline, trans-2-methyl-8a- acetoxy-4a-(3-methoxyphenyl)-6α-[N-methyl-(3,4-dichlorophenylacetamido)]decahydroisoquinoline, trans-2-methyl- 8a-acetoxy-4a-(3-methoxyphenyl)-6α-(N-methylbenzamido)decahydroisoquinoline, trans-2-methyl-8a-acetoxy- 4a-(3-methoxyphenyl)-6α-[N-methyl-(2- naphthamido)]decahydroisoquinoline, trans-2-methyl-8a-acetoxy-4a- (3-methoxyphenyl)-6α-[N-isobutyl-3- trifluoromethylcinnamamido)] decahydroisoquinoline, trans-2- methyl-8a-acetoxy-4a-(3-methoxyphenyl)-6α-[N-isobutyl-(6- phenylhexanamido)]decahydroisoquinoline, trans-2- methyl-8a- acetoxy-4a-(3-methoxyphenyl)-6α-[N-isobutyl-(3,4- dichlorophenylacetamido)]decahydroisoquinoline, trans-2-methyl- 8a-acetoxy-4a-(3-methoxyphenyl)-6α-(N- isobutylbenzamido)decahydroisoquinoline, trans-2-methyl-8a- acetoxy-4a-(3-methoxyphenyl)-6α-[N-isobutyl-(2- naphthamido)]decahydroisoquinoline, trans-2-methyl-8a-methoxy-4a-(3-methoxyphenyl)-6α-(3- trifluoromethylcinnamamido)decahydroisoquinoline, trans-2- methyl-8a-methoxy-4a-(3-methoxyphenyl)-6α-(6- phenylhexanamido) decahydroisoquinoline, trans-2-methyl-8a- methoxy-4a-(3-methoxyphenyl)-6α-(3,4- dichlorophenylacetamido)decahydroisoquinoline, trans-2-methyl-8a- methoxy-4a-(3-methoxyphenyl)-6α-benzamidodecahydroisoquinoline, trans-2-methyl-8a-methoxy-4a-(3-methoxyphenyl)-6α-(2- naphthamido)decahydroisoquinoline, trans-2-methyl-8-methoxy-4a-(3-methoxyphenyl)-6α-[N-methyl-3- trifluoromethylcinnamamido)]decahydroisoquinoline, trans-2- methyl-8a-methoxy-4a-(3-methoxyphenyl)-6α-[N-methyl-(6- phenylhexanamido)]decahydroisoquinoline, trans-2-methyl-8a- methoxy-4a-(3-methoxyphenyl)-6α-[N-methyl-(3,4- dichlorophenylacetamido)]decahydroisoquinoline, trans-2-methyl- 8a-methoxy-4a-(3-methoxyphenyl)-6α-(N- methylbenzamido)decahydroisoquinoline, trans-2-methyl-8a-methoxy- 4a-(3-methoxyphenyl)-6α-[N-methyl-(2- naphthamido)]decahydroisoquinoline, trans-2-methyl-8a-methoxy-4a- (3-methoxyphenyl)-6α-[N-isobutyl-3- trifluoromethylcinnamamido)] decahydroisoquinoline, trans-2- methyl-8a-methoxy-4a-(3-methoxyphenyl)-6α-[N-isobutyl-(6- phenylhexanamido)]decahydroisoquinoline, trans-2-methyl-8a- methoxy-4a-(3-methoxyphenyl)-6α-[N-isobutyl-(3,4- dichlorophenylacetamido)] decahydroisoquinoline, trans-2-methyl- 8-methoxy-4a-(3-methoxyphenyl)-6α-(N- isobutylbenzamido)decahydroisoquinoline, trans-2-methyl-8a- methoxy-4a-(3-methoxyphenyl)-6α-[N-isobutyl-(2- naphthamido)]decahydroisoquinoline, trans-2-methyl-4a-(3- acetoxyphenyl)-6α-(3- trifluoromethylcinnamamido)decahydroisoquinoline, trans-2- methyl-4a-(3-acetoxyphenyl)-6α-(6- phenylhexanamido)decahydroisoquinoline, trans-2-methyl-4a-(3- acetoxyphenyl)-6α-(3,4- dichlorophenylacetamido)decahydroisoquinoline, trans-2-methyl- 4a-(3-acetoxyphenyl)-6α-benzamidodecahydroisoquinoline, trans-2- methyl-4a-(3-acetoxyphenyl)-6α-(2- naphthamido)decahydroisoquinoline, trans-2-methyl-4a-(3- acetoxyphenyl)-6α-[N-methyl-3- trifluoromethylcinnamamido)]decahydroisoquinoline, trans-2- methyl-4a-(3-acetoxyphenyl)-6α-[N-methyl-(6- phenylhexanamido)]decahydroisoquinoline, trans-2- methyl-4a-(3- acetoxyphenyl)-6α-[N-methyl-(3,4- dichlorophenylacetamido)]decahydroisoquinoline, trans-2-methyl- 4a-(3-acetoxyphenyl)-6a-(N- methylbenzamido)decahydroisoquinoline, trans-2- methyl-4a-(3- acetoxyphenyl)-6α-[N-methyl-(2- naphthamido)]decahydroisoquinoline, trans-2-methyl-4a-(3- acetoxyphenyl)-6a-[N-isobutyl-3- trifluoromethylcinnamamido)]decahydroisoquinoline, trans-2- methyl-4a-(3-acetoxyphenyl)-6α-[N-isobutyl-(6- phenylhexanamido)]decahydroisoquinoline, trans-2- methyl-4a-(3- acetoxyphenyl)-6α-[N-isobutyl-(3,4- dichlorophenylacetamido)]decahydroisoquinoline, trans- 2-methyl- 4a-(3-acetoxyphenyl)-6α-(N- isobutylbenzamido)decahydroisoquinoline, trans-2- methyl-4a-(3- acetoxyphenyl)-6α-[N-isobutyl-(2- naphthamido)]decahydroisoquinoline, trans-2-methyl-8a- hydroxy-4a-(3-acetoxyphenyl)-6α-(3- trifluoromethylcinnamamido)decahydroisoquinoline, trans-2- methyl-8a-hydroxy-4a-(3-acetoxyphenyl)-6α-(6- phenylhexanamido)decahydroisoquinoline, trans-2- methyl-8a- hydroxy-4a-(3-acetoxyphenyl)-6α-(3,4- dichlorophenylacetamido)decahydroisoquinoline, trans- 2-methyl-8a- hydroxy-4a-(3-acetoxyphenyl)-6α-benzamidodecahydroisoquinoline, trans-2-methyl-8a- hydroxy-4a-(3-acetoxyphenyl)-6α-(2- naphthamido)decahydroisoquinoline, trans-2-methyl-8a-hydroxy-4a- (3-acetoxyphenyl)-6α-[N-methyl-3- trifluoromethylcinnamamido)]decahydroisoquinoline, trans-2- methyl-8a-hydroxy-4a-(3-acetoxyphenyl)-6α- [N-methyl-(6- phenylhexanamido)] decahydroisoquinoline, trans-2-methyl-8a- hydroxy-4a-(3-acetoxyphenyl)-6α-[N-methyl-(3,4- dichlorophenylacetamido)]decahydroisoquinoline, trans- 2-methyl- 8a-hydroxy-4a-(3-acetoxyphenyl)-6α-(N- methylbenzamido)decahydroisoquinoline, trans-2- methyl-8a-hydroxy- 4a-(3-acetoxyphenyl)-6α-[N-methyl-(2- naphthamido)]decahydroisoquinoline, trans- 2-methyl-8a-hydroxy-4a- (3-acetoxyphenyl)-6α-[N- isobutyl-3- trifluoromethylcinnamamido)]decahydroisoquinoline, trans-2- methyl-8a-hydroxy-4a-(3-acetoxyphenyl)-6α-[N-isobutyl-(6- phenylhexanamido)]decahydroisoquinoline, trans-2- methyl-8a- hydroxy-4a-(3-acetoxyphenyl)-6α-[N- isobutyl-(3,4- dichlorophenylacetamido)]decahydroisoquinoline, trans-2-methyl- 8-hydroxy-4a-(3- acetoxyphenyl)-6α-(N- isobutylbenzamido)decahydroisoquinoline, trans-2-methyl-8a- hydroxy-4a-(3-acetoxyphenyl)-6α-[N-isobutyl-(2- naphthamido)]decahydroisoquinoline, trans-2-methyl-8a-acetoxy-4a-(3-acetoxyphenyl)-6α-(3- trifluoromethylcinnamamido)decahydroisoquinoline, trans-2- methyl-8a-acetoxy-4a-(3-acetoxyphenyl)-6α-(6- phenylhexanamido)decahydroisoquinoline, trans-2-methyl-8a- acetoxy-4a-(3-acetoxyphenyl)-6α-(3,4- dichlorophenylacetamido)decahydroisoquinoline, trans-2-methyl-8a- acetoxy-4a-(3-acetoxyphenyl)-6α-benzamidodecahydroisoquinoline, trans-2-methyl-8a-acetoxy-4a-(3-acetoxyphenyl)-6α-(2- naphthamido)decahydroisoquinoline, trans-2-methyl-8a- acetoxy-4a- (3-acetoxyphenyl)-6α-[N-methyl-3- trifluoromethylcinnamamido)]decahydroisoquinoline, trans-2- methyl-8a-acetoxy-4a-(3-acetoxyphenyl)-6α-[N- methyl-(6- phenylhexanamido)]decahydroisoquinoline, trans-2-methyl-8a- acetoxy-4a-(3-acetoxyphenyl)-6α-[N- methyl-(3,4- dichlorophenylacetamido)] decahydroisoquinoline, trans-2-methyl- 8a-acetoxy-4a-(3-acetoxyphenyl)-6α-(N- methylbenzamido)decahydroisoquinoline, trans-2-methyl-8a-acetoxy- 4a-(3-acetoxyphenyl)-6α-[N-methyl-(2- naphthamido)] decahydroisoquinoline, trans-2-methyl-8a-acetoxy-4a- (3-acetoxyphenyl)-6α-[N-isobutyl-3- trifluoromethylcinnamamido)]decahydroisoquinoline, trans-2- methyl-8a-acetoxy-4a-(3-acetoxyphenyl)-6α-[N- isobutyl-(6- phenylhexanamido)]decahydroisoquinoline, trans-2-methyl-8a- acetoxy-4a-(3-acetoxyphenyl)-6α-[N- isobutyl-(3,4- dichlorophenylacetamido)]decahydroisoquinoline, trans-2-methyl- 8a-acetoxy-4a-(3-acetoxyphenyl)-6α-(N- isobutylbenzamido)decahydroisoquinoline, trans-2-methyl-8a- acetoxy-4a-(3-acetoxyphenyl)-6α-[N-isobutyl-(2- naphthamido)]decahydroisoquinoline, trans-2-methyl-8a-methoxy-4a-(3-acetoxyphenyl)-6α-(3- trifluoromethylcinnamamido)

decahydroisoquinoline, trans-2- methyl-8a-methoxy-4a-(3-acetoxyphenyl)-6α-(6- phenylhexanamido) decahydroisoquinoline, trans-2-methyl-8a- methoxy-4a-(3-acetoxyphenyl)-6α-(3,4- dichlorophenylacetamido) decahydroisoquinoline, trans-2-methyl-8a- methoxy-4a-(3-acetoxyphenyl)-6α-benzamidodecahydroisoquinoline, trans-2-methyl-8a-methoxy-4a-(3-acetoxyphenyl)-6α-(2-naphthamido)decahydroisoquinoline, trans-2-methyl-8a-methoxy-4a- (3-acetoxyphenyl)-6α-[N-methyl-3-trifluoromethylcinnamamido)]decahydroisoquinoline, trans-2- methyl-8a-methoxy-4a-(3-acetoxyphenyl)-6α-[N-methyl-(6- phenylhexanamido)]decahydroisoquinoline, trans-2-methyl-8a- methoxy-4a-(3-acetoxyphenyl)-6α-[N-methyl-(3,4-dichlorophenylacetamido)]decahydroisoquinoline, trans-2-methyl- 8a-methoxy-4a-(3-acetoxyphenyl)-6α-(N-methylbenzamido)decahydroisoquinoline, trans-2-methyl-8a-methoxy- 4a-(3-acetoxyphenyl)-6α-[N-methyl-(2- naphthamido)]decahydroisoquinoline, trans-2-methyl-8a-methoxy-4a- (3-acetoxyphenyl)-6α-[N-isobutyl-3- trifluoromethylcinnamamido)] decahydroisoquinoline, trans-2- methyl-8a-methoxy-4a-(3-acetoxyphenyl)-6α-[N-isobutyl-(6-phenylhexanamido)]decahydroisoquinoline, trans-2-methyl-8a- methoxy-4a-(3-acetoxyphenyl)-6α-[N-isobutyl-(3,4- dichlorophenylacetamido)] decahydroisoquinoline, trans-2-methyl- 8a-methoxy-4a-(3-acetoxyphenyl)-6α-(N- isobutylbenzamido) decahydroisoquinoline, trans-2-methyl-8a- methoxy-4a-(3-acetoxyphenyl)-6α-[N-isobutyl-(2- naphthamido)] decahydroisoquinoline, trans-2-cyclopropylmethyl-4a-(3-hydroxyphenyl)-6β-(3- trifluoromethylcinnamamido) decahydroisoquinoline, trans-2- cyclopropylmethyl-4a-(3-hydroxyphenyl)-6β-(6- phenylhexanamido) decahydroisoquinoline, trans-2- cyclopropylmethyl-4a-(3-hydroxyphenyl)-6β-(3,4- dichlorophenylacetamido) decahydroisoquinoline, trans-2- cyclopropylmethyl-4a-(3-hydroxyphenyl)-6β-benzamidodecahydroisoquinoline, trans-2-cyclopropylmethyl-4a-(3- hydroxyphenyl)-6β-(2- naphthamido)decahydroisoquinoline, trans-2-cyclopropylmethyl-4a-(3-hydroxyphenyl)-6β-[N-methyl-3- trifluoromethylcinnamamido)] decahydroisoquinoline, trans-2- cyclopropylmethyl-4a-(3-hydroxyphenyl)-6β-[N-methyl-(6- phenylhexanamido)]decahydroisoquinoline, trans-2-cyclopropylmethyl-4a-(3-hydroxyphenyl)-6β-[N-methyl-(3,4- dichlorophenylacetamido)]decahydroisoquinoline, trans-2- cyclopropylmethyl-4a-(3-hydroxyphenyl)-6β-(N- methylbenzamido)decahydroisoquinoline, trans-2- cyclopropylmethyl-4a-(3-hydroxyphenyl)-6β-[N-methyl-(2- naphthamido)]decahydroisoquinoline, trans-2-cyclopropylmethyl- 4a-(3-hydroxyphenyl)-6β-[N-isobutyl-3- trifluoromethylcinnamamido)]decahydroisoquinoline, trans-2- cyclopropylmethyl-4a-(3-hydroxyphenyl)-6β-[N-isobutyl-(6-phenylhexanamido)]decahydroisoquinoline, trans-2- cyclopropylmethyl-4a-(3-hydroxyphenyl)-6β-[N-isobutyl-(3,4- dichlorophenylacetamido)] decahydroisoquinoline, trans-2- cyclopropylmethyl-4a-(3-hydroxyphenyl)-6β-(N- isobutylbenzamido) decahydroisoquinoline, trans-2- cyclopropylmethyl-4a-(3-hydroxyphenyl)-6β-[N-isobutyl-(2- naphthamido)] decahydroisoquinoline, trans-2-cyclopropylmethyl-8a-hydroxy-4a-(3-hydroxyphenyl)-6β-(3- trifluoromethylcinnamamido)decahydroisoquinoline, trans-2- cyclopropylmethyl-8a-hydroxy-4a-(3-hydroxyphenyl)-6β-(6- phenylhexanamido) decahydroisoquinoline, trans-2- cyclopropylmethyl-8a-hydroxy-4a-(3-hydroxyphenyl)-6β-(3,4- dichlorophenylacetamido)decahydroisoquinoline, trans-2- cyclopropylmethyl-8a-hydroxy-4a-(3-hydroxyphenyl) -6β- benzamidodecahydroisoquinoline, trans-2- cyclopropylmethyl-8a- hydroxy-4a-(3-hydroxyphenyl)-6β-(2- naphthamido)decahydroisoquinoline, trans-2- cyclopropylmethyl-8a- hydroxy-4a-(3-hydroxyphenyl)-6β-[N-methyl-3- trifluoromethylcinnamamido)] decahydroisoquinoline, trans-2- cyclopropylmethyl-8a-hydroxy-4a-(3-hydroxyphenyl)-6β-[N-methyl-(6-phenylhexanamido)]decahydroisoquinoline, trans-2- cyclopropylmethyl-8a-hydroxy-4a-(3-hydroxyphenyl)-6β-[N-methyl- (3,4-dichlorophenylacetamido)] decahydroisoquinoline, trans-2- cyclopropylmethyl-8a-hydroxy-4a-(3-hydroxyphenyl)-6β-(N-methylbenzamido)decahydroisoquinoline, trans-2- cyclopropylmethyl-8a-hydroxy-4a-(3-hydroxyphenyl)-6β-[N-methyl- (2-naphthamido)]decahydroisoquinoline, trans-2- cyclopropylmethyl-8a-hydroxy-4a-(3-hydroxyphenyl)-6β-[N-isobutyl-3-trifluoromethylcinnamamido)]decahydroisoquinoline, trans-2- cyclopropylmethyl-8a-hydroxy-4a-(3-hydroxyphenyl)-6β-[N-isobutyl- (6-phenylhexanamido)] decahydroisoquinoline, trans-2- cyclopropylmethyl-8a-hydroxy-4a-(3-hydroxyphenyl)-6β-[N-isobutyl- (3,4-dichlorophenylacetamido)]decahydroisoquinoline, trans-2- cyclopropylmethyl-8-hydroxy-4a-(3-hydroxyphenyl)-6β-(N- isobutylbenzamido)decahydroisoquinoline, trans-2- cyclopropylmethyl-8a-hydroxy-4a-(3-hydroxyphenyl) -6β-[N-isobutyl- (2-naphthamido)] decahydroisoquinoline, trans-2-cyclopropylmethyl-8a- acetoxy-4a-(3-hydroxyphenyl)-6β-(3- trifluoromethylcinnamamido)decahydroisoquinoline, trans-2- cyclopropylmethyl-8a-acetoxy-4a-(3- hydroxyphenyl)-6β-(6- phenylhexanamido) decahydroisoquinoline, trans-2- cyclopropylmethyl-8a- acetoxy-4a-(3-hydroxyphenyl)-6β-(3,4- dichlorophenylacetamido)decahydroisoquinoline, trans-2- cyclopropylmethyl-8a-acetoxy-4a-(3-hydroxyphenyl)- 6β- benzamidodecahydroisoquinoline, trans-2- cyclopropylmethyl-8- acetoxy-4a-(3-hydroxyphenyl)-6β- (2- naphthamido)decahydroisoquinoline, trans-2- cyclopropylmethyl-8- acetoxy-4a-(3-hydroxyphenyl)-6β- [N-methyl-3- trifluoromethylcinnamamido)] decahydroisoquinoline, trans-2- cyclopropylmethyl-8a- acetoxy-4a-(3-hydroxyphenyl)-6β-[N-methyl- (6-phenylhexanamido)]decahydroisoquinoline, trans-2- cyclopropylmethyl-8a-acetoxy-4a-(3-hydroxyphenyl)- 6β-[N-methyl- (3,4-dichlorophenylacetamido)] decahydroisoquinoline, trans-2- cyclopropylmethyl-8a- acetoxy-4a-(3-hydroxyphenyl)-6β-(N- methylbenzamido)decahydroisoquinoline, trans-2- cyclopropylmethyl-8a-acetoxy-4a-(3-hydroxyphenyl)- 6β-[N-methyl- (2-naphthamido)]decahydroisoquinoline, trans-2- cyclopropylmethyl-8a-acetoxy-4a-(3- hydroxyphenyl)-6β-[N-isobutyl- 3-trifluoromethylcinnamamido)]decahydroisoquinoline, trans-2- cyclopropylmethyl-8a-acetoxy-4a-(3- hydroxyphenyl)-6β-[N-isobutyl- (6-phenylhexanamido)] decahydroisoquinoline, trans-2- cyclopropylmethyl-8a- acetoxy-4a-(3-hydroxyphenyl)-6β-[N-isobutyl- (3,4-dichlorophenylacetamido)]decahydroisoquinoline, trans- 2- cyclopropylmethyl-8a-acetoxy-4a-(3-hydroxyphenyl)- 6β-(N- isobutylbenzamido)decahydroisoquinoline, trans- 2- cyclopropylmethyl-8a-acetoxy-4a-(3-hydroxyphenyl)-

6β-[N-isobutyl- (2-naphthamido)]decahydroisoquinoline, trans-2-cyclopropylmethyl-8a-methoxy-4a-(3-hydroxyphenyl)-6β-(3- trifluoromethylcinnamamido) decahydroisoquinoline, trans-2- cyclopropylmethyl-8a-methoxy-4a-(3-hydroxyphenyl)-6β-(6-phenylhexanamido)decahydroisoquinoline, trans-2-cyclopropylmethyl-8a-methoxy-4a-(3-hydroxyphenyl)-6β-(3,4- dichlorophenylacetamido) decahydroisoquinoline, trans-2- cyclopropylmethyl-8a-methoxy-4a-(3-hydroxyphenyl)-6β-benzamidodecahydroisoquinoline, trans-2-cyclopropylmethyl-8a- methoxy-4a-(3-hydroxyphenyl)-6β-(2- naphthamido)decahydroisoquinoline, trans-2-cyclopropylmethyl-8a- methoxy-4a-(3-hydroxyphenyl)-6β-[N-methyl-3- trifluoromethylcinnamamido)] decahydroisoquinoline, trans-2- cyclopropylmethyl-8a-methoxy-4a-(3-hydroxyphenyl)-6β-[N-methyl-(6-phenylhexanamido)]decahydroisoquinoline, trans-2-cyclopropylmethyl-8a-methoxy-4a-(3-hydroxyphenyl)-6β-[N-methyl- (3,4-dichlorophenylacetamido)] decahydroisoquinoline, trans-2- cyclopropylmethyl-8a-methoxy-4a-(3-hydroxyphenyl)-6β-(N-methylbenzamido)decahydroisoquinoline, trans-2-cyclopropylmethyl-8a-methoxy-4a-(3-hydroxyphenyl)-6β-[N-methyl- (2-naphthamido)]decahydroisoquinoline, trans-2- cyclopropylmethyl-8a-methoxy-4a-(3-hydroxyphenyl)-6β-[N-isobutyl-3-trifluoromethylcinnamamido)]decahydroisoquinoline, trans-2- cyclopropylmethyl-8a-methoxy-4a-(3-hydroxyphenyl)-6β-[N-isobutyl- (6-phenylhexanamido)] decahydroisoquinoline, trans-2- cyclopropylmethyl-8a-methoxy-4a-(3-hydroxyphenyl)-6β-[N-isobutyl- (3,4-dichlorophenylacetamido)]decahydroisoquinoline, trans-2- cyclopropylmethyl-8a-methoxy-4a-(3-hydroxyphenyl) -6β-(N- isobutylbenzamido)decahydroisoquinoline, trans-2- cyclopropylmethyl-8a-methoxy-4a-(3-hydroxyphenyl)-6β-[N-isobutyl- (2-naphthamido)] decahydroisoquinoline, trans-2-cyclopropylmethyl-4a-(3-methoxyphenyl)-6β-(3- trifluoromethylcinnamamido) decahydroisoquinoline, trans-2- cyclopropylmethyl-4a-(3-methoxyphenyl)-6β-(6- phenylhexanamido) decahydroisoquinoline, trans-2- cyclopropylmethyl-4a-(3-methoxyphenyl)-6β-(3,4- dichlorophenylacetamido) decahydroisoquinoline, trans-2- cyclopropylmethyl-4a-(3-methoxyphenyl)-6β-benzamidodecahydroisoquinoline, trans-2-cyclopropylmethyl-4a-(3- methoxyphenyl)-6β-(2-naphthamido)decahydroisoquinoline, trans-2-cyclopropylmethyl-4a-(3-methoxyphenyl)-6β-[N-methyl-3- trifluoromethylcinnamamido)] decahydroisoquinoline, trans-2- cyclopropylmethyl-4a-(3-methoxyphenyl)-6β-[N-methyl-(6-phenylhexanamido)]decahydroisoquinoline, trans-2-cyclopropylmethyl-4a-(3-methoxyphenyl)-6β-[N-methyl-(3,4- dichlorophenylacetamido)] decahydroisoquinoline, trans-2- cyclopropylmethyl-4a-(3-methoxyphenyl)-6β-(N- methylbenzamido) decahydroisoquinoline, trans-2- cyclopropylmethyl-4a-(3-methoxyphenyl)-6β-[N-methyl-(2- naphthamido)] decahydroisoquinoline, trans-2-cyclopropylmethyl- 4a-(3-methoxyphenyl)-6β-[N-isobutyl-3-trifluoromethylcinnamamido)]decahydroisoquinoline, trans-2- cyclopropylmethyl-4a-(3-methoxyphenyl)-6β-[N-isobutyl-(6- phenylhexanamido)] decahydroisoquinoline, trans-2- cyclopropylmethyl-4a-(3-methoxyphenyl)-6β-[N-isobutyl-(3,4-dichlorophenylacetamido)]decahydroisoquinoline, trans-2- cyclopropylmethyl-4a-(3-methoxyphenyl)-6β-(N-isobutylbenzamido)decahydroisoquinoline, trans-2-cyclopropylmethyl-4a-(3-methoxyphenyl)-6β-[N-isobutyl-(2- naphthamido)]decahydroisoquinoline, trans-2-cyclopropylmethyl-8a-hydroxy-4a-(3-methoxyphenyl)-6β-(3- trifluoromethylcinnamamido) decahydroisoquinoline, trans-2- cyclopropylmethyl-8a-hydroxy-4a-(3-methoxyphenyl)-6β-(6- phenylhexanamido)decahydroisoquinoline, trans-2- cyclopropylmethyl-8a-hydroxy-4a-(3-methoxyphenyl)-6β-(3,4- dichlorophenylacetamido) decahydroisoquinoline, trans-2- cyclopropylmethyl-8a-hydroxy-4a-(3-methoxyphenyl)-6β-benzamidodecahydroisoquinoline, trans-2- cyclopropylmethyl-8a- hydroxy-4a-(3-methoxyphenyl)-6β-(2- naphthamido)decahydroisoquinoline, trans-2-cyclopropylmethyl-8a- hydroxy-4a-(3-methoxyphenyl)-6β-[N-methyl-3- trifluoromethylcinnamamido)] decahydroisoquinoline, trans-2- cyclopropylmethyl-8a-hydroxy-4a-(3-methoxyphenyl)-6β-[N-methyl-(6-phenylhexanamido)]decahydroisoquinoline, trans-2-cyclopropylmethyl-8a-hydroxy-4a-(3-methoxyphenyl)-6β-[N-methyl- (3,4-dichlorophenylacetamido)] decahydroisoquinoline, trans-2- cyclopropylmethyl-8a-hydroxy-4a-(3-methoxyphenyl)-6β-(N-methylbenzamido)decahydroisoquinoline, trans-2-cyclopropylmethyl-8a-hydroxy-4a-(3-methoxyphenyl)-6β-[N-methyl- (2-naphthamido)]decahydroisoquinoline, trans-2- cyclopropylmethyl-8a-hydroxy-4a-(3-methoxyphenyl)-6β-[N-isobutyl-3-trifluoromethylcinnamamido)]decahydroisoquinoline, trans-2- cyclopropylmethyl-8a-hydroxy-4a-(3-methoxyphenyl)-6β-[N-isobutyl- (6-phenylhexanamido)] decahydroisoquinoline, trans-2- cyclopropylmethyl-8a-hydroxy-4a-(3-methoxyphenyl)-6β-[N-isobutyl- (3,4-dichlorophenylacetamido)]decahydroisoquinoline, trans-2- cyclopropylmethyl-8a-hydroxy-4a-(3-methoxyphenyl) -6β-(N- isobutylbenzamido)decahydroisoquinoline, trans-2- cyclopropylmethyl-8a-hydroxy-4a-(3-methoxyphenyl)-6β-[N-isobutyl- (2-naphthamido)] decahydroisoquinoline, trans-2-cyclopropylmethyl-8a-acetoxy-4a-(3-methoxyphenyl)-6β-(3- trifluoromethylcinnamamido)decahydroisoquinoline, trans-2- cyclopropylmethyl-8a-acetoxy-4a-(3-methoxyphenyl)-6β-(6- phenylhexanamido) decahydroisoquinoline, trans-2- cyclopropylmethyl-8a-acetoxy-4a-(3-methoxyphenyl)-6β-(3,4- dichlorophenylacetamido)decahydroisoquinoline, trans-2- cyclopropylmethyl-8a-acetoxy-4a-(3-methoxyphenyl)-6β- benzamidodecahydroisoquinoline, trans-2- cyclopropylmethyl-8- acetoxy-4a-(3-methoxyphenyl)-6β-(2- naphthamido)decahydroisoquinoline, trans-2- cyclopropylmethyl-8- acetoxy-4a-(3-methoxyphenyl)-6β-[N-methyl-3- trifluoromethylcinnamamido)] decahydroisoquinoline, trans-2- cyclopropylmethyl-8a-acetoxy-4a-(3-methoxyphenyl)-6β-[N-methyl-(6-phenylhexanamido)]decahydroisoquinoline, trans-2-cyclopropylmethyl-8a-acetoxy-4a-(3-methoxyphenyl)-6β-[N-methyl- (3,4-dichlorophenylacetamido)] decahydroisoquinoline, trans-2- cyclopropylmethyl-8a-acetoxy-4a-(3-methoxyphenyl)-6β-(N-methylbenzamido)decahydroisoquinoline, trans-2-cyclopropylmethyl-8a-acetoxy-4a-(3-methoxyphenyl)-6β-[N-methyl- (2-naphthamido)]decahydroisoquinoline, trans-2- cyclopropylmethyl-8a-acetoxy-4a-(3-methoxyphenyl)-6β-[N-isobutyl-3-trifluoromethylcinnamamido)]decahydroisoquinoline, trans-2- cyclopropylmethyl-8a-acetoxy-4a-(3-methoxyphenyl)-6β-[N-isobutyl- (6-phenylhexanamido)] decahydroisoquinoline, trans-2- cyclopropylmethyl-8a-acetoxy-4a-(3-methoxyphenyl)-6β-[N-isobutyl- (3,4-dichlorophenylacetamido)]decahydroisoquinoline, trans-2- cyclopropylmethyl-8a-acetoxy-4a-(3-methoxyphenyl)-6β-(N- isobutylbenzamido)decahydroisoquinoline, trans-2- cyclopropylmethyl-8a-acetoxy-4a-(3-methoxyphenyl)-6β-[N-isobutyl- (2-naphthamido)]decahydroisoquinoline, trans-2-cyclopropylmethyl-8a-methoxy-4a-(3-methoxyphenyl)-6β-(3- trifluoromethylcinnamamido) decahydroisoquinoline, trans-2- cyclopropylmethyl-8a-methoxy-4a-(3-methoxyphenyl)-6β-(6-phenylhexanamido)decahydroisoquinoline, trans-2-cyclopropylmethyl-8a-methoxy-4a-(3-methoxyphenyl)-6β-(3,4- dichlorophenylacetamido) decahydroisoquinoline, trans-2- cyclopropylmethyl-8a-methoxy-4a-(3-methoxyphenyl)-6β-benzamidodecahydroisoquinoline, trans-2-cyclopropylmethyl-8- methoxy-4a-(3-methoxyphenyl)-6β-(2- naphthamido)decahydroisoquinoline, trans-2-cyclopropylmethyl-8- methoxy-4a-(3-methoxyphenyl)-6β-[N-methyl-3- trifluoromethylcinnamamido)] decahydroisoquinoline, trans-2- cyclopropylmethyl-8a-methoxy-4a-(3-methoxyphenyl)-6β-[N-methyl-(6-phenylhexanamido)]decahydroisoquinoline, trans-2-cyclopropylmethyl-8a-methoxy-4a-(3-methoxyphenyl)-6β-[N-methyl- (3,4-dichlorophenylacetamido)] decahydroisoquinoline, trans-2- cyclopropylmethyl-8a-methoxy-4a-(3-methoxyphenyl)-6β-(N-methylbenzamido)decahydroisoquinoline, trans-2-cyclopropylmethyl-8a-methoxy-4a-(3-methoxyphenyl)-6β-[N-methyl- (2-naphthamido)]decahydroisoquinoline, trans-2- cyclopropylmethyl-8a-methoxy-4a-(3-methoxyphenyl)-6β-[N-isobutyl- 3-trifluoromethylcinnamamido)]decahydroisoquinoline, trans-2- cyclopropylmethyl-8a-methoxy-4a-(3-methoxyphenyl)-6β-[N-isobutyl- (6-phenylhexanamido)] decahydroisoquinoline, trans-2- cyclopropylmethyl-8a-methoxy-4a-(3-methoxyphenyl)-6β-[N-isobutyl- (3,4-dichlorophenylacetamido)]decahydroisoquinoline, trans-2- cyclopropylmethyl-8a-methoxy-4a-(3-methoxyphenyl)-6β-(N- isobutylbenzamido) decahydroisoquinoline, trans-2- cyclopropylmethyl-8a-methoxy-4a-(3-methoxyphenyl)-6β-[N-isobutyl- (2-naphthamido)]decahydroisoquinoline, trans-2-cyclopropylmethyl-4a-(3-acetoxyphenyl)-6β-(3-trifluoromethylcinnamamido)decahydroisoquinoline, trans-2- cyclopropylmethyl-4a-(3-acetoxyphenyl)-6β-(6-phenylhexanamido)decahydroisoquinoline, trans-2- cyclopropylmethyl-4a-(3-acetoxyphenyl)-6β-(3,4-dichlorophenylacetamido)decahydroisoquinoline, trans-2- cyclopropylmethyl-4a-(3-acetoxyphenyl)-6β-benzamidodecahydroisoquinoline, trans-2-cyclopropylmethyl-4a-(3- acetoxyphenyl)-6β-(2-naphthamido)decahydroisoquinoline, trans-2-cyclopropylmethyl-4a-(3-acetoxyphenyl)-6β-[N-methyl-3- trifluoromethylcinnamamido)] decahydroisoquinoline, trans-2- cyclopropylmethyl-4a-(3-acetoxyphenyl)-6β-[N-methyl-(6- phenylhexanamido)]decahydroisoquinoline, trans-2- cyclopropylmethyl-4a-(3-acetoxyphenyl)-6β-[N-methyl-(3,4-dichlorophenylacetamido)]decahydroisoquinoline, trans-2- cyclopropylmethyl-4a-(3-acetoxyphenyl)-6β-(N-methylbenzamido)decahydroisoquinoline, trans-2- cyclopropylmethyl-4a-(3-acetoxyphenyl)-6β-[N-methyl-(2- naphthamido)]decahydroisoquinoline, trans-2-cyclopropylmethyl- 4a-(3-acetoxyphenyl)-6β-[N-isobutyl-3- trifluoromethylcinnamamido)] decahydroisoquinoline, trans-2- cyclopropylmethyl-4a-(3-acetoxyphenyl)-6β-[N-isobutyl-(6-phenylhexanamido)]decahydroisoquinoline, trans-2-cyclopropylmethyl-4a-(3-acetoxyphenyl)-6β-[N-isobutyl-(3,4- dichlorophenylacetamido)] decahydroisoquinoline, trans-2- cyclopropylmethyl-4a-(3-acetoxyphenyl)-6β-(N- isobutylbenzamido) decahydroisoquinoline, trans-2- cyclopropylmethyl-4a-(3-acetoxyphenyl)-6β-[N-isobutyl-(2- naphthamido)] decahydroisoquinoline, trans-2-cyclopropylmethyl-8a-hydroxy-4a-(3-acetoxyphenyl)-6β-(3- trifluoromethylcinnamamido)decahydroisoquinoline, trans-2- cyclopropylmethyl-8a-hydroxy-4a-(3-acetoxyphenyl)-6β-(6- phenylhexanamido) decahydroisoquinoline, trans-2- cyclopropylmethyl-8a-hydroxy-4a-(3-acetoxyphenyl)-6β-(3,4-dichlorophenylacetamido)decahydroisoquinoline, trans-2- cyclopropylmethyl-8a-hydroxy-4a-(3-acetoxyphenyl)-6β- benzamidodecahydroisoquinoline, trans-2- cyclopropylmethyl-8- hydroxy-4a-(3-acetoxyphenyl)-6β-(2- naphthamido)decahydroisoquinoline, trans-2-cyclopropylmethyl-8- hydroxy-4a-(3-acetoxyphenyl)-6β-[N-methyl-3- trifluoromethylcinnamamido)] decahydroisoquinoline, trans-2- cyclopropylmethyl-8a-hydroxy-4a-(3-acetoxyphenyl)-6β-[N-methyl-(6-phenylhexanamido)]decahydroisoquinoline, trans-2-cyclopropylmethyl-8a-hydroxy-4a-(3-acetoxyphenyl)-6β-[N-methyl- (3,4-dichlorophenylacetamido)] decahydroisoquinoline, trans-2- cyclopropylmethyl-8a-hydroxy-4a-(3-acetoxyphenyl)-6β-(N-methylbenzamido)decahydroisoquinoline, trans-2-cyclopropylmethyl-8a-hydroxy-4a-(3-acetoxyphenyl)-6β-[N-methyl- (2-naphthamido)]decahydroisoquinoline, trans-2- cyclopropylmethyl-8a-hydroxy-4a-(3-acetoxyphenyl)-6β-[N-isobutyl- 3-trifluoromethylcinnamamido)]decahydroisoquinoline, trans-2- cyclopropylmethyl-8a-hydroxy-4a-(3-acetoxyphenyl)-6β-[N-isobutyl- (6-phenylhexanamido)] decahydroisoquinoline, trans-2- cyclopropylmethyl-8a-hydroxy-4a-(3-acetoxyphenyl)-6β-[N-isobutyl- (3,4-dichlorophenylacetamido)]decahydroisoquinoline, trans-2- cyclopropylmethyl-8a-hydroxy-4a-(3-acetoxyphenyl)-6β-(N- isobutylbenzamido)decahydroisoquinoline, trans-2- cyclopropylmethyl-8a-hydroxy-4a-(3-acetoxyphenyl)-6β-[N-isobutyl- (2-naphthamido)]decahydroisoquinoline, trans-2-cyclopropylmethyl-8a-acetoxy-4a-(3-acetoxyphenyl)-6β-(3- trifluoromethylcinnamamido) decahydroisoquinoline, trans-2- cyclopropylmethyl-8a-acetoxy-4a-(3-acetoxyphenyl)-6β-(6-phenylhexanamido)decahydroisoquinoline, trans-2-cyclopropylmethyl-8a-acetoxy-4a-(3-acetoxyphenyl)-6β-(3,4- dichlorophenylacetamido)decahydroisoquinoline, trans-2- cyclopropylmethyl-8a-acetoxy-4a-(3-acetoxyphenyl)-6β- benzamidodecahydroisoquinoline, trans-2-cyclopropylmethyl-8a- acetoxy-4a-(3-acetoxyphenyl)-6β-(2- naphthamido) decahydroisoquinoline, trans-2-cyclopropylmethyl-8a- acetoxy-4a-(3-acetoxyphenyl)-6β-[N-methyl-3- trifluoromethylcinnamamido)]decahydroisoquinoline, trans-2- cyclopropylmethyl-8a-acetoxy-4a-(3-acetoxyphenyl)-6β-[N-methyl- (6-phenylhexanamido)] decahydroisoquinoline, trans-2- cyclopropylmethyl-8a-acetoxy-4a-(3-acetoxyphenyl)-6β-[N-methyl- (3,4-dichlorophenylacetamido)]decahydroisoquinoline, trans-2- cyclopropylmethyl-8a-acetoxy-4a-(3-acetoxyphenyl)-

6β-(N- methylbenzamido)decahydroisoquinoline, trans-2- cyclopropylmethyl-8a-acetoxy-4a-(3-acetoxyphenyl)-6β-[N-methyl- (2-naphthamido)]decahydroisoquinoline, trans-2- cyclopropylmethyl-8a-acetoxy-4a-(3-acetoxyphenyl)-6β-[N-isobutyl-3-trifluoromethylcinnamamido)]decahydroisoquinoline, trans-2- cyclopropylmethyl-8a-acetoxy-4a-(3-acetoxyphenyl)-6β-[N-isobutyl- (6-phenylhexanamido)]decahydroisoquinoline, trans-2- cyclopropylmethyl-8a-acetoxy-4a-(3-acetoxyphenyl)-6β-[N-isobutyl- (3,4-dichlorophenylacetamido)]decahydroisoquinoline, trans-2- cyclopropylmethyl-8a-acetoxy-4a-(3-acetoxyphenyl)-6β-(N- isobutylbenzamido)decahydroisoquinoline, trans-2- cyclopropylmethyl-8a-acetoxy-4a-(3-acetoxyphenyl)-6β-[N-isobutyl- (2-naphthamido)]decahydroisoquinoline, trans-2-cyclopropylmethyl-8a-methoxy-4a-(3-acetoxyphenyl)-6β-(3- trifluoromethylcinnamamido) decahydroisoquinoline, trans-2- cyclopropylmethyl-8a-methoxy-4a-(3-acetoxyphenyl)-6β-(6-phenylhexanamido)decahydroisoquinoline, trans-2- cyclopropylmethyl-8a-methoxy-4a-(3-acetoxyphenyl)-6β-(3,4- dichlorophenylacetamido) decahydroisoquinoline, trans-2- cyclopropylmethyl-8a-methoxy-4a-(3-acetoxyphenyl)-6β-benzamidodecahydroisoquinoline, trans-2- cyclopropylmethyl-8- methoxy-4a-(3-acetoxyphenyl)-6β-(2- naphthamido)decahydroisoquinoline, trans-2- cyclopropylmethyl-8- methoxy-4a-(3-acetoxyphenyl)-6β-[N-methyl-3- trifluoromethylcinnamamido)]decahydroisoquinoline, trans-2- cyclopropylmethyl-8a-methoxy-4a-(3-acetoxyphenyl)-6β-[N-methyl-(6-phenylhexanamido)]decahydroisoquinoline, trans-2- cyclopropylmethyl-8a-methoxy-4a-(3-acetoxyphenyl)-6β-[N-methyl- (3,4-dichlorophenylacetamido)]decahydroisoquinoline, trans-2- cyclopropylmethyl-8a-methoxy-4a-(3-acetoxyphenyl)-6β-(N-methylbenzamido)decahydroisoquinoline, trans-2- cyclopropylmethyl-8a-methoxy-4a-(3-acetoxyphenyl)-6β-[N-methyl- (2-naphthamido)]decahydroisoquinoline, trans-2- cyclopropylmethyl-8a-methoxy-4a-(3-acetoxyphenyl)-6β-[N-isobutyl-3-trifluoromethylcinnamamido)]decahydroisoquinoline, trans-2- cyclopropylmethyl-8a-methoxy-4a-(3-acetoxyphenyl)-6β-[N-isobutyl- (6-phenylhexanamido)]decahydroisoquinoline, trans-2- cyclopropylmethyl-8a-methoxy-4a-(3-acetoxyphenyl)-6β-[N-isobutyl- (3,4-dichlorophenylacetamido)]decahydroisoquinoline, trans-2- cyclopropylmethyl-8a-methoxy-4a-(3-acetoxyphenyl)-6β-(N- isobutylbenzamido)decahydroisoquinoline, trans-2- cyclopropylmethyl-8a-methoxy-4a-(3-acetoxyphenyl)-6β-[N-isobutyl- (2-naphthamido)]decahydroisoquinoline, trans-2-allyl-4a-(3-hydroxyphenyl)-6β-(3- trifluoromethylcinnamamido)decahydroisoquinoline, trans-2-allyl- 4a-(3-hydroxyphenyl)-6β-(6-phenylhexanamido)decahydroisoquinoline, trans-2-allyl-4a-(3- hydroxyphenyl)-6β-(3,4-dichlorophenylacetamido)decahydroisoquinoline, trans-2-allyl-4a- (3-hydroxyphenyl)-6β-benzamidodecahydroisoquinoline, trans-2- allyl-4a-(3-hydroxyphenyl)-6β-(2- naphthamido) decahydroisoquinoline, trans-2-allyl-4a-(3-hydroxyphenyl)-6β-[N-methyl-3-trifluoromethylcinnamamido)]decahydroisoquinoline, trans-2- allyl-4a-(3-hydroxyphenyl)-6β-[N-methyl-(6-phenylhexanamido)]decahydroisoquinoline, trans-2-allyl-4a-(3- hydroxyphenyl)-6β-[N-methyl-(3,4-dichlorophenylacetamido)]decahydroisoquinoline, trans-2-allyl- 4a-(3-hydroxyphenyl)-6β-(N- methylbenzamido) decahydroisoquinoline, trans-2-allyl-4a-(3-hydroxyphenyl)-6β-[N-methyl-(2- naphthamido)] decahydroisoquinoline, trans-2-allyl-4a-(3-hydroxyphenyl)-6β-[N-isobutyl-3-trifluoromethylcinnamamido)]decahydroisoquinoline, trans-2- allyl-4a-(3-hydroxyphenyl)-6β-[N-isobutyl-(6-phenylhexanamido)]decahydroisoquinoline, trans-2-allyl-4a-(3- hydroxyphenyl)-6β-[N-isobutyl-(3,4-dichlorophenylacetamido)]decahydroisoquinoline, trans-2-allyl- 4a-(3-hydroxyphenyl)-6β-(N-isobutylbenzamido)decahydroisoquinoline, trans-2-allyl-4a-(3- hydroxyphenyl)-6β-[N-isobutyl-(2- naphthamido) ]decahydroisoquinoline, trans-2-allyl-8a-hydroxy-4a-(3-hydroxyphenyl)-6β-(3- trifluoromethylcinnamamido) decahydroisoquinoline, trans-2-allyl- 8a-hydroxy-4a-(3-hydroxyphenyl)-6β-(6- phenylhexanamido) decahydroisoquinoline, trans-2-allyl-8a-hydroxy- 4a-(3-hydroxyphenyl)-6β-(3,4- dichlorophenylacetamido) decahydroisoquinoline, trans-2-allyl-8a- hydroxy-4a-(3-hydroxyphenyl)-6β-benzamidodecahydroisoquinoline, trans-2-allyl-8a-hydroxy-4a-(3-hydroxyphenyl)-6β-(2-naphthamido)decahydroisoquinoline, trans-2-allyl-8a-hydroxy-4a- (3-hydroxyphenyl)-6β-[N-methyl-3-trifluoromethylcinnamamido)]decahydroisoquinoline, trans-2- allyl-8a-hydroxy-4a-(3-hydroxyphenyl)-6β-[N-methyl-(6- phenylhexanamido)]decahydroisoquinoline, trans-2-allyl-8a- hydroxy-4a-(3-hydroxyphenyl)-6β-[N-methyl-(3,4- dichlorophenylacetamido)] decahydroisoquinoline, trans-2-allyl-8a- hydroxy-4a-(3-hydroxyphenyl)-6β-(N- methylbenzamido) decahydroisoquinoline, trans-2-allyl-8a-hydroxy- 4a-(3-hydroxyphenyl)-6β-[N-methyl-(2- naphthamido)] decahydroisoquinoline, trans-2-allyl-8a-hydroxy-4a-(3-hydroxyphenyl)-6β-[N-isobutyl-3-trifluoromethylcinnamamido)]decahydroisoquinoline, trans-2- allyl-8a-hydroxy-4a-(3-hydroxyphenyl)-6β-[N-isobutyl-(6- phenylhexanamido)]decahydroisoquinoline, trans-2-allyl-8a- hydroxy-4a-(3-hydroxyphenyl)-6β-[N-isobutyl-(3,4- dichlorophenylacetamido)] decahydroisoquinoline, trans-2-allyl-8a- hydroxy-4a-(3-hydroxyphenyl)-6β-(N- isobutylbenzamido) decahydroisoquinoline, trans-2-allyl-8a- hydroxy-4a-(3-hydroxyphenyl)-6β-[N-isobutyl-(2- naphthamido)] decahydroisoquinoline, trans-2-allyl-8a-acetoxy-4a-(3-hydroxyphenyl)-6β-(3- trifluoromethylcinnamamido) decahydroisoquinoline, trans-2-allyl- 8a-acetoxy-4a-(3-hydroxyphenyl)-6β(6- phenylhexanamido) decahydroisoquinoline, trans-2-allyl-8a-acetoxy- 4a-(3-hydroxyphenyl)-6β-(3,4- dichlorophenylacetamido) decahydroisoquinoline, trans-2-allyl-8a- acetoxy-4a-(3-hydroxyphenyl)-6β-benzamidodecahydroisoquinoline, trans-2-allyl-8a-acetoxy-4a-(3-hydroxyphenyl)-6β-(2-naphthamido)decahydroisoquinoline, trans-2-allyl-8a-acetoxy-4a- (3-hydroxyphenyl)-6β-[N-methyl-3-trifluoromethylcinnamamido)]decahydroisoquinoline, trans-2- allyl-8a-acetoxy-4a-(3-hydroxyphenyl)-6β-[N-methyl-(6- phenylhexanamido)]decahydroisoquinoline, trans-2-allyl-8a- acetoxy-4a-(3-hydroxyphenyl)-6β-[N-methyl-(3,4- dichlorophenylacetamido)] decahydroisoquinoline, trans-2-allyl-8- acetoxy-4a-(3-hydroxyphenyl)-6β-(N- methylbenzamido) decahydroisoquinoline, trans-2-allyl-8a-acetoxy- 4a-(3-hydroxyphenyl)-6β-[N-methyl-(2- naphthamido)] decahydroisoquinoline, trans-2-allyl-8a-acetoxy-4a- (3-hydroxyphenyl)-6β-[N-isobutyl-3-trifluoromethylcinnamamido)]decahydroisoquinoline, trans-2- allyl-8a-acetoxy-4a-(3-hydroxyphenyl)-6β-[N-isobutyl-(6- phenylhexanamido)]decahydroisoquinoline, trans-2-allyl-8a- acetoxy-4a-(3-hydroxyphenyl)-6β-[N-isobutyl-(3,4- dichlorophenylacetamido)] decahydroisoquinoline, trans-2-allyl-8a- acetoxy-4a-(3-hydroxyphenyl)-6β-(N- isobutylbenzamido) decahydroisoquinoline, trans-2-allyl-8a- acetoxy-4a-(3-hydroxyphenyl)-6β-[N-isobutyl-(2- naphthamido)] decahydroisoquinoline, trans-2-allyl-8a-methoxy-4a-(3-hydroxyphenyl)-6β-(3- trifluoromethylcinnamamido) decahydroisoquinoline, trans-2-allyl- 8a-methoxy-4a-(3-hydroxyphenyl)-6β-(6- phenylhexanamido) decahydroisoquinoline, trans-2-allyl-8a-methoxy- 4a-(3-hydroxyphenyl)-6β-(3,4- dichlorophenylacetamido) decahydroisoquinoline, trans-2-allyl-8a- methoxy-4a-(3- hydroxyphenyl)-6β-benzamidodecahydroisoquinoline, trans-2-allyl-8a-methoxy-4a-(3-hydroxyphenyl)-6β-(2- naphthamido)decahydroisoquinoline, trans-2-allyl-8a-methoxy-4a- (3-hydroxyphenyl)-6β-[N-methyl-3- trifluoromethylcinnamamido)]decahydroisoquinoline, trans-2- allyl-8a-methoxy-4a-(3-hydroxyphenyl)-6β-[N-methyl-(6- phenylhexanamido)]decahydroisoquinoline, trans-2-allyl-8a- methoxy-4a-(3-hydroxyphenyl)-6β-[N-methyl-(3,4- dichlorophenylacetamido)] decahydroisoquinoline, trans-2-allyl-8a- methoxy-4a-(3-hydroxyphenyl)-6β-(N- methylbenzamido) decahydroisoquinoline, trans-2-allyl-8a-methoxy- 4a-(3-hydroxyphenyl)-6β-[N-methyl-(2- naphthamido)] decahydroisoquinoline, trans-2-allyl-8a-methoxy-4a-(3-hydroxyphenyl)-6β-[N-isobutyl-3- trifluoromethylcinnamamido)]decahydroisoquinoline, trans-2- allyl-8a-methoxy-4a-(3-hydroxyphenyl)-6β-[N-isobutyl-(6- phenylhexanamido)]decahydroisoquinoline, trans-2-allyl-8a- methoxy-4a-(3-hydroxyphenyl)-6β-[N-isobutyl-(3,4- dichlorophenylacetamido)] decahydroisoquinoline, trans-2-allyl-8a- methoxy-4a-(3-hydroxyphenyl)-6β-(N- isobutylbenzamido) decahydroisoquinoline, trans-2-allyl-8a- methoxy-4a-(3-hydroxyphenyl)-6β-[N-isobutyl-(2- naphthamido)] decahydroisoquinoline, trans-2-allyl-4a-(3-methoxyphenyl)-6β-(3- trifluoromethylcinnamamido) decahydroisoquinoline, trans-2-allyl- 4a-(3-methoxyphenyl)-6β-(6- phenylhexanamido) decahydroisoquinoline, trans-2-allyl-4a-(3-methoxyphenyl)-6β-(3,4- dichlorophenylacetamido) decahydroisoquinoline, trans-2-allyl-4a- (3-methoxyphenyl)-6β-benzamidodecahydroisoquinoline, trans-2- allyl-4a-(3-methoxyphenyl)-6β-(2- naphthamido) decahydroisoquinoline, trans-2-allyl-4a-(3- methoxyphenyl)-6β-[N-methyl-3- trifluoromethylcinnamamido)]decahydroisoquinoline, trans-2- allyl-4a-(3-methoxyphenyl)-6β-[N-methyl-(6- phenylhexanamido)]decahydroisoquinoline, trans-2- allyl-4a-(3- methoxyphenyl)-6β-[N-methyl-(3,4- dichlorophenylacetamido)]decahydroisoquinoline, trans-2-allyl- 4a-(3-methoxyphenyl)-6β-(N- methylbenzamido) decahydroisoquinoline, trans-2-allyl-4a-(3-methoxyphenyl)-6β-[N-methyl-(2- naphthamido)] decahydroisoquinoline, trans-2-allyl-4a-(3- methoxyphenyl)-6β-[N-isobutyl-3- trifluoromethylcinnamamido)]decahydroisoquinoline, trans-2- allyl-4a-(3-methoxyphenyl)-6β-[N-isobutyl-(6- phenylhexanamido)]decahydroisoquinoline, trans-2-allyl-4a-(3- methoxyphenyl)-6β-[N-isobutyl-(3,4- dichlorophenylacetamido)]decahydroisoquinoline, trans-2-allyl- 4a-(3-methoxyphenyl)-6β-(N- isobutylbenzamido)decahydroisoquinoline, trans-2-allyl-4a-(3- methoxyphenyl)-6β-[N-isobutyl-(2- naphthamido)]decahydroisoquinoline, trans-2-allyl-8a-hydroxy-4a-(3-methoxyphenyl)-6β-(3- trifluoromethylcinnamamido) decahydroisoquinoline, trans-2-allyl- 8a-hydroxy-4a-(3-methoxyphenyl)-6β-(6- phenylhexanamido) decahydroisoquinoline, trans-2-allyl-8a-hydroxy- 4a-(3-methoxyphenyl)-6β-(3,4- dichlorophenylacetamido) decahydroisoquinoline, trans-2-allyl-8a- hydroxy-4a-(3-methoxyphenyl)-6β-benzamidodecahydroisoquinoline, trans-2-allyl-8a-hydroxy-4a-(3-methoxyphenyl)-6β-(2- naphthamido)decahydroisoquinoline, trans-2-allyl-8-hydroxy-4a- (3-methoxyphenyl)-6β-[N-methyl-3- trifluoromethylcinnamamido)]decahydroisoquinoline, trans-2- allyl-8-hydroxy-4a-(3-methoxyphenyl)-6β-[N-methyl-(6- phenylhexanamido)]decahydroisoquinoline, trans-2-allyl-8a- hydroxy-4a-(3-methoxyphenyl)-6β-[N-methyl-(3,4- dichlorophenylacetamido)] decahydroisoquinoline, trans-2-allyl-8a- hydroxy-4a-(3-methoxyphenyl)-6β-(N- methylbenzamido) decahydroisoquinoline, trans-2-allyl-8a-hydroxy- 4a-(3-methoxyphenyl)-6β-[N-methyl-(2- naphthamido)] decahydroisoquinoline, trans-2-allyl-8a-hydroxy-4a- (3-methoxyphenyl)-6β-[N-isobutyl-3- trifluoromethylcinnamamido)]decahydroisoquinoline, trans-2- allyl-8-hydroxy-4a-(3-methoxyphenyl)-6β-[N-isobutyl-(6- phenylhexanamido)]decahydroisoquinoline, trans-2-allyl-8a- hydroxy-4a-(3-methoxyphenyl)-6β-[N-isobutyl-(3,4- dichlorophenylacetamido)] decahydroisoquinoline, trans-2-allyl-8a- hydroxy-4a-(3-methoxyphenyl)-6β-(N- isobutylbenzamido) decahydroisoquinoline, trans-2-allyl-8a- hydroxy-4a-(3-methoxyphenyl)-6β-[N-isobutyl-(2- naphthamido)] decahydroisoquinoline, trans-2-allyl-8a-acetoxy-4a-(3- methoxyphenyl)-6β-(3- trifluoromethylcinnamamido) decahydroisoquinoline, trans-2-allyl- 8a-acetoxy-4a-(3-methoxyphenyl)-6β-(6- phenylhexanamido) decahydroisoquinoline, trans-2-allyl-8a-acetoxy- 4a-(3-methoxyphenyl)-6β-(3,4- dichlorophenylacetamido) decahydroisoquinoline, trans-2-allyl-8a- acetoxy-4a-(3-methoxyphenyl)-6β-benzamidodecahydroisoquinoline, trans-2-allyl-8a-acetoxy-4a-(3-methoxyphenyl)-6β-(2- naphthamido)decahydroisoquinoline, trans-2-allyl-8a- acetoxy-4a- (3-methoxyphenyl)-6β-[N-methyl-3- trifluoromethylcinnamamido)]decahydroisoquinoline, trans-2- allyl-8a-acetoxy-4a-(3-methoxyphenyl)-6β-[N-methyl-(6- phenylhexanamido)]decahydroisoquinoline, trans-2-allyl-8a- acetoxy-4a-(3-methoxyphenyl)-6β-[N-methyl-(3,4- dichlorophenylacetamido)] decahydroisoquinoline, trans-2-allyl-8a- acetoxy-4a-(3-methoxyphenyl)-6β-(N- methylbenzamido) decahydroisoquinoline, trans-2-allyl-8a-acetoxy- 4a-(3-methoxyphenyl)-6β-[N-methyl-(2- naphthamido)] decahydroisoquinoline, trans-2-allyl-8a-acetoxy-4a- (3-methoxyphenyl)-6β-[N-isobutyl-3- trifluoromethylcinnamamido)]decahydroisoquinoline, trans-2- allyl-8a-acetoxy-4a-(3-methoxyphenyl)-6β-[N-isobutyl-(6- phenylhexanamido)]decahydroisoquinoline, trans-2-allyl-8a- acetoxy-4a-(3-methoxyphenyl)-6β-[N-isobutyl-(3,4- dichlorophenylacetamido)] decahydroisoquinoline, trans-2-allyl-8a- acetoxy-4a-(3-methoxyphenyl)-6β-(N- isobutylbenzamido) decahydroisoquinoline, trans-2-allyl-8a- acetoxy-4a-(3-methoxyphenyl)-6β-[N-isobutyl-(2- naphthamido)] decahydroisoquinoline, trans-2-allyl-8a-methoxy-4a-(3- methoxyphenyl)-6β-(3- trifluoromethylcinnamamido) decahydroisoquinoline, trans-2-allyl- 8a-methoxy-4a-(3- methoxyphenyl)-6β-(6- phenylhexanamido) decahydroisoquinoline, trans-2-allyl-8a-methoxy- 4a-(3-methoxyphenyl)-6β-(3,4- dichlorophenylacetamido) decahydroisoquinoline, trans-2-allyl-8a- methoxy-4a-(3-methoxyphenyl)-6β-benzamidodecahydroisoquinoline, trans-2-allyl-8a-methoxy-4a-(3-methoxyphenyl)-6β-(2-naphthamido)decahydroisoquinoline, trans-2-allyl-8a-methoxy-4a- (3-methoxyphenyl)-6β-[N-methyl-3-trifluoromethylcinnamamido)]decahydroisoquinoline, trans-2- allyl-8a-methoxy-4a-(3-methoxyphenyl)-6β-[N-methyl-(6- phenylhexanamido)]decahydroisoquinoline, trans-2-allyl-8a- methoxy-4a-(3-methoxyphenyl)-6β-[N-methyl-(3,4- dichlorophenylacetamido)] decahydroisoquinoline, trans-2-allyl-8a- methoxy-4a-(3-methoxyphenyl)-6β-(N- methylbenzamido) decahydroisoquinoline, trans-2-allyl-8a-methoxy- 4a-(3-methoxyphenyl)-6β-[N-methyl-(2- naphthamido)] decahydroisoquinoline, trans-2-allyl-8a-methoxy-4a- (3-methoxyphenyl)-6β-[N-isobutyl-3-trifluoromethylcinnamamido)]decahydroisoquinoline, trans-2- allyl-8a-methoxy-4a-(3-methoxyphenyl)-6β-[N-isobutyl-(6- phenylhexanamido)]decahydroisoquinoline, trans-2-allyl-8a- methoxy-4a-(3-methoxyphenyl)-6β-[N-isobutyl-(3,4- dichlorophenylacetamido)] decahydroisoquinoline, trans-2-allyl-8a- methoxy-4a-(3-methoxyphenyl)-6β-(N- isobutylbenzamido) decahydroisoquinoline, trans-2-allyl-8a- methoxy-4a-(3-methoxyphenyl)-6β-[N-isobutyl-(2- naphthamido)] decahydroisoquinoline, trans-2-allyl-4a-(3-acetoxyphenyl)-6β-(3- trifluoromethylcinnamamido) decahydroisoquinoline, trans-2-allyl- 4a-(3-acetoxyphenyl)-6β-(6- phenylhexanamido) decahydroisoquinoline, trans-2-allyl-4a-(3-acetoxyphenyl)-6β-(3,4- dichlorophenylacetamido) decahydroisoquinoline, trans-2-allyl-4a- (3-acetoxyphenyl)-6β-benzamidodecahydroisoquinoline, trans-2- allyl-4a-(3-acetoxyphenyl)-6β-(2- naphthamido) decahydroisoquinoline, trans-2-allyl-4a-(3-acetoxyphenyl)-6β-[N-methyl-3-trifluoromethylcinnamamido)]decahydroisoquinoline, trans-2- allyl-4a-(3-acetoxyphenyl)-6β-[N-methyl-(6-phenylhexanamido)]decahydroisoquinoline, trans-2-allyl-4a-(3- acetoxyphenyl)-6β-[N-methyl-(3,4-dichlorophenylacetamido)]decahydroisoquinoline, trans-2-allyl- 4a-(3-acetoxyphenyl)-6β-(N- methylbenzamido) decahydroisoquinoline, trans-2-allyl-4a-(3-acetoxyphenyl)-6β-[N-methyl-(2- naphthamido)] decahydroisoquinoline, trans-2-allyl-4a-(3-acetoxyphenyl)-6β-[N-isobutyl-3-trifluoromethylcinnamamido)]decahydroisoquinoline, trans-2- allyl-4a-(3-acetoxyphenyl)-6β-[N-isobutyl-(6-phenylhexanamido)]decahydroisoquinoline, trans-2-allyl-4a-(3- acetoxyphenyl)-6β-[N-isobutyl-(3,4-dichlorophenylacetamido)]decahydroisoquinoline, trans-2-allyl- 4a-(3-acetoxyphenyl)-6β-(N- isobutylbenzamido) decahydroisoquinoline, trans-2-allyl-4a-(3-acetoxyphenyl)-6β-[N-isobutyl-(2- naphthamido)] decahydroisoquinoline, trans-2-allyl-8a-hydroxy-4a-(3-acetoxyphenyl)-6β-(3- trifluoromethylcinnamamido) decahydroisoquinoline, trans-2-allyl- 8a-hydroxy-4a-(3-acetoxyphenyl)-6β-(6- phenylhexanamido) decahydroisoquinoline, trans-2-allyl-8a-hydroxy- 4a-(3-acetoxyphenyl)-6β-(3,4- dichlorophenylacetamido) decahydroisoquinoline, trans-2-allyl-8a- hydroxy-4a-(3-acetoxyphenyl)-6β-benzamidodecahydroisoquinoline, trans-2-allyl-8-hydroxy-4a-(3-acetoxyphenyl)-6β-(2- naphthamido)decahydroisoquinoline, trans-2-allyl-8a-hydroxy-4a- (3-acetoxyphenyl)-6β-[N-methyl-3-trifluoromethylcinnamamido)]decahydroisoquinoline, trans-2- allyl-8-hydroxy-4a-(3-acetoxyphenyl)-6β-[N-methyl-(6- phenylhexanamido)]decahydroisoquinoline, trans-2-allyl-8a- hydroxy-4a-(3-acetoxyphenyl)-6β-[N-methyl-(3,4- dichlorophenylacetamido)] decahydroisoquinoline, trans-2-allyl-8a- hydroxy-4a-(3-acetoxyphenyl)-6β-(N- methylbenzamido) decahydroisoquinoline, trans-2-allyl-8a-hydroxy- 4a-(3-acetoxyphenyl)-6β-[N-methyl-(2- naphthamido)] decahydroisoquinoline, trans-2-allyl-8a-hydroxy-4a- (3-acetoxyphenyl)-6β-[N-isobutyl-3-trifluoromethylcinnamamido)]decahydroisoquinoline, trans-2- allyl-8a-hydroxy-4a-(3-acetoxyphenyl)-6β-[N-isobutyl-(6- phenylhexanamido)]decahydroisoquinoline, trans-2-allyl-8a- hydroxy-4a-(3-acetoxyphenyl)-6β-[N-isobutyl-(3,4- dichlorophenylacetamido)] decahydroisoquinoline, trans-2-allyl-8a- hydroxy-4a-(3-acetoxyphenyl)-6β-(N- isobutylbenzamido) decahydroisoquinoline, trans-2-allyl-8a- hydroxy-4a-(3-acetoxyphenyl)-6β-[N-isobutyl-(2- naphthamido)] decahydroisoquinoline, trans-2-allyl-8a-acetoxy-4a-(3-acetoxyphenyl)-6β-(3- trifluoromethylcinnamamido) decahydroisoquinoline, trans-2-allyl- 8a-acetoxy-4a-(3-acetoxyphenyl)-6β-(6- phenylhexanamido) decahydroisoquinoline, trans-2-allyl-8a-acetoxy- 4a-(3-acetoxyphenyl)-6β-(3,4- dichlorophenylacetamido) decahydroisoquinoline, trans-2-allyl-8a- acetoxy-4a-(3-acetoxyphenyl)-6β-benzamidodecahydroisoquinoline, trans-2-allyl-8a-acetoxy-4a-(3-acetoxyphenyl)-6β-(2- naphthamido)decahydroisoquinoline, trans-2-allyl-8a-acetoxy-4a- (3-acetoxyphenyl)-6β-[N-methyl-3-trifluoromethylcinnamamido)]decahydroisoquinoline, trans-2- allyl-8a-acetoxy-4a-(3-acetoxyphenyl)-6β-[N-methyl-(6- phenylhexanamido)]decahydroisoquinoline, trans-2-allyl-8a- acetoxy-4a-(3-acetoxyphenyl)-6β-[N-methyl-(3,4- dichlorophenylacetamido)] decahydroisoquinoline, trans-2-allyl-8a- acetoxy-4a-(3-acetoxyphenyl)-6β-(N- methylbenzamido) decahydroisoquinoline, trans-2-allyl-8a-acetoxy- 4a-(3-acetoxyphenyl)-6β-[N-methyl-(2- naphthamido)] decahydroisoquinoline, trans-2-allyl-8a-acetoxy-4a- (3-acetoxyphenyl)-6β-[N-isobutyl-3-trifluoromethylcinnamamido)]decahydroisoquinoline, trans-2- allyl-8a-acetoxy-4a-(3-acetoxyphenyl)-6β-[N-isobutyl-(6- phenylhexanamido)]decahydroisoquinoline, trans-2-allyl-8a- acetoxy-4a-(3-acetoxyphenyl)-6β-[N-isobutyl-(3,4- dichlorophenylacetamido)] decahydroisoquinoline, trans-2-allyl-8a- acetoxy-4a-(3-acetoxyphenyl)-6β-(N- isobutylbenzamido) decahydroisoquinoline, trans-2-allyl-8a- acetoxy-4a-(3-acetoxyphenyl)-6β-[N-isobutyl-(2- naphthamido)] decahydroisoquinoline, trans-2-allyl-8a-methoxy-4a-(3-acetoxyphenyl)-6β-(3- trifluoromethylcinnamamido) decahydroisoquinoline, trans-2-allyl- 8-methoxy-4a-(3-acetoxyphenyl)-6β-(6- phenylhexanamido) decahydroisoquinoline, trans-2-allyl-8a-methoxy- 4a-(3-acetoxyphenyl)-6β-(3,4- dichlorophenylacetamido) decahydroisoquinoline, trans-2-allyl-8a- methoxy-4a-(3-acetoxyphenyl)-6β-benzamidodecahydroisoquinoline, trans-2-allyl-8a-methoxy-4a-(3-acetoxyphenyl)-6β-(2- naphthamido)decahydroisoquinoline, trans-2-allyl-8a-methoxy-4a- (3-acetoxyphenyl)-6β-[N-methyl-3-trifluoromethylcinnamamido)]decahydroisoquinoline, trans-2- allyl-8a-methoxy-4a-(3-acetoxyphenyl)-6β-[N-methyl-(6- phenylhexanamido)]decahydroisoquinoline, trans-2-allyl-8a- methoxy-4a-(3-acetoxyphenyl)-6β-[N- methyl-(3,4- dichlorophenylacetamido)]
decahydroisoquinoline, trans-2-allyl-8a- methoxy-4a-(3-
acetoxyphenyl)-6β-(N- methylbenzamido)
decahydroisoquinoline, trans-2-allyl-8a-methoxy- 4a-(3-
acetoxyphenyl)-6β-[N-methyl-(2- naphthamido)]
decahydroisoquinoline, trans-2-allyl-8a-methoxy-4a-
(3-acetoxyphenyl)-6β-[N-isobutyl-3-
trifluoromethylcinnamamido)]decahydroisoquinoline,
trans-2- allyl-8a-methoxy-4a-(3-acetoxyphenyl)-6β-[N-
isobutyl-(6- phenylhexanamido)]decahydroisoquinoline,
trans-2-allyl-8a- methoxy-4a-(3-acetoxyphenyl)-6β-[N-
isobutyl-(3,4- dichlorophenylacetamido)]
decahydroisoquinoline, trans-2-allyl-8a- methoxy-4a-(3-
acetoxyphenyl)-6β-(N- isobutylbenzamido)
decahydroisoquinoline, trans-2-allyl-8a- methoxy-4a-(3-
acetoxyphenyl)-6β-[N-isobutyl-(2- naphthamido)]
decahydroisoquinoline, trans-2-methyl-4a-(3-
hydroxyphenyl)-6β-(3- trifluoromethylcinnamamido)
decahydroisoquinoline, trans-2- methyl-4a-(3-
hydroxyphenyl)-6β-(6- phenylhexanamido)
decahydroisoquinoline, trans-2-methyl-4a-(3-
hydroxyphenyl)-6β-(3,4- dichlorophenylacetamido)
decahydroisoquinoline, trans-2-methyl- 4a-(3-
hydroxyphenyl)-6β-benzamidodecahydroisoquinoline,
trans-2- methyl-4a-(3-hydroxyphenyl)-6β-(2-
naphthamido)decahydroisoquinoline, trans-2-methyl-4a-
(3- hydroxyphenyl)-6β-[N-methyl-3-
trifluoromethylcinnamamido)]decahydroisoquinoline,
trans-2- methyl-4a-(3-hydroxyphenyl)-6β-[N-methyl-(6-
phenylhexanamido)]decahydroisoquinoline, trans-2-
methyl-4a-(3- hydroxyphenyl)-6β-[N-methyl-(3,4-
dichlorophenylacetamido)]decahydroisoquinoline, trans-
2-methyl- 4a-(3-hydroxyphenyl)-6β-(N-
methylbenzamido)decahydroisoquinoline, trans-2-
methyl-4a-(3- hydroxyphenyl)-6β-[N-methyl-(2-
naphthamido)]decahydroisoquinoline, trans-2-methyl-4a-
(3- hydroxyphenyl)-6β-[N-isobutyl-3-
trifluoromethylcinnamamido)]decahydroisoquinoline,
trans-2- methyl-4a-(3-hydroxyphenyl)-6β-[N-isobutyl-
(6- phenylhexanamido)]decahydroisoquinoline, trans-2-
methyl-4a-(3- hydroxyphenyl)-6β-[N-isobutyl-(3,4-
dichlorophenylacetamido)]decahydroisoquinoline, trans-
2-methyl- 4a-(3-hydroxyphenyl)-6β-(N-
isobutylbenzamido)decahydroisoquinoline, trans-2-
methyl-4a-(3- hydroxyphenyl)-6β-[N-isobutyl-(2-
naphthamido)]decahydroisoquinoline, trans-2-methyl-8a-
hydroxy-4a-(3-hydroxyphenyl)-6β-(3-
trifluoromethylcinnamido)decahydroisoquinoline,
trans-2- methyl-8a-hydroxy-4a-(3-hydroxyphenyl)-6β-
(6- phenylhexanamido)decahydroisoquinoline, trans-2-
methyl-8a- hydroxy-4a-(3-hydroxyphenyl)-6β-(3,4-
dichlorophenylacetamido)decahydroisoquinoline, trans-
2-methyl-8a- hydroxy-4a-(3-hydroxyphenyl)-6β-
benzamidodecahydroisoquinoline, trans-2-methyl-8a-
hydroxy-4a-(3-hydroxyphenyl)-6β-(2- naphthamido)
decahydroisoquinoline, trans-2-methyl-8a-hydroxy-4a-
(3-hydroxyphenyl)-6β-[N-methyl-3-
trifluoromethylcinnamamido)]decahydroisoquinoline,
trans-2- methyl-8a-hydroxy-4a-(3-hydroxyphenyl)-6β-
[N-methyl-(6- phenylhexanamido)]
decahydroisoquinoline, trans-2-methyl-8a- hydroxy-4a-
(3-hydroxyphenyl)-6β-[N-methyl-(3,4-
dichlorophenylacetamido)]decahydroisoquinoline, trans-
2-methyl- 8-hydroxy-4a-(3-hydroxyphenyl)-6β-(N-
methylbenzamido)decahydroisoquinoline, trans-2-
methyl-8a-hydroxy- 4a-(3-hydroxyphenyl)-6β-[N-
methyl-(2- naphthamido)]decahydroisoquinoline, trans-
2-methyl-8a-hydroxy-4a- (3-hydroxyphenyl)-6β-[N-
isobutyl-3- trifluoromethylcinnamamido)]
decahydroisoquinoline, trans-2- methyl-8a-hydroxy-4a-
(3-hydroxyphenyl)-6β-[N-isobutyl-(6-
phenylhexanamido)]decahydroisoquinoline, trans-2-
methyl-8a- hydroxy-4a-(3-hydroxyphenyl)-6β-[N-
isobutyl-(3,4- dichlorophenylacetamido)]
decahydroisoquinoline, trans-2-methyl- 8a-hydroxy-4a-
(3-hydroxyphenyl)-6β-(N- isobutylbenzamido)
decahydroisoquinoline, trans-2-methyl-8a- hydroxy-4a-
(3-hydroxyphenyl)-6β-[N-isobutyl-(2- naphthamido)]
decahydroisoquinoline, trans-2-methyl-8a-acetoxy-4a-(3-
hydroxyphenyl)-6β-(3- trifluoromethylcinnamamido)
decahydroisoquinoline, trans-2- methyl-8a-acetoxy-4a-
(3-hydroxyphenyl)-6β-(6- phenylhexanamido)
decahydroisoquinoline, trans-2-methyl-8a- acetoxy-4a-
(3-hydroxyphenyl)-6β-(3,4- dichlorophenylacetamido)
decahydroisoquinoline, trans-2-methyl-8a- acetoxy-4a-
(3-hydroxyphenyl)-6β-
benzamidodecahydroisoquinoline, trans-2-methyl-8a-
acetoxy-4a-(3-hydroxyphenyl)-6β-(2- naphthamido)
decahydroisoquinoline, trans-2-methyl-8a-acetoxy-4a-
(3-hydroxyphenyl)-6β-[N-methyl-3-
trifluoromethylcinnamamido)]decahydroisoquinoline,
trans-2- methyl-8a-acetoxy-4a-(3-hydroxyphenyl)-6β-
[N-methyl-(6- phenylhexanamido)]
decahydroisoquinoline, trans-2-methyl-8a- acetoxy-4a-
(3-hydroxyphenyl)-6β-[N-methyl-(3,4-
dichlorophenylacetamido)]decahydroisoquinoline, trans-
2-methyl- 8a-acetoxy-4a-(3-hydroxyphenyl)-6β-(N-
methylbenzamido)decahydroisoquinoline, trans-2-
methyl-8a-acetoxy- 4a-(3-hydroxyphenyl)-6β-[N-
methyl-(2- naphthamido)]decahydroisoquinoline, trans-
2-methyl-8a-acetoxy-4a- (3-hydroxyphenyl)-6β-[N-
isobutyl-3- trifluoromethylcinnamamido)]
decahydroisoquinoline, trans-2- methyl-8a-acetoxy-4a-
(3-hydroxyphenyl)-6β-[N-isobutyl-(6-
phenylhexanamido)]decahydroisoquinoline, trans-2-
methyl-8a- acetoxy-4a-(3-hydroxyphenyl)-6β-[N-
isobutyl-(3,4- dichlorophenylacetamido)]
decahydroisoquinoline, trans-2-methyl- 8a-acetoxy-4a-
(3-hydroxyphenyl)-6β-(N- isobutylbenzamido)
decahydroisoquinoline, trans-2-methyl-8a- acetoxy-4a-
(3-hydroxyphenyl)-6β-[N-isobutyl-(2- naphthamido)]
decahydroisoquinoline, trans-2-methyl-8a-methoxy-4a-
(3-hydroxyphenyl)-6β-(3- trifluoromethylcinnamamido)
decahydroisoquinoline, trans-2- methyl-8a-methoxy-4a-
(3-hydroxyphenyl)-6β-(6- phenylhexanamido)
decahydroisoquinoline, trans-2-methyl-8a- methoxy-4a-
(3-hydroxyphenyl)-6β-(3,4- dichlorophenylacetamido)
decahydroisoquinoline, trans-2-methyl-8a- methoxy-4a-
(3-hydroxyphenyl)-6β-
benzamidodecahydroisoquinoline, trans-2-methyl-8a-
methoxy-4a-(3-hydroxyphenyl)-6β-(2- naphthamido)
decahydroisoquinoline, trans-2-methyl-8a-methoxy-4a-
(3-hydroxyphenyl)-6β-[N-methyl-3-
trifluoromethylcinnamamido)]decahydroisoquinoline,
trans-2- methyl-8a-methoxy-4a-(3-hydroxyphenyl)-6β-
[N-methyl-(6- phenylhexanamido)]
decahydroisoquinoline, trans-2-methyl-8a- methoxy-4a-
(3-hydroxyphenyl)-6β-[N-methyl-(3,4-
dichlorophenylacetamido)]decahydroisoquinoline, trans-
2-methyl- 8-methoxy-4a-(3-hydroxyphenyl)-6β-(N-
methylbenzamido)decahydroisoquinoline, trans-2-
methyl-8a-methoxy- 4a-(3-hydroxyphenyl)-6β-[N-
methyl-(2- naphthamido)]decahydroisoquinoline, trans-
2-methyl-8a-methoxy-4a- (3-hydroxyphenyl)-6β-[N- isobutyl-3- trifluoromethylcinnamamido)]
decahydroisoquinoline, trans-2- methyl-8a-methoxy-4a-
(3-hydroxyphenyl)-6β-[N-isobutyl-(6-
phenylhexanamido)]decahydroisoquinoline, trans-2-
methyl-8a- methoxy-4a-(3-hydroxyphenyl)-6β-[N-
isobutyl-(3,4- dichlorophenylacetamido)]
decahydroisoquinoline, trans-2-methyl- 8a-methoxy-4a-
(3-hydroxyphenyl)-6β-(N- isobutylbenzamido)
decahydroisoquinoline, trans-2-methyl-8a- methoxy-4a-
(3-hydroxyphenyl)-6β-[N-isobutyl-(2- naphthamido)]
decahydroisoquinoline, trans-2-methyl-4a-(3-
methoxyphenyl)-6β-(3- trifluoromethylcinnamamido)
decahydroisoquinoline, trans-2- methyl-4a-(3-
methoxyphenyl)-6β-(6- phenylhexanamido)
decahydroisoquinoline, trans-2-methyl-4a-(3-
methoxyphenyl)-6β-(3,4-dichlorophenylacetamido)
decahydroisoquinoline, trans-2-methyl- 4a-(3-
methoxyphenyl)-6β-benzamidodecahydroisoquinoline,
trans-2- methyl-4a-(3-methoxyphenyl)-6β-(2-
naphthamido)decahydroisoquinoline, trans-2-methyl-4a-
(3- methoxyphenyl)-6β-[N-methyl-3-
trifluoromethylcinnamamido)]decahydroisoquinoline,
trans-2- methyl-4a-(3-methoxyphenyl)-6β-[N-methyl-(6-
phenylhexanamido)]decahydroisoquinoline, trans-2-
methyl-4a-(3- methoxyphenyl)-6β-[N-methyl-(3,4-
dichlorophenylacetamido)]decahydroisoquinoline, trans-
2-methyl- 4a-(3-methoxyphenyl)-6β-(N-
methylbenzamido)decahydroisoquinoline, trans-2-
methyl-4a-(3- methoxyphenyl)-6β-[N-methyl-(2-
naphthamido)]decahydroisoquinoline, trans-2-methyl-4a-
(3- methoxyphenyl)-6β-[N-isobutyl-3-
trifluoromethylcinnamamido)]decahydroisoquinoline,
trans-2- methyl-4a-(3-methoxyphenyl)-6β-[N-isobutyl-
(6- phenylhexanamido)]decahydroisoquinoline, trans-2-
methyl-4a-(3- methoxyphenyl)-6β-[N-isobutyl-(3,4-
dichlorophenylacetamido)]decahydroisoquinoline, trans-
2-methyl- 4a-(3-methoxyphenyl)-6β-(N-
isobutylbenzamido)decahydroisoquinoline, trans-2-
methyl-4a-(3- methoxyphenyl)-6β-[N-isobutyl-(2-
naphthamido)]decahydroisoquinoline, trans-2-methyl-8a-
hydroxy-4a-(3-methoxyphenyl)-6β-(3-
trifluoromethylcinnamamido)decahydroisoquinoline,
trans-2- methyl-8a-hydroxy-4a-(3-methoxyphenyl)-6β-
(6- phenylhexanamido)decahydroisoquinoline, trans-2-
methyl-8a- hydroxy-4a-(3-methoxyphenyl)-6β-(3,4-
dichlorophenylacetamido)decahydroisoquinoline, trans-
2-methyl-8a- hydroxy-4a-(3-methoxyphenyl)-6β-
benzamidodecahydroisoquinoline, trans-2-methyl-8a-
hydroxy-4a-(3-methoxyphenyl)-6β-(2- naphthamido)
decahydroisoquinoline, trans-2-methyl-8a-hydroxy-4a-
(3-methoxyphenyl)-6β-[N-methyl-3-
trifluoromethylcinnamamido)]decahydroisoquinoline,
trans-2- methyl-8a-hydroxy-4a-(3-methoxyphenyl)-6β-
[N-methyl-(6- phenylhexanamido)]
decahydroisoquinoline, trans-2-methyl-8a- hydroxy-4a-
(3-methoxyphenyl)-6β-[N-methyl-(3,4-
dichlorophenylacetamido)]decahydroisoquinoline, trans-
2-methyl- 8a-hydroxy-4a-(3-methoxyphenyl)-6β-(N-
methylbenzamido)decahydroisoquinoline, trans-2-
methyl-8a-hydroxy- 4a-(3-methoxyphenyl)-6β-[N-
methyl-(2- naphthamido)]decahydroisoquinoline, trans-
2-methyl-8a-hydroxy-4a- (3-methoxyphenyl)-6β-[N-
isobutyl-3- trifluoromethylcinnamamido)]
decahydroisoquinoline, trans-2- methyl-8a-hydroxy-4a-
(3-methoxyphenyl)-6β-[N-isobutyl-(6-
phenylhexanamido)]decahydroisoquinoline, trans-2-
methyl-8a- hydroxy-4a-(3-methoxyphenyl)-6β-[N-
isobutyl-(3,4- dichlorophenylacetamido)]
decahydroisoquinoline, trans-2-methyl- 8a-hydroxy-4a-
(3-methoxyphenyl)-6β-(N- isobutylbenzamido)
decahydroisoquinoline, trans-2-methyl-8a- hydroxy-4a-
(3-methoxyphenyl)-6β-[N-isobutyl-(2- naphthamido)]
decahydroisoquinoline, trans-2-methyl-8a-acetoxy-4a-(3-
methoxyphenyl)-6β-(3- trifluoromethylcinnamamido)
decahydroisoquinoline, trans-2- methyl-8a-acetoxy-4a-
(3-methoxyphenyl)-6β-(6- phenylhexanamido)
decahydroisoquinoline, trans-2-methyl-8a- acetoxy-4a-
(3-methoxyphenyl)-6β-(3,4- dichlorophenylacetamido)
decahydroisoquinoline, trans-2-methyl-8a- acetoxy-4a-
(3-methoxyphenyl)-6β-
benzamidodecahydroisoquinoline, trans-2-methyl-8a-
acetoxy-4a-(3-methoxyphenyl)-6β-(2- naphthamido)
decahydroisoquinoline, trans-2-methyl-8a-acetoxy-4a-
(3-methoxyphenyl)-6β-[N-methyl-3-
trifluoromethylcinnamamido)]decahydroisoquinoline,
trans-2- methyl-8a-acetoxy-4a-(3-methoxyphenyl)-6β-
[N-methyl-(6- phenylhexanamido)]
decahydroisoquinoline, trans-2-methyl-8a- acetoxy-4a-
(3-methoxyphenyl)-6β-[N-methyl-(3,4-
dichlorophenylacetamido)]decahydroisoquinoline, trans-
2-methyl- 8a-acetoxy-4a-(3-methoxyphenyl)-6β-(N-
methylbenzamido)decahydroisoquinoline, trans-2-
methyl-8-aacetoxy- 4a-(3-methoxyphenyl)-6β-[N-
methyl-(2- naphthamido)]decahydroisoquinoline, trans-
2-methyl-8a-acetoxy-4a- (3-methoxyphenyl)-6β-[N-
isobutyl-3- trifluoromethylcinnamamido)]
decahydroisoquinoline, trans-2- methyl-8a-acetoxy-4a-
(3-methoxyphenyl)-6β-[N-isobutyl-(6-
phenylhexanamido)]decahydroisoquinoline, trans-2-
methyl-8a- acetoxy-4a-(3-methoxyphenyl)-6β-[N-
isobutyl-(3,4- dichlorophenylacetamido)]
decahydroisoquinoline, trans-2-methyl- 8a-acetoxy-4a-
(3-methoxyphenyl)-6β-(N- isobutylbenzamido)
decahydroisoquinoline, trans-2-methyl-8a- acetoxy-4a-
(3-methoxyphenyl)-6β-[N-isobutyl-(2- naphthamido)]
decahydroisoquinoline, trans-2-methyl-8a-methoxy-4a-
(3-methoxyphenyl)-6β-(3- trifluoromethylcinnamamido)
decahydroisoquinoline, trans-2- methyl-8a-methoxy-4a-
(3-methoxyphenyl)-6β-(6- phenylhexanamido)
decahydroisoquinoline, trans-2-methyl-8a- methoxy-4a-
(3-methoxyphenyl)-6β-(3,4- dichlorophenylacetamido)
decahydroisoquinoline, trans-2-methyl-8a- methoxy-4a-
(3-methoxyphenyl)-6β-
benzamidodecahydroisoquinoline, trans-2-methyl-8a-
methoxy-4a-(3-methoxyphenyl)-6β-(2- naphthamido)
decahydroisoquinoline, trans-2-methyl-8a-methoxy-4a-
(3-methoxyphenyl)-6β-[N-methyl-3-
trifluoromethylcinnamamido)]decahydroisoquinoline,
trans-2- methyl-8a-methoxy-4a-(3-methoxyphenyl)-6β-
[N-methyl-(6- phenylhexanamido)]
decahydroisoquinoline, trans-2-methyl-8a- methoxy-4a-
(3-methoxyphenyl)-6β-[N-methyl-(3,4-
dichlorophenylacetamido)]decahydroisoquinoline, trans-
2-methyl- 8a-methoxy-4a-(3-methoxyphenyl)-6β-(N-
methylbenzamido)decahydroisoquinoline, trans-2-
methyl-8a-methoxy- 4a-(3-methoxyphenyl)-6β-[N-
methyl-(2- naphthamido)]decahydroisoquinoline, trans-
2-methyl-8a-methoxy-4a- (3-methoxyphenyl)-6β-[N-
isobutyl-3- trifluoromethylcinnamamido)]
decahydroisoquinoline, trans-2- methyl-8a-methoxy-4a-
(3-methoxyphenyl)-6β-[N-isobutyl-(6-
phenylhexanamido)]decahydroisoquinoline, trans-2-
methyl-8a- methoxy-4a-(3-methoxyphenyl)-6β-[N-
isobutyl-(3,4- dichlorophenylacetamido)]

decahydroisoquinoline, trans-2-methyl- 8a-methoxy-4a-(3-methoxyphenyl)-6β-(N- isobutylbenzamido) decahydroisoquinoline, trans-2-methyl-8a- methoxy-4a-(3-methoxyphenyl)-6β-[N-isobutyl-(2- naphthamido)] decahydroisoquinoline, trans-2-methyl-4a-(3- acetoxyphenyl)-6β-(3- trifluoromethylcinnamamido) decahydroisoquinoline, trans-2- methyl-4a-(3-acetoxyphenyl)-6β-(6- phenylhexanamido) decahydroisoquinoline, trans-2-methyl-4a-(3-acetoxyphenyl)-6β-(3,4- dichlorophenylacetamido) decahydroisoquinoline, trans-2-methyl- 4a-(3-acetoxyphenyl)-6β-benzamidodecahydroisoquinoline, trans-2- methyl-4a-(3-acetoxyphenyl)-6β-(2-naphthamido)decahydroisoquinoline, trans-2-methyl-4a-(3- acetoxyphenyl)-6β-[N-methyl-3- trifluoromethylcinnamamido)]decahydroisoquinoline, trans-2- methyl-4a-(3-acetoxyphenyl)-6β-[N-methyl-(6- phenylhexanamido)]decahydroisoquinoline, trans-2-methyl-4a-(3- acetoxyphenyl)-6β-[N-methyl-(3,4-dichlorophenylacetamido)]decahydroisoquinoline, trans-2-methyl- 4a-(3-acetoxyphenyl)-6β-(N-methylbenzamido)decahydroisoquinoline, trans-2-methyl-4a-(3- acetoxyphenyl)-6β-[N-methyl-(2-naphthamido)]decahydroisoquinoline, trans-2-methyl-4a-(3- acetoxyphenyl)-6β-[N-isobutyl-3-trifluoromethylcinnamamido)]decahydroisoquinoline, trans-2- methyl-4a-(3-acetoxyphenyl)-6β-[N-isobutyl-(6-phenylhexanamido)]decahydroisoquinoline, trans-2-methyl-4a-(3- acetoxyphenyl)-6β-[N-isobutyl-(3,4-dichlorophenylacetamido)]decahydroisoquinoline, trans-2-methyl- 4a-(3-acetoxyphenyl)-6β-(N-isobutylbenzamido)decahydroisoquinoline, trans-2-methyl-4a-(3- acetoxyphenyl)-6β-[N-isobutyl-(2-naphthamido)]decahydroisoquinoline, trans-2-methyl-8a-hydroxy-4a-(3-acetoxyphenyl)-6β-(3-trifluoromethylcinnamamido)decahydroisoquinoline, trans-2- methyl-8a-hydroxy-4a-(3-acetoxyphenyl)-6β-(6-phenylhexanamido)decahydroisoquinoline, trans-2-methyl-8a- hydroxy-4a-(3-acetoxyphenyl)-6β-(3,4-dichlorophenylacetamido)decahydroisoquinoline, trans-2-methyl-8a- hydroxy-4a-(3-acetoxyphenyl)-6β-benzamidodecahydroisoquinoline, trans-2-methyl-8a-hydroxy-4a-(3-acetoxyphenyl)-6β-(2- naphthamido) decahydroisoquinoline, trans-2-methyl-8a-hydroxy-4a-(3-acetoxyphenyl)-6β-[N-methyl-3- trifluoromethylcinnamamido)]decahydroisoquinoline, trans-2- methyl-8a-hydroxy-4a-(3-acetoxyphenyl)-6β-[N-methyl-(6- phenylhexanamido)] decahydroisoquinoline, trans-2-methyl-8a- hydroxy-4a-(3-acetoxyphenyl)-6β-[N-methyl-(3,4- dichlorophenylacetamido)]decahydroisoquinoline, trans-2-methyl- 8a-hydroxy-4a-(3-acetoxyphenyl)-6β-(N-methylbenzamido)decahydroisoquinoline, trans-2-methyl-8a-hydroxy- 4a-(3-acetoxyphenyl)-6β-[N-methyl-(2- naphthamido)]decahydroisoquinoline, trans-2-methyl-8a-hydroxy-4a- (3-acetoxyphenyl)-6β-[N-isobutyl-3- trifluoromethylcinnamamido)] decahydroisoquinoline, trans-2- methyl-8a-hydroxy-4a-(3-acetoxyphenyl)-6β-[N-isobutyl-(6-phenylhexanamido)]decahydroisoquinoline, trans-2- methyl-8a- hydroxy-4a-(3-acetoxyphenyl)-6β-[N-isobutyl-(3,4- dichlorophenylacetamido)] decahydroisoquinoline, trans-2-methyl- 8a-hydroxy-4a-(3-acetoxyphenyl)-6β-(N- isobutylbenzamido) decahydroisoquinoline, trans-2-methyl-8a- hydroxy-4a-(3-acetoxyphenyl)-6β-[N-isobutyl-(2- naphthamido)] decahydroisoquinoline, trans-2-methyl-8a-acetoxy-4a-(3-acetoxyphenyl)-6β-(3- trifluoromethylcinnamamido) decahydroisoquinoline, trans-2- methyl-8a-acetoxy-4a-(3-acetoxyphenyl)-6β-(6- phenylhexanamido) decahydroisoquinoline, trans-2-methyl-8a- acetoxy-4a-(3-acetoxyphenyl)-6β-(3,4- dichlorophenylacetamido) decahydroisoquinoline, trans-2-methyl-8a- acetoxy-4a-(3-acetoxyphenyl)-6β-benzamidodecahydroisoquinoline, trans-2-methyl-8a-acetoxy-4a-(3-acetoxyphenyl)-6β-(2-naphthamido)decahydroisoquinoline, trans-2-methyl-8-acetoxy-4a- (3-acetoxyphenyl)-6β-[N-methyl-3-trifluoromethylcinnamamido)]decahydroisoquinoline, trans-2- methyl-8a-acetoxy-4a-(3-acetoxyphenyl)-6β-[N-methyl-(6- phenylhexanamido)]decahydroisoquinoline, trans-2-methyl-8a- acetoxy-4a-(3-acetoxyphenyl)-6β-[N-methyl-(3,4- dichlorophenylacetamido)] decahydroisoquinoline, trans-2-methyl- 8a-acetoxy-4a-(3-acetoxyphenyl)-6β-(N- methylbenzamido) decahydroisoquinoline, trans-2-methyl-8a-acetoxy- 4a-(3-acetoxyphenyl)-6β-[N-methyl-(2- naphthamido)] decahydroisoquinoline, trans-2-methyl-8a-acetoxy-4a- (3-acetoxyphenyl)-6β-[N-isobutyl-3-trifluoromethylcinnamamido)]decahydroisoquinoline, trans-2- methyl-8a-acetoxy-4a-(3-acetoxyphenyl)-6β-[N-isobutyl-(6- phenylhexanamido)]decahydroisoquinoline, trans-2-methyl-8a- acetoxy-4a-(3-acetoxyphenyl)-6β-[N-isobutyl-(3,4- dichlorophenylacetamido)] decahydroisoquinoline, trans-2-methyl- 8a-acetoxy-4a-(3-acetoxyphenyl)-6β-(N- isobutylbenzamido) decahydroisoquinoline, trans-2-methyl-8a- acetoxy-4a-(3-acetoxyphenyl)-6β-(N-isobutyl-(2- naphthamido)] decahydroisoquinoline, trans-2-methyl-8a-methoxy-4a-(3-acetoxyphenyl)-6β-(3- trifluoromethylcinnamamido) decahydroisoquinoline, trans-2- methyl-8a-methoxy-4a-(3-acetoxyphenyl)-6β-(6- phenylhexanamido) decahydroisoquinoline, trans-2-methyl-8a- methoxy-4a-(3-acetoxyphenyl)-6β-(3,4- dichlorophenylacetamido) decahydroisoquinoline, trans-2-methyl-8a- methoxy-4a-(3-acetoxyphenyl)-6β-benzamidodecahydroisoquinoline, trans-2-methyl-8a-methoxy-4a-(3-acetoxyphenyl)-6β-(2-naphthamido)decahydroisoquinoline, trans-2-methyl-8a-methoxy-4a- (3-acetoxyphenyl)-6β-[N-methyl-3-trifluoromethylcinnamamido)]decahydroisoquinoline, trans-2- methyl-8a-methoxy-4a-(3-acetoxyphenyl)-6β-[N-methyl-(6- phenylhexanamido)] decahydroisoquinoline, trans-2-methyl-8a- methoxy-4a-(3-acetoxyphenyl)-6β-[N-methyl-(3,4-dichlorophenylacetamido)]decahydroisoquinoline, trans-2-methyl- 8a-methoxy-4a-(3-acetoxyphenyl)-6β-(N-methylbenzamido)decahydroisoquinoline, trans-2-methyl-8a-methoxy- 4a-(3-acetoxyphenyl)-6β-[N-methyl-(2- naphthamido)]decahydroisoquinoline, trans-2-methyl-8a-methoxy-4a- (3-acetoxyphenyl)-6β-[N-isobutyl-3- trifluoromethylcinnamamido)] decahydroisoquinoline, trans-2- methyl-8a-methoxy-4a-(3-acetoxyphenyl)-6β-[N-isobutyl-(6-phenylhexanamido)]decahydroisoquinoline, trans-2- methyl-8a- methoxy-4a-(3-acetoxyphenyl)-6α-[N-isobutyl-(3,4- dichlorophenylacetamido)] decahydroisoquinoline, trans-2-methyl- 8a-methoxy-4a-(3-acetoxyphenyl)-6β-(N- isobutylbenzamido) decahydroisoquinoline, trans-2-methyl-8a- methoxy-4a-(3-acetoxyphenyl)-6β-[N-isobutyl-(2- naphthamido)] decahydroisoquinoline, trans-2-cyclopropylmethyl-4a-(3-hydroxyphenyl)-6α-[trans-β-(3- furyl)acrylamido] decahydroisoquinoline, trans-2- cyclopropylmethyl-4a-(3-hydroxyphenyl)-6α-[trans-β-(4-bromo-2- thienyl) acrylamido]decahydroisoquinoline, trans-2- cyclopropylmethyl-4a-(3-hydroxyphenyl)-6α-[trans-β-(2-methyl-3- furyl)acrylamido]decahydroisoquinoline, trans-2- cyclopropylmethyl-4a-(3-hydroxyphenyl)-6α-(3-methoxycinnnamamido)decahydroisoquinoline, trans-2-cyclopropylmethyl-4a-(3-hydroxyphenyl)-6α-(3-trifluoromethoxycinnnamamido)decahydroisoquinoline, trans-2- cyclopropylmethyl-4a-(3-hydroxyphenyl)-6α-(3-hydroxycinnnamamido)decahydroisoquinoline, trans-2-cyclopropylmethyl-4a-(3-hydroxyphenyl)-6α-(4-trifluoromethylphenylpropiolamido) decahydroisoquinoline, trans- 2-cyclopropylmethyl-4a-(3-hydroxyphenyl)-6α-(3- methylphenylpropiolamido) decahydroisoquinoline, trans-2- cyclopropylmethyl-4a-(3-hydroxyphenyl)-6α-(3,4-dimethylphenylpropiolamido)decahydroisoquinoline, trans-2- cyclopropylmethyl-4a-(3-hydroxyphenyl)-6α-(benzyloxycarboxamido)decahydroisoquinoline, trans-2-cyclopropylmethyl-4a-(3-hydroxyphenyl)-6α-[N-methyl-[trans-β-(3- furyl)acrylamido]] decahydroisoquinoline, trans-2- cyclopropylmethyl-4a-(3-hydroxyphenyl)-6α-[N-methyl-[trans-β-(4- bromo-2-thienyl)acrylamido]]decahydroisoquinoline, trans-2-cyclopropylmethyl-4a-(3-hydroxyphenyl)-6α-[N-methyl-[trans-β-(2- methyl-3-furyl)acrylamido]] decahydroisoquinoline, trans-2- cyclopropylmethyl-4a-(3-hydroxyphenyl)-6α-[N-methyl-(3-methoxycinnnamamido)]decahydroisoquinoline, trans-2-cyclopropylmethyl-4a-(3-hydroxyphenyl)-6α-[N-methyl-(3- trifluoromethoxycinnnamamido)] decahydroisoquinoline, trans-2- cyclopropylmethyl-4a-(3-hydroxyphenyl)-6α-[N-methyl-(3-hydroxycinnnamamido)]decahydroisoquinoline, trans-2-cyclopropylmethyl-4a-(3-hydroxyphenyl)-6α-[N-methyl-(4- trifluoromethylphenylpropiolamido)] decahydroisoquinoline, trans- 2-cyclopropylmethyl-4a-(3-hydroxyphenyl)-6α-[N-methyl-(3-methylphenylpropiolamido)]decahydroisoquinoline, trans-2- cyclopropylmethyl-4a-(3-hydroxyphenyl)-6α-[N-methyl-(3,4- dimethylphenylpropiolamido)] decahydroisoquinoline, trans-2- cyclopropylmethyl-4a-(3-hydroxyphenyl)-6α-[N-methyl-(benzyloxycarboxamido)]decahydroisoquinoline, trans-2-cyclopropylmethyl-8a-hydroxy-4a-(3-hydroxyphenyl)-6α- [trans-β-(3-furyl)acrylamido]decahydroisoquinoline, trans-2- cyclopropylmethyl-8a-hydroxy-4a-(3-hydroxyphenyl)-6α-[trans-β- (4-bromo-2-thienyl) acrylamido]decahydroisoquinoline, trans-2-cyclopropylmethyl-8a-hydroxy-4a-(3-hydroxyphenyl)-6α-[trans-β- (2-methyl-3-furyl)acrylamido] decahydroisoquinoline, trans-2- cyclopropylmethyl-8a-hydroxy-4a-(3-hydroxyphenyl)-6α-(3-methoxycinnnamamido)decahydroisoquinoline, trans-2-cyclopropylmethyl-8a-hydroxy-4a-(3-hydroxyphenyl)-6α-(3- trifluoromethoxycinnnamamido) decahydroisoquinoline, trans-2- cyclopropylmethyl-8a-hydroxy-4a-(3-hydroxyphenyl)-6α-(3-hydroxycinnnamamido)decahydroisoquinoline, trans-2-cyclopropylmethyl-8a-hydroxy-4a-(3-hydroxyphenyl)-6α-(4- trifluoromethylphenylpropiolamido) decahydroisoquinoline, trans- 2-cyclopropylmethyl-8a-hydroxy-4a-(3-hydroxyphenyl) -6α-(3- methylphenylpropiolamido)decahydroisoquinoline, trans-2- cyclopropylmethyl-8a-hydroxy-4a-(3-hydroxyphenyl)-6α-(3,4- dimethylphenylpropiolamido) decahydroisoquinoline, trans-2- cyclopropylmethyl-8a-hydroxy-4a-(3-hydroxyphenyl) -6α-[N- methyl-(benzyloxycarboxamido)]decahydroisoquinoline, trans-2-cyclopropylmethyl-8a-hydroxy-4a-(3-hydroxyphenyl)-6α-[N-methyl- [trans-β-(3-furyl)acrylamido]] decahydroisoquinoline, trans-2- cyclopropylmethyl-8a-hydroxy-4a-(3-hydroxyphenyl)-6α-[N-methyl- [trans-β-(4-bromo-2-thienyl)acrylamido]]decahydroisoquinoline, trans-2-cyclopropylmethyl-8a-hydroxy-4a-(3-hydroxyphenyl)-6α-[N- methyl-[trans-β-(2-methyl-3-furyl)acrylamido]]decahydroisoquinoline, trans-2- cyclopropylmethyl-8a-hydroxy-4a-(3-hydroxyphenyl)-6α-[N-methyl- (3-methoxycinnnamamido)] decahydroisoquinoline, trans-2- cyclopropylmethyl-8a-hydroxy-4a-(3-hydroxyphenyl)-6α-[N-methyl- (3-trifluoromethoxycinnnamamido)] decahydroisoquinoline, trans-2- cyclopropylmethyl-8a-hydroxy-4a-(3-hydroxyphenyl)-6α-[N-methyl- (3-hydroxycinnnamamido)]decahydroisoquinoline, trans-2- cyclopropylmethyl-8a-hydroxy-4a-(3-hydroxyphenyl) -6α-[N-methyl- (4-trifluoromethylphenylpropiolamido)] decahydroisoquinoline, trans-2-cyclopropylmethyl-8a-hydroxy-4a-(3-hydroxyphenyl)-6α-[N- methyl-(3-methylphenylpropiolamido)]decahydroisoquinoline, trans-2-cyclopropylmethyl-8a-hydroxy-4a-(3-hydroxyphenyl)-6α-[N- methyl-(3,4-dimethylphenylpropiolamido)]decahydroisoquinoline, trans-2-cyclopropylmethyl-8a-hydroxy-4a-(3-hydroxyphenyl) -6α-[N- methyl-(benzyloxycarboxamido)]decahydroisoquinoline, trans-2-cyclopropylmethyl-8a-acetoxy-4a-(3-hydroxyphenyl)-6α- [trans-β-(3-furyl)acrylamido]decahydroisoquinoline, trans-2- cyclopropylmethyl-8a-acetoxy-4a-(3-hydroxyphenyl)-6α-[trans-β- (4-bromo-2-thienyl) acrylamido]decahydroisoquinoline, trans-2-cyclopropylmethyl-8a-acetoxy-4a-(3-hydroxyphenyl)-6α-[trans-β- (2-methyl-3-furyl)acrylamido] decahydroisoquinoline, trans-2- cyclopropylmethyl-8a-acetoxy-4a-(3-hydroxyphenyl)-6α-(3-methoxycinnnamamido)decahydroisoquinoline, trans-2-cyclopropylmethyl-8a-acetoxy-4a-(3-hydroxyphenyl)-6α-(3- trifluoromethoxycinnnamamido) decahydroisoquinoline, trans-2- cyclopropylmethyl-8a-acetoxy-4a-(3-hydroxyphenyl)-6α-(3-hydroxycinnnamamido)decahydroisoquinoline, trans-2-cyclopropylmethyl-8a-acetoxy-4a-(3-hydroxyphenyl)-6α-(4- trifluoromethylphenylpropiolamido) decahydroisoquinoline, trans- 2-cyclopropylmethyl-8a-acetoxy-4a-(3-hydroxyphenyl)-6α-(3-methylphenylpropiolamido)decahydroisoquinoline, trans-2- cyclopropylmethyl-8a-acetoxy-4a-(3-hydroxyphenyl)-6α-(3,4- dimethylphenylpropiolamido) decahydroisoquinoline, trans-2- cyclopropylmethyl-8a-acetoxy-4a-(3-hydroxyphenyl)-6α-(benzyloxycarboxamido)decahydroisoquinoline, trans-2-cyclopropylmethyl-8a-acetoxy-4a-(3-hydroxyphenyl)-6α-[N-methyl- [trans-β-(3-furyl)acrylamido]] decahydroisoquinoline, trans-2- cyclopropylmethyl-8a-acetoxy-4a-(3-hydroxyphenyl)-6α-[N-methyl- [trans-β-(4-bromo-2-thienyl)acrylamido]]decahydroisoquinoline, trans-2-cyclopropylmethyl-8a-acetoxy-4a-(3-hydroxyphenyl)-6α-[N- methyl-[trans-β-(2-methyl-3-furyl)acrylamido]]decahydroisoquinoline, trans-2- cyclopropylmethyl-8a-acetoxy-4a-(3-hydroxyphenyl)-6α-[N-methyl- (3-methoxycinnnamamido)] decahydroisoquinoline, trans-2- cyclopropylmethyl-8a-acetoxy-4a-(3-hydroxyphenyl)-6α-[N-methyl- (3-trifluoromethoxycinnnamamido)] decahydroisoquinoline, trans-2- cyclopropylmethyl-8a-acetoxy-4a-(3-hydroxyphenyl)-6α-[N-methyl- (3-hydroxycinnnamamido)]decahydroisoquinoline, trans-2- cyclopropylmethyl-8a-acetoxy-4a-(3-hydroxyphenyl)-6α-[N-methyl- (4-trifluoromethylphenylpropiolamido)] decahydroisoquinoline, trans-2-cyclopropylmethyl-8a-acetoxy-4a-(3-hydroxyphenyl)-6α-[N- methyl-(3-methylphenylpropiolamido)]decahydroisoquinoline, trans-2-cyclopropylmethyl-8a-acetoxy-4a-(3-hydroxyphenyl)-6α-[N- methyl-(3,4-dimethylphenylpropiolamido)]decahydroisoquinoline, trans-2-cyclopropylmethyl-8a-acetoxy-4a-(3-hydroxyphenyl)-6α-[N- methyl-(benzyloxycarboxamido)]decahydroisoquinoline, trans-2-cyclopropylmethyl-8a-methoxy-4a-(3-hydroxyphenyl)-6α- [trans-β-(3-furyl)acrylamido]decahydroisoquinoline, trans-2-cyclopropylmethyl-8a-methoxy-4a-(3-hydroxyphenyl)-6α-[trans-β- (4-bromo-2-thienyl)acrylamido] decahydroisoquinoline, trans-2- cyclopropylmethyl-8a-methoxy-4a-(3-hydroxyphenyl)-6α-[trans-β- (2-methyl-3-furyl)acrylamido]decahydroisoquinoline, trans-2-cyclopropylmethyl-8a-methoxy-4a-(3-hydroxyphenyl)-6α-(3- methoxycinnnamamido)decahydroisoquinoline, trans-2- cyclopropylmethyl-8a-methoxy-4a-(3-hydroxyphenyl)-6α-(3- trifluoromethoxycinnnamamido) decahydroisoquinoline, trans-2- cyclopropylmethyl-8a-methoxy-4a-(3-hydroxyphenyl)-6α-(3-hydroxycinnnamamido)decahydroisoquinoline, trans-2-cyclopropylmethyl-8a-methoxy-4a-(3-hydroxyphenyl)-6α-(4- trifluoromethylphenylpropiolamido) decahydroisoquinoline, trans-2-cyclopropylmethyl-8a-methoxy-4a-(3-hydroxyphenyl)-6α-(3- methylphenylpropiolamido)decahydroisoquinoline, trans-2- cyclopropylmethyl-8a-methoxy-4a-(3-hydroxyphenyl)-6α-(3,4- dimethylphenylpropiolamido) decahydroisoquinoline, trans-2- cyclopropylmethyl-8a-methoxy-4a-(3-hydroxyphenyl)-6α- (benzyloxycarboxamido)decahydroisoquinoline, trans-2-cyclopropylmethyl-8a-methoxy-4a-(3-hydroxyphenyl)-6α-[N-methyl- [trans-β-(3-furyl)acrylamido]] decahydroisoquinoline, trans-2- cyclopropylmethyl-8a-methoxy-4a-(3-hydroxyphenyl)-6α-[N-methyl- [trans-β-(4-bromo-2-thienyl)acrylamido]]decahydroisoquinoline, trans-2-cyclopropylmethyl-8a-methoxy-4a-(3-hydroxyphenyl)-6α-[N- methyl-[trans-β-(2-methyl-3-furyl)acrylamido]]decahydroisoquinoline, trans-2- cyclopropylmethyl-8a-methoxy-4a-(3-hydroxyphenyl)-6α-[N-methyl- (3-methoxycinnnamamido)]decahydroisoquinoline, trans-2- cyclopropylmethyl-8a-methoxy-4a-(3-hydroxyphenyl)-6α-[N-methyl- (3-trifluoromethoxycinnnamamido)] decahydroisoquinoline, trans-2- cyclopropylmethyl-8a-methoxy-4a-(3-hydroxyphenyl)-6α-[N-methyl- (3-hydroxycinnnamamido)]decahydroisoquinoline, trans-2- cyclopropylmethyl-8a-methoxy-4a-(3-hydroxyphenyl)-6α-[N-methyl-(4- trifluoromethylphenylpropiolamido)]decahydroisoquinoline, trans-2-cyclopropylmethyl-8a-methoxy-4a-(3-hydroxyphenyl)-6α-[N-methyl-(3-methylphenylpropiolamido)]decahydroisoquinoline, trans-2- cyclopropylmethyl-8a-methoxy-4a-(3-hydroxyphenyl)-6α-[N-methyl-(3,4- dimethylphenylpropiolamido)]decahydroisoquinoline, trans-2- cyclopropylmethyl-8a-methoxy-4a-(3-hydroxyphenyl)-6α-[N-methyl- (benzyloxycarboxamido)]decahydroisoquinoline, trans-2-cyclopropylmethyl-8a-hydroxy-4a-(3-methoxyphenyl)-6α- [trans-β-(3-furyl)acrylamido]decahydroisoquinoline, trans-2- cyclopropylmethyl-8a-hydroxy-4a-(3-methoxyphenyl)-6α-[trans-β- (4-bromo-2-thienyl) acrylamido]decahydroisoquinoline, trans-2-cyclopropylmethyl-8a-hydroxy-4a-(3-methoxyphenyl)-6α-[trans-β- (2-methyl-3-furyl)acrylamido] decahydroisoquinoline, trans-2- cyclopropylmethyl-8a-hydroxy-4a-(3-methoxyphenyl)-6α-(3- methoxycinnnamamido)decahydroisoquinoline, trans-2- cyclopropylmethyl-8a-hydroxy-4a-(3-methoxyphenyl)-6α-(3- trifluoromethoxycinnnamamido) decahydroisoquinoline, trans-2- cyclopropylmethyl-8a-hydroxy-4a-(3-methoxyphenyl)-6α-(3- hydroxycinnnamamido)decahydroisoquinoline, trans-2- cyclopropylmethyl-8a-hydroxy-4a-(3-methoxyphenyl)-6α-(4- trifluoromethylphenylpropiolamido) decahydroisoquinoline, trans- 2-cyclopropylmethyl-8a-hydroxy-4a-(3-methoxyphenyl)-6α-(3- methylphenylpropiolamido)decahydroisoquinoline, trans-2- cyclopropylmethyl-8a-hydroxy-4a-(3-methoxyphenyl)-6α-(3,4- dimethylphenylpropiolamido)decahydroisoquinoline, trans-2- cyclopropylmethyl-8a-hydroxy-4a-(3-methoxyphenyl)-6α- (benzyloxycarboxamido)decahydroisoquinoline, trans-2- cyclopropylmethyl-8a-hydroxy-4a-(3-methoxyphenyl)-6α-[N-methyl- [trans-β-(3-furyl)acrylamido]] decahydroisoquinoline, trans-2- cyclopropylmethyl-8a-hydroxy-4a-(3-methoxyphenyl)-6α-[N-methyl- [trans-β-(4-bromo-2-thienyl)acrylamido]]decahydroisoquinoline, trans-2-cyclopropylmethyl-8a-hydroxy-4a-(3-methoxyphenyl)-6α-[N- methyl-[trans-β-(2-methyl-3-furyl)acrylamido]]decahydroisoquinoline, trans-2-cyclopropylmethyl-8a-hydroxy-4a-(3-methoxyphenyl)-6α-[N-methyl- (3-methoxycinnnamamido)] decahydroisoquinoline, trans-2- cyclopropylmethyl-8a-hydroxy-4a-(3-methoxyphenyl)-6α-[N-methyl-(3-trifluoromethoxycinnnamamido)] decahydroisoquinoline, trans-2- cyclopropylmethyl-8a-hydroxy-4a-(3-methoxyphenyl)-6α-[N-methyl- (3-hydroxycinnnamamido)]decahydroisoquinoline, trans-2- cyclopropylmethyl-8a-hydroxy-4a-(3-methoxyphenyl)-6α-[N-methyl- (4-trifluoromethylphenylpropiolamido)] decahydroisoquinoline, trans-2-cyclopropylmethyl-8a-hydroxy-4a-(3-methoxyphenyl)-6α-[N- methyl-(3-methylphenylpropiolamido)]decahydroisoquinoline, trans-2-cyclopropylmethyl-8a-hydroxy-4a-(3-methoxyphenyl)-6α-[N- methyl-(3,4-dimethylphenylpropiolamido)]decahydroisoquinoline, trans-2-cyclopropylmethyl-8a-hydroxy-4a-(3-methoxyphenyl)-6α-[N- methyl-(benzyloxycarboxamido)]decahydroisoquinoline, trans-2-cyclopropylmethyl-8a-acetoxy-4a-(3-methoxyphenyl)-6α- [trans-β-(3-furyl)acrylamido]decahydroisoquinoline, trans-2- cyclopropylmethyl-8a-acetoxy-4a-(3-methoxyphenyl)-6α-[trans-β- (4-bromo-2-thienyl)acrylamido]decahydroisoquinoline, trans-2-cyclopropylmethyl-8a-acetoxy-4a-(3-methoxyphenyl)-6α-[trans-β- (2-methyl-3-furyl)acrylamido]decahydroisoquinoline, trans-2- cyclopropylmethyl-8a-acetoxy-4a-(3-methoxyphenyl)-6α-(3-methoxycinnnamamido)decahydroisoquinoline, trans-2-cyclopropylmethyl-8a-acetoxy-4a-(3-methoxyphenyl)-6α-(3- trifluoromethoxycinnnamamido) decahydroisoquinoline, trans-2- cyclopropylmethyl-8a-acetoxy-4a-(3-methoxyphenyl)-6α-(3-hydroxycinnnamamido)decahydroisoquinoline, trans-2-cyclopropylmethyl-8a-acetoxy-4a-(3-methoxyphenyl)-6α-(4- trifluoromethylphenylpropiolamido) decahydroisoguinoline, trans- 2-cyclopropylmethyl-8a-acetoxy-4a-(3-methoxyphenyl)-6α-(3-methylphenylpropiolamido)decahydroisoquinoline, trans-2- cyclopropylmethyl-8a-acetoxy-4a-(3-methoxyphenyl)-6α-(3,4- dimethylphenylpropiolamido) decahydroisoquinoline, trans-2- cyclopropylmethyl-8a-acetoxy-4a-(3-methoxyphenyl)-6α-(benzyloxycarboxamido)decahydroisoquinoline, trans-2-cyclopropylmethyl-8a-acetoxy-4a-(3-methoxyphenyl)-6α-[N-methyl- [trans-β-(3-furyl)acrylamido]] decahydroisoquinoline, trans-2- cyclopropylmethyl-8a-acetoxy-4a-(3-methoxyphenyl)-6α-[N-methyl- [trans-β-(4-bromo-2-thienyl)acrylamido]]decahydroisoquinoline, trans-2-cyclopropylmethyl-8a-acetoxy-4a-(3-methoxyphenyl)-6αa-[N- methyl-[trans-β-(2-methyl-3-furyl)acrylamido]]decahydroisoquinoline, trans-2- cyclopropylmethyl-8a-acetoxy-4a-(3-methoxyphenyl)-6α-[N-methyl- (3-methoxycinnnamamido)] decahydroisoquinoline, trans-2- cyclopropylmethyl-8a-acetoxy-4a-(3-methoxyphenyl)-6α-[N-methyl-(3-trifluoromethoxycinnnamamido)] decahydroisoquinoline, trans-2- cyclopropylmethyl-8a-acetoxy-4a-(3-methoxyphenyl)-6α-[N-methyl- (3-hydroxycinnnamamido)]decahydroisoquinoline, trans-2- cyclopropylmethyl-8a-acetoxy-4a-(3-methoxyphenyl)-6α-[N-methyl- (4-trifluoromethylphenylpropiolamido)] decahydroisoquinoline, trans-2-cyclopropylmethyl-8a-acetoxy-4a-(3-methoxyphenyl)-6α-[N- methyl-(3-methylphenylpropiolamido)]decahydroisoquinoline, trans-2-cyclopropylmethyl-8a-acetoxy-4a-(3-methoxyphenyl)-6α-[N- methyl-(3,4-dimethylphenylpropiolamido)]decahydroisoquinoline, trans-2-cyclopropylmethyl-8a-acetoxy-4a-(3-methoxyphenyl)-6α-[N- methyl-(benzyloxycarboxamido)]decahydroisoquinoline, trans-2-cyclopropylmethyl-8a-methoxy-4a-(3-methoxyphenyl) -6α- [trans-β-(3-furyl)acrylamido] decahydroisoquinoline, trans-2- cyclopropylmethyl-8a-methoxy-4a-(3-methoxyphenyl)-6α-[trans-β- (4-bromo-2-thienyl)acrylamido]decahydroisoquinoline, trans-2-cyclopropylmethyl-8a-methoxy-4a-(3-methoxyphenyl)-6α-[trans-β- (2-methyl-3-furyl)acrylamido] decahydroisoquinoline, trans-2- cyclopropylmethyl-8a-methoxy-4a-(3-methoxyphenyl)-6α-(3-methoxycinnnamamido)decahydroisoquinoline, trans-2- cyclopropylmethyl-8a-methoxy-4a-(3-methoxyphenyl)-6α-(3- trifluoromethoxycinnnamamido) decahydroisoquinoline, trans-2- cyclopropylmethyl-8a-methoxy-4a-(3-methoxyphenyl)-6α-(3-hydroxycinnnamamido)decahydroisoquinoline, trans-2- cyclopropylmethyl-8a-methoxy-4a-(3-methoxyphenyl)-6α-(4- trifluoromethylphenylpropiolamido) decahydroisoquinoline, trans- 2-cyclopropylmethyl-8a-methoxy-4a-(3-methoxyphenyl)-6α-(3-methylphenylpropiolamido)decahydroisoquinoline, trans-2- cyclopropylmethyl-8a-methoxy-4a-(3-methoxyphenyl)-6α-(3,4- dimethylphenylpropiolamido) decahydroisoquinoline, trans-2- cyclopropylmethyl-8a-methoxy-4a-(3-methoxyphenyl)-6α- (benzyloxycarboxamido)decahydroisoquinoline, trans-2-cyclopropylmethyl-8a-methoxy-4a-(3-methoxyphenyl)-6α-[N-methyl- [trans-β-(3-furyl)acrylamido]] decahydroisoquinoline, trans-2- cyclopropylmethyl-8a-methoxy-4a-(3-methoxyphenyl)-6α-[N-methyl- [trans-β-(4-bromo-2-thienyl)acrylamido]]decahydroisoquinoline, trans-2-cyclopropylmethyl-8a-methoxy-4a-(3-methoxyphenyl)-6α-[N- methyl-[trans-β-(2-methyl-3-furyl)acrylamido]]decahydroisoquinoline, trans-2- cyclopropylmethyl-8a-methoxy-4a-(3-methoxyphenyl)-6α-[N-methyl- (3-methoxycinnnamamido)] decahydroisoquinoline, trans-2- cyclopropylmethyl-8a-methoxy-4a-(3-methoxyphenyl)-6α-[N-methyl-(3-trifluoromethoxycinnnamamido)] decahydroisoquinoline, trans-2- cyclopropylmethyl-8a-methoxy-4a-(3-methoxyphenyl)-6α-[N-methyl-(3-hydroxycinnnamamido)]decahydroisoquinoline, trans-2- cyclopropylmethyl-8a-methoxy-4a-(3-methoxyphenyl)-6α-[N-methyl- (4-trifluoromethylphenylpropiolamido)] decahydroisoquinoline, trans-2-cyclopropylmethyl-8a-methoxy-4a-(3-methoxyphenyl)-6α-[N- methyl-(3-methylphenylpropiolamido)]decahydroisoquinoline, trans-2-cyclopropylmethyl-8a-methoxy-4a-(3-methoxyphenyl)-6α-[N- methyl-(3,4-dimethylphenylpropiolamido)]decahydroisoquinoline, trans-2-cyclopropylmethyl-8a-methoxy-4a-(3-methoxyphenyl)-6α-[N- methyl-(benzyloxycarboxamido)]decahydroisoquinoline, trans-2-cyclopropylmethyl-4a-(3-acetoxyphenyl)-6α-[trans-β-(3- furyl)acrylamido]decahydroisoquinoline, trans-2- cyclopropylmethyl-4a-(3-acetoxyphenyl)-6α-[trans-β-(4-bromo-2- thienyl)acrylamido]decahydroisoquinoline, trans-2- cyclopropylmethyl-4a-(3-acetoxyphenyl)-6α-[trans-β-(2-methyl-3- furyl)acrylamido] decahydroisoquinoline, trans-2- cyclopropylmethyl-4a-(3-acetoxyphenyl)-6α-(3- methoxycinnnamamido) decahydroisoquinoline, trans-2- cyclopropylmethyl-4a-(3-acetoxyphenyl)-6α-(3- trifluoromethoxycinnnamamido)decahydroisoquinoline, trans-2- cyclopropylmethyl-4a-(3-acetoxyphenyl)-6α-(3- hydroxycinnamamido)decahydroisoquinoline, trans-2- cyclopropylmethyl-4a-(3-acetoxyphenyl)-6α-(4- trifluoromethylphenylpropiolamido) decahydroisoquinoline, trans- 2-cyclopropylmethyl-4a-(3-acetoxyphenyl)-6α-(3- methylphenylpropiolamido) decahydroisoquinoline, trans-2- cyclopropylmethyl-4a-(3-acetoxyphenyl)-6α-(3,4- dimethylphenylpropiolamido)decahydroisoquinoline, trans-2- cyclopropylmethyl-4a-(3-acetoxyphenyl)-6α-(benzyloxycarboxamido) decahydroisoquinoline, trans-2- cyclopropylmethyl-4a-(3-acetoxyphenyl)-6α-[N-methyl-[trans-β-(3- furyl)acrylamido]]decahydroisoquinoline, trans-2- cyclopropylmethyl-4a-(3-acetoxyphenyl)-6α-[N-methyl-[trans-β-(4- bromo-2-thienyl)acrylamido]] decahydroisoquinoline, trans-2- cyclopropylmethyl-4a-(3-acetoxyphenyl)-6α-[N-methyl-[trans-β-(2- methyl-3-furyl)acrylamido]]decahydroisoquinoline, trans-2- cyclopropylmethyl-4a-(3-acetoxyphenyl)-6α-[N-methyl-(3- methoxycinnnamamido)] decahydroisoquinoline, trans-2- cyclopropylmethyl-4a-(3-acetoxyphenyl)-6α-[N-methyl-(3- trifluoromethoxycinnnamamido)]decahydroisoquinoline, trans-2- cyclopropylmethyl-4a-(3-acetoxyphenyl)-6α-[N-methyl-(3- hydroxycinnnamamido)] decahydroisoquinoline, trans-2- cyclopropylmethyl-4a-(3-acetoxyphenyl)-6α-[N-methyl-(4- trifluoromethylphenylpropiolamido)] decahydroisoquinoline, trans- 2-cyclopropylmethyl-4a-(3-acetoxyphenyl)-6α-[N-methyl-(3- methylphenylpropiolamido)]decahydroisoquinoline, trans-2- cyclopropylmethyl-4a-(3-acetoxyphenyl)-6α-[N-methyl-(3,4- dimethylphenylpropiolamido)] decahydroisoquinoline, trans-2- cyclopropylmethyl-4a-(3-acetoxyphenyl)-6α-[N-methyl-(benzyloxycarboxamido)]decahydroisoquinoline, trans-2-cyclopropylmethyl-8a-hydroxy-4a-(3-acetoxyphenyl)-6α- [trans-β-(3-furyl)acrylamido]decahydroisoquinoline, trans-2- cyclopropylmethyl-8a-hydroxy-4a-(3-acetoxyphenyl)-6α-[trans-β- (4-bromo-2-thienyl) acrylamido]decahydroisoquinoline, trans-2- cyclopropylmethyl-8a-hydroxy-4a-(3-acetoxyphenyl)-6α-[trans-β- (2-methyl-3-furyl)acrylamido] decahydroisoquinoline, trans-2- cyclopropylmethyl-8a-hydroxy-4a-(3-acetoxyphenyl)-6α-(3- methoxycinnnamamido)decahydroisoquinoline, trans-2- cyclopropylmethyl-8a-hydroxy-4a-(3-acetoxyphenyl)-6α-(3- trifluoromethoxycinnnamamido)decahydroisoquinoline, trans-2- cyclopropylmethyl-8a-hydroxy-4a-(3-acetoxyphenyl)-6α-(3- hydroxycinnnamamido)decahydroisoquinoline, trans-2- cyclopropylmethyl-8a-hydroxy-4a-(3-acetoxyphenyl)-6α-(4- trifluoromethylphenylpropiolamido) decahydroisoquinoline, trans- 2-cyclopropylmethyl-8a-hydroxy-4a-(3-acetoxyphenyl)-6α-(3- methylphenylpropiolamido)decahydroisoquinoline, trans-2- cyclopropylmethyl-8a-hydroxy-4a-(3-acetoxyphenyl)-6α-(3,4- dimethylphenylpropiolamido) decahydroisoquinoline, trans-2- cyclopropylmethyl-8a-hydroxy-4a-(3-acetoxyphenyl)-6α- (benzyloxycarboxamido)decahydroisoquinoline, trans-2- cyclopropylmethyl-8a-hydroxy-4a-(3-acetoxyphenyl)-6α-[N-methyl- [trans-β-(3-furyl)acrylamido]] decahydroisoquinoline, trans-2- cyclopropylmethyl-8a-hydroxy-4a-(3-acetoxyphenyl)-6α-[N-methyl- [trans-β-(4-bromo-2-thienyl)acrylamido]]decahydroisoquinoline, trans-2-cyclopropylmethyl-8a-hydroxy-4a-(3-acetoxyphenyl)-6α-[N- methyl-[trans-β-(2-methyl-3-furyl)acrylamido]]decahydroisoquinoline, trans-2- cyclopropylmethyl-8a-hydroxy-4a-(3-acetoxyphenyl)-6α-[N-methyl- (3-methoxycinnnamamido)] decahydroisoquinoline, trans-2- cyclopropylmethyl-8a-hydroxy-4a-(3-acetoxyphenyl)-6α-[N-methyl- (3-trifluoromethoxycinnnamamido)] decahydroisoquinoline, trans-2- cyclopropylmethyl-8a-hydroxy-4a-(3-acetoxyphenyl) -6α-[N-methyl- (3-hydroxycinnnamamido)]decahydroisoquinoline, trans-2- cyclopropylmethyl-8a-hydroxy-4a-(3-acetoxyphenyl)-6α-[N-methyl- (4-trifluoromethylphenylpropiolamido)] decahydroisoquinoline, trans-2-cyclopropylmethyl-8a-hydroxy-4a-(3-acetoxyphenyl)-6α-[N- methyl-(3-methylphenylpropiolamido)]decahydroisoquinoline, trans-2-cyclopropylmethyl-8a-hydroxy-4a-(3-acetoxyphenyl)-6α-[N- methyl-(3,4-dimethylphenylpropiolamido)]decahydroisoquinoline, trans-2-cyclopropylmethyl-8a-hydroxy-4a-(3-acetoxyphenyl)-6α-[N- methyl-(benzyloxycarboxamido)]decahydroisoquinoline, trans-2-cyclopropylmethyl-8a-acetoxy-4a-(3-acetoxyphenyl)-6α- [trans-β-(3-furyl)acrylamido]decahydroisoquinoline, trans-2- cyclopropylmethyl-8a-acetoxy-4a-(3-acetoxyphenyl)-6α-[trans-β- (4-bromo-2-thienyl)acrylamido] decahydroisoquinoline, trans-2- cyclopropylmethyl-8a-acetoxy-4a-(3-acetoxyphenyl)-6α-[trans-β- (2-methyl-3-furyl)acrylamido]decahydroisoquinoline, trans-2- cyclopropylmethyl-8a-acetoxy-4a-(3-acetoxyphenyl)-6α-(3- methoxycinnnamamido)decahydroisoquinoline, trans-2- cyclopropylmethyl-8a-acetoxy-4a-(3-acetoxyphenyl)-6α-(3- trifluoromethoxycinnnamamido) decahydroisoquinoline, trans-2- cyclopropylmethyl-8a-acetoxy-4a-(3-acetoxyphenyl)-6α-(3- hydroxycinnnamamido)decahydroisoquinoline, trans-2- cyclopropylmethyl-8a-acetoxy-4a-(3-acetoxyphenyl)-6α-(4- trifluoromethylphenylpropiolamido) decahydroisoquinoline, trans- 2-cyclopropylmethyl-8a-acetoxy-4a-(3-acetoxyphenyl)-6α-(3- methylphenylpropiolamido)decahydroisoquinoline, trans-2- cyclopropylmethyl-8a-acetoxy-4a-(3-acetoxyphenyl)-6α-(3,4- dimethylphenylpropiolamido) decahydroisoquinoline, trans-2- cyclopropylmethyl-8a-acetoxy-4a-(3-acetoxyphenyl)-6α- (benzyloxycarboxamido)decahydroisoquinoline, trans-2- cyclopropylmethyl-8a-acetoxy-4a-(3-acetoxyphenyl)-6α-[N-methyl- [trans-β-(3-furyl)acrylamido]] decahydroisoquinoline, trans-2- cyclopropylmethyl-8a-acetoxy-4a-(3-acetoxyphenyl)-6α-[N-methyl- [trans-β-(4-bromo-2-thienyl)acrylamido]]decahydroisoquinoline, trans-2-cyclopropylmethyl-8a-acetoxy-4a-(3-acetoxyphenyl)-6α-[N- methyl-[trans-β-(2-methyl-3-furyl)acrylamido]]decahydroisoquinoline, trans-2- cyclopropylmethyl-8a-acetoxy-4a-(3-acetoxyphenyl)-6α-[N-methyl- (3-methoxycinnnamamido)] decahydroisoquinoline, trans-2- cyclopropylmethyl-8a-acetoxy-4a-(3-acetoxyphenyl)-6α-[N-methyl- (3-trifluoromethoxycinnnamamido)]

decahydroisoquinoline, trans-2- cyclopropylmethyl-8a-acetoxy-4a-(3-acetoxyphenyl)-6α-[N-methyl-(3-hydroxycinnnamamido)]decahydroisoquinoline, trans-2- cyclopropylmethyl-8a-acetoxy-4a-(3-acetoxyphenyl)-6α-[N-methyl- (4-trifluoromethylphenylpropiolamido)] decahydroisoquinoline, trans-2-cyclopropylmethyl-8a-acetoxy-4a-(3-acetoxyphenyl)-6α-[N- methyl-(3-methylphenylpropiolamido)]decahydroisoquinoline, trans-2-cyclopropylmethyl-8a-acetoxy-4a-(3-acetoxyphenyl)-6α-[N- methyl-(3,4-dimethylphenylpropiolamido)]decahydroisoquinoline, trans-2-cyclopropylmethyl-8a-acetoxy-4a-(3-acetoxyphenyl)-6α-[N- methyl-(benzyloxycarboxamido)]decahydroisoquinoline, trans-2-cyclopropylmethyl-8a-methoxy-4a-(3-acetoxyphenyl)-6α- [trans-β-(3-furyl)acrylamido]decahydroisoquinoline, trans-2-cyclopropylmethyl-8a-methoxy-4a-(3-acetoxyphenyl)-6α-[trans-β- (4-bromo-2-thienyl)acrylamido] decahydroisoquinoline, trans-2- cyclopropylmethyl-8a-methoxy-4a-(3-acetoxyphenyl)-6α-[trans-β- (2-methyl-3-furyl)acrylamido]decahydroisoquinoline, trans-2-cyclopropylmethyl-8a-methoxy-4a-(3-acetoxyphenyl)-6α-(3- methoxycinnnamamido)decahydroisoquinoline, trans-2- cyclopropylmethyl-8a-methoxy-4a-(3-acetoxyphenyl)-6α-(3- trifluoromethoxycinnnamamido) decahydroisoquinoline, trans-2- cyclopropylmethyl-8a-methoxy-4a-(3-acetoxyphenyl)-6α-(3-hydroxycinnnamamido)decahydroisoquinoline, trans-2-cyclopropylmethyl-8a-methoxy-4a-(3-acetoxyphenyl)-6α-(4- trifluoromethylphenylpropiolamido) decahydroisoquinoline, trans- 2-cyclopropylmethyl-8a-methoxy-4a-(3-acetoxyphenyl)-6α-(3-methylphenylpropiolamido)decahydroisoquinoline, trans-2- cyclopropylmethyl-8a-methoxy-4a-(3-acetoxyphenyl)-6α-(3,4- dimethylphenylpropiolamido) decahydroisoquinoline, trans-2- cyclopropylmethyl-8a-methoxy-4a-(3-acetoxyphenyl)-6α-(benzyloxycarboxamido)decahydroisoquinoline, trans-2-cyclopropylmethyl-8a-methoxy-4a-(3-acetoxyphenyl)-6α-[N-methyl- [trans-β-(3-furyl)acrylamido]] decahydroisoquinoline, trans-2- cyclopropylmethyl-8a-methoxy-4a-(3-acetoxyphenyl)-6α-[N-methyl- [trans-β-(4-bromo-2-thienyl)acrylamido]]decahydroisoquinoline, trans-2-cyclopropylmethyl-8a-methoxy-4a-(3-acetoxyphenyl)-6α-[N- methyl-[trans-β-(2-methyl-3-furyl)acrylamido]]decahydroisoquinoline, trans-2-cyclopropylmethyl-8a-methoxy-4a-(3-acetoxyphenyl)-6α-[N-methyl- (3-methoxycinnnamamido)] decahydroisoquinoline, trans-2- cyclopropylmethyl-8a-methoxy-4a-(3-acetoxyphenyl)-6α-[N-methyl- (3-trifluoromethoxycinnnamamido)] decahydroisoquinoline, trans-2- cyclopropylmethyl-8a-methoxy-4a-(3-acetoxyphenyl)-6α-[N-methyl- (3-hydroxycinnnamamido)]decahydroisoquinoline, trans-2- cyclopropylmethyl-8a-methoxy-4a-(3-acetoxyphenyl)-6α-[N-methyl- (4-trifluoromethylphenylpropiolamido)] decahydroisoquinoline, trans-2-cyclopropylmethyl-8a-methoxy-4a-(3-acetoxyphenyl)-6α-[N- methyl-(3-methylphenylpropiolamido)]decahydroisoquinoline, trans-2-cyclopropylmethyl-8a-methoxy-4a-(3-acetoxyphenyl)-6α-[N- methyl-(3,4-dimethylphenylpropiolamido)]decahydroisoquinoline, trans-2-cyclopropylmethyl-8a-methoxy-4a-(3-acetoxyphenyl)-6α-[N- methyl-(benzyloxycarboxamido)]decahydroisoquinoline, trans-2-allyl-4a-(3-hydroxyphenyl)-6α-[trans-β-(3- furyl)acrylamido]decahydroisoquinoline, trans-2-allyl-4a-(3-hydroxyphenyl)-6α-[trans-β-(4-bromo-2- thienyl)acrylamido]decahydroisoquinoline, trans-2-allyl-4a-(3-hydroxyphenyl)-6α-[trans-β-(2-methyl-3- furyl)acrylamido]decahydroisoquinoline, trans-2-allyl-4a-(3-hydroxyphenyl)-6α-(3-methoxycinnnamamido) decahydroisoquinoline, trans-2-allyl-4a-(3-hydroxyphenyl)-6α-(3- trifluoromethoxycinnnamamido) decahydroisoquinoline, trans-2- allyl-4a-(3-hydroxyphenyl)-6α-(3- hydroxycinnnamamido) decahydroisoquinoline, trans-2-allyl-4a-(3-hydroxyphenyl)-6α-(4- trifluoromethylphenylpropiolamido) decahydroisoquinoline, trans- 2-allyl-4a-(3-hydroxyphenyl)-6α-(3- methylphenylpropiolamido) decahydroisoquinoline, trans-2-allyl- 4a-(3-hydroxyphenyl)-6α-(3,4- dimethylphenylpropiolamido) decahydroisoquinoline, trans-2-allyl- 4a-(3-hydroxyphenyl)-6α- (benzyloxycarboxamido) decahydroisoquinoline, trans-2-allyl-4a-(3-hydroxyphenyl)-6α-[N-methyl-[trans-β-(3- furyl)acrylamido]]decahydroisoquinoline, trans-2-allyl-4a-(3-hydroxyphenyl)-6α-[N-methyl-[trans-β-(4-bromo-2-thienyl)acrylamido]]decahydroisoquinoline, trans-2-allyl-4a-(3- hydroxyphenyl)-6α-[N-methyl-[trans-β-(2-methyl-3- furyl)acrylamido]]decahydroisoquinoline, trans-2-allyl-4a-(3- hydroxyphenyl)-6α-[N-methyl-(3-methoxycinnnamamido)]decahydroisoquinoline, trans-2-allyl-4a-(3- hydroxyphenyl)-6α-[N-methyl-(3-trifluoromethoxycinnnamamido)]decahydroisoquinoline, trans-2- allyl-4a-(3-hydroxyphenyl)-6α-[N-methyl-(3-hydroxycinnnamamido)]decahydroisoquinoline, trans-2-allyl-4a-(3- hydroxyphenyl)-6α-[N-methyl-(4-trifluoromethylphenylpropiolamido)] decahydroisoquinoline, trans- 2-allyl-4a-(3-hydroxyphenyl)-6α-[N-methyl-(3-methylphenylpropiolamido)]decahydroisoquinoline, trans-2-allyl- 4a-(3-hydroxyphenyl)-6α-[N-methyl-(3,4-dimethylphenylpropiolamido)]decahydroisoquinoline, trans-2- allyl-4a-(3-hydroxyphenyl)-6α-[N-methyl-(benzyloxycarboxamido)]decahydroisoquinoline, trans-2-allyl-8a-hydroxy-4a-(3-hydroxyphenyl)-6α-[trans-β-(3- furyl)acrylamido]decahydroisoquinoline, trans-2-allyl-8a- hydroxy-4a-(3-hydroxyphenyl)-6α-[trans-β-(4-bromo-2- thienyl)acrylamido]decahydroisoquinoline, trans-2-allyl-8a- hydroxy-4a-(3-hydroxyphenyl)-6α-[trans-β-(2-methyl-3- furyl)acrylamido] decahydroisoquinoline, trans-2-allyl-8a- hydroxy-4a-(3-hydroxyphenyl)-6α-(3- methoxycinnnamamido) decahydroisoquinoline, trans-2-allyl-8a- hydroxy-4a-(3-hydroxyphenyl)-6a-(3- trifluoromethoxycinnnamamido) decahydroisoquinoline, trans-2- allyl-8a-hydroxy-4a-(3-hydroxyphenyl)-6α-(3- hydroxycinnnamamido) decahydroisoquinoline, trans-2-allyl-8a- hydroxy-4a-(3-hydroxyphenyl)-6α-(4- trifluoromethylphenylpropiolamido) decahydroisoquinoline, trans- 2-allyl-8a-hydroxy-4a-(3-hydroxyphenyl)-6α-(3- methylphenylpropiolamido) decahydroisoquinoline, trans-2-allyl- 8a-hydroxy-4a-(3-hydroxyphenyl)-6α-(3,4- dimethylphenylpropiolamido) decahydroisoquinoline, trans-2-allyl- 8a-hydroxy-4a-(3-hydroxyphenyl)-6α- (benzyloxycarboxamido) decahydroisoquinoline, trans-2-allyl-8a- hydroxy-4a-(3-hydroxyphenyl)-6α-[N-methyl-[trans-β-(3- furyl)acrylamido]]decahydroisoquinoline, trans-2-allyl-8a-hydroxy-4a-(3-hydroxyphenyl)-6α-[N-methyl-[trans-β-(4-bromo-2- thienyl)acrylamido]]decahydroisoquinoline, trans-2-allyl-8a- hydroxy-4a-(3-hydroxyphenyl)-6α-[N- methyl-[trans-p-(2-methyl-3- furyl)acrylamido]]
decahydroisoquinoline, trans-2-allyl-8a- hydroxy-4a-(3-
hydroxyphenyl)-6α-[N-methyl-(3-
methoxycinnnamamido)]decahydroisoquinoline, trans-2-
allyl-8a- hydroxy-4a-(3-hydroxyphenyl)-6α-[N-methyl-
(3- trifluoromethoxycinnnamamido)]
decahydroisoquinoline, trans-2- allyl-8a-hydroxy-4a-(3-
hydroxyphenyl)-6α-[N-methyl-(3-
hydroxycinnnamamido)]decahydroisoquinoline, trans-2-
allyl-8a- hydroxy-4a-(3-hydroxyphenyl)-6α-[N-methyl-
(4- trifluoromethylphenylpropiolamido)]
decahydroisoquinoline, trans- 2-allyl-8a-hydroxy-4a-(3-
hydroxyphenyl)-6α-[N-methyl-(3-
methylphenylpropiolamido)]decahydroisoquinoline,
trans-2-allyl- 8a-hydroxy-4a-(3-hydroxyphenyl)-6α-[N-
methyl-(3,4- dimethylphenylpropiolamido)]
decahydroisoquinoline, trans-2- allyl-8a-hydroxy-4a-(3-
hydroxyphenyl)-6α-[N-methyl- (benzyloxycarboxamido)
]decahydroisoquinoline, trans-2-allyl-8a-acetoxy-4a-(3-
hydroxyphenyl)-6α-[trans-β-(3- furyl)acrylamido]
decahydroisoquinoline, trans-2-allyl-8a- acetoxy-4a-(3-
hydroxyphenyl)-6α-[trans-β-(4-bromo-2- thienyl)
acrylamido]decahydroisoquinoline, trans-2-allyl-8a-
acetoxy-4a-(3-hydroxyphenyl)-6α-[trans-β-(2-methyl-3-
furyl)acrylamido]decahydroisoquinoline, trans-2-allyl-
8a- acetoxy-4a-(3-hydroxyphenyl)-6α-(3-
methoxycinnnamamido)decahydroisoquinoline, trans-2-
allyl-8a- acetoxy-4a-(3-hydroxyphenyl)-6α-(3-
trifluoroinethoxycinnnamamido)decahydroisoquinoline,
trans-2- allyl-8a-acetoxy-4a-(3-hydroxyphenyl)-6α-(3-
hydroxycinnnamamido)decahydroisoquinoline, trans-2-
allyl-8a- acetoxy-4a-(3-hydroxyphenyl)-6α-(4-
trifluoromethylphenylpropiolamido)
decahydroisoquinoline, trans-2-allyl-8a-acetoxy-4a-(3-
hydroxyphenyl)-6α-(3- methylphenylpropiolamido)
decahydroisoquinoline, trans-2-allyl- 8a-acetoxy-4a-(3-
hydroxyphenyl)-6α-(3,4- dimethylphenylpropiolamido)
decahydroisoquinoline, trans-2-allyl- 8a-acetoxy-4a-(3-
hydroxyphenyl)-6α- (benzyloxycarboxamido)
decahydroisoquinoline, trans-2-allyl-8a- acetoxy-4a-(3-
hydroxyphenyl)-6α-[N-methyl-[trans-β-(3- furyl)
acrylamido]]decahydroisoquinoline, trans-2-allyl-8a-
acetoxy-4a-(3-hydroxyphenyl)-6α-[N-methyl-[trans-β-
(4-bromo-2- thienyl)acrylamido]]decahydroisoquinoline,
trans-2-allyl-8a- acetoxy-4a-(3-hydroxyphenyl)-6α-[N-
methyl-[trans-β-(2-methyl-3- furyl)acrylamido]]
decahydroisoquinoline, trans-2-allyl-8a- acetoxy-4a-(3-
hydroxyphenyl)-6α-[N-methyl-(3-
methoxycinnnamamido)]decahydroisoquinoline, trans-2-
allyl-8a- acetoxy-4a-(3-hydroxyphenyl)-6α-[N-methyl-
(3- trifluoromethoxycinnnamamido)]
decahydroisoquinoline, trans-2- allyl-8a-acetoxy-4a-(3-
hydroxyphenyl)-6α-[N-methyl-(3-
hydroxycinnnamamido)]decahydroisoquinoline, trans-2-
allyl-8a- acetoxy-4a-(3-hydroxyphenyl)-6α-[N-methyl-
(4- trifluoromethylphenylpropiolamido)]
decahydroisoquinoline, trans- 2-allyl-8a-acetoxy-4a-(3-
hydroxyphenyl)-6α-[N-methyl-(3-
methylphenylpropiolamido)l]decahydroisoquinoline,
trans-2-allyl- 8a-acetoxy-4a-(3-hydroxyphenyl)-6a-[N-
methyl-(3,4- dimethylphenylpropiolamido)]
decahydroisoquinoline, trans-2- allyl-8a-acetoxy-4a-(3-
hydroxyphenyl)-6α-[N-methyl- (benzyloxycarboxamido)
]decahydroisoquinoline, trans-2-allyl-8a-methoxy-4a-(3-
hydroxyphenyl)-6α-[trans-β-(3- furyl)acrylamido]
decahydroisoquinoline, trans-2-allyl-8a- methoxy-4a-(3-
hydroxyphenyl)-6α-[trans-β-(4-bromo-2- thienyl)
acrylamido]decahydroisoquinoline, trans-2-allyl-8a-
methoxy-4a-(3-hydroxyphenyl)-6α-[trans-β-(2-
methyl-3- furyl)acrylamido]decahydroisoquinoline,
trans-2-allyl-8a- methoxy-4a-(3-hydroxyphenyl)-6α-(3-
methoxycinnnamamido)decahydroisoquinoline, trans-2-
allyl-8a- methoxy-4a-(3-hydroxyphenyl)-6α-(3-
trifluoromethoxycinnnamamido)decahydroisoquinoline,
trans-2- allyl-8a-methoxy-4a-(3-hydroxyphenyl)-6α-(3-
hydroxycinnnamamido)decahydroisoquinoline, trans-2-
allyl-8a- methoxy-4a-(3-hydroxyphenyl)-6α-(4-
trifluoromethylphenylpropiolamido)
decahydroisoquinoline, trans- 2-allyl-8a-methoxy-4a-(3-
hydroxyphenyl)-6α(3- methylphenylpropiolamido)
decahydroisoquinoline, trans-2-allyl- 8a-methoxy-4a-(3-
hydroxyphenyl)-6α-(3,4- dimethylphenylpropiolamido)
decahydroisoquinoline, trans-2-allyl- 8a-methoxy-4a-(3-
hydroxyphenyl)-6α- (benzyloxycarboxamido)
decahydroisoquinoline, trans-2-allyl-8a- methoxy-4a-(3-
hydroxyphenyl)-6α-[N-methyl-[trans-β-(3- furyl)
acrylamido]]decahydroisoquinoline, trans-2-allyl-8a-
methoxy-4a-(3-hydroxyphenyl)-6α-[N-methyl-[trans-β-
(4-bromo-2- thienyl)acrylamido]]decahydroisoquinoline,
trans-2-allyl-8a- methoxy-4a-(3-hydroxyphenyl)-6α-[N-
methyl-[trans-β-(2-methyl-3- furyl)acrylamido]]
decahydroisoquinoline, trans-2-allyl-8a- methoxy-4a-(3-
hydroxyphenyl)-6α-[N-methyl-(3-
methoxycinnnamamido)]decahydroisoquinoline, trans-2-
allyl-8a- methoxy-4a-(3-hydroxyphenyl)-6α-[N-methyl-
(3- trifluoromethoxycinnnamamido)]
decahydroisoquinoline, trans-2- allyl-8a-methoxy-4a-(3-
hydroxyphenyl)-6α-[N-methyl-(3-
hydroxycinnnamamido)]decahydroisoquinoline, trans-2-
allyl-8a- methoxy-4a-(3-hydroxyphenyl)-6α-[N-methyl-
(4- trifluoromethylphenylpropiolamido)]
decahydroisoquinoline, trans- 2-allyl-8a-methoxy-4a-(3-
hydroxyphenyl)-6α-[N-methyl-(3-
methylphenylpropiolamido)]decahydroisoquinoline,
trans-2-allyl- 8a-methoxy-4a-(3-hydroxyphenyl)-6α-[N-
methyl-(3,4- dimethylphenylpropiolamido)]
decahydroisoquinoline, trans-2- allyl-8a-methoxy-4a-(3-
hydroxyphenyl)-6α-[N-methyl- (benzyloxycarboxamido)
]decahydroisoquinoline, trans-2-allyl-4a-(3-
methoxyphenyl)-6α-[trans-β-(3- furyl)acrylamido]
decahydroisoquinoline, trans-2-allyl-4a-(3-
methoxyphenyl)-6α-[trans-β-(4-bromo-2- thienyl)
acrylamido]decahydroisoquinoline, trans-2-allyl-4a-(3-
methoxyphenyl)-6α-[trans-β-(2-methyl-3- furyl)
acrylamido]decahydroisoquinoline, trans-2-allyl-4a-(3-
methoxyphenyl)-6α-(3-methoxycinnnamamido)
decahydroisoquinoline, trans-2-allyl-4a-(3-
methoxyphenyl)-6α-(3- trifluoromethoxycinnnamamido)
decahydroisoquinoline, trans-2- allyl-4a-(3-
methoxyphenyl)-6α-(3- hydroxycinnnamamido)
decahydroisoquinoline, trans-2-allyl-4a-(3-
methoxyphenyl)-6α-(4-
trifluoromethylphenylpropiolamido)
decahydroisoquinoline, trans- 2-allyl-4a-(3-
methoxyphenyl)-6α-(3- methylphenylpropiolamido)
decahydroisoquinoline, trans-2-allyl- 4a-(3-
methoxyphenyl)-6α-(3,4- dimethylphenylpropiolamido)
decahydroisoquinoline, trans-2-allyl- 4a-(3-
methoxyphenyl)-6α- (benzyloxycarboxamido)
decahydroisoquinoline, trans-2-allyl-4a-
(3-methoxyphenyl)-6α-[N-methyl-[trans-β-(3- furyl)
acrylamido]]decahydroisoquinoline, trans-2-allyl-4a-(3-
methoxyphenyl)-6α-[N-methyl-[trans-β-(4-bromo-2-
thienyl)acrylamido]]decahydroisoquinoline, trans-2- allyl-4a-(3- methoxyphenyl)-6α-[N-methyl-[trans-β-(2-methyl-3- furyl)acrylamido]]decahydroisoquinoline, trans-2-allyl-4a-(3- methoxyphenyl)-6α-[N-methyl-(3-methoxycinnnamamido)]decahydroisoquinoline, trans-2-allyl-4a-(3- methoxyphenyl)-6α-[N-methyl-(3- trifluoromethoxycinnnamamido)]decahydroisoquinoline, trans-2- allyl-4a-(3-methoxyphenyl)-6α-[N-methyl-(3-hydroxycinnnamamido)]decahydroisoquinoline, trans-2-allyl-4a-(3- methoxyphenyl)-6α-[N-methyl-(4-trifluoromethylphenylpropiolamido)] decahydroisoquinoline, trans- 2-allyl-4a-(3-methoxyphenyl)-6α-[N-methyl-(3-methylphenylpropiolamido)]decahydroisoquinoline, trans-2-allyl- 4a-(3-methoxyphenyl)-6α-[N-methyl-(3,4-dimethylphenylpropiolamido)]decahydroisoquinoline, trans-2- allyl-4a-(3-methoxyphenyl)-6α-[N-methyl-(benzyloxycarboxamido)]decahydroisoquinoline, trans-2-allyl-8a-hydroxy-4a-(3-methoxyphenyl)-6α-[trans-β-(3- furyl)acrylamido]decahydroisoquinoline, trans-2-allyl-8a- hydroxy-4a-(3-methoxyphenyl)-6α-[trans-β-(4-bromo-2- thienyl)acrylamido]decahydroisoquinoline, trans-2-allyl-8a- hydroxy-4a-(3-methoxyphenyl)-6α-[trans-β-(2-methyl-3- furyl)acrylamido] decahydroisoquinoline, trans-2-allyl-8a- hydroxy-4a-(3-methoxyphenyl)-6α-(3- methoxycinnamamido) decahydroisoquinoline, trans-2-allyl-8a- hydroxy-4a-(3-methoxyphenyl)-6α-(3- trifluoromethoxycinnnamamido) decahydroisoquinoline, trans-2- allyl-8a-hydroxy-4a-(3-methoxyphenyl)-6α-(3- hydroxycinnnamamido) decahydroisoquinoline, trans-2-allyl-8a- hydroxy-4a-(3-methoxyphenyl)-6α-(4-trifluoromethylphenylpropiolamido) decahydroisoquinoline, trans- 2-allyl-8a-hydroxy-4a-(3-methoxyphenyl)-6α-(3- methylphenylpropiolamido) decahydroisoquinoline, trans-2-allyl- 8a-hydroxy-4a-(3-methoxyphenyl)-6α-(3,4- dimethylphenylpropiolamido) decahydroisoquinoline, trans-2-allyl- 8a-hydroxy-4a-(3-methoxyphenyl) -6α- (benzyloxycarboxamido) decahydroisoquinoline, trans-2-allyl-8a- hydroxy-4a-(3-methoxyphenyl)-6α-[N-methyl-[trans-β-(3- furyl) acrylamido]]decahydroisoquinoline, trans-2-allyl-8a-hydroxy-4a-(3-methoxyphenyl)-6α-[N-methyl-[trans-β-(4-bromo-2- thienyl)acrylamido]]decahydroisoquinoline, trans-2-allyl-8a- hydroxy-4a-(3-methoxyphenyl)-6α-[N-methyl-[trans-β-(2-methyl-3- furyl)acrylamido]] decahydroisoquinoline, trans-2-allyl-8a- hydroxy-4a-(3-methoxyphenyl)-6α-[N-methyl-(3-methoxycinnnamamido)]decahydroisoquinoline, trans-2-allyl-8a- hydroxy-4a-(3-methoxyphenyl)-6α-[N-methyl-(3- trifluoromethoxycinnnamamido)] decahydroisoquinoline, trans-2- allyl-8a-hydroxy-4a-(3-methoxyphenyl)-6α-[N-methyl-(3-hydroxycinnnamamido)]decahydroisoquinoline, trans-2-allyl-8a- hydroxy-4a-(3-methoxyphenyl)-6α-[N-methyl-(4- trifluoromethylphenylpropiolamido)] decahydroisoquinoline, trans-2-allyl-8a-hydroxy-4a-(3-methoxyphenyl)-6α-[N-methyl-(3-methylphenylpropiolamido)]decahydroisoquinoline, trans-2-allyl- 8a-hydroxy-4a-(3-methoxyphenyl)-6α-[N-methyl-(3,4- dimethylphenylpropiolamido)] decahydroisoquinoline, trans-2- allyl-8a-hydroxy-4a-(3-methoxyphenyl)-6α-[N-methyl-(benzyloxycarboxamido)]decahydroisoquinoline, trans-2-allyl-8a-acetoxy-4a-(3-methoxyphenyl)-6α-[trans-β-(3- furyl)acrylamido]decahydroisoquinoline, trans-2-allyl-8a- acetoxy-4a-(3-methoxyphenyl)-6α-[trans-β-(4-bromo-2- thienyl)acrylamido]decahydroisoquinoline, trans-2-allyl-8a- acetoxy-4a-(3-methoxyphenyl)-6α-[trans-β-(2-methyl-3- furyl)acrylamido] decahydroisoquinoline, trans-2-allyl-8a- acetoxy-4a-(3-methoxyphenyl)-6α-(3- methoxycinnamamido) decahydroisoquinoline, trans-2-allyl-8a- acetoxy-4a-(3-methoxyphenyl)-6α-(3- trifluoromethoxycinnnamamido) decahydroisoquinoline, trans-2- allyl-8a-acetoxy-4a-(3-methoxyphenyl)-6α-(3- hydroxycinnnamamido) decahydroisoquinoline, trans-2-allyl-8a- acetoxy-4a-(3-methoxyphenyl) -6α-(4-trifluoromethylphenylpropiolamido) decahydroisoquinoline, trans- 2-allyl-8a-acetoxy-4a-(3-methoxyphenyl)-6α-(3- methylphenylpropiolamido) decahydroisoquinoline, trans-2-allyl- 8a-acetoxy-4a-(3-methoxyphenyl)-6α-(3,4- dimethylphenylpropiolamido) decahydroisoquinoline, trans-2-allyl- 8a-acetoxy-4a-(3-methoxyphenyl)-6α- (benzyloxycarboxamido) decahydroisoquinoline, trans-2-allyl-8a- acetoxy-4a-(3-methoxyphenyl)-6α-[N-methyl-[trans-β-(3- furyl) acrylamido]]decahydroisoquinoline, trans-2-allyl-8a-acetoxy-4a-(3-methoxyphenyl)-6α-[N-methyl-[trans-β-(4-bromo-2- thienyl)acrylamido]]decahydroisoquinoline, trans-2-allyl-8a- acetoxy-4a-(3-methoxyphenyl)-6α-[N-methyl-[trans-β-(2-methyl-3- furyl)acrylamido]] decahydroisoquinoline, trans-2-allyl-8a- acetoxy-4a-(3-methoxyphenyl)-6α-[N-methyl-(3- methoxycinnnamamido)]decahydroisoquinoline, trans-2- allyl-8a-acetoxy-4a-(3-methoxyphenyl)-6α-[N-methyl-(3- trifluoromethoxycinnnamamido)] decahydroisoquinoline, trans-2- allyl-8a-acetoxy-4a-(3-methoxyphenyl)-6α-[N-methyl-(3-hydroxycinnnamamido)]decahydroisoquinoline, trans-2-allyl-8a- acetoxy-4a-(3-methoxyphenyl)-6α-[N-methyl-(4- trifluoromethylphenylpropiolamido)] decahydroisoquinoline, trans- 2-allyl-8a-acetoxy-4a-(3-methoxyphenyl)-6α-[N-methyl-(3-methylphenylpropiolamido)]decahydroisoquinoline, trans-2-allyl- 8a-acetoxy-4a-(3-methoxyphenyl)-6α-[N-methyl-(3,4- dimethylphenylpropiolamido)] decahydroisoquinoline, trans-2- allyl-8a-acetoxy-4a-(3-methoxyphenyl)-6α-[N-methyl-(benzyloxycarboxamido)]decahydroisoquinoline, trans-2-allyl-8a-methoxy-4a-(3-methoxyphenyl)-6α-[trans-β-(3- furyl)acrylamido]decahydroisoquinoline, trans-2-allyl-8a- methoxy-4a-(3-methoxyphenyl)-6α-[trans-β-(4-bromo-2- thienyl)acrylamido]decahydroisoquinoline, trans-2-allyl-8a- methoxy-4a-(3-methoxyphenyl)-6α-[trans-β-(2-methyl-3- furyl)acrylamido] decahydroisoquinoline, trans-2-allyl-8a- methoxy-4a-(3-methoxyphenyl)-6α-(3- methoxycinnnamamido) decahydroisoquinoline, trans-2-allyl-8a- methoxy-4a-(3-methoxyphenyl)-6α-(3- trifluoromethoxycinnnamamido) decahydroisoquinoline, trans-2-allyl-8a-methoxy-4a-(3-methoxyphenyl)-6α-(3- hydroxycinnnamamido) decahydroisoquinoline, trans-2-allyl-8a- methoxy-4a-(3-methoxyphenyl)-6α-(4-trifluoromethylphenylpropiolamido) decahydroisoquinoline, trans- 2-allyl-8a-methoxy-4a-(3-methoxyphenyl)-6α-(3- methylphenylpropiolamido) decahydroisoquinoline, trans-2-allyl- 8a-methoxy-4a-(3-methoxyphenyl)-6α-(3,4- dimethylphenylpropiolamido) decahydroisoquinoline, trans-2-allyl- 8a-methoxy-4a-(3-methoxyphenyl)-6α- (benzyloxycarboxamido) decahydroisoquinoline, trans-2-allyl-8a- methoxy-4a-(3-methoxyphenyl)-6α-[N-methyl-[trans-β-(3- furyl) acrylamido]]decahydroisoquinoline, trans-2-allyl-8a-methoxy-4a-(3-methoxyphenyl)-6α-[N-methyl-[trans-β-

(4-bromo-2- thienyl)acrylamido]]decahydroisoquinoline, trans-2-allyl-8a- methoxy-4a-(3-methoxyphenyl)-6α-[N-methyl-[trans-β-(2-methyl-3- furyl)acrylamido]] decahydroisoquinoline, trans-2-allyl-8a- methoxy-4a-(3-methoxyphenyl)-6α-[N-methyl-(3- methoxycinnnamamido)]decahydroisoquinoline, trans-2-allyl-8a- methoxy-4a-(3-methoxyphenyl)-6α-[N-methyl-(3- trifluoromethoxycinnnamamido)] decahydroisoquinoline, trans-2- allyl-8a-methoxy-4a-(3-methoxyphenyl)-6α-[N-methyl-(3- hydroxycinnnamamido)]decahydroisoquinoline, trans-2-allyl-8a- methoxy-4a-(3-methoxyphenyl)-6α-[N-methyl-(4- trifluoromethylphenylpropiolamido)] decahydroisoquinoline, trans- 2-allyl-8a-methoxy-4a-(3-methoxyphenyl)-6α-[N-methyl-(3- methylphenylpropiolamido)]decahydroisoquinoline, trans-2-allyl- 8a-methoxy-4a-(3-methoxyphenyl)-6α-[N-methyl-(3,4- dimethylphenylpropiolamido)] decahydroisoquinoline, trans-2-allyl-8a-methoxy-4a-(3-methoxyphenyl)-6α-[N-methyl-(benzyloxycarboxamido)]decahydroisoquinoline, trans-2-allyl-4a-(3-acetoxyphenyl)-6α-[trans-β-(3- furyl)acrylamido]decahydroisoquinoline, trans-2-allyl-4a-(3-acetoxyphenyl)-6α-[trans-β-(4-bromo-2- thienyl)acrylamido]decahydroisoquinoline, trans-2-allyl-4a-(3-acetoxyphenyl)-6α-[trans-β-(2-methyl-3- furyl)acrylamido]decahydroisoquinoline, trans-2-allyl-4a-(3-acetoxyphenyl)-6α-(3-methoxycinnnamamido) decahydroisoquinoline, trans-2-allyl-4a-(3-acetoxyphenyl)-6α-(3- trifluoromethoxycinnnamamido) decahydroisoquinoline, trans-2- allyl-4a-(3-acetoxyphenyl)-6α-(3- hydroxycinnnamamido) decahydroisoquinoline, trans-2-allyl-4a-(3-acetoxyphenyl)-6α-(4- trifluoromethylphenylpropiolamido) decahydroisoquinoline, trans- 2-allyl-4a-(3-acetoxyphenyl)-6α-(3- methylphenylpropiolamido) decahydroisoquinoline, trans-2-allyl- 4a-(3-acetoxyphenyl)-6α-(3,4- dimethylphenylpropiolamido) decahydroisoquinoline, trans-2-allyl- 4a-(3-acetoxyphenyl)-6α- (benzyloxycarboxamido) decahydroisoquinoline, trans-2-allyl-4a-(3-acetoxyphenyl)-6α-[N-methyl-[trans-β-(3- furyl)acrylamido]]decahydroisoquinoline, trans-2-allyl-4a-(3-acetoxyphenyl)-6α-[N-methyl-[trans-β-(4-bromo-2- thienyl)acrylamido]]decahydroisoquinoline, trans-2-allyl-4a-(3- acetoxyphenyl)-6α-[N-methyl-[trans-β-(2-methyl-3- furyl)acrylamido]]decahydroisoquinoline, trans-2-allyl-4a-(3- acetoxyphenyl)-6α-[N-methyl-(3-methoxycinnnamamido)]decahydroisoquinoline, trans-2-allyl-4a-(3- acetoxyphenyl)-6α-[N-methyl-(3-trifluoromethoxycinnnamamido)]decahydroisoquinoline, trans-2- allyl-4a-(3-acetoxyphenyl)-6α-[N-methyl-(3-hydroxycinnnamamido)]decahydroisoquinoline, trans-2- allyl-4a-(3- acetoxyphenyl)-6α-[N-methyl-(4- trifluoromethylphenylpropiolamido)] decahydroisoquinoline, trans- 2-allyl-4a-(3-acetoxyphenyl)-6α-[N-methyl-(3-methylphenylpropiolamido)]decahydroisoquinoline, trans-2-allyl- 4a-(3-acetoxyphenyl)-6α-[N-methyl-(3,4-dimethylphenylpropiolamido)]decahydroisoquinoline, trans-2- allyl-4a-(3-acetoxyphenyl)-6α-[N-methyl-(benzyloxycarboxamido)]decahydroisoquinoline, trans-2-allyl-8a-hydroxy-4a-(3-acetoxyphenyl)-6α-[trans-β-(3-furyl)acrylamido]decahydroisoquinoline, trans-2-allyl-8a- hydroxy-4a-(3-acetoxyphenyl)-6α-[trans-β-(4-bromo-2- thienyl)acrylamido]decahydroisoquinoline, trans-2-allyl-8a- hydroxy-4a-(3-acetoxyphenyl)-6α-[trans-β-(2-methyl-3- furyl)acrylamido] decahydroisoquinoline, trans-2-allyl-8a- hydroxy-4a-(3-acetoxyphenyl)-6α-(3- methoxycinnnamamido) decahydroisoquinoline, trans-2-allyl-8a- hydroxy-4a-(3-acetoxyphenyl)-6α-(3- trifluoromethoxycinnnamamido) decahydroisoquinoline, trans-2- allyl-8a-hydroxy-4a-(3-acetoxyphenyl)-6α-(3- hydroxycinnnamamido) decahydroisoquinoline, trans-2-allyl-8a- hydroxy-4a-(3-acetoxyphenyl)-6α-(4- trifluoromethylphenylpropiolamido) decahydroisoquinoline, trans- 2-allyl-8a-hydroxy-4a-(3-acetoxyphenyl)-6α-(3- methylphenylpropiolamido) decahydroisoquinoline, trans-2-allyl-8a-hydroxy-4a-(3-acetoxyphenyl)-6α-(3,4- dimethylphenylpropiolamido) decahydroisoquinoline, trans-2-allyl- 8a-hydroxy-4a-(3-acetoxyphenyl)-6α- (benzyloxycarboxamido) decahydroisoquinoline, trans-2-allyl-8a- hydroxy-4a-(3-acetoxyphenyl)-6α-[N-methyl-[trans-μ-(3- furyl)acrylamido]]decahydroisoquinoline, trans-2-allyl-8a-hydroxy-4a-(3-acetoxyphenyl)-6α-(N-methyl-[trans-β-(4-bromo-2- thienyl)acrylamido]]decahydroisoquinoline, trans-2-allyl-8a- hydroxy-4a-(3-acetoxyphenyl)-6α-[N-methyl-[trans-β-(2-methyl-3- furyl)acrylamido]] decahydroisoquinoline, trans-2-allyl-8a- hydroxy-4a-(3-acetoxyphenyl)-6α-[N-methyl-(3-methoxycinnnamamido)]decahydroisoquinoline, trans-2-allyl-8a- hydroxy-4a-(3-acetoxyphenyl)-6α-[N-methyl-(3- trifluoromethoxycinnnamamido)] decahydroisoquinoline, trans-2- allyl-8a-hydroxy-4a-(3-acetoxyphenyl)-6α-[N-methyl-(3-hydroxycinnnamamido)]decahydroisoquinoline, trans-2- allyl-8a- hydroxy-4a-(3-acetoxyphenyl)-6α-[N-methyl-(4- trifluoromethylphenylpropiolamido)] decahydroisoquinoline, trans- 2-allyl-8a-hydroxy-4a-(3-acetoxyphenyl)-6α-[N-methyl-(3-methylphenylpropiolamido)]decahydroisoquinoline, trans-2-allyl- 8a-hydroxy-4a-(3-acetoxyphenyl)-6α-[N-methyl-(3,4- dimethylphenylpropiolamido)] decahydroisoquinoline, trans-2- allyl-8a-hydroxy-4a-(3-acetoxyphenyl)-6α-[N-methyl- (benzyloxycarboxamido)]decahydroisoquinoline, trans-2-allyl-8a-acetoxy-4a-(3-acetoxyphenyl)-6α-[trans-β-(3- furyl)acrylamido] decahydroisoquinoline, trans-2-allyl-8a- acetoxy-4a-(3-acetoxyphenyl)-6α-[trans-β-(4-bromo-2- thienyl)acrylamido]decahydroisoquinoline, trans-2-allyl-8a-acetoxy-4a-(3-acetoxyphenyl)-6α-[trans-β-(2-methyl-3-furyl)acrylamido]decahydroisoquinoline, trans-2-allyl- 8a- acetoxy-4a-(3-acetoxyphenyl)-6α-(3- methoxycinnnamamido)decahydroisoquinoline, trans-2-allyl-8a- acetoxy-4a-(3-acetoxyphenyl)-6α-(3- trifluoromethoxycinnnamamido)decahydroisoquinoline, trans-2- allyl-8a-acetoxy-4a-(3-acetoxyphenyl)-6α-(3-hydroxycinnnamamido)decahydroisoquinoline, trans-2- allyl-8a- acetoxy-4a-(3-acetoxyphenyl)-6α-(4-trifluoromethylphenylpropiolamido) decahydroisoquinoline, trans- 2-allyl-8a-acetoxy-4a-(3-acetoxyphenyl)-6α-(3- methylphenylpropiolamido) decahydroisoquinoline, trans-2-allyl- 8a-acetoxy-4a-(3-acetoxyphenyl)-6α-(3,4- dimethylphenylpropiolamido) decahydroisoquinoline, trans-2-allyl- 8a-acetoxy-4a-(3-acetoxyphenyl)-6α- (benzyloxycarboxamido) decahydroisoquinoline, trans-2-allyl-8a- acetoxy-4a-(3-acetoxyphenyl)-6α-[N-methyl-[trans-β-(3- furyl)acrylamido]]decahydroisoquinoline, trans-2-allyl-8a-acetoxy-4a-(3-acetoxyphenyl)-6α-[N-methyl-[trans-β-(4-bromo-2- thienyl)acrylamido]]decahydroisoquinoline, trans-2-allyl-8a- acetoxy-4a-(3-acetoxyphenyl)-6α-[N-methyl-[trans-β-(2-methyl-3- furyl)acrylamido]] decahydroisoquinoline, trans-2-allyl-8a- acetoxy-4a-(3-acetoxyphenyl)-6α-[N-methyl-(3-methoxycinnnamamido)]decahydroisoquinoline, trans-2-allyl-8a- acetoxy-4a-(3-acetoxyphenyl)-6α-[N-methyl-(3- trifluoromethoxycinnnamamido)] decahydroisoquinoline, trans-2- allyl-8a-acetoxy-4a-(3-acetoxyphenyl)-6α-[N-methyl-(3-hydroxycinnnamamido)]decahydroisoquinoline, trans-2- allyl-8a-acetoxy-4a-(3-acetoxyphenyl)-6α-[N-methyl-(4-trifluoromethylphenylpropiolamido)] decahydroisoquinoline, trans- 2-allyl-8a-acetoxy-4a-(3-acetoxyphenyl)-6α-[N-methyl-(3-methylphenylpropiolamido)]decahydroisoquinoline, trans-2-allyl- 8a-acetoxy-4a-(3-acetoxyphenyl)-6α-[N-methyl-(3,4- dimethylphenylpropiolamido)] decahydroisoquinoline, trans-2- allyl-8a-acetoxy-4a-(3-acetoxyphenyl)-6α-[N-methyl- (benzyloxycarboxamido)]decahydroisoquinoline, trans-2-allyl-8a-methoxy-4a-(3-acetoxyphenyl)-6α-[trans-β-(3- furyl)acrylamido] decahydroisoquinoline, trans-2-allyl-8a- methoxy-4a-(3-acetoxyphenyl)-6α-[trans-β-(4-bromo-2- thienyl)acrylamido]decahydroisoquinoline, trans-2-allyl-8a-methoxy-4a-(3-acetoxyphenyl)-6α-[trans-β-(2-methyl-3-furyl)acrylamido]decahydroisoquinoline, trans-2-allyl-8a- methoxy-4a-(3-acetoxyphenyl)-6α-(3-methoxycinnnamamido)decahydroisoquinoline, trans-2-allyl-8a- methoxy-4a-(3-acetoxyphenyl)-6α-(3-trifluoromethoxycinnnamamido)decahydroisoquinoline, trans-2- allyl-8a-methoxy-4a-(3-acetoxyphenyl)-6α-(3-hydroxycinnnamamido)decahydroisoquinoline, trans-2-allyl-8a- methoxy-4a-(3-acetoxyphenyl)-6α-(4-trifluoromethylphenylpropiolamido) decahydroisoquinoline, trans- 2-allyl-8a-methoxy-4a-(3-acetoxyphenyl)-6α-(3- methylphenylpropiolamido) decahydroisoquinoline, trans-2-allyl- 8a-methoxy-4a-(3-acetoxyphenyl)-6α-(3,4- dimethylphenylpropiolamido) decahydroisoquinoline, trans-2-allyl- 8a-methoxy-4a-(3-acetoxyphenyl)-6α- (benzyloxycarboxamido) decahydroisoquinoline, trans-2-allyl-8a-methoxy-4a-(3-acetoxyphenyl)-6α-[N-methyl-[trans-β-(3- furyl)acrylamido]]decahydroisoquinoline, trans-2-allyl-8a-methoxy-4a-(3-acetoxyphenyl)-6α-[N-methyl-[trans-β-(4-bromo-2- thienyl)acrylamido]]decahydroisoquinoline, trans-2-allyl-8a- methoxy-4a-(3-acetoxyphenyl)-6α-[N-methyl-[trans-β-(2-methyl-3- furyl)acrylamido]] decahydroisoquinoline, trans-2-allyl-8a- methoxy-4a-(3-acetoxyphenyl)-6α-[N-methyl-(3-methoxycinnnamamido)]decahydroisoquinoline, trans-2- allyl-8a- methoxy-4a-(3-acetoxyphenyl)-6α-[N-methyl-(3- trifluoromethoxycinnnamamido)] decahydroisoquinoline, trans-2- allyl-8a-methoxy-4a-(3-acetoxyphenyl)-6α-[N-methyl-(3-hydroxycinnnamamido)]decahydroisoquinoline, trans-2-allyl-8a- methoxy-4a-(3-acetoxyphenyl)-6α-[N-methyl-(4- trifluoromethylphenylpropiolamido)] decahydroisoquinoline, trans- 2-allyl-8a-methoxy-4a-(3-acetoxyphenyl)-6α-[N-methyl-(3-methylphenylpropiolamido)]decahydroisoquinoline, trans-2-allyl- 8a-methoxy-4a-(3-acetoxyphenyl)-6α-[N-methyl-(3,4- dimethylphenylpropiolamido)] decahydroisoquinoline, trans-2-allyl-8a-methoxy-4a-(3-acetoxyphenyl)-6α-[N-methyl- (benzyloxycarboxamido)]decahydroisoquinoline, trans-2-cyclopropylmethyl-4a-(3-hydroxyphenyl)-6α-[trans-β-(3- furyl)acrylamido] decahydroisoquinoline, trans-2- cyclopropylmethyl-4a-

(3-hydroxyphenyl)-6α-[trans-β-(4-bromo-2- thienyl) acrylamido]decahydroisoquinoline, trans-2-cyclopropylmethyl-4a-(3-hydroxyphenyl)-6α-[trans-β-(2-methyl-3- furyl)acrylamido]decahydroisoquinoline, trans-2- cyclopropylmethyl-4a-(3-hydroxyphenyl)-6β-(3-methoxycinnnamamido)decahydroisoquinoline, trans-2-cyclopropylmethyl-4a-(3-hydroxyphenyl)-6β-(3-trifluoromethoxycinnnamamido)decahydroisoquinoline, trans-2-cyclopropylmethyl-4a-(3-hydroxyphenyl)-6β-(3-hydroxycinnnamamido)decahydroisoquinoline, trans-2-cyclopropylmethyl-4a-(3-hydroxyphenyl)-6β-(4- trifluoromethylphenylpropiolamido) decahydroisoquinoline, trans-2-cyclopropylmethyl-4a-(3-hydroxyphenyl)-6β-(3-methylphenylpropiolamido) decahydroisoquinoline, trans-2-cyclopropylmethyl-4a-(3-hydroxyphenyl)-6β-(3,4-dimethylphenylpropiolamido) decahydroisoquinoline, trans-2-cyclopropylmethyl-4a-(3-hydroxyphenyl)-6β-(benzyloxycarboxamido) decahydroisoquinoline, trans-2-cyclopropylmethyl-4a-(3-hydroxyphenyl)-6β-[N-methyl-[trans-β-(3-furyl) acrylamido]]decahydroisoquinoline, trans-2-cyclopropylmethyl-4a-(3-hydroxyphenyl)-6β-[N-methyl-[trans-β-(4-bromo-2-thienyl)acrylamido]] decahydroisoquinoline, trans-2-cyclopropylmethyl-4a-(3-hydroxyphenyl)-6β-[N-methyl-[trans-β-(2-methyl-3-furyl)acrylamido]]decahydroisoquinoline, trans-2-cyclopropylmethyl-4a-(3-hydroxyphenyl)-6β-[N-methyl-(3-methoxycinnnamamido)]decahydroisoquinoline, trans-2-cyclopropylmethyl-4a-(3-hydroxyphenyl)-6β-[N-methyl-(3-trifluoromethoxycinnnamamido)] decahydroisoquinoline, trans-2-cyclopropylmethyl-4a-(3-hydroxyphenyl)-6β-[N-methyl-(3-hydroxycinnnamamido)]decahydroisoquinoline, trans-2-cyclopropylmethyl-4a-(3-hydroxyphenyl)-6β-[N-methyl-(4-trifluoromethylphenylpropiolamido)] decahydroisoquinoline, trans-2-cyclopropylmethyl-4a-(3-hydroxyphenyl)-6β-[N-methyl-(3-methylphenylpropiolamido)]decahydroisoquinoline, trans-2-cyclopropylmethyl-4a-(3-hydroxyphenyl)-6β-[N-methyl-(3,4-dimethylphenylpropiolamido)] decahydroisoquinoline, trans-2-cyclopropylmethyl-4a-(3-hydroxyphenyl)-6β-[N-methyl-(benzyloxycarboxamido)] decahydroisoquinoline, trans-2-cyclopropylmethyl-8a-hydroxy-4a-(3-hydroxyphenyl)-6β-[trans-β-(3-furyl) acrylamido]decahydroisoquinoline, trans-2-cyclopropylmethyl-8a-hydroxy-4a-(3-hydroxyphenyl)-6β-[trans-β-(4-bromo-2-thienyl)acrylamido] decahydroisoquinoline, trans-2-cyclopropylmethyl-8a-hydroxy-4a-(3-hydroxyphenyl)-6β-[trans-β-(2-methyl-3-furyl)acrylamido]decahydroisoquinoline, trans-2-cyclopropylmethyl-8a-hydroxy-4a-(3-hydroxyphenyl)-6β-(3-methoxycinnnamamido)decahydroisoquinoline, trans-2-cyclopropylmethyl-8a-hydroxy-4a-(3-hydroxyphenyl)-6β-(3-trifluoromethoxycinnnamamido) decahydroisoquinoline, trans-2-cyclopropylmethyl-8a-hydroxy-4a-(3-hydroxyphenyl)-6β-(3-hydroxycinnnamamido)decahydroisoquinoline, trans-2-cyclopropylmethyl-8a-hydroxy-4a-(3-hydroxyphenyl)-6β-(4-trifluoromethylphenylpropiolamido) decahydroisoquinoline, trans-2-cyclopropylmethyl-8a-hydroxy-4a-(3-hydroxyphenyl)-6β-(3-methylphenylpropiolamido)decahydroisoquinoline, trans-2-cyclopropylmethyl-8a-hydroxy-4a-(3-hydroxyphenyl)-6β-(3,4-dimethylphenylpropiolamido) decahydroisoquinoline, trans-2-cyclopropylmethyl-8a-hydroxy-4a-(3-hydroxyphenyl)-6β-(benzyloxycarboxamido)decahydroisoquinoline, trans-2- cyclopropylmethyl-8a-hydroxy-4a-(3-hydroxyphenyl)-6β-[N-methyl-[trans-β-(3-furyl)acrylamido]]decahydroisoquinoline, trans-2-cyclopropylmethyl-8a-hydroxy-4a-(3-hydroxyphenyl)-6β-[N-methyl-[trans-β-(4-bromo-2-thienyl)acrylamido]]decahydroisoquinoline, trans-2-cyclopropylmethyl-8a-hydroxy-4a-(3-hydroxyphenyl)-6β-[N-methyl-[trans-β-(2-methyl-3-furyl)acrylamido]]decahydroisoquinoline, trans-2-cyclopropylmethyl-8a-hydroxy-4a-(3-hydroxyphenyl)-6β-[N-methyl-(3-methoxycinnnamamido)]decahydroisoquinoline, trans-2-cyclopropylmethyl-8a-hydroxy-4a-(3-hydroxyphenyl)-6β-[N-methyl-(3-trifluoromethoxycinnnamamido)]decahydroisoquinoline, trans-2-cyclopropylmethyl-8a-hydroxy-4a-(3-hydroxyphenyl)-6β-[N-methyl-(3-hydroxycinnnamamido)]decahydroisoquinoline, trans-2-cyclopropylmethyl-8a-hydroxy-4a-(3-hydroxyphenyl)-6β-[N-methyl-(4-trifluoromethylphenylpropiolamido)]decahydroisoquinoline, trans-2-cyclopropylmethyl-8a-hydroxy-4a-(3-hydroxyphenyl)-6β-[N-methyl-(3-methylphenylpropiolamido)]decahydroisoquinoline, trans-2-cyclopropylmethyl-8a-hydroxy-4a-(3-hydroxyphenyl)-6β-[N-methyl-(3,4-dimethylphenylpropiolamido)]decahydroisoquinoline, trans-2-cyclopropylmethyl-8a-hydroxy-4a-(3-hydroxyphenyl)-6β-[N-methyl-(benzyloxycarboxamido)]decahydroisoquinoline, trans-2-cyclopropylmethyl-8a-acetoxy-4a-(3-hydroxyphenyl)-6β-[trans-β-(3-furyl)acrylamido]decahydroisoquinoline, trans-2-cyclopropylmethyl-8a-acetoxy-4a-(3-hydroxyphenyl)-6β-[trans-β-(4-bromo-2-thienyl)acrylamido]decahydroisoquinoline, trans-2-cyclopropylmethyl-8a-acetoxy-4a-(3-hydroxyphenyl)-6β-[trans-β-(2-methyl-3-furyl)acrylamido]decahydroisoquinoline, trans-2-cyclopropylmethyl-8a-acetoxy-4a-(3-hydroxyphenyl)-6β-(3-methoxycinnnamamido)decahydroisoquinoline, trans-2-cyclopropylmethyl-8a-acetoxy-4a-(3-hydroxyphenyl)-6β-(3-trifluoromethoxycinnnamamido)decahydroisoquinoline, trans-2-cyclopropylmethyl-8a-acetoxy-4a-(3-hydroxyphenyl)-6β-(3-hydroxycinnnamamido)decahydroisoquinoline, trans-2-cyclopropylmethyl-8a-acetoxy-4a-(3-hydroxyphenyl)-6β-(4-trifluoromethylphenylpropiolamido)decahydroisoquinoline, trans-2-cyclopropylmethyl-8a-acetoxy-4a-(3-hydroxyphenyl)-6β-(3-methylphenylpropiolamido)decahydroisoquinoline, trans-2-cyclopropylmethyl-8a-acetoxy-4a-(3-hydroxyphenyl)-6β-(3,4-dimethylphenylpropiolamido)decahydroisoquinoline, trans-2-cyclopropylmethyl-8a-acetoxy-4a-(3-hydroxyphenyl)-6β-(benzyloxycarboxamido)decahydroisoquinoline, trans-2-cyclopropylmethyl-8a-acetoxy-4a-(3-hydroxyphenyl)-6β-[N-methyl-[trans-β-(3-furyl)acrylamido]]decahydroisoquinoline, trans-2-cyclopropylmethyl-8a-acetoxy-4a-(3-hydroxyphenyl)-6β-[N-methyl-[trans-β-(4-bromo-2-thienyl)acrylamido]]decahydroisoquinoline, trans-2-cyclopropylmethyl-8a-acetoxy-4a-(3-hydroxyphenyl)-6β-[N-methyl-[trans-β-(2-methyl-3-furyl)acrylamido]]decahydroisoquinoline, trans-2-cyclopropylmethyl-8a-acetoxy-4a-(3-hydroxyphenyl)-6β-[N-methyl-(3-methoxycinnnamamido)]decahydroisoquinoline, trans-2-cyclopropylmethyl-8a-acetoxy-4a-(3-hydroxyphenyl)-6β-[N-methyl-(3-trifluoromethoxycinnnamamido)]decahydroisoquinoline, trans-2-cyclopropylmethyl-8a-acetoxy-4a-(3-hydroxyphenyl)-6β-[N-methyl-(3-hydroxycinnnamamido)]decahydroisoquinoline, trans-2-cyclopropylmethyl-8a-acetoxy-4a-(3-hydroxyphenyl)-6β-[N-methyl-(4-trifluoromethylphenylpropiolamido)]decahydroisoquinoline, trans-2-cyclopropylmethyl-8a-acetoxy-4a-(3-hydroxyphenyl)-6β-[N-methyl-(3-methylphenylpropiolamido)]decahydroisoquinoline, trans-2-cyclopropylmethyl-8a-acetoxy-4a-(3-hydroxyphenyl)-6β-[N-methyl-(3,4-dimethylphenylpropiolamido)]decahydroisoquinoline, trans-2-cyclopropylmethyl-8a-acetoxy-4a-(3-hydroxyphenyl)-6β-[N-methyl-(benzyloxycarboxamido)]decahydroisoquinoline, trans-2-cyclopropylmethyl-8a-methoxy-4a-(3-hydroxyphenyl)-6β-[trans-β-(3-furyl)acrylamido]decahydroisoquinoline, trans-2-cyclopropylmethyl-8a-methoxy-4a-(3-hydroxyphenyl)-6β-[trans-β-(4-bromo-2-thienyl)acrylamido]decahydroisoquinoline, trans-2-cyclopropylmethyl-8a-methoxy-4a-(3-hydroxyphenyl)-6β-[trans-β-(2-methyl-3-furyl)acrylamido]decahydroisoquinoline, trans-2-cyclopropylmethyl-8a-methoxy-4a-(3-hydroxyphenyl)-6β-(3-methoxycinnnamamido)decahydroisoquinoline, trans-2-cyclopropylmethyl-8a-methoxy-4a-(3-hydroxyphenyl)-6β-(3-trifluoromethoxycinnnamamido)decahydroisoquinoline, trans-2-cyclopropylmethyl-8a-methoxy-4a-(3-hydroxyphenyl)-6β-(3-hydroxycinnnamamido)decahydroisoquinoline, trans-2-cyclopropylmethyl-8a-methoxy-4a-(3-hydroxyphenyl)-6β-(4-trifluoromethylphenylpropiolamido)decahydroisoquinoline, trans-2-cyclopropylmethyl-8a-methoxy-4a-(3-hydroxyphenyl)-6β-(3-methylphenylpropiolamido)decahydroisoquinoline, trans-2-cyclopropylmethyl-8a-methoxy-4a-(3-hydroxyphenyl)-6β-(3,4-dimethylphenylpropiolamido)decahydroisoquinoline, trans-2-cyclopropylmethyl-8a-methoxy-4a-(3-hydroxyphenyl)-6β-(benzyloxycarboxamido)decahydroisoquinoline, trans-2-cyclopropylmethyl-8a-methoxy-4a-(3-hydroxyphenyl)-6β-[N-methyl-[trans-β-(3-furyl)acrylamido]]decahydroisoquinoline, trans-2-cyclopropylmethyl-8a-methoxy-4a-(3-hydroxyphenyl)-6β-[N-methyl-[trans-β-(4-bromo-2-thienyl)acrylamido]]decahydroisoquinoline, trans-2-cyclopropylmethyl-8a-methoxy-4a-(3-hydroxyphenyl)-6β-[N-methyl-[trans-β-(2-methyl-3-furyl)acrylamido]]decahydroisoquinoline, trans-2-cyclopropylmethyl-8a-methoxy-4a-(3-hydroxyphenyl)-6β-[N-methyl-(3-methoxycinnnamamido)]decahydroisoquinoline, trans-2-cyclopropylmethyl-8a-methoxy-4a-(3-hydroxyphenyl)-6β-[N-methyl-(3-trifluoromethoxycinnnamamido)]decahydroisoquinoline, trans-2-cyclopropylmethyl-8a-methoxy-4a-(3-hydroxyphenyl)-6β-[N-methyl-(3-hydroxycinnnamamido)]decahydroisoquinoline, trans-2-cyclopropylmethyl-8a-methoxy-4a-(3-hydroxyphenyl)-6β-[N-methyl-(4-trifluoromethylphenylpropiolamido)]decahydroisoquinoline, trans-2-cyclopropylmethyl-8a-methoxy-4a-(3-hydroxyphenyl)-6β-[N-methyl-(3-methylphenylpropiolamido)]decahydroisoquinoline, trans-2-cyclopropylmethyl-8a-methoxy-4a-(3-hydroxyphenyl)-6β-[N-methyl-(3,4-dimethylphenylpropiolamido)]decahydroisoquinoline, trans-2-cyclopropylmethyl-8a-methoxy-4a-(3-hydroxyphenyl)-6β-[N-methyl-(benzyloxycarboxamido)]decahydroisoquinoline, trans-2-cyclopropylmethyl-4a-(3-methoxyphenyl)-6β-[trans-β-(3-furyl)acrylamido]decahydroisoquinoline, trans-2-cyclopropylmethyl-4a-(3-methoxyphenyl)-6β-[trans-β-(4-bromo-2-thienyl)acrylamido]decahydroisoquinoline, trans-2-cyclopropylmethyl-4a-(3-methoxyphenyl)-6β-[trans-β-

(2-methyl-3-furyl)acrylamido]decahydroisoquinoline, trans-2-cyclopropylmethyl-4a-(3-methoxyphenyl)-6β-(3-methoxycinnnamamido)decahydroisoquinoline, trans-2-cyclopropylmethyl-4a-(3-methoxyphenyl)-6β-(3-trifluoromethoxycinnnamamido)decahydroisoquinoline, trans-2-cyclopropylmethyl-4a-(3-methoxyphenyl)-6β-(3-hydroxycinnnamamido)decahydroisoquinoline, trans-2-cyclopropylmethyl-4a-(3-methoxyphenyl)-6β-(4-trifluoromethylphenylpropiolamido)decahydroisoquinoline, trans-2-cyclopropylmethyl-4a-(3-methoxyphenyl)-6β-(3-methylphenylpropiolamido)decahydroisoquinoline, trans-2-cyclopropylmethyl-4a-(3-methoxyphenyl)-6β-(3,4-dimethylphenylpropiolamido)decahydroisoquinoline, trans-2-cyclopropylmethyl-4a-(3-methoxyphenyl)-6β-(benzyloxycarboxamido)decahydroisoquinoline, trans-2-cyclopropylmethyl-4a-(3-methoxyphenyl)-6β-[N-methyl-[trans-β-(3-furyl)acrylamido]]decahydroisoquinoline, trans-2-cyclopropylmethyl-4a-(3-methoxyphenyl)-6β-[N-methyl-[trans-β-(4-bromo-2-thienyl)acrylamido]]decahydroisoquinoline, trans-2-cyclopropylmethyl-4a-(3-methoxyphenyl)-6β-[N-methyl-[trans-β-(2-methyl-3-furyl)acrylamido]]decahydroisoquinoline, trans-2-cyclopropylmethyl-4a-(3-methoxyphenyl)-6β-[N-methyl-(3-methoxycinnnamamido)]decahydroisoquinoline, trans-2-cyclopropylmethyl-4a-(3-methoxyphenyl)-6β-[N-methyl-(3-trifluoromethoxycinnnamamido)]decahydroisoquinoline, trans-2-cyclopropylmethyl-4a-(3-methoxyphenyl)-6β-[N-methyl-(3-hydroxycinnnamamido)]decahydroisoquinoline, trans-2-cyclopropylmethyl-4a-(3-methoxyphenyl)-6β-[N-methyl-(4-trifluoromethylphenylpropiolamido)]decahydroisoquinoline, trans-2-cyclopropylmethyl-4a-(3-methoxyphenyl)-6β-[N-methyl-(3-methylphenylpropiolamido)]decahydroisoquinoline, trans-2-cyclopropylmethyl-4a-(3-methoxyphenyl)-6β-[N-methyl-(3,4-dimethylphenylpropiolamido)]decahydroisoquinoline, trans-2-cyclopropylmethyl-4a-(3-methoxyphenyl)-6β-[N-methyl-(benzyloxycarboxamido)]decahydroisoquinoline, trans-2-cyclopropylmethyl-8a-hydroxy-4a-(3-methoxyphenyl)-6β-[trans-β-(3-furyl)acrylamido]decahydroisoquinoline, trans-2-cyclopropylmethyl-8a-hydroxy-4a-(3-methoxyphenyl)-6β-[trans-β-(4-bromo-2-thienyl)acrylamido]decahydroisoquinoline, trans-2-cyclopropylmethyl-8a-hydroxy-4a-(3-methoxyphenyl)-6β-[trans-β-(2-methyl-3-furyl)acrylamido]decahydroisoquinoline, trans-2-cyclopropylmethyl-8a-hydroxy-4a-(3-methoxyphenyl)-6β-(3-methoxycinnnamamido)decahydroisoquinoline, trans-2-cyclopropylmethyl-8a-hydroxy-4a-(3-methoxyphenyl)-6β-(3-trifluoromethoxycinnnamamido)decahydroisoquinoline, trans-2-cyclopropylmethyl-8a-hydroxy-4a-(3-methoxyphenyl)-6β-(3-hydroxycinnnamamido)decahydroisoquinoline, trans-2-cyclopropylmethyl-8a-hydroxy-4a-(3-methoxyphenyl)-6β-(4-trifluoromethylphenylpropiolamido)decahydroisoquinoline, trans-2-cyclopropylmethyl-8a-hydroxy-4a-(3-methoxyphenyl)-6β-(3-methylphenylpropiolamido)decahydroisoquinoline, trans-2-cyclopropylmethyl-8a-hydroxy-4a-(3-methoxyphenyl)-6β-(3,4-dimethylphenylpropiolamido)decahydroisoquinoline, trans-2-cyclopropylmethyl-8a-hydroxy-4a-(3-methoxyphenyl)-6β-(benzyloxycarboxamido)decahydroisoquinoline, trans-2-cyclopropylmethyl-8a-hydroxy-4a-(3-methoxyphenyl)-6β-[N-methyl-[trans-β-(3-furyl)acrylamido]]decahydroisoquinoline, trans-2-cyclopropylmethyl-8a-hydroxy-4a-(3-methoxyphenyl)-6β-[N-methyl-[trans-β-(4-bromo-2-thienyl)acrylamido]]decahydroisoquinoline, trans-2-cyclopropylmethyl-8a-hydroxy-4a-(3-methoxyphenyl)-6β-[N-methyl-[trans-β-(2-methyl-3-furyl)acrylamido]]decahydroisoquinoline, trans-2-cyclopropylmethyl-8a-hydroxy-4a-(3-methoxyphenyl)-6β-[N-methyl-(3-methoxycinnnamamido)]decahydroisoquinoline, trans-2-cyclopropylmethyl-8a-hydroxy-4a-(3-methoxyphenyl)-6β-[N-methyl-(3-trifluoromethoxycinnnamamido)]decahydroisoquinoline, trans-2-cyclopropylmethyl-8a-hydroxy-4a-(3-methoxyphenyl)-6β-[N-methyl-(3-hydroxycinnnamamido)]decahydroisoquinoline, trans-2-cyclopropylmethyl-8a-hydroxy-4a-(3-methoxyphenyl)-6β-[N-methyl-(4-trifluoromethylphenylpropiolamido)]decahydroisoquinoline, trans-2-cyclopropylmethyl-8a-hydroxy-4a-(3-methoxyphenyl)-6β-[N-methyl-(3-methylphenylpropiolamido)]decahydroisoquinoline, trans-2-cyclopropylmethyl-8a-hydroxy-4a-(3-methoxyphenyl)-6β-[N-methyl-(3,4-dimethylphenylpropiolamido)]decahydroisoquinoline, trans-2-cyclopropylmethyl-8a-hydroxy-4a-(3-methoxyphenyl)-6β-[N-methyl-(benzyloxycarboxamido)]decahydroisoquinoline, trans-2-cyclopropylmethyl-8a-acetoxy-4a-(3-methoxyphenyl)-6β-[trans-β-(3-furyl)acrylamido]decahydroisoquinoline, trans-2-cyclopropylmethyl-8a-acetoxy-4a-(3-methoxyphenyl)-6β-[trans-β-(4-bromo-2-thienyl)acrylamido]decahydroisoquinoline, trans-2-cyclopropylmethyl-8a-acetoxy-4a-(3-methoxyphenyl)-6β-[trans-β-(2-methyl-3-furyl)acrylamido]decahydroisoquinoline, trans-2-cyclopropylmethyl-8a-acetoxy-4a-(3-methoxyphenyl)-6β-(3-methoxycinnnamamido)decahydroisoquinoline, trans-2-cyclopropylmethyl-8a-acetoxy-4a-(3-methoxyphenyl)-6β-(3-trifluoromethoxycinnnamamido)decahydroisoquinoline, trans-2-cyclopropylmethyl-8a-acetoxy-4a-(3-methoxyphenyl)-6β-(3-hydroxycinnnamamido)decahydroisoquinoline, trans-2-cyclopropylmethyl-8a-acetoxy-4a-(3-methoxyphenyl)-6β-(4-trifluoromethylphenylpropiolamido)decahydroisoquinoline, trans-2-cyclopropylmethyl-8a-acetoxy-4a-(3-methoxyphenyl)-6β-(3-methylphenylpropiolamido)decahydroisoquinoline, trans-2-cyclopropylmethyl-8a-acetoxy-4a-(3-methoxyphenyl)-6β-(3,4-dimethylphenylpropiolamido)decahydroisoquinoline, trans-2-cyclopropylmethyl-8a-acetoxy-4a-(3-methoxyphenyl)-6β-(benzyloxycarboxamido)decahydroisoquinoline, trans-2-cyclopropylmethyl-8a-acetoxy-4a-(3-methoxyphenyl)-6β-[N-methyl-[trans-β-(3-furyl)acrylamido]]decahydroisoquinoline, trans-2-cyclopropylmethyl-8a-acetoxy-4a-(3-methoxyphenyl)-6β-[N-methyl-[trans-β-(4-bromo-2-thienyl)acrylamido]]decahydroisoquinoline, trans-2-cyclopropylmethyl-8a-acetoxy-4a-(3-methoxyphenyl)-6β-[N-methyl-[trans-β-(2-methyl-3-furyl)acrylamido]]decahydroisoquinoline, trans-2-cyclopropylmethyl-8a-acetoxy-4a-(3-methoxyphenyl)-6β-[N-methyl-(3-methoxycinnnamamido)]decahydroisoquinoline, trans-2-cyclopropylmethyl-8a-acetoxy-4a-(3-methoxyphenyl)-6β-[N-methyl-(3-trifluoromethoxycinnnamamido)]decahydroisoquinoline, trans-2-cyclopropylmethyl-8a-acetoxy-4a-(3-methoxyphenyl)-6β-[N-methyl-(3-hydroxycinnnamamido)]decahydroisoquinoline, trans-2-cyclopropylmethyl-8a-acetoxy-4a-(3-methoxyphenyl)-6β-[N-methyl-(4-trifluoromethylphenylpropiolamido)]

decahydroisoquinoline, trans-2-cyclopropylmethyl-8a-acetoxy-4a-(3-methoxyphenyl)-6β-[N-methyl-(3-methylphenylpropiolamido)]decahydroisoquinoline, trans-2-cyclopropylmethyl-8a-acetoxy-4a-(3-methoxyphenyl)-6β-[N-methyl-(3,4-dimethylphenylpropiolamido)]decahydroisoquinoline, trans-2-cyclopropylmethyl-8a-acetoxy-4a-(3-methoxyphenyl)-6β-[N-methyl-(benzyloxycarboxamido)]decahydroisoquinoline, trans-2-cyclopropylmethyl-8a-methoxy-4a-(3-methoxyphenyl)-6β-[trans-β-(3-furyl)acrylamido]decahydroisoquinoline, trans-2-cyclopropylmethyl-8a-methoxy-4a-(3-methoxyphenyl)-6β-[trans-β-(4-bromo-2-thienyl)acrylamido]decahydroisoquinoline, trans-2-cyclopropylmethyl-8a-methoxy-4a-(3-methoxyphenyl)-6β-[trans-β-(2-methyl-3-furyl)acrylamido]decahydroisoquinoline, trans-2-cyclopropylmethyl-8a-methoxy-4a-(3-methoxyphenyl)-6β-(3-methoxycinnnamamido)decahydroisoquinoline, trans-2-cyclopropylmethyl-8a-methoxy-4a-(3-methoxyphenyl)-6β-(3-trifluoromethoxycinnnamamido)decahydroisoquinoline, trans-2-cyclopropylmethyl-8a-methoxy-4a-(3-methoxyphenyl)-6β-(3-hydroxycinnnamamido)decahydroisoquinoline, trans-2-cyclopropylmethyl-8a-methoxy-4a-(3-methoxyphenyl)-6β-(4-trifluoromethylphenylpropiolamido)decahydroisoquinoline, trans-2-cyclopropylmethyl-8a-methoxy-4a-(3-methoxyphenyl)-6β-(3-methylphenylpropiolamido)decahydroisoquinoline, trans-2-cyclopropylmethyl-8a-methoxy-4a-(3-methoxyphenyl)-6β-(3,4-dimethylphenylpropiolamido)decahydroisoquinoline, trans-2-cyclopropylmethyl-8a-methoxy-4a-(3-methoxyphenyl)-6β-(benzyloxycarboxamido)decahydroisoquinoline, trans-2-cyclopropylmethyl-8a-methoxy-4a-(3-methoxyphenyl)-6β-[N-methyl-[trans-β-(3-furyl)acrylamido]]decahydroisoquinoline, trans-2-cyclopropylmethyl-8a-methoxy-4a-(3-methoxyphenyl)-6β-[N-methyl-[trans-β-(4-bromo-2-thienyl)acrylamido]]decahydroisoquinoline, trans-2-cyclopropylmethyl-8a-methoxy-4a-(3-methoxyphenyl)-6β-[N-methyl-[trans-β-(2-methyl-3-furyl)acrylamido]]decahydroisoquinoline, trans-2-cyclopropylmethyl-8a-methoxy-4a-(3-methoxyphenyl)-6β-[N-methyl-(3-methoxycinnnamamido)]decahydroisoquinoline, trans-2-cyclopropylmethyl-8a-methoxy-4a-(3-methoxyphenyl)-6β-[N-methyl-(4-trifluoromethylphenylpropiolamido)]decahydroisoquinoline, trans-2-cyclopropylmethyl-8a-methoxy-4a-(3-methoxyphenyl)-6β-[N-methyl-(3-hydroxycinnnamamido)]decahydroisoquinoline, trans-2-cyclopropylmethyl-8a-methoxy-4a-(3-methoxyphenyl)-6β-[N-methyl-(3-methylphenylpropiolamido)]decahydroisoquinoline, trans-2-cyclopropylmethyl-8a-methoxy-4a-(3-methoxyphenyl)-6β-[N-methyl-(benzyloxycarboxamido)]decahydroisoquinoline, trans-2-cyclopropylmethyl-4a-(3-acetoxyphenyl)-6β-[trans-β-(3-furyl)acrylamido]decahydroisoquinoline, trans-2-cyclopropylmethyl-4a-(3-acetoxyphenyl)-6β-[trans-β-(4-bromo-2-thienyl)acrylamido]decahydroisoquinoline, trans-2-cyclopropylmethyl-4a-(3-acetoxyphenyl)-6β-[trans-β-(2-methyl-3-furyl)acrylamido]decahydroisoquinoline, trans-2-cyclopropylmethyl-4a-(3-acetoxyphenyl)-6β-(3-methoxycinnnamamido)decahydroisoquinoline, trans-2-cyclopropylmethyl-4a-(3-acetoxyphenyl)-6β-(3-trifluoromethoxycinnnamamido)decahydroisoquinoline, trans-2-cyclopropylmethyl-4a-(3-acetoxyphenyl)-6β-(3-hydroxycinnnamamido)decahydroisoquinoline, trans-2-cyclopropylmethyl-4a-(3-acetoxyphenyl)-6β-(4-trifluoromethylphenylpropiolamido)decahydroisoquinoline, trans-2-cyclopropylmethyl-4a-(3-acetoxyphenyl)-6β-(3-methylphenylpropiolamido)decahydroisoquinoline, trans-2-cyclopropylmethyl-4a-(3-acetoxyphenyl)-6β-(3,4-dimethylphenylpropiolamido)decahydroisoquinoline, trans-2-cyclopropylmethyl-4a-(3-acetoxyphenyl)-6β-(benzyloxycarboxamido)decahydroisoquinoline, trans-2-cyclopropylmethyl-4a-(3-acetoxyphenyl)-6β-[N-methyl-[trans-β-(3-furyl)acrylamido]]decahydroisoquinoline, trans-2-cyclopropylmethyl-4a-(3-acetoxyphenyl)-6β-[N-methyl-[trans-β-(4-bromo-2-thienyl)acrylamido]]decahydroisoquinoline, trans-2-cyclopropylmethyl-4a-(3-acetoxyphenyl)-6β-[N-methyl-[trans-β-(2-methyl-3-furyl)acrylamido]]decahydroisoquinoline, trans-2-cyclopropylmethyl-4a-(3-acetoxyphenyl)-6β-[N-methyl-(3-methoxycinnnamamido)]decahydroisoquinoline, trans-2-cyclopropylmethyl-4a-(3-acetoxyphenyl)-6β-[N-methyl-(3-trifluoromethoxycinnnamamido)]decahydroisoquinoline, trans-2-cyclopropylmethyl-4a-(3-acetoxyphenyl)-6β-[N-methyl-(3-hydroxycinnnamamido)]decahydroisoquinoline, trans-2-cyclopropylmethyl-4a-(3-acetoxyphenyl)-6β-[N-methyl-(4-trifluoromethylphenylpropiolamido)]decahydroisoquinoline, trans-2-cyclopropylmethyl-4a-(3-acetoxyphenyl)-6β-[N-methyl-(3-methylphenylpropiolamido)]decahydroisoquinoline, trans-2-cyclopropylmethyl-4a-(3-acetoxyphenyl)-6β-[N-methyl-(3,4-dimethylphenylpropiolamido)]decahydroisoquinoline, trans-2-cyclopropylmethyl-4a-(3-acetoxyphenyl)-6β-[N-methyl(benzyloxycarboxamido)]decahydroisoquinoline, trans-2-cyclopropylmethyl-8a-hydroxy-4a-(3-acetoxyphenyl)-6β-[trans-β-(3-furyl)acrylamido]decahydroisoquinoline, trans-2-cyclopropylmethyl-8a-hydroxy-4a-(3-acetoxyphenyl)-6β-[trans-β-(4-bromo-2-thienyl)acrylamido]decahydroisoquinoline, trans-2-cyclopropylmethyl-8a-hydroxy-4a-(3-acetoxyphenyl)-6β-[trans-β-(2-methyl-3-furyl)acrylamido]decahydroisoquinoline, trans-2-cyclopropylmethyl-8a-hydroxy-4a-(3-acetoxyphenyl)-6β-(3-methoxycinnnamamido)decahydroisoquinoline, trans-2-cyclopropylmethyl-8a-hydroxy-4a-(3-acetoxyphenyl)-6β-(3-trifluoromethoxycinnnamamido)decahydroisoquinoline, trans-2-cyclopropylmethyl-8a-hydroxy-4a-(3-acetoxyphenyl)-6β-(3-hydroxycinnnamamido)decahydroisoquinoline, trans-2-cyclopropylmethyl-8a-hydroxy-4a-(3-acetoxyphenyl)-6β-(4-trifluoromethylphenylpropiolamido)decahydroisoquinoline, trans-2-cyclopropylmethyl-8a-hydroxy-4a-(3-acetoxyphenyl)-6β-(3-methylphenylpropiolamido)decahydroisoquinoline, trans-2-cyclopropylmethyl-8a-hydroxy-4a-(3-acetoxyphenyl)-6β-(3,4-dimethylphenylpropiolamido)decahydroisoquinoline, trans-2-cyclopropylmethyl-8a-hydroxy-4a-(3-acetoxyphenyl)-6β-(benzyloxycarboxamido)decahydroisoquinoline, trans-2-cyclopropylmethyl-8a-hydroxy-4a-(3-acetoxyphenyl)-6β-[N-methyl-[trans-β-(3-furyl)acrylamido]]decahydroisoquinoline, trans-2-cyclopropylmethyl-8a-hydroxy-4a-(3-acetoxyphenyl)-6β-[N-methyl-[trans-β-(4-bromo-2-thienyl)acrylamido]]decahydroisoquinoline, trans-2-cyclopropylmethyl-8a-hydroxy-4a-(3-acetoxyphenyl)-6β-[N-methyl-[trans-β-(2-methyl-3-furyl)acrylamido]]decahydroisoquinoline, trans-2-cyclopropylmethyl-8a-hydroxy-4a-(3-acetoxyphenyl)-6β-[N-methyl-(3-methoxycinnnamamido)] decahydroisoquinoline, trans-2-cyclopropylmethyl-8a-hydroxy-4a-(3-acetoxyphenyl)-6β-[N-methyl-(3-trifluoromethoxycinnnamamido)]decahydroisoquinoline, trans-2-cyclopropylmethyl-8a-hydroxy-4a-(3-acetoxyphenyl)-6β-[N-methyl-(3-hydroxycinnnamamido)]decahydroisoquinoline, trans-2-cyclopropylmethyl-8a-hydroxy-4a-(3-acetoxyphenyl)-6β-[N-methyl-(4-trifluoromethylphenylpropiolamido)] decahydroisoquinoline, trans-2-cyclopropylmethyl-8a-hydroxy-4a-(3-acetoxyphenyl)-6β-[N-methyl-(3-methylphenylpropiolamido)]decahydroisoquinoline, trans-2-cyclopropylmethyl-8a-hydroxy-4a-(3-acetoxyphenyl)-6β-[N-methyl-(3,4-dimethylphenylpropiolamido)]decahydroisoquinoline, trans-2-cyclopropylmethyl-8a-hydroxy-4a-(3-acetoxyphenyl)-6(-[N-methyl-(benzyloxycarboxamido)] decahydroisoquinoline, trans-2-cyclopropylmethyl-8a-acetoxy-4a-(3-acetoxyphenyl)-6β-[trans-β-(3-furyl) acrylamido]decahydroisoquinoline, trans-2-cyclopropylmethyl-8a-acetoxy-4a-(3-acetoxyphenyl)-6β-[trans-β-(4-bromo-2-thienyl)acrylamido] decahydroisoquinoline, trans-2-cyclopropylmethyl-8a-acetoxy-4a-(3-acetoxyphenyl)-6β-[trans-β-(2-methyl-3-furyl)acrylamido]decahydroisoquinoline, trans-2-cyclopropylmethyl-8a-acetoxy-4a-(3-acetoxyphenyl)-6β-(3-methoxycinnnamamido)decahydroisoquinoline, trans-2-cyclopropylmethyl-8a-acetoxy-4a-(3-acetoxyphenyl)-6β-(3-trifluoromethoxycinnnamamido) decahydroisoquinoline, trans-2-cyclopropylmethyl-8a-acetoxy-4a-(3-acetoxyphenyl)-6β-(3-hydroxycinnnamamido)decahydroisoquinoline, trans-2-cyclopropylmethyl-8a-acetoxy-4a-(3-acetoxyphenyl)-6β-(4-trifluoromethylphenylpropiolamido) decahydroisoquinoline, trans-2-cyclopropylmethyl-8a-acetoxy-4a-(3-acetoxyphenyl)-6β-(3-methylphenylpropiolamido)decahydroisoquinoline, trans-2-cyclopropylmethyl-8a-acetoxy-4a-(3-acetoxyphenyl)-6β-(3,4-dimethylphenylpropiolamido) decahydroisoquinoline, trans-2-cyclopropylmethyl-8a-acetoxy-4a-(3-acetoxyphenyl)-6β-(benzyloxycarboxamido)decahydroisoquinoline, trans-2-cyclopropylmethyl-8a-acetoxy-4a-(3-acetoxyphenyl)-6β-[N-methyl-[trans-β-(3-furyl)acrylamido]] decahydroisoquinoline, trans-2-cyclopropylmethyl-8a-acetoxy-4a-(3-acetoxyphenyl)-6β-[N-methyl-[trans-β-(4-bromo-2-thienyl)acrylamido]]decahydroisoquinoline, trans-2-cyclopropylmethyl-8a-acetoxy-4a-(3-acetoxyphenyl)-6β-[N-methyl-[trans-β-(2-methyl-3-furyl)acrylamido]]decahydroisoquinoline, trans-2-cyclopropylmethyl-8a-acetoxy-4a-(3-acetoxyphenyl)-6β-[N-methyl-(3-methoxycinnnamamido)] decahydroisoquinoline, trans-2-cyclopropylmethyl-8a-acetoxy-4a-(3-acetoxyphenyl)-6β-[N-methyl-(3-trifluoromethoxycinnnamamido)]decahydroisoquinoline, trans-2-cyclopropylmethyl-8a-acetoxy-4a-(3-acetoxyphenyl)-6β-[N-methyl-(3-hydroxycinnnamamido)]decahydroisoquinoline, trans-2-cyclopropylmethyl-8a-acetoxy-4a-(3-acetoxyphenyl)-6β-[N-methyl-(4-trifluoromethylphenylpropiolamido)] decahydroisoquinoline, trans-2-cyclopropylmethyl-8a-acetoxy-4a-(3-acetoxyphenyl)-6β-[N-methyl-(3-methylphenylpropiolamido)]decahydroisoquinoline, trans-2-cyclopropylmethyl-8a-acetoxy-4a-(3-acetoxyphenyl)-6β-[N-methyl-(3,4-dimethylphenylpropiolamido)]decahydroisoquinoline, trans-2-cyclopropylmethyl-8a-acetoxy-4a-(3-acetoxyphenyl)-6β-[N-methyl-(benzyloxycarboxamido)] decahydroisoquinoline, trans-2-cyclopropylmethyl-8a-methoxy-4a-(3-acetoxyphenyl)-6β-[trans-β-(3-furyl) acrylamido]decahydroisoquinoline, trans-2-cyclopropylmethyl-8a-methoxy-4a-(3-acetoxyphenyl)-6β-[trans-β-(4-bromo-2-thienyl)acrylamido] decahydroisoquinoline, trans-2-cyclopropylmethyl-8a-methoxy-4a-(3-acetoxyphenyl)-6β-[trans-β-(2-methyl-3-furyl)acrylamido]decahydroisoquinoline, trans-2-cyclopropylmethyl-8a-methoxy-4a-(3-acetoxyphenyl)-6β-(3-methoxycinnnamamido)decahydroisoquinoline, trans-2-cyclopropylmethyl-8a-methoxy-4a-(3-acetoxyphenyl)-6β-(3-trifluoromethoxycinnnamamido) decahydroisoquinoline, trans-2-cyclopropylmethyl-8a-methoxy-4a-(3-acetoxyphenyl)-6β-(3-hydroxycinnnamamido)decahydroisoquinoline, trans-2-cyclopropylmethyl-8a-methoxy-4a-(3-acetoxyphenyl)-6β-(4-trifluoromethylphenylpropiolamido) decahydroisoquinoline, trans-2-cyclopropylmethyl-8a-methoxy-4a-(3-acetoxyphenyl)-6β-(3-methylphenylpropiolamido)decahydroisoquinoline, trans-2-cyclopropylmethyl-8a-methoxy-4a-(3-acetoxyphenyl)-6β-(3,4-dimethylphenylpropiolamido) decahydroisoquinoline, trans-2-cyclopropylmethyl-8a-methoxy-4a-(3-acetoxyphenyl)-6β-(benzyloxycarboxamido)decahydroisoquinoline, trans-2-cyclopropylmethyl-8a-methoxy-4a-(3-acetoxyphenyl)-6β-[N-methyl-[trans-β-(3-furyl)acrylamido]] decahydroisoquinoline, trans-2-cyclopropylmethyl-8a-methoxy-4a-(3-acetoxyphenyl)-6β-[N-methyl-[trans-β-(4-bromo-2-thienyl)acrylamido]]decahydroisoquinoline, trans-2-cyclopropylmethyl-8a-methoxy-4a-(3-acetoxyphenyl)-6β-[N-methyl-[trans-β-(2-methyl-3-furyl)acrylamido]]decahydroisoquinoline, trans-2-cyclopropylmethyl-8a-methoxy-4a-(3-acetoxyphenyl)-6β-[N-methyl-(3-methoxycinnnamamido)] decahydroisoquinoline, trans-2-cyclopropylmethyl-8a-methoxy-4a-(3-acetoxyphenyl)-6β-[N-methyl-(3-trifluoromethoxycinnnamamido)]decahydroisoquinoline, trans-2-cyclopropylmethyl-8a-methoxy-4a-(3-acetoxyphenyl)-6β-[N-methyl-(3-hydroxycinnnamamido)]decahydroisoquinoline, trans-2-cyclopropylmethyl-8a-methoxy-4a-(3-acetoxyphenyl)-6β-[N-methyl-(4-trifluoromethylphenylpropiolamido)] decahydroisoquinoline, trans-2-cyclopropylmethyl-8a-methoxy-4a-(3-acetoxyphenyl)-6β-[N-methyl-(3-methylphenylpropiolamido)]decahydroisoquinoline, trans-2-cyclopropylmethyl-8a-methoxy-4a-(3-acetoxyphenyl)-6β-[N-methyl-(3,4-dimethylphenylpropiolamido)]decahydroisoquinoline, trans-2-cyclopropylmethyl-8a-methoxy-4a-(3-acetoxyphenyl)-6β-[N-methyl-(benzyloxycarboxamido)] decahydroisoquinoline, trans-2-allyl-4a-(3-hydroxyphenyl)-6β-[trans-β-(3-furyl)acrylamido] decahydroisoquinoline, trans-2-allyl-4a-(3-hydroxyphenyl)-6β-[trans-β-(4-bromo-2-thienyl) acrylamido]decahydroisoquinoline, trans-2-allyl-4a-(3-hydroxyphenyl)-6β-[trans-pi-(2-methyl-3-furyl) acrylamido]decahydroisoquinoline, trans-2-allyl-4a-(3-hydroxyphenyl)-6β-(3-methoxycinnnamamido) decahydroisoquinoline, trans-2-allyl-4a-(3-hydroxyphenyl)-6β-(3-trifluoromethoxycinnnamamido) decahydroisoquinoline, trans-2-allyl-4a-(3- hydroxyphenyl)-6β-(3-hydroxycinnnamamido) decahydroisoquinoline, trans-2-allyl-4a-(3-hydroxyphenyl)-6β-(4-trifluoromethylphenylpropiolamido) decahydroisoquinoline, trans-2-allyl-4a-(3-hydroxyphenyl)-6β-(3-methylphenylpropiolamido) decahydroisoquinoline, trans-2-allyl-4a-(3-hydroxyphenyl)-6β-(3,4-dimethylphenylpropiolamido) decahydroisoquinoline, trans-2-allyl-4a-(3-hydroxyphenyl)-6β-(benzyloxycarboxamido) decahydroisoquinoline, trans-2-allyl-4a-(3-hydroxyphenyl)-6β-[N-methyl-[trans-β-(3-furyl)acrylamido]]decahydroisoquinoline, trans-2-allyl-4a-(3-hydroxyphenyl)-6β-[N-methyl-[trans-β-(4-bromo-2-thienyl)acrylamido]]decahydroisoquinoline, trans-2-allyl-4a-(3-hydroxyphenyl)-6β-[N-methyl-[trans-β-(2-methyl-3-furyl)acrylamido]]decahydroisoquinoline, trans-2-allyl-4a-(3-hydroxyphenyl)-6β-[N-methyl-(3-methoxycinnnamamido)]decahydroisoquinoline, trans-2-allyl-4a-(3-hydroxyphenyl)-6β-[N-methyl-(3-trifluoromethoxycinnnamamido)]decahydroisoquinoline, trans-2-allyl-4a-(3-hydroxyphenyl)-6β-[N-methyl-(3-hydroxycinnnamamido)]decahydroisoquinoline, trans-2-allyl-4a-(3-hydroxyphenyl)-6β-[N-methyl-(4-trifluoromethylphenylpropiolamido)] decahydroisoquinoline, trans-2-allyl-4a-(3-hydroxyphenyl)-6β-[N-methyl-(3-methylphenylpropiolamido)]decahydroisoquinoline, trans-2-allyl-4a-(3-hydroxyphenyl)-6β-[N-methyl-(3,4-dimethylphenylpropiolamido)]decahydroisoquinoline, trans-2-allyl-4a-(3-hydroxyphenyl)-6β-[N-methyl-(benzyloxycarboxamido)]decahydroisoquinoline, trans-2-allyl-8a-hydroxy-4a-(3-hydroxyphenyl)-6β-[trans-β-(3-furyl)acrylamido]decahydroisoquinoline, trans-2-allyl-8a-hydroxy-4a-(3-hydroxyphenyl)-6β-([trans-β-(4-bromo-2-thienyl)acrylamido]decahydroisoquinoline, trans-2-allyl-8a-hydroxy-4a-(3-hydroxyphenyl)-6β-[trans-β-(2-methyl-3-furyl) acrylamido] decahydroisoquinoline, trans-2-allyl-8a-hydroxy-4a-(3-hydroxyphenyl)-6β-(3-methoxycinnnamamido) decahydroisoquinoline, trans-2-allyl-8a-hydroxy-4a-(3-hydroxyphenyl)-6β-(3-trifluoromethoxycinnnamamido) decahydroisoquinoline, trans-2-allyl-8a-hydroxy-4a-(3-hydroxyphenyl)-6β-(3-hydroxycinnnamamido) decahydroisoquinoline, trans-2-allyl-8a-hydroxy-4a-(3-hydroxyphenyl)-6β-(4-trifluoromethylphenylpropiolamido) decahydroisoquinoline, trans-2-allyl-8a-hydroxy-4a-(3-hydroxyphenyl)-6β-(3-methylphenylpropiolamido) decahydroisoquinoline, trans-2-allyl-8a-hydroxy-4a-(3-hydroxyphenyl)-6β-(3,4-dimethylphenylpropiolamido) decahydroisoquinoline, trans-2-allyl-8a-hydroxy-4a-(3-hydroxyphenyl)-6β-(benzyloxycarboxamido) decahydroisoquinoline, trans-2-allyl-8a-hydroxy-4a-(3-hydroxyphenyl)-6β-[N-methyl-[trans-β-(3-furyl)acrylamido]]decahydroisoquinoline, trans-2-allyl-8a-hydroxy-4a-(3-hydroxyphenyl)-6β-[N-methyl-[trans-β-(4-bromo-2-thienyl)acrylamido]]decahydroisoquinoline, trans-2-allyl-8a-hydroxy-4a-(3-hydroxyphenyl)-6β-[N-methyl-[trans-β-(2-methyl-3-furyl)acrylamido]] decahydroisoquinoline, trans-2-allyl-8a-hydroxy-4a-(3-hydroxyphenyl)-6β-[N-methyl-(3-methoxycinnnamamido)]decahydroisoquinoline, trans-2-allyl-8a-hydroxy-4a-(3-hydroxyphenyl)-6β-[N-methyl-(3-trifluoromethoxycinnnamamido)] decahydroisoquinoline, trans-2-allyl-8a-hydroxy-4a-(3-hydroxyphenyl)-6β-[N-methyl-(3-hydroxycinnnamamido)]decahydroisoquinoline, trans-2-allyl-8a-hydroxy-4a-(3-hydroxyphenyl)-6β-[N-methyl-(4-trifluoromethylphenylpropiolamido)] decahydroisoquinoline, trans-2-allyl-8a-hydroxy-4a-(3-hydroxyphenyl)-6β-[N-methyl-(3-methylphenylpropiolamido)]decahydroisoquinoline, trans-2-allyl-8a-hydroxy-4a-(3-hydroxyphenyl)-6β-[N-methyl-(3,4-dimethylphenylpropiolamido)] decahydroisoquinoline, trans-2-allyl-8a-hydroxy-4a-(3-hydroxyphenyl)-6β-[N-methyl-(benzyloxycarboxamido)] decahydroisoquinoline, trans-2-allyl-8a-acetoxy-4a-(3-hydroxyphenyl)-6β-[trans-β-(3-furyl)acrylamido] decahydroisoquinoline, trans-2-allyl-8a-acetoxy-4a-(3-hydroxyphenyl)-6β-[trans-β-(4-bromo-2-thienyl) acrylamido]decahydroisoquinoline, trans-2-allyl-8a-acetoxy-4a-(3-hydroxyphenyl)-6β-[trans-β-(2-methyl-3-furyl)acrylamido]decahydroisoquinoline, trans-2-allyl-8a-acetoxy-4a-(3-hydroxyphenyl)-6β-(3-methoxycinnnamamido)decahydroisoquinoline, trans-2-allyl-8a-acetoxy-4a-(3-hydroxyphenyl)-6β-(3-trifluoromethoxycinnnamamido)decahydroisoquinoline, trans-2-allyl-8a-acetoxy-4a-(3-hydroxyphenyl)-6β-(3-hydroxycinnnamamido)decahydroisoquinoline, trans-2-allyl-8a-acetoxy-4a-(3-hydroxyphenyl)-6β-(4-trifluoromethylphenylpropiolamido) decahydroisoquinoline, trans-2-allyl-8a-acetoxy-4a-(3-hydroxyphenyl)-6β-(3-methylphenylpropiolamido) decahydroisoquinoline, trans-2-allyl-8a-acetoxy-4a-(3-hydroxyphenyl)-6β-(3,4-dimethylphenylpropiolamido) decahydroisoquinoline, trans-2-allyl-8a-acetoxy-4a-(3-hydroxyphenyl)-6β-(benzyloxycarboxamido) decahydroisoquinoline, trans-2-allyl-8a-acetoxy-4a-(3-hydroxyphenyl)-6β-[N-methyl-[trans-β-(3-furyl)acrylamido]]decahydroisoquinoline, trans-2-allyl-8a-acetoxy-4a-(3-hydroxyphenyl)-6β-[N-methyl-[trans-β-(4-bromo-2-thienyl)acrylamido]]decahydroisoquinoline, trans-2-allyl-8a-acetoxy-4a-(3-hydroxyphenyl)-6β-[N-methyl-[trans-β-(2-methyl-3-furyl)acrylamido]] decahydroisoquinoline, trans-2-allyl-8a-acetoxy-4a-(3-hydroxyphenyl)-6β-[N-methyl-(3-methoxycinnnamamido)]decahydroisoquinoline, trans-2-allyl-8a-acetoxy-4a-(3-hydroxyphenyl)-6β-[N-methyl-(3-trifluoromethoxycinnnamamido)] decahydroisoquinoline, trans-2-allyl-8a-acetoxy-4a-(3-hydroxyphenyl)-6β-[N-methyl-(3-hydroxycinnnamamido)]decahydroisoquinoline, trans-2-allyl-8a-acetoxy-4a-(3-hydroxyphenyl)-6β-[N-methyl-(4-trifluoromethylphenylpropiolamido)] decahydroisoquinoline, trans-2-allyl-8a-acetoxy-4a-(3-hydroxyphenyl)-6β-[N-methyl-(3-methylphenylpropiolamido)]decahydroisoquinoline, trans-2-allyl-8a-acetoxy-4a-(3-hydroxyphenyl)-6β-[N-methyl-(3,4-dimethylphenylpropiolamido)] decahydroisoquinoline, trans-2-allyl-8a-acetoxy-4a-(3-hydroxyphenyl)-6β-[N-methyl-(benzyloxycarboxamido)] decahydroisoquinoline, trans-2-allyl-8a-methoxy-4a-(3-hydroxyphenyl)-6β-[trans-β-(3-furyl)acrylamido] decahydroisoquinoline, trans-2-allyl-8a-methoxy-4a-(3-hydroxyphenyl)-6β-[trans-β-(4-bromo-2-thienyl) acrylamido]decahydroisoquinoline, trans-2-allyl-8a-methoxy-4a-(3-hydroxyphenyl)-6β-[trans-β-(2-methyl-3-furyl)acrylamido]decahydroisoquinoline, trans-2-allyl-8a-methoxy-4a-(3-hydroxyphenyl)-6β-(3-methoxycinnnamamido)decahydroisoquinoline, trans-2-allyl-8a-methoxy-4a-(3-hydroxyphenyl)-6β-(3-trifluoromethoxycinnnamamido)decahydroisoquinoline, trans-2-allyl-8a-methoxy-4a-(3-hydroxyphenyl)-6β-(3- hydroxycinnnamamido)decahydroisoquinoline, trans-2-allyl-8a-methoxy-4a-(3-hydroxyphenyl)-6β-(4-trifluoromethylphenylpropiolamido)decahydroisoquinoline, trans-2-allyl-8a-methoxy-4a-(3-hydroxyphenyl)-6β-(3-methylphenylpropiolamido) decahydroisoquinoline, trans-2-allyl-8a-methoxy-4a-(3-hydroxyphenyl)-6β-(3,4-dimethylphenylpropiolamido) decahydroisoquinoline, trans-2-allyl-8a-methoxy-4a-(3-hydroxyphenyl)-6β-(benzyloxycarboxamido) decahydroisoquinoline, trans-2-allyl-8a-methoxy-4a-(3-hydroxyphenyl)-6β-[N-methyl-[trans-β-(3-furyl)acrylamido]]decahydroisoquinoline, trans-2-allyl-8a-methoxy-4a-(3-hydroxyphenyl)-6β-[N-methyl-[trans-β-(4-bromo-2-thienyl)acrylamido]]decahydroisoquinoline, trans-2-allyl-8a-methoxy-4a-(3-hydroxyphenyl)-6β-[N-methyl-[trans-β-(2-methyl-3-furyl)acrylamido]] decahydroisoquinoline, trans-2-allyl-8a-methoxy-4a-(3-hydroxyphenyl)-6β-[N-methyl-(3-methoxycinnnamamido)]decahydroisoquinoline, trans-2-allyl-8a-methoxy-4a-(3-hydroxyphenyl)-6β-[N-methyl-(3-trifluoromethoxycinnnamamido)] decahydroisoquinoline, trans-2-allyl-8a-methoxy-4a-(3-hydroxyphenyl)-6β-[N-methyl-(3-hydroxycinnnamamido)]decahydroisoquinoline, trans-2-allyl-8a-methoxy-4a-(3-hydroxyphenyl)-6β-[N-methyl-(4-trifluoromethylphenylpropiolamido)] decahydroisoquinoline, trans-2-allyl-8a-methoxy-4a-(3-hydroxyphenyl)-6β-[N-methyl-(3-methylphenylpropiolamido)]decahydroisoquinoline, trans-2-allyl-8a-methoxy-4a-(3-hydroxyphenyl)-6β-[N-methyl-(3,4-dimethylphenylpropiolamido)] decahydroisoquinoline, trans-2-allyl-8a-methoxy-4a-(3-hydroxyphenyl)-6β-[N-methyl-(benzyloxycarboxamido)] decahydroisoquinoline, trans-2-allyl-4a-(3-methoxyphenyl)-6β-[trans-β-(3-furyl)acrylamido] decahydroisoquinoline, trans-2-allyl-4a-(3-methoxyphenyl)-6β-[trans-β-(4-bromo-2-thienyl)acrylamido]decahydroisoquinoline, trans-2-allyl-4a-(3-methoxyphenyl)-6β-[trans-β-(2-methyl-3-furyl)acrylamido]decahydroisoquinoline, trans-2-allyl-4a-(3-methoxyphenyl)-6β-(3-methoxycinnnamamido) decahydroisoquinoline, trans-2-allyl-4a-(3-methoxyphenyl)-6β-(3-trifluoromethoxycinnnamamido) decahydroisoquinoline, trans-2-allyl-4a-(3-methoxyphenyl)-6β-(3-hydroxycinnnamamido) decahydroisoquinoline, trans-2-allyl-4a-(3-methoxyphenyl)-6β-(4-trifluoromethylphenylpropiolamido) decahydroisoquinoline, trans-2-allyl-4a-(3-methoxyphenyl)-6β-(3-methylphenylpropiolamido) decahydroisoquinoline, trans-2-allyl-4a-(3-methoxyphenyl)-6β-(3,4-dimethylphenylpropiolamido) decahydroisoquinoline, trans-2-allyl-4a-(3-methoxyphenyl)-6β-(benzyloxycarboxamido) decahydroisoquinoline, trans-2-allyl-4a-(3-methoxyphenyl)-6β-[N-methyl-[trans-β-(3-furyl)acrylamido]]decahydroisoquinoline, trans-2-allyl-4a-(3-methoxyphenyl)-6β-[N-methyl-[trans-β-(4-bromo-2-thienyl)acrylamido]]decahydroisoquinoline, trans-2-allyl-4a-(3-methoxyphenyl)-6β-[N-methyl-[trans-β-(2-methyl-3-furyl)acrylamido]]decahydroisoquinoline, trans-2-allyl-4a-(3-methoxyphenyl)-6β-[N-methyl-(3-methoxycinnnamamido)]decahydroisoquinoline, trans-2-allyl-4a-(3-methoxyphenyl)-6β-[N-methyl-(3-trifluoromethoxycinnnamamido)]decahydroisoquinoline, trans-2-allyl-4a-(3-methoxyphenyl)-6β-[N-methyl-(3-hydroxycinnnamamido)]decahydroisoquinoline, trans-2-allyl-4a-(3-methoxyphenyl)-6β-[N-methyl-(4-trifluoromethylphenylpropiolamido)]decahydroisoquinoline, trans-2-allyl-4a-(3-methoxyphenyl)-6β-[N-methyl-(3-methylphenylpropiolamido)]decahydroisoquinoline, trans-2-allyl-4a-(3-methoxyphenyl)-6β-[N-methyl-(3,4-dimethylphenylpropiolamido)]decahydroisoquinoline, trans-2-allyl-4a-(3-methoxyphenyl)-6β-[N-methyl-(benzyloxycarboxamido)]decahydroisoquinoline, trans-2-allyl-8a-hydroxy-4a-(3-methoxyphenyl)-6β-[trans-β-(3-furyl)acrylamido]decahydroisoquinoline, trans-2-allyl-8a-hydroxy-4a-(3-methoxyphenyl)-6β-[trans-β-(4-bromo-2-thienyl)acrylamido]decahydroisoquinoline, trans-2-allyl-8a-hydroxy-4a-(3-methoxyphenyl)-6β-[trans-β-(2-methyl-3-furyl)acrylamido] decahydroisoquinoline, trans-2-allyl-8a-hydroxy-4a-(3-methoxyphenyl)-6β-(3-methoxycinnnamamido) decahydroisoquinoline, trans-2-allyl-8a-hydroxy-4a-(3-methoxyphenyl)-6β-(3-trifluoromethoxycinnnamamido) decahydroisoquinoline, trans-2-allyl-8a-hydroxy-4a-(3-methoxyphenyl)-6β-(3-hydroxycinnnamamido) decahydroisoquinoline, trans-2-allyl-8a-hydroxy-4a-(3-methoxyphenyl)-6β-(4-trifluoromethylphenylpropiolamido) decahydroisoquinoline, trans-2-allyl-8a-hydroxy-4a-(3-methoxyphenyl)-6β-(3-methylphenylpropiolamido) decahydroisoquinoline, trans-2-allyl-8a-hydroxy-4a-(3-methoxyphenyl)-6β-(3,4-dimethylphenylpropiolamido) decahydroisoquinoline, trans-2-allyl-8a-hydroxy-4a-(3-methoxyphenyl)-6β-(benzyloxycarboxamido) decahydroisoquinoline, trans-2-allyl-8a-hydroxy-4a-(3-methoxyphenyl)-6β-[N-methyl-[trans-β-(3-furyl)acrylamido]]decahydroisoquinoline, trans-2-allyl-8a-hydroxy-4a-(3-methoxyphenyl)-6β-[N-methyl-[trans-β-(4-bromo-2-thienyl)acrylamido]]decahydroisoquinoline, trans-2-allyl-8a-hydroxy-4a-(3-methoxyphenyl)-6β-[N-methyl-[trans-β-(2-methyl-3-furyl)acrylamido]] decahydroisoquinoline, trans-2-allyl-8a-hydroxy-4a-(3-methoxyphenyl)-6β-[N-methyl-(3-methoxycinnnamamido)]decahydroisoquinoline, trans-2-allyl-8a-hydroxy-4a-(3-methoxyphenyl)-6β-[N-methyl-(3-trifluoromethoxycinnnamamido)] decahydroisoquinoline, trans-2-allyl-8a-hydroxy-4a-(3-methoxyphenyl)-6β-[N-methyl-(3-hydroxycinnnamamido)]decahydroisoquinoline, trans-2-allyl-8a-hydroxy-4a-(3-methoxyphenyl)-6β-[N-methyl-(4-trifluoromethylphenylpropiolamido)] decahydroisoquinoline, trans-2-allyl-8a-hydroxy-4a-(3-methoxyphenyl)-6β-[N-methyl-(3-methylphenylpropiolamido)]decahydroisoquinoline, trans-2-allyl-8a-hydroxy-4a-(3-methoxyphenyl)-6β-[N-methyl-(3,4-dimethylphenylpropiolamido)] decahydroisoquinoline, trans-2-allyl-8a-hydroxy-4a-(3-methoxyphenyl)-6β-[N-methyl-(benzyloxycarboxamido)]decahydroisoquinoline, trans-2-allyl-8a-acetoxy-4a-(3-methoxyphenyl)-6β-[trans-β-(3-furyl)acrylamido] decahydroisoquinoline, trans-2-allyl-8a-acetoxy-4a-(3-methoxyphenyl)-6β-[trans-β-(4-bromo-2-thienyl)acrylamido]decahydroisoquinoline, trans-2-allyl-8a-acetoxy-4a-(3-methoxyphenyl)-6β-[trans-β-(2-methyl-3-furyl)acrylamido]decahydroisoquinoline, trans-2-allyl-8a-acetoxy-4a-(3-methoxyphenyl)-6β-(3-methoxycinnnamamido)decahydroisoquinoline, trans-2-allyl-8a-acetoxy-4a-(3-methoxyphenyl)-6β-(3-trifluoromethoxycinnnamamido)decahydroisoquinoline, trans-2-allyl-8a-acetoxy-4a-(3-methoxyphenyl)-6β-(3-hydroxycinnnamamido)decahydroisoquinoline, trans-2- allyl-8a-acetoxy-4a-(3-methoxyphenyl)-6β-(4-trifluoromethylphenylpropiolamido)decahydroisoquinoline, trans-2-allyl-8a-acetoxy-4a-(3-methoxyphenyl)-6β-(3-methylphenylpropiolamido)decahydroisoquinoline, trans-2-allyl-8a-acetoxy-4a-(3-methoxyphenyl)-6β-(3,4-dimethylphenylpropiolamido)decahydroisoquinoline, trans-2-allyl-8a-acetoxy-4a-(3-methoxyphenyl)-6β-(benzyloxycarboxamido)decahydroisoquinoline, trans-2-allyl-8a-acetoxy-4a-(3-methoxyphenyl)-6β-[N-methyl-[trans-β-(3-furyl)acrylamido]]decahydroisoquinoline, trans-2-allyl-8a-acetoxy-4a-(3-methoxyphenyl)-6β-[N-methyl-[trans-β-(4-bromo-2-thienyl)acrylamido]]decahydroisoquinoline, trans-2-allyl-8a-acetoxy-4a-(3-methoxyphenyl)-6β-[N-methyl-[trans-β-(2-methyl-3-furyl)acrylamido]]decahydroisoquinoline, trans-2-allyl-8a-acetoxy-4a-(3-methoxyphenyl)-6β-[N-methyl-(3-methoxycinnnamamido)]decahydroisoquinoline, trans-2-allyl-8a-acetoxy-4a-(3-methoxyphenyl)-6β-[N-methyl-(3-trifluoromethoxycinnnamamido)]decahydroisoquinoline, trans-2-allyl-8a-acetoxy-4a-(3-methoxyphenyl)-6β-[N-methyl-(3-hydroxycinnnamamido)]decahydroisoquinoline, trans-2-allyl-8a-acetoxy-4a-(3-methoxyphenyl)-6β-[N-methyl-(4-trifluoromethylphenylpropiolamido)]decahydroisoquinoline, trans-2-allyl-8a-acetoxy-4a-(3-methoxyphenyl)-6β-[N-methyl-(3-methylphenylpropiolamido)]decahydroisoquinoline, trans-2-allyl-8a-acetoxy-4a-(3-methoxyphenyl)-6β-[N-methyl-(3,4-dimethylphenylpropiolamido)]decahydroisoquinoline, trans-2-allyl-8a-acetoxy-4a-(3-methoxyphenyl)-6β-[N-methyl-(benzyloxycarboxamido)]decahydroisoquinoline, trans-2-allyl-8a-methoxy-4a-(3-methoxyphenyl)-6β-[trans-β-(3-furyl)acrylamido]decahydroisoquinoline, trans-2-allyl-8a-methoxy-4a-(3-methoxyphenyl)-6β-[trans-β-(4-bromo-2-thienyl)acrylamido]decahydroisoquinoline, trans-2-allyl-8a-methoxy-4a-(3-methoxyphenyl)-6β-[trans-β-(2-methyl-3-furyl)acrylamido]decahydroisoquinoline, trans-2-allyl-8a-methoxy-4a-(3-methoxyphenyl)-6β-(3-methoxycinnnamamido)decahydroisoquinoline, trans-2-allyl-8a-methoxy-4a-(3-methoxyphenyl)-6β-(3-trifluoromethoxycinnnamamido)decahydroisoquinoline, trans-2-allyl-8a-methoxy-4a-(3-methoxyphenyl)-6β-(3-hydroxycinnnamamido)decahydroisoquinoline, trans-2-allyl-8a-methoxy-4a-(3-methoxyphenyl)-6β-(4-trifluoromethylphenylpropiolamido)decahydroisoquinoline, trans-2-allyl-8a-methoxy-4a-(3-methoxyphenyl)-6β-(3-methylphenylpropiolamido)decahydroisoquinoline, trans-2-allyl-8a-methoxy-4a-(3-methoxyphenyl)-6β-(3,4-dimethylphenylpropiolamido)decahydroisoquinoline, trans-2-allyl-8a-methoxy-4a-(3-methoxyphenyl)-6β-(benzyloxycarboxamido)decahydroisoquinoline, trans-2-allyl-8a-methoxy-4a-(3-methoxyphenyl)-6β-[N-methyl-[trans-β-(3-furyl)acrylamido]]decahydroisoquinoline, trans-2-allyl-8a-methoxy-4a-(3-methoxyphenyl)-6β-[N-methyl-[trans-β-(4-bromo-2-thienyl)acrylamido]]decahydroisoquinoline, trans-2-allyl-8a-methoxy-4a-(3-methoxyphenyl)-6β-[N-methyl-[trans-β-(2-methyl-3-furyl)acrylamido]]decahydroisoquinoline, trans-2-allyl-8a-methoxy-4a-(3-methoxyphenyl)-6β-[N-methyl-(3-methoxycinnnamamido)]decahydroisoquinoline, trans-2-allyl-8a-methoxy-4a-(3-methoxyphenyl)-6β-[N-methyl-(3-trifluoromethoxycinnnamamido)]decahydroisoquinoline, trans-2-allyl-8a-methoxy-4a-(3-methoxyphenyl)-6β-[N-methyl-(3-hydroxycinnnamamido)]decahydroisoquinoline, trans-2-allyl-8a-methoxy-4a-(3-methoxyphenyl)-6β-[N-methyl-(4-trifluoromethylphenylpropiolamido)]decahydroisoquinoline, trans-2-allyl-8a-methoxy-4a-(3-methoxyphenyl)-6β-[N-methyl-(3-methylphenylpropiolamido)]decahydroisoquinoline, trans-2-allyl-8a-methoxy-4a-(3-methoxyphenyl)-6β-[N-methyl-(3,4-dimethylphenylpropiolamido)]decahydroisoquinoline, trans-2-allyl-8a-methoxy-4a-(3-methoxyphenyl)-6β-[N-methyl-(benzyloxycarboxamido)]decahydroisoquinoline, trans-2-allyl-4a-(3-acetoxyphenyl)-6β-[trans-β-(3-furyl)acrylamido]decahydroisoquinoline, trans-2-allyl-4a-(3-acetoxyphenyl)-6β-[trans-β-(4-bromo-2-thienyl)acrylamido]decahydroisoquinoline, trans-2-allyl-4a-(3-acetoxyphenyl)-6β-[trans-β-(2-methyl-3-furyl)acrylamido]decahydroisoquinoline, trans-2-allyl-4a-(3-acetoxyphenyl)-6β-(3-methoxycinnnamamido)decahydroisoquinoline, trans-2-allyl-4a-(3-acetoxyphenyl)-6β-(3-trifluoromethoxycinnnamamido)decahydroisoquinoline, trans-2-allyl-4a-(3-acetoxyphenyl)-6β-(3-hydroxycinnnamamido)decahydroisoquinoline, trans-2-allyl-4a-(3-acetoxyphenyl)-6β-(4-trifluoromethylphenylpropiolamido)decahydroisoquinoline, trans-2-allyl-4a-(3-acetoxyphenyl)-6β-(3-methylphenylpropiolamido)decahydroisoquinoline, trans-2-allyl-4a-(3-acetoxyphenyl)-6β-(3,4-dimethylphenylpropiolamido)decahydroisoquinoline, trans-2-allyl-4a-(3-acetoxyphenyl)-6β-(benzyloxycarboxamido)decahydroisoquinoline, trans-2-allyl-4a-(3-acetoxyphenyl)-6β-[N-methyl-[trans-β-(3-furyl)acrylamido]]decahydroisoquinoline, trans-2-allyl-4a-(3-acetoxyphenyl)-6β-[N-methyl-[trans-β-(4-bromo-2-thienyl)acrylamido]]decahydroisoquinoline, trans-2-allyl-4a-(3-acetoxyphenyl)-6β-[N-methyl-[trans-β-(2-methyl-3-furyl)acrylamido]]decahydroisoquinoline, trans-2-allyl-4a-(3-acetoxyphenyl)-6β-[N-methyl-(3-methoxycinnnamamido)]decahydroisoquinoline, trans-2-allyl-4a-(3-acetoxyphenyl)-6β-[N-methyl-(3-trifluoromethoxycinnnamamido)]decahydroisoquinoline, trans-2-allyl-4a-(3-acetoxyphenyl)-6β-[N-methyl-(3-hydroxycinnnamamido)]decahydroisoquinoline, trans-2-allyl-4a-(3-acetoxyphenyl)-6β-[N-methyl-(4-trifluoromethylphenylpropiolamido)]decahydroisoquinoline, trans-2-allyl-4a-(3-acetoxyphenyl)-6β-[N-methyl-(3-methylphenylpropiolamido)]decahydroisoquinoline, trans-2-allyl-4a-(3-acetoxyphenyl)-6β-[N-methyl-(3,4-dimethylphenylpropiolamido)]decahydroisoquinoline, trans-2-allyl-4a-(3-acetoxyphenyl)-6β-[N-methyl-(benzyloxycarboxamido)]decahydroisoquinoline, trans-2-allyl-8a-hydroxy-4a-(3-acetoxyphenyl)-6β-[trans-β-(3-furyl)acrylamido]decahydroisoquinoline, trans-2-allyl-8a-hydroxy-4a-(3-acetoxyphenyl)-6β-[trans-β-(4-bromo-2-thienyl)acrylamido]decahydroisoquinoline, trans-2-allyl-8a-hydroxy-4a-(3-acetoxyphenyl)-6β-[trans-β-(2-methyl-3-furyl)acrylamido]decahydroisoquinoline, trans-2-allyl-8a-hydroxy-4a-(3-acetoxyphenyl)-6β-(3-methoxycinnnamamido)decahydroisoquinoline, trans-2-allyl-8a-hydroxy-4a-(3-acetoxyphenyl)-6β-(3-trifluoromethoxycinnnamamido)decahydroisoquinoline, trans-2-allyl-8a-hydroxy-4a-(3-acetoxyphenyl)-6β-(3-hydroxycinnnamamido)decahydroisoquinoline, trans-2-allyl-8a-hydroxy-4a-(3-acetoxyphenyl)-6β-(4-trifluoromethylphenylpropiolamido)

decahydroisoquinoline, trans-2-allyl-8a-hydroxy-4a-(3-acetoxyphenyl)-6β-(3-methylphenylpropiolamido) decahydroisoquinoline, trans-2-allyl-4a-hydroxy-4a-(3-acetoxyphenyl)-6β-(3,4-dimethylphenylpropiolamido) decahydroisoquinoline, trans-2-allyl-4a-hydroxy-4a-(3-acetoxyphenyl)-6β-(benzyloxycarboxamido) decahydroisoquinoline, trans-2-allyl-8a-hydroxy-4a-(3-acetoxyphenyl)-6β-[N-methyl-[trans-β-(3-furyl)acrylamido]]decahydroisoquinoline, trans-2-allyl-8a-hydroxy-4a-(3-acetoxyphenyl)-6β-[N-methyl-[trans-β-(4-bromo-2-thienyl)acrylamido]]decahydroisoquinoline, trans-2-allyl-8a-hydroxy-4a-(3-acetoxyphenyl)-6β-[N-methyl-[trans-β-(2-methyl-3-furyl)acrylamido]] decahydroisoquinoline, trans-2-allyl-8a-hydroxy-4a-(3-acetoxyphenyl)-6β-[N-methyl-(3-methoxycinnnamamido)]decahydroisoquinoline, trans-2-allyl-8a-hydroxy-4a-(3-acetoxyphenyl)-6β-[N-methyl-(3-trifluoromethoxycinnnamamido)] decahydroisoquinoline, trans-2-allyl-8a-hydroxy-4a-(3-acetoxyphenyl)-6β-[N-methyl-(3-hydroxycinnnamamido)]decahydroisoquinoline, trans-2-allyl-8a-hydroxy-4a-(3-acetoxyphenyl)-6β-[N-methyl-(4-trifluoromethylphenylpropiolamido)] decahydroisoquinoline, trans-2-allyl-8a-hydroxy-4a-(3-acetoxyphenyl)-6β-[N-methyl-(3-methylphenylpropiolamido)]decahydroisoquinoline, trans-2-allyl-8a-hydroxy-4a-(3-acetoxyphenyl)-6β-[N-methyl-(3,4-dimethylphenylpropiolamido)] decahydroisoquinoline, trans-2-allyl-8a-hydroxy-4a-(3-acetoxyphenyl)-6β-[N-methyl-(benzyloxycarboxamido)] decahydroisoquinoline, trans-2-allyl-8a-acetoxy-4a-(3-acetoxyphenyl)-6β-[trans-β-(3-furyl)acrylamido] decahydroisoquinoline, trans-2-allyl-8a-acetoxy-4a-(3-acetoxyphenyl)-6β-[trans-β-(4-bromo-2-thienyl)acrylamido]decahydroisoquinoline, trans-2-allyl-8a-acetoxy-4a-(3-acetoxyphenyl)-6β-[trans-β-(2-methyl-3-furyl)acrylamido]decahydroisoquinoline, trans-2-allyl-8a-acetoxy-4a-(3-acetoxyphenyl)-6β-(3-methoxycinnnamamido)decahydroisoquinoline, trans-2-allyl-8a-acetoxy-4a-(3-acetoxyphenyl)-6β-(3-trifluoromethoxycinnnamamido)decahydroisoquinoline, trans-2-allyl-8a-acetoxy-4a-(3-acetoxyphenyl)-6β-(3-hydroxycinnnamamido)decahydroisoquinoline, trans-2-allyl-8a-acetoxy-4a-(3-acetoxyphenyl)-6β-(4-trifluoromethylphenylpropiolamido) decahydroisoquinoline, trans-2-allyl-8a-acetoxy-4a-(3-acetoxyphenyl)-6β-(3-methylphenylpropiolamido) decahydroisoquinoline, trans-2-allyl-8a-acetoxy-4a-(3-acetoxyphenyl)-6β-(3,4-dimethylphenylpropiolamido) decahydroisoquinoline, trans-2-allyl-8a-acetoxy-4a-(3-acetoxyphenyl)-6β-(benzyloxycarboxamido) decahydroisoquinoline, trans-2-allyl-8a-acetoxy-4a-(3-acetoxyphenyl)-6β-[N-methyl-[trans-β-(3-furyl)acrylamido]]decahydroisoquinoline, trans-2-allyl-8a-acetoxy-4a-(3-acetoxyphenyl)-6β-[N-methyl-[trans-β-(4-bromo-2-thienyl)acrylamido]]decahydroisoquinoline, trans-2-allyl-8a-acetoxy-4a-(3-acetoxyphenyl)-6β-[N-methyl-[trans-β-(2-methyl-3-furyl)acrylamido]] decahydroisoquinoline, trans-2-allyl-8a-acetoxy-4a-(3-acetoxyphenyl)-6β-[N-methyl-(3-methoxycinnnamamido)]decahydroisoquinoline, trans-2-allyl-8a-acetoxy-4a-(3-acetoxyphenyl)-6β-[N-methyl-(3-trifluoromethoxycinnnamamido)] decahydroisoquinoline, trans-2-allyl-8a-acetoxy-4a-(3-acetoxyphenyl)-6β-[N-methyl-(3-hydroxycinnnamamido)]decahydroisoquinoline, trans-2-allyl-8a-acetoxy-4a-(3-acetoxyphenyl)-6β-[N-methyl-(4-trifluoromethylphenylpropiolamido)] decahydroisoquinoline, trans-2-allyl-8a-acetoxy-4a-(3-acetoxyphenyl)-6β-[N-methyl-(3-methylphenylpropiolamido)]decahydroisoquinoline, trans-2-allyl-8a-acetoxy-4a-(3-acetoxyphenyl)-6β-[N-methyl-(3,4-dimethylphenylpropiolamido)] decahydroisoquinoline, trans-2-allyl-8a-methoxy-4a-(3-acetoxyphenyl)-6β-[N-methyl-(benzyloxycarboxamido)] decahydroisoquinoline, but the present invention is not limited to these compounds. The compounds incorporated in the present invention includes (+), (−), and (+) isomers of these.

In practice, compounds of general formula (I) incorporated in the present invention can be obtained by the following methods:

Among the compounds of general formula (I) incorporated in the present invention, those in which A is —XC(=Y)—, —XC(=Y)Z—, or $XSO_2$— (wherein X is $NR^4$ or O, Y is O or S, Z is O or NH, and $R^4$ is as defined above) can be practically obtained by the following method:

CHART 1

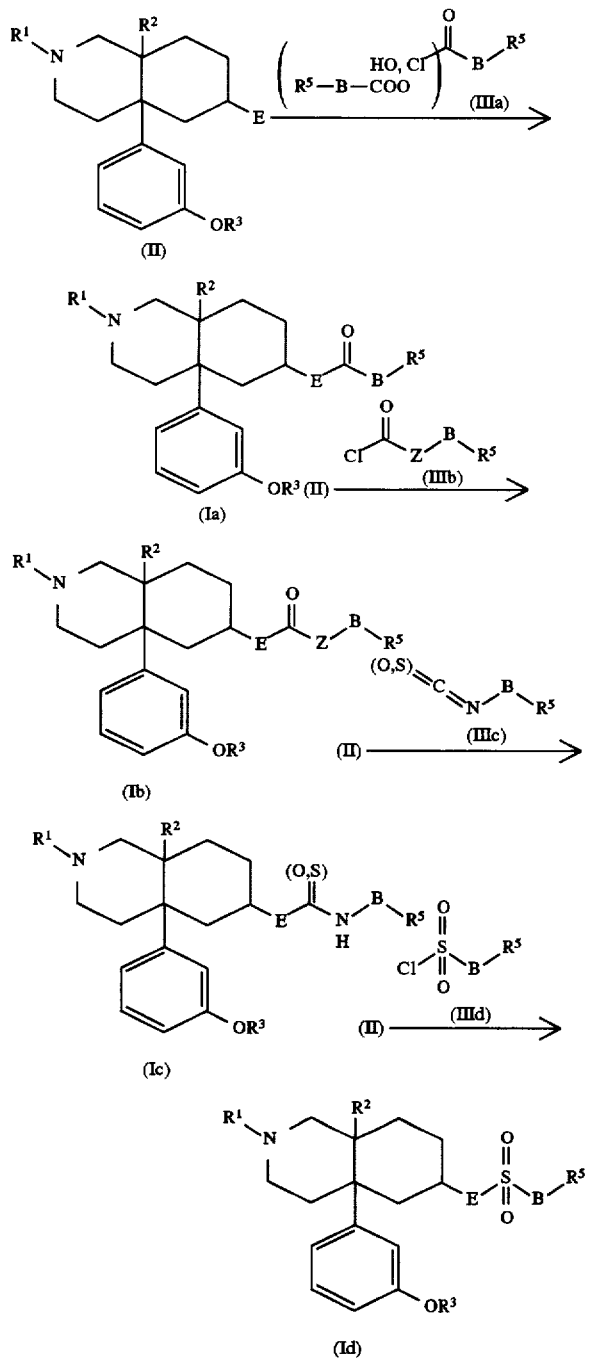

In general, such compounds can be obtained by condensation of a 6-amino body or a 6-hydroxy body, both of which have a general formula (II) (wherein $R^1$, $R^2$ and $R^3$ are as defined above; and E is $NHR^4$ ($R^4$ is as defined above) or OH), with a carboxylic acid derivative having a general formula (IIIa) (wherein B and $R^5$ are as defined above), a formic acid derivative having a general formula (IIIb) (wherein Z, B and $R^5$ are as defined above), an isocyanic acid or an isothiocyanic acid derivative having a general formula (IIIc) (wherein B and $R^5$ are as defined above), or with a sulfonic acid derivative having a general formula (IIId) (wherein B and $R^5$ are as defined above), as is shown in Chart 1.

In practice, the 6-amino body used for the above condensation can be obtained by the following step:

CHART 2

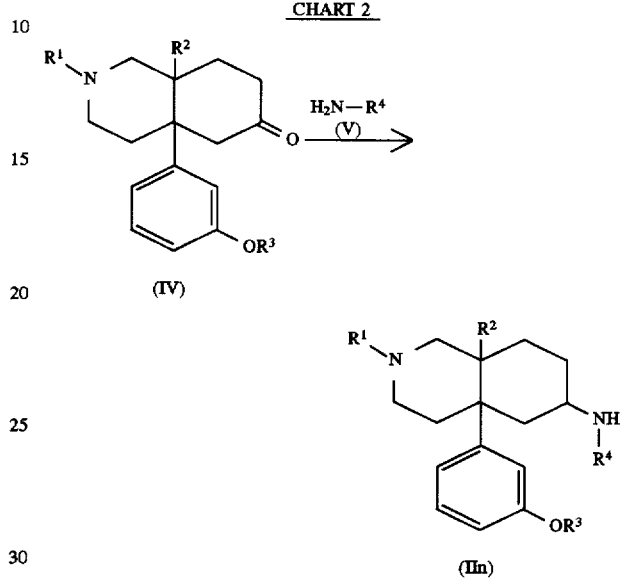

As is shown in Chart 2, the 6-amino body having a general formula (IIn) (wherein $R^1$, $R^2$ and $R^3$ are as defined above; and $R^4$ is as defined above, except for exclusion of hydrogen) can be obtained by mixing a 6-keto body having a general formula (IV) (wherein $R^1$, $R^2$ and $R^3$ are as defined above) and a primary amine having a general formula (V) (wherein $R^4$ is as defined above, except for exclusion of hydrogen) in a solvent, followed by hydrogenation in the presence of an appropriate amount of an acid and a metal catalyst or reduction using a metal hydride reductant in the presence of an acid.

Among the 6-amino bodies having the general formula (IIn) shown in Chart 2, a trans-6α-amino body having a general formula (IIt α) (wherein $R^1$, $R^2$ and $R^3$ are as defined above; and $R^4$ is as defined above, except for exclusion of hydrogen), in which the ring juncture positions of the decahydroisoquinoline skeleton are fused in a trans form and stereochemistry of the 6-position is α, or a trans-6β-amino body of general formula (IIt β) (wherein $R^1$, $R^2$ and $R^3$ are as defined above; and $R^4$ is as defined above, except for exclusion of hydrogen), in which the the ring juncture positions of the decahydroisoquinoline skeleton are fused in a trans form and stereochemistry of the 6-position is β can be similarly obtained by using a trans-6-keto body [disclosed in Japanese Unexamined Patent Publication Nos. 4-275288, 4-297458, 5-155857, and the like] having a general formula (IVt) (wherein $R^1$, $R^2$ and $R^3$ are as defined above) in which the ring juncture positions of the decahydroisoquinoline skeleton are fused in a trans form, and a primary amine having the general formula (V), as is shown in Chart 3.

CHART 3

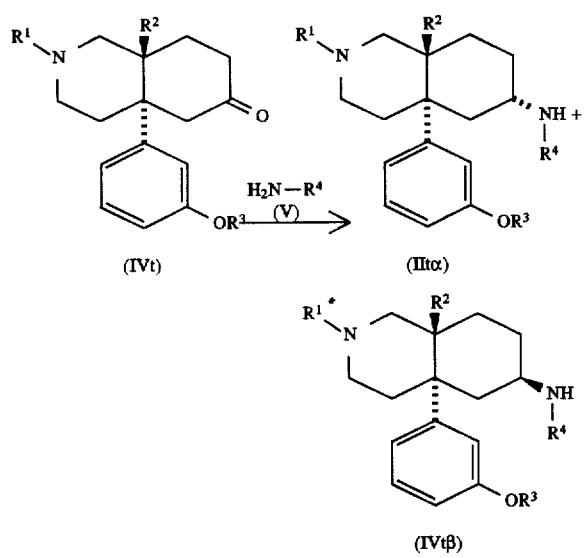

Among the above methods, hydrogenation or reduction by sodium triacetoxyborohydride is preferred for highly selectively obtaining a trans-6α-amino body having the general formula (IIt α). However, reduction by other metal hydride reductants is advantageous in that the a body having the general formula (IIt α) and the β body having the general formula (IIt β) can be occasionally obtained at the same time and the desired stereoisomer compound can be obtained using general isolation and purification methods, although the ratio of the resulting isomers varies according to the substrate. This method is also useful when a substrate used for obtaining an amino body has a functional group, such as olefin, that is reactive under hydrogenation conditions.

In the case of reduction by hydrogenation, the amine is used in an amount of 1 to 30 equivalents, preferably 1 to 10 equivalents. Any solvent, for example, an alcohol such as methanol or ethanol, an ether such as THF, ether, DME, or dioxane, or an aromatic hydrocarbon such as benzene or toluene can be used as the reaction solvent, as long as it is inactive under hydrogenation conditions; and among these, an alcohol is preferable and methanol is particularly preferable. Any acid, for example, an inorganic acid such as hydrochloric acid, hydrobromic acid, sulfuric acid, or phosphoric acid, a sulfonic acid such as methanesulfonic acid, benzenesulfonic acid, or p-toluenesulfonic acid, or an organic carboxylic acid such as benzoic acid, acetic acid, or oxalic acid, can be used as the coexisting acid, so far as it generally forms a salt with an amine; and among these, hydrochloric acid, sulfuric acid, acetic acid, and methanesulfonic acid are preferable and, in general, satisfactory results can be obtained by using hydrochloric acid in an amount of 1 equivalent less than the total amount of a base. These acids may be added to the reaction system by making a salt with the substrate or the reagent beforehand. In some cases, the reaction can be conducted without using any of these acids. Although, any catalyst which is used for general hydrogenation, for example, a platinum catalyst such as platinum oxide or platinum hydroxide, a palladium catalyst such as palladium hydroxide or palladium-carbon, or a nickel catalyst such as Raney nickel, can be employed as the metal catalyst, a platinum catalyst, in particular platinum oxide, is preferable. The reaction temperature is −30° C. to 80° C. and preferably −10° C. to 50° C.; the hydrogen pressure is 1 to 100 atm and preferably 1 to 30 atm; and in general, satisfactory results can be obtained at room temperature and atmospheric pressure.

When reduction is conducted using a metal hydride, the amine is used in an amount of 1 to 30 equivalents and, preferably, 1 to 15 equivalents. As the solvent, an alcohol such as methanol or ethanol, an ether such as THF, ether, DME, or dioxane, an aromatic hydrocarbon such as benzene or toluene, or halogen such as dichloromethane or 1,2-dichloroethane can be used; and among these, an alcohol is preferable and methanol is particularly preferable. THF, dichloroethane, and the like are preferably used when using a certain kind of reductants. Any acid, for example, an inorganic acid such as hydrochloric acid, hydrobromic acid, sulfuric acid, or phosphoric acid, a sulfonic acid such as methanesulfonic acid, or p-toluenesulfonic acid, or an organic acid such as benzoic acid, acetic acid, or oxalic acid, can be used, so far as it generally forms a salt with an amine; and among these, hydrochloric acid, sulfuric acid, acetic acid, and methanesulfonic acid are preferable. Furthermore, these acids may be added to the reaction system by making a salt with the substrate or reagent beforehand. In some cases, the reaction can be conducted without using any of these acids. The reaction can be carried out using a metal hydride reductant relatively stable even when being with an acid, and examples of the reductant are sodium borohydride, sodium cyanoborohydride, zinc borohydride, sodium triacetoxyborohydride, tetramethylammonium triacetoxyborohydride, and borane-pyridine. In particular, sodium cyanoborohydride in methanol and sodium triacetoxyborohydride in THF or dichloroethane are preferable. Although the reaction temperature is −30° C. to 100° C. and preferably −10° C. to 50° C., satisfactory results can be generally obtained at room temperature.

Among trans-6β-amino bodies of general formula (IIt β), a trans-6β-amino body of general formula (IIth β) (wherein $R^1$, $R^2$ and $R^3$ are as defined above) in which $R^4$ is hydrogen can be obtained in a further stereoselective way from a trans-6-keto body having the general formula (IVt) (wherein $R^1$, $R^2$ and $R^3$ are as defined above) by the steps shown in Chart 4.

CHART 4

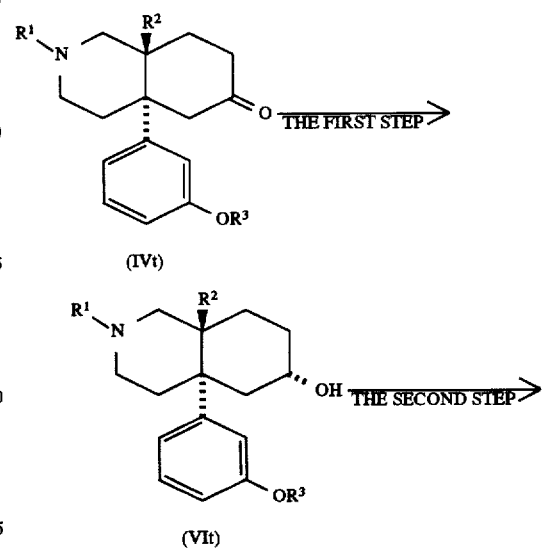

-continued
CHART 4

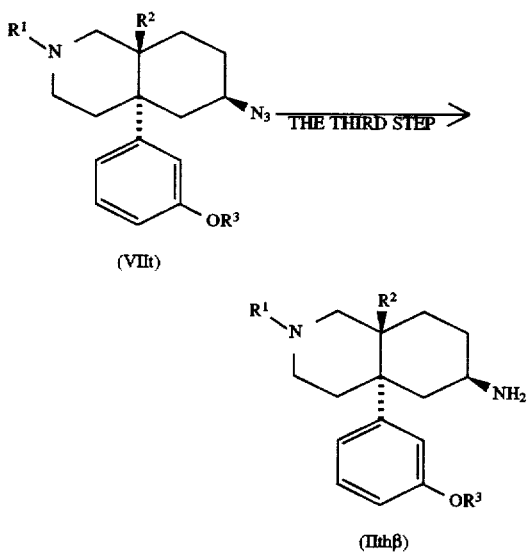

In the first step, the ketone moiety of a trans-6-keto body of general formula (IVt) (wherein $R^1$ and $R^2$ are as defined above; and $R^3$ is as defined above or trisubstituted silyl) is converted into a trans-6α-hydroxy body of general formula (VIt) (wherein $R^1$, $R^2$ and $R^3$ are as defined above) by reduction using a metal hydride reductant or reduction by hydrogenation under the presence of an acid and a metal catalyst. Although sodium borohydride, sodium cyanoborohydride, zinc borohydride, sodium triacetoxyborohydride, L-Selectride, and lithium aluminum hydride can be used as the metal hydride reductant, satisfactory results can be obtained by sodium borohydride. As the solvent, an alcohol such as methanol or ethanol, or an ether such as THF, ether, DME, or dioxane can be used; and an alcohol, in particular methanol, is preferable. In the case of hydrogenation, as the solvent, an alcohol such as methanol or ethanol, or an ether such as THF, ether, or dioxane is preferable; and an alcohol, in particular methanol, is preferable. As the coexisting acid, an inorganic acid such as hydrochloric acid, hydrobromic acid, sulfuric acid, or phosphoric acid, a sulfonic acid such as methanesulfonic acid or p-toluenesulfonic acid, or an organic acid such as benzoic acid, acetic acid, or oxalic acid, can be used; and hydrochloric acid and acetic acid are particularly preferable. Although, any metal catalyst used for general hydrogenation, for example, a platinum catalyst such as platinum oxide or platinum hydroxide, a palladium catalyst such as palladium hydroxide or palladium-carbon, or a nickel catalyst such as Raney nickel, can be used as the metal catalyst, a platinum catalyst, in particular platinum oxide, is preferable. The reaction temperature is –30° C. to 80° C. and preferably –10° C. to 50° C.; the hydrogen pressure is 1 to 100 atm and preferably 1 to 30 atm; and in general, satisfactory results can be obtained at room temperature and atmospheric pressure.

In the second step, the trans-6α-hydroxy body of general formula (VIt) is converted into a trans-6β-azide body of general formula (VIIt) (wherein $R^1$, $R^2$ and $R^3$ are as defined above) by substituting the hydroxy group of the trans-6α-hydroxy body by an azide group with inversion of stereochemistry. According to a method of direct reaction of the trans-6α-hydroxy body, a hydrogen azide is employed and a combination of an azodicarboxylate and triphenylphosphine is used as an activator [O. Mitsunobu, Synthesis, 1 (1981)]. In this case, a hydrocarbon such as benzene or toluene is preferably used as the reaction solvent, and a diethyl azodicarboxylate or a diisopropyl azodicarboxylate is preferably used as an azodicarboxylate. Moreover, the substitution can be conducted more readily by converting the hydroxy group to a leaving group such as a sulfonate ester, etc. according to a conventional method before reacting with a metal azide. Preferred leaving groups are methanesulfonate, benzenesulfonate, and p-toluenesulfonate in this case. In general, highly polar solvents are preferable, and DMF, DMSO, HMPA, acetone, water, and mixtures thereof are particularly preferable. Lithium azide and sodium azide are most preferable as the metal azide. In some cases, a reaction additive such as ammonium chloride or trimethylsilyl chloride is preferably added. Although the reaction temperature is 0° C. to 200° C. and preferably 40° C. to 150° C., the reaction can be conducted at a reflux temperature in a simple way.

In the third step, the azide moiety of the trans-6β-azide body of general formula (VIIt) (wherein $R^1$, $R^2$ and $R^3$ are as defined above) is converted into a trans-6β-amino body of general formula (IIthβ) (wherein $R^1$, $R^2$ and $R^3$ are as defined above) by reduction using a metal hydride reductant or reduction by hydrogenation in the presence of an acid and a metal catalyst. Although sodium borohydride, sodium cyanoborohydride, zinc borohydride, sodium triacetoxyborohydride, L-Selectride, and lithium aluminum hydride can be used as the metal hydride reductant, satisfactory results can be obtained using sodium borohydride. An alcohol such as methanol or ethanol, or an ether such as THF, ether, DME, or dioxane can be used as the solvent; and an alcohol, in particular methanol, is preferable. In the case of hydrogenation, an alcohol such as methanol or ethanol, or an ether such as THF, ether, or dioxane is preferably used as the reaction solvent; and an alcohol, in particular methanol, is preferable. The coexisting acid includes inorganic acids such as hydrochloric acid, hydrobromic acid, sulfuric acid, and phosphoric acid, sulfonic acids such as methanesulfonic acid and p-toluenesulfonic acid, and organic acids such as benzoic acid, acetic acid, and oxalic acid; and hydrochloric acid and acetic acid are preferable among these. Although, any metal catalyst used for general hydrogenation, for example, a platinum catalyst such as platinum oxide or platinum hydroxide, a palladium catalyst such as palladium hydroxide or palladium-carbon, or a nickel catalyst such as Raney nickel, can be used as the metal catalyst, a platinum catalyst, in particular platinum oxide, is preferable. The reaction temperature is –30° C. to 80° C. and preferably –10° C. to 50° C.; the hydrogen pressure is 1 to 100 atm and preferably 1 to 30 atm; and in general, satisfactory results can be obtained at room temperature and atmospheric pressure.

When a trans-6-keto body is used, that is included in the trans-6-keto bodies having the general formula (IVt) and that has a general formula (IVtp) (wherein $R^1$, $R^2$ and $R^3$ are as defined above) in which $R^3$ is hydrogen, as is shown in Chart 5, it is occasionally preferable to convert the trans-6-keto body into another trans-6-keto body having a general formula (IVtg) (wherein $R^1$ and $R^2$ are as defined above; and G is trisubstituted silyl group) in which G is introduced to protect the active hydrogen in the phenolic hydroxy group before subjecting the trans-6-keto body to the steps shown in Chart 4.

G can be introduced by a reaction with silyl chloride in the presence of a base. Trimethylsilyl chloride, triphenylsilyl chloride, t-butyldimethylsilyl chloride, and diphenylmethylsilyl chloride can be used as the silyl chloride, and t-butyldimethylsilyl chloride is preferable. The base used for the reaction includes tertiary amines such as triethylamine, diisopropylethylamine, and Proton Sponge, pyridine, dimethylaminopyridine, and imidazole; and among these, imidazole is preferable. Although the reaction solvent includes halocarbons such as dichloromethane, chloroform, carbon tetrachloride, and 1,2-dichloroethane, ethers such as ether, THF, DME, and dioxane, and pyridine; DMF and dichloromethane are preferable. The reaction can be conducted at a temperature ranging from −80° C. to 100° C. and, in particular, satisfactory results can be obtained from 0° C. to the vicinity of room temperature.

CHART 5

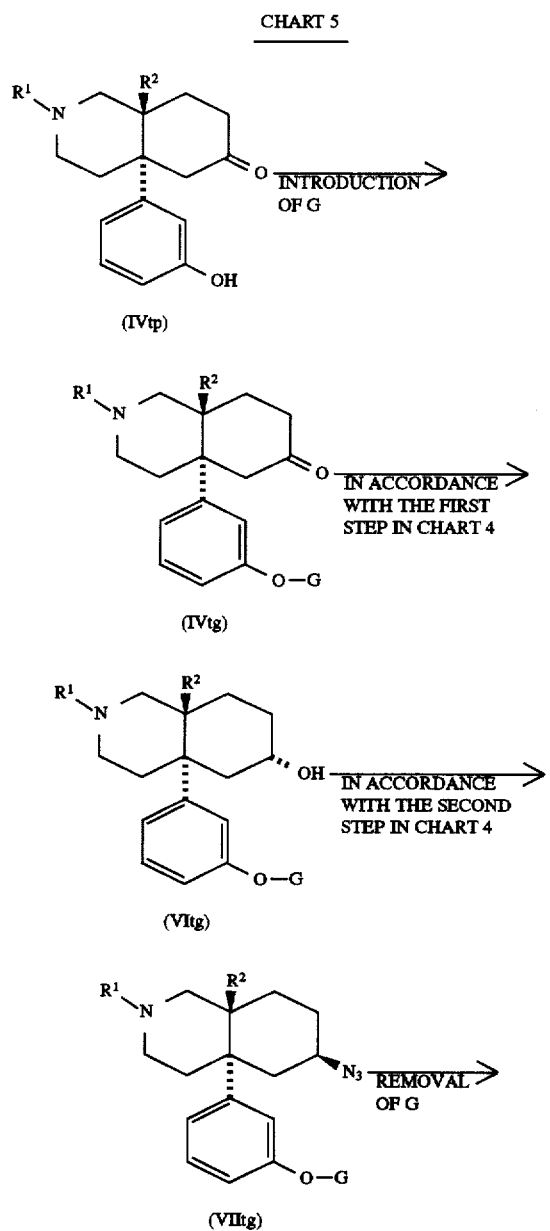

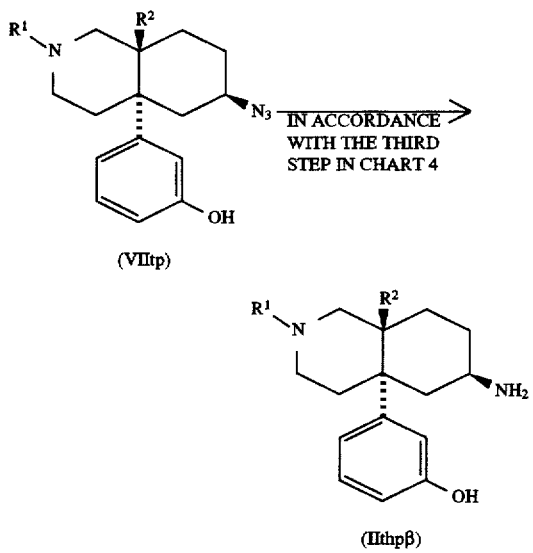

The following reduction process of the trans-6-keto body having the general formula (IVtg) (wherein $R^1$ and $R^2$ are as defined above; and G is a trisubstituted silyl group) to a trans-6β-hydroxy body having a general formula (VItg) (wherein $R^1$ and $R^2$ are as defined above; and G is a trisubstituted silyl group) and the introduction process of an azide group into a trans-6β-azide body having a general formula (VIItg) (wherein $R^1$ and $R^2$ are as defined above; and G is trisubstituted silyl group) can be carried out according to the first and second steps shown in Chart 4, respectively.

The step for converting a trans-6β-azide body having the general formula (VIItg) (wherein $R^1$ and $R^2$ are as defined above; and G is a trisubstituted silyl group) into another trans-6β-azide body having a general formula (VIItp) (wherein $R^1$ and $R^2$ are as defined above) by removing the protective trisubstituted silyl group G can be conducted according to a conventional method. In general, an acid such as hydrochloric acid, sulfuric acid, acetic acid, or hydrofluoric acid; a quaternary ammonium salt such as tetrabutylammonium fluoride, tetrabutylammonium chloride, and pyridinium hydrofluoride; or a base such as sodium hydroxide, potassium hydroxide, and potassium carbonate are used for the conversion. However, in general, the conversion can be sufficiently conducted by using 1 to 20 equivalents, in particular 1 to 5 equivalents, of hydrochloric acid or tetrabutylammonium fluoride. Ethers such as THF, ether, DME, and dioxane, halocarbons such as dichloromethane and chloroform, acetonitrile, and the like are used as the reaction solvent; and THF is preferable among these. The reaction can be conducted at a temperature ranging from −20° C. to 100° C. and, in general, satisfactory results can be obtained at room temperature.

The above step is followed by a conversion step of the trans-6β-azide body having a general formula (VIItp) (wherein $R^1$ and $R^2$ are as defined above) to a trans-6β-amino body having a general formula (IIthp β) (wherein $R^1$ and $R^2$ are as defined above) by reducing the azide moiety of the trans-6β-azide body. This step can be conducted according to the third step shown in Chart 4.

Among compounds having the corresponding general formulae (Ia), (Ib), (Ic), and (Id) shown in Chart 1, in each of which formulae E is $NR^4$, a compound having a general formula (Ina) (wherein $R^1$, $R^2$, $R^3$, $R^4$, $R^5$ and B are as defined above), a compound having a general formula (Inb) (wherein $R^1$, $R^2$, $R^3$, $R^4$, $R^5$, B and Z are as defined above), a compound having a general formula (Inc) (wherein $R^1$, $R^2$, $R^3$, $R^4$, $R^5$ and B are as defined above), and a compound having a general formula (Ind) (wherein $R^1$, $R^2$, $R^3$, $R^4$, $R^5$ and B are as defined above) can be obtained by condensation of a 6-amino body which has the general formula (IIn) (wherein $R^1$, $R^2$, $R^3$, and $R^4$ are as defined above) and which is obtained by the method shown in Chart 2 with: a carboxylic acid or a derivative thereof having a general formula (IIIa) (wherein B and $R^5$ are as defined above); a formic acid derivative having a general formula (IIIb) (wherein Z, B and $R^5$ are as defined above); an isocyanic acid or isothiocyanic acid derivative having a general formula (IIIc) (wherein B and $R^5$ are as defined above); a sulfonic acid derivative having a general formula (IIId) (wherein B and $R^5$ are as defined above); or the like.

CHART 6

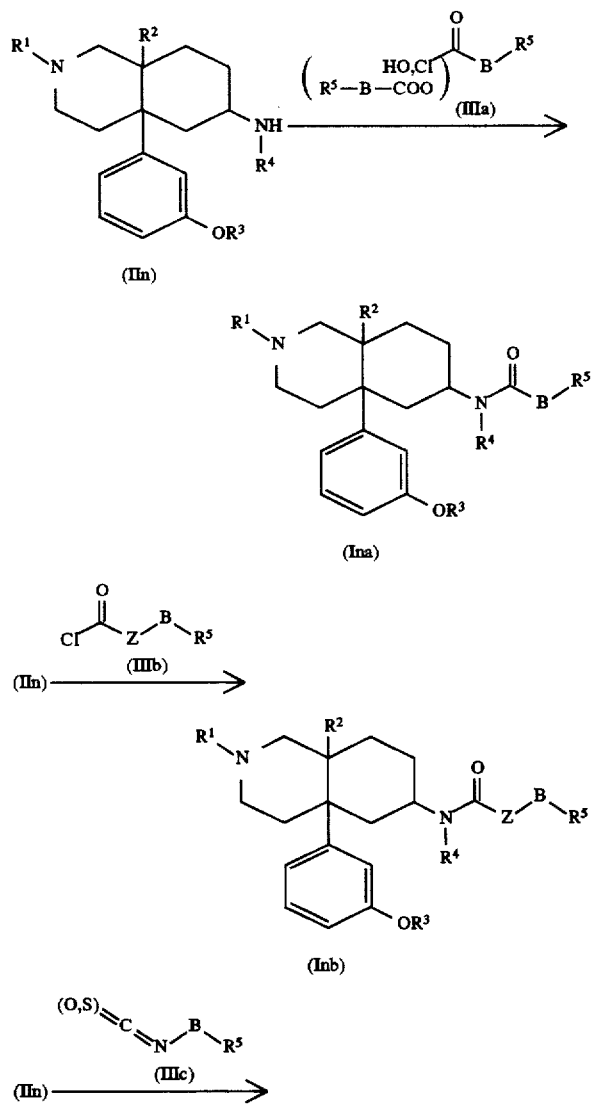

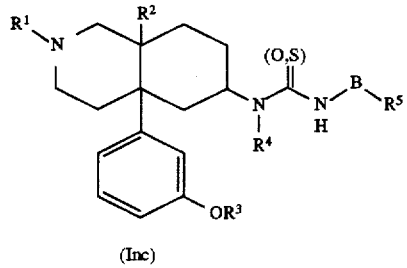

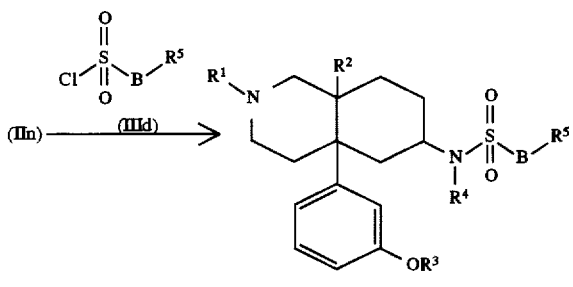

Condensation with a carboxylic acid derivative (IIIa) can be conducted by subjecting the 6-amino body (IIn) to a reaction with the corresponding acid chloride or acid anhydride in the presence of a base or a reaction with a carboxylic acid per se using N,N'-dichlorohexylcarbodiimide (hereinafter referred to as DCC), 1,1'-carbonyldiimidazole, bis-(2-oxo-3-oxazolidinyl)phosphinic chloride (hereinafter referred to as BOPCl), or the like. The acid chloride and acid anhydride are each used in an amount of 1 to 20 equivalents and, preferably, 1 to 5 equivalents. The solvent used for the above reaction includes halocarbons such as dichloromethane, chloroform, carbon tetrachloride, and 1,2-dichloroethane, ethers such as ether, THF, DME, and dioxane, pyridine, water, and mixtures thereof; and dichloromethane, chloroform, and a THF-water mixture are preferable when an acid chloride is used, and pyridine is preferably employed as both a base and a solvent when an acid anhydride is used. The base employed for the reaction includes tertiary amines such as triethylamine, diisopropylethylamine, and Proton Sponge, organic bases such as pyridine, dimethylaminopyridine, and imidazole, and inorganic bases such as potassium carbonate, sodium carbonate, sodium hydrogencarbonate, sodium hydroxide, and potassium hydroxide; and, in general, satisfactory results can be obtained by using 1 to 20 equivalents, preferably 1 to 5 equivalents, of triethylamine when the solvent is chloroform, and by using 1 to 20 equivalents, preferably 1 to 5 equivalents, of potassium carbonate, sodium carbonate, or sodium hydrogencarbonate when the solvent is a THF-water mixture. The reaction can be conducted at a temperature ranging from −80° C. to 100° C. and, in particular, satisfactory results can be obtained from 0° C. to the vicinity of room temperature. DCC, as a condensing agent, is used in an amount of 1 to 20 equivalents, preferably 1 to 5 equivalents; and the solvent used for the reaction includes halocarbons such as dichloromethane, chloroform, carbon tetrachloride, and 1,2-dichloroethane, ethers such as ether, THF, DME, and dioxane; and dichloromethane and chloroform are preferable among these. The coexisting base used for the reaction includes tertiary amines such as triethylamine, diisopropylethylamine, and Proton Sponge, organic bases such as pyridine, dimethylaminopyridine, and imidazole; and 0.01 to 2 equivalents of dimethylaminopyridine is particularly preferable. The reaction can be conducted at a temperature ranging from −80° C. to 100° C. and, in particular, satisfactory results can be obtained from 0° C. to the vicinity of room temperature. 1,1'-carbonyldiimidazole, as a condensing agent, is used in an amount of 1 to 20 equivalents, preferably 1 to 5 equivalents; and the solvent used for the reaction includes ethers such as ether, THF, DME, and dioxane, and halocarbons such as dichloromethane, chloroform, carbon tetrachloride, and 1,2-dichloroethane; and THF is particularly preferable. The reaction can be conducted at a temperature ranging from −20° C. to 120° C. and, in particular, from the vicinity of room temperature to 100° C. is preferable. BOPCl, as a condensing agent, is used in an amount of 1 to 20 equivalents, preferably 1 to 5 equivalents; and the solvent used for the reaction includes halocarbons such as dichloromethane, chloroform, carbon tetrachloride, and 1,2-dichloroethane, ethers such as ether, THF, DME, and dioxane with dichloromethane and chloroform being preferred. The coexisting base used for the reaction includes tertiary amines such as triethylamine, diisopropylethylamine, Proton Sponge, and N-ethylpiperidine, and organic bases such as pyridine, dimethylaminopyridine, and imidazole; and 1 to 20 equivalents, preferably 1 to 5 equivalents, of N-ethylpiperidine is particularly preferable. The reaction can be conducted at a temperature ranging from −80° C. to 100° C. and, in particular, satisfactory results can be obtained at 0° C. to 50° C.

Condensation with a formic acid derivative (IIIb) can be carried out by subjecting the 6-amino body (IIn) to a reaction with 1 to 20 equivalents, preferably 1 to 5 equivalents, of the corresponding acid chloride in the presence of a base. The solvent used for the reaction includes halocarbons such as dichloromethane, chloroform, carbon tetrachloride, and 1,2-dichloroethane, ethers such as ether, THF, DME, and dioxane, pyridine, water, and mixtures thereof; and chloroform and a THF-water mixture are preferable. The base used for the reaction includes: tertiary amines such as triethylamine, diisopropylethylamine, and Proton Sponge; organic bases such as pyridine, dimethylaminopyridine, and imidazole; and inorganic bases such as potassium carbonate, sodium carbonate, and sodium hydrogencarbonate. In general, satisfactory results can be obtained by using 1 to 20 equivalents, preferably 1 to 5 equivalents, of triethylamine when the solvent is chloroform, and by using 1 to 20 equivalents, preferably 1 to 5 equivalents, of potassium carbonate, sodium carbonate, or sodium hydrogencarbonate when the solvent is a THF-water mixture. The reaction can be conducted at a temperature ranging from −80° C. to 100° C. and, in particular, satisfactory results can be obtained from 0° C. to the vicinity of room temperature.

Condensation with an isocyanic acid or an isothiocyanic acid derivative (IIIb) can be carried out by subjecting the 6-amino body (IIn) to a reaction with 1 to 20 equivalents, preferably 1 to 5 equivalents, of the corresponding isocyanate in the presence of a base. The solvent used for the reaction includes halocarbons such as dichloromethane, chloroform, carbon tetrachloride, and 1,2-dichloroethane, and ethers such as ether, THF, DME, and dioxane; and chloroform is preferable among these. The reaction can be conducted at a temperature ranging from −80° C. to 100° C. and, in particular, satisfactory results can be obtained from 0° C. to the vicinity of room temperature.

Condensation with a sulfonic acid derivative (IIId) can be carried out by subjecting the 6-amino body (IIn) to a reaction with 1 to 20 equivalents, preferably 1 to 5 equivalents, of the corresponding sulfonyl chloride in the presence of a base. The base used for the reaction includes tertiary amines such as triethylamine, disopropylethylamine, and Proton Sponge, pyridine, dimethylaminopyridine, and imidazole; the solvent used for the reaction includes halocarbons such as dichloromethane, chloroform, carbon tetrachloride, and 1,2-dichloroethane, ethers such as ether, THF, DME, and dioxane, and pyridine; and pyridine is preferably used as both a base and a solvent. The reaction can be conducted at a temperature ranging from −80° C. to 100° C. and, in particular, satisfactory results can be obtained from 0° C. to the vicinity of room temperature.

If a 6-amino body, that is included in those having the general formula (IIn) in which $R^3$ is hydrogen and that has a general formula (IInp) (wherein $R^1$, $R^2$, and $R^4$ are as defined above), is used in the steps shown in Chart 6, the phenolic hydroxy group of the 6-amino body occasionally reacts with a carboxylic acid derivative of general formula (IIIa), a formic acid derivative of general formula (IIIb), and an isocyanic acid or isothiocyanic acid derivative of general formula (IIIc) to give a compound having the corresponding general formulae (VIIIna), (VIIInb), and (VIIInc) (wherein $R^1$, $R^2$, $R^4$, $R^5$, B, and Z are as defined above) shown in Charts 7 to 9; therefore, after conducting the first step in a similar manner to that shown in Chart 6, an alkali treatment is carried out as the second step to obtain the target compounds of general formulae (Inap), (Inbp), and (Incp) (wherein $R^1$, $R^2$, $R^4$, $R^5$, B, and Z are as defined above).

CHART 7

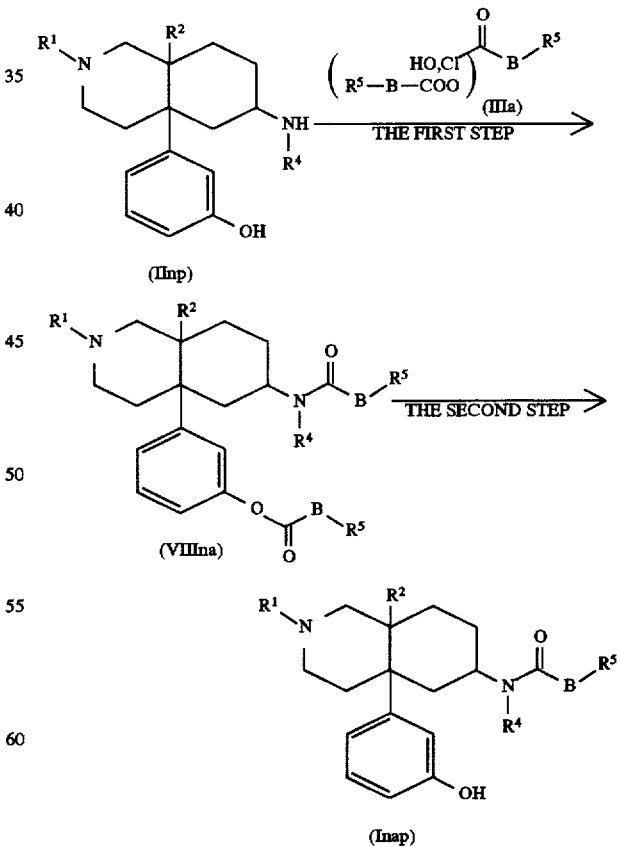

CHART 8

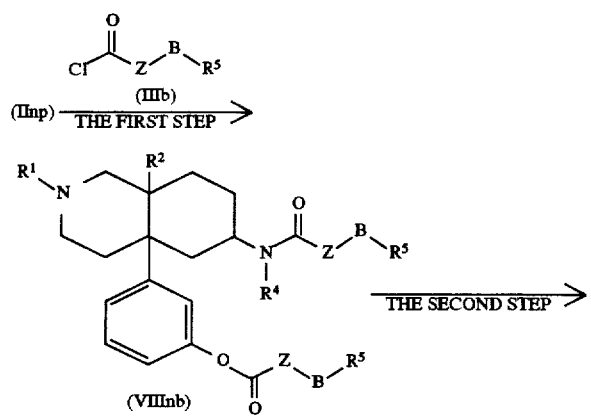

CHART 9

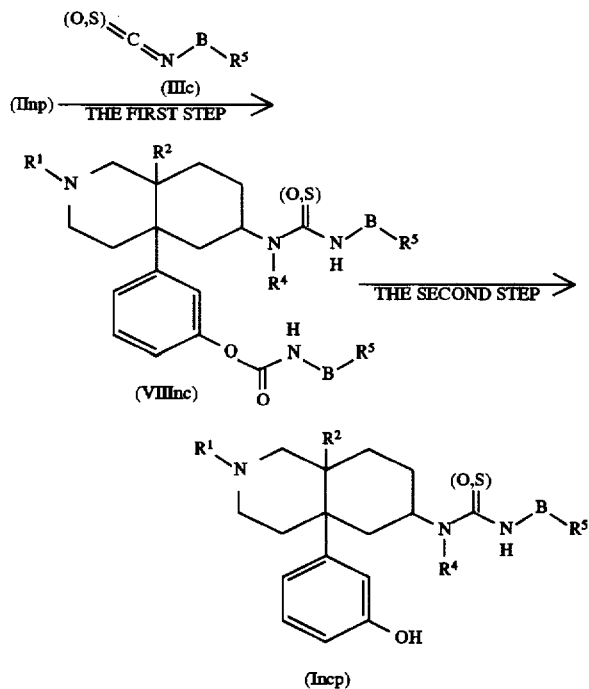

Water, an alcohol such as methanol or ethanol, or an ether such as ether, THF, DME, dioxane, or a mixture thereof is used as the reaction solvent of the second step; and if sufficient solubility can not be obtained, a halocarbon such as dichloromethane or chloroform may be added in an appropriate way. An inorganic base such as potassium carbonate, sodium carbonate, sodium hydrogencarbonate, sodium hydroxide, or potassium hydroxide is used as the base; and in general, potassium carbonate, sodium hydroxide, or the like is used in an amount of 1 to 20 equivalents, and preferably 1 to 10 equivalents. The reaction can be conducted at a temperature ranging from −80° C. to 100° C. and, in particular, satisfactory results can be obtained at 0° C. to 50° C.

If a 6-amino body, that is included in those having the general formula (IIn) in which $R^3$ is hydrogen, is condensed with a sulfonic acid derivative of general formula (IIId) in the steps shown in Chart 6, desirable results can be obtained by using a 6-amino body of general formula (IIng) (wherein $R^1$, $R^2$, $R^4$, and G are as defined above) in which the phenolic hydroxy group is protected by a tri-substituted silyl group G, as is shown in Chart 10. This method is also applicable to condensation with a carboxylic acid derivative of general formula (IIIa), a formic acid derivative of general formula (IIIb), and an isocyanic acid or isothiocyanic acid derivative of general formula (IIIc).

CHART 10

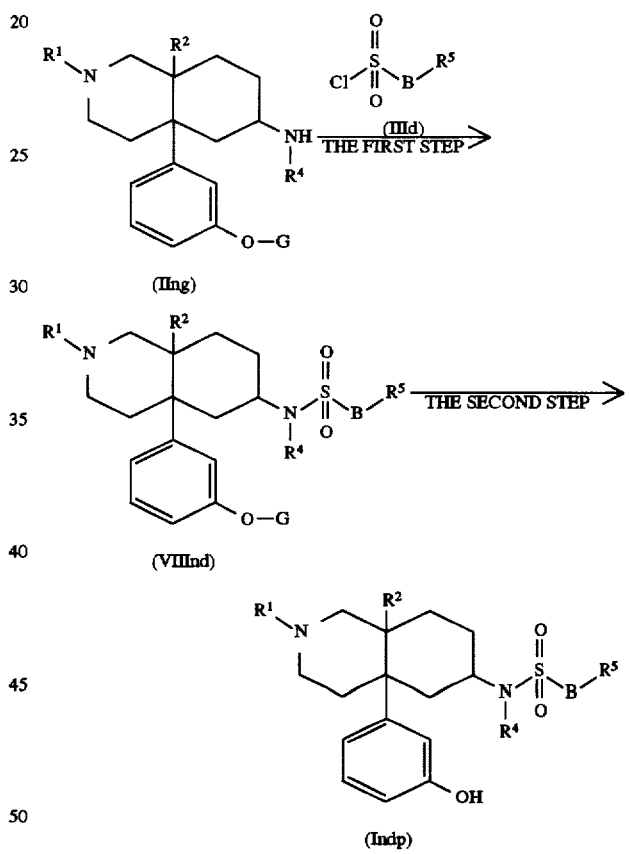

In other words, after converting the 6-amino body to a compound of general formula (VIIInd) (wherein $R^1$, $R^2$, $R^4$, $R^5$, B and G are as defined above) by carrying out the first step in a similar way to that shown in Chart 8, the tri-substituted silyl group G is removed during the second step so as to obtain a compound general formula (Indp) (wherein $R^1$, $R^2$, $R^4$, $R^5$, and B are as defined above). For removing the silyl group in the second step, an acid such as hydrochloric acid, sulfuric acid, acetic acid, or hydrofluoric acid; a quaternary ammonium salt such as tetrabutylammonium fluoride, tetrabutylammonium chloride, and pyridinium hydrofluoride; or a base such as sodium hydroxide, potassium hydroxide, and potassium carbonate can be used; and in general, the removal of the silyl group can be sufficiently carried out using 1 to 20 equivalents, in particular 1 to 5 equivalents, of hydrochloric acid or tetrabutylammonium fluoride. Ethers such as THF, ether, DME, and dioxane, halocarbons such as dichloromethane and chloroform, acetonitrile, and the like are used as the reaction solvent; and THF is preferable among these. The reaction can be conducted at a temperature ranging from −20° C. to 100° C. and, in general, satisfactory results can be obtained at room temperature.

Among the compounds of general formula (I), a 6-amino body of general formula (Ine) (wherein $R^1$, $R^2$, $R^3$, $R^4$, $R^5$, and B are as defined above) in which A is —$NR^4$—$CH_2$— can be obtained by reducing a 6-amide body of general formula (Ina) shown in Chart 6 using a metal hydride reductant, as is shown in Chart 11.

Among compounds having the corresponding general formulae (Ia), (Ib), (Ic), and (Id) shown in Chart 1, in each of which E is O, a compound having a general formula (Ioa) (wherein $R^1$, $R^2$, $R^3$, $R^5$ and B are as defined above), a compound having a general formula (Iob) (wherein $R^1$, $R^2$, $R^3$, $R^5$, B, and Z are as defined above), a compound having a general formula (Ioc) (wherein $R^1$, $R^2$, $R^3$, $R^5$ and B are as defined above), and a compound having a general formula (Iod) (wherein $R^1$, $R^2$, $R^3$, $R^5$ and B are as defined above) can be obtained by condensation of a 6-hydroxy body of general formula (IIo) (wherein $R^1$, $R^2$, and $R^3$ are as defined above) with: a carboxylic acid or a derivative thereof having the general formula (IIIa) (wherein B and $R^5$ are as defined above); a formic acid derivative having the general formula

CHART 11

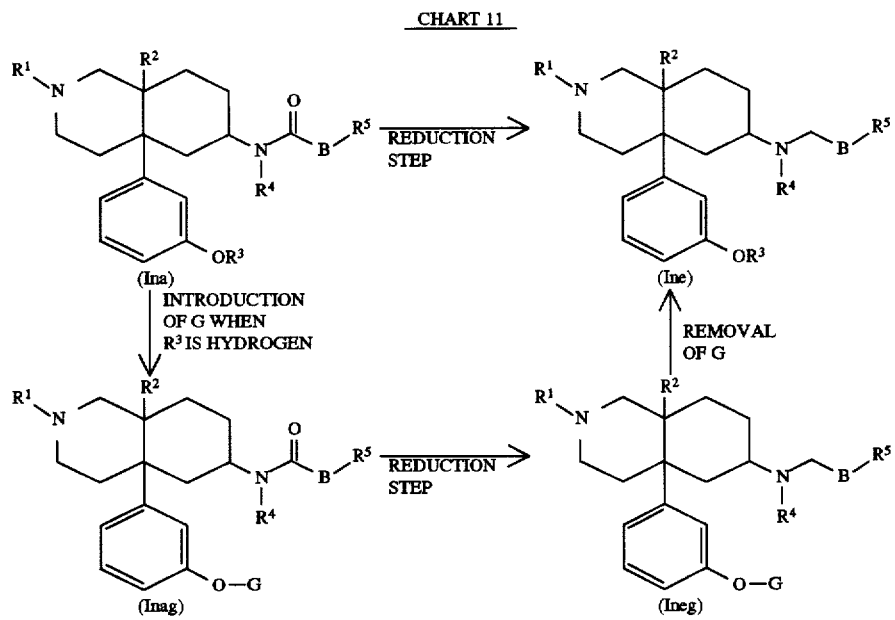

A metal hydride compound having strong reducing power such as lithium aluminum hydride, diisobutyl aluminum hydride, aluminum hydride, lithium borohydride, or diborane can be used as the metal hydride reductant; and 1 to 20 equivalents, in particular, 1 to 5 equivalents, of diborane is preferably employed. When lithium aluminum hydride, lithium borohydride, or diborane is used, an ether such as THF, DME, ether, or dioxane can be used as the solvent; and THF is preferable. When diisobutyl aluminum hydride or aluminum hydride is used, an aromatic hydrocarbon such as benzene or toluene is preferably employed. The reaction can be conducted at a temperature ranging from −40° C. to 120° C. and preferably 0° C. to 80° C. When $R^3$ of the 6-amide body having the general formula (Ina) is hydrogen, more preferable results can be obtained by the following method: the 6-amide body is converted to a 6-amino body, in which a tri-substituted silyl group G has been introduced to the phenolic hydroxy group according to the above method shown in Chart 5 and which has a general formula (Inag) (wherein $R^1$, $R^2$, $R^4$, $R^5$, B, and G are as defined above); the resultant is converted to a 6-amino body of general formula (Ineg) (wherein $R^1$, $R^2$, $R^4$, $R^5$, B, and G are as defined above) by the above reduction step; and then the tri-substituted silyl group G is removed according to the method shown in Chart 5.

(IIIb) (wherein Z, B and $R^5$ are as defined above); an isocyanic acid or isothiocyanic acid derivative having the general formula (IIIc) (wherein B and $R^5$ are as defined above); a sulfonic acid derivative having the general formula (IIId) (wherein B and $R^5$ are as defined above); or the like. The condensation reaction can be carried out in accordance with the methods used for obtaining the compounds of general formulae (Ina), (Inb), (Inc), and (Ind), in each of which E is $NR^4$, as is shown in Chart 6.

CHART 12

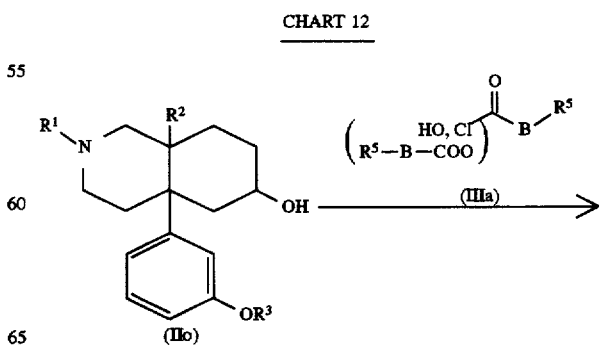

CHART 12

-continued

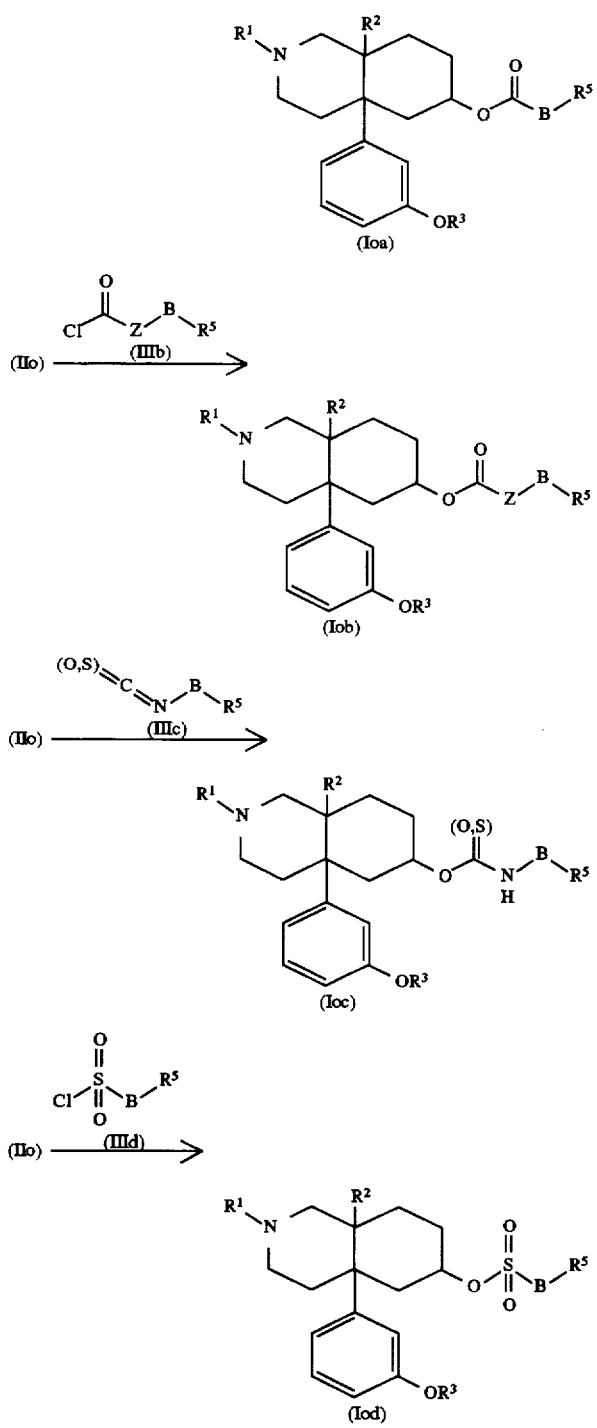

If a 6-hydroxy body of general formula (IIop) (wherein R¹, R², and R⁴ are as defined above) included in those having the general formula (IIo) in which R³ is hydrogen is used in the steps shown in Chart 12, the phenolic hydroxy group of the 6-hydroxy body occasionally reacts with a carboxylic acid derivative of general formula (IIIa), a formic acid derivative of general formula (IIIb), and an isocyanic acid or isothiocyanic acid derivative of general formula (IIIc) to give a compound having the corresponding general formulae (VIIIoa), (VIIIob), and (VIIIoc) (wherein R¹, R², R⁵, B, and Z are as defined above) shown in Charts 13 to 15; therefore, after conducting the first step in a similar manner to that shown in Chart 12, an alkali treatment is carried out as the second step to obtain the target compounds.

CHART 13

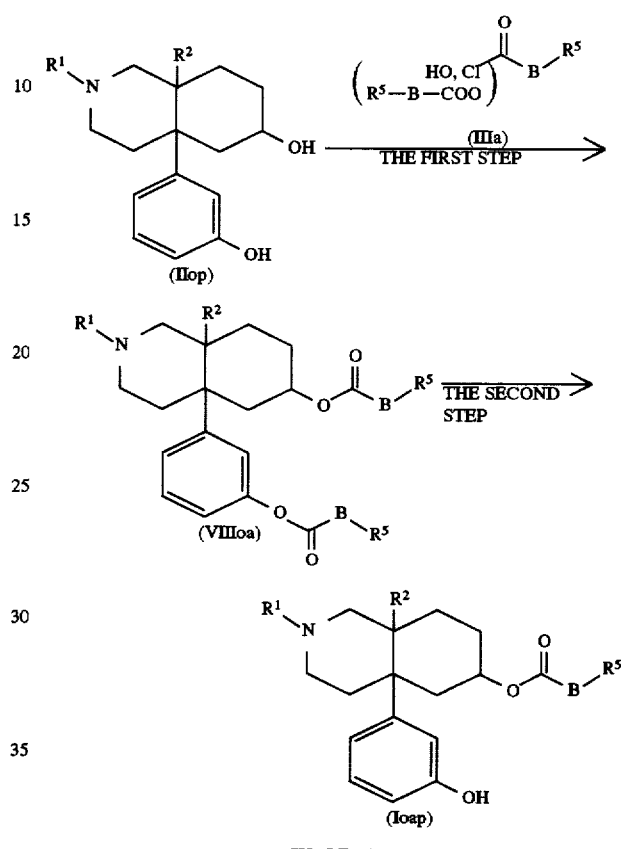

CHART 14

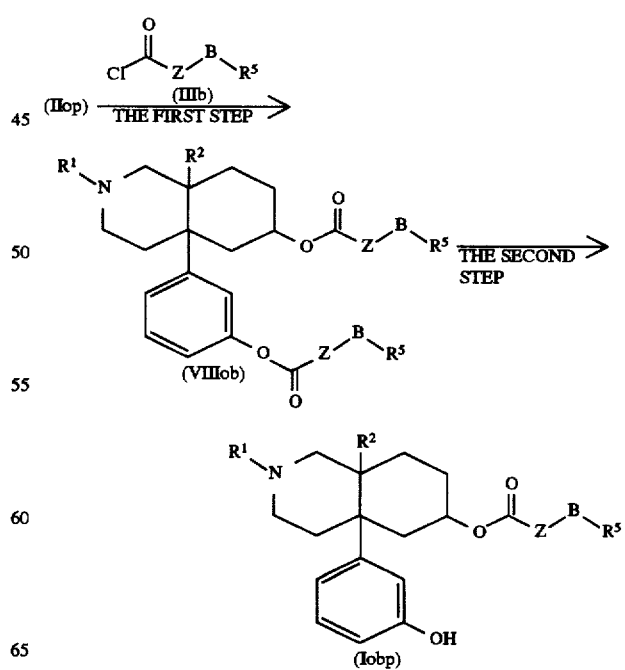

-continued
CHART 15

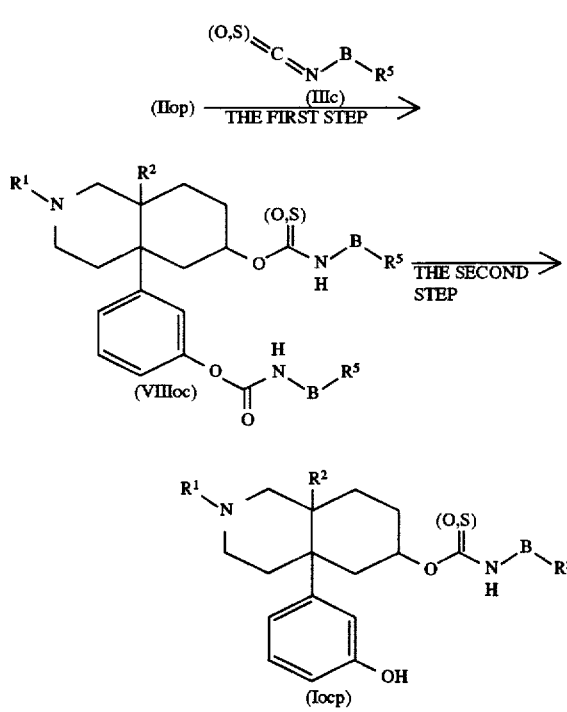

The above second step can be conducted in accordance with the methods employed for obtaining the compounds of general formulae (Inap), (Inbp), and (Incp) shown in Charts 7 to 9. However, solvolysis of the 6-position occasionally occurs and, in such a case, the reaction temperature is lowered or the reaction time is shortened.

If a 6-hydroxy body, that is included in those having the general formula (IIo) in which $R^3$ is hydrogen, is condensed with a sulfonic acid derivative of general formula (IIId) in the steps shown in Chart 12, preferable results can be obtained by using a 6-hydroxy body of general formula (IIog) (wherein $R^1$, $R^2$, and G are as defined above) in which the phenolic hydroxy group is protected beforehand by a tri-substituted silyl group G, as is shown in the steps shown in Chart 16. This method is also applicable to condensation with a carboxylic acid derivative of general formula (IIIa), a formic acid derivative of general formula (IIIb), and an isocyanic acid or isothiocyanic acid derivative of general formula (IIIc).

CHART 16

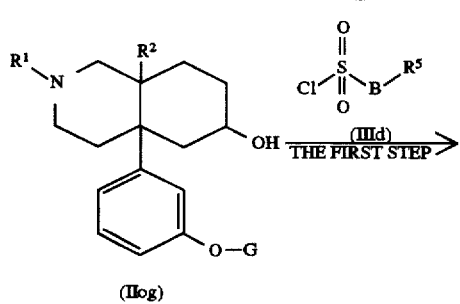

-continued
CHART 16

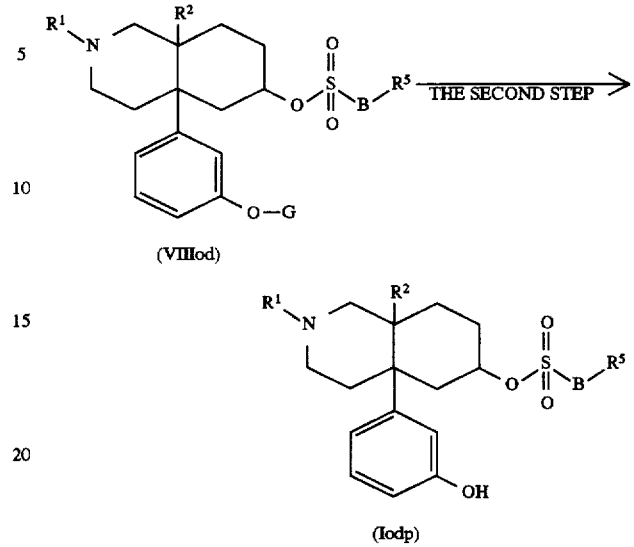

In other words, after converting the 6-hydroxy body to a compound of general formula (VIIIod) (wherein $R^1$, $R^2$, $R^5$, B and G are as defined above) by carrying out the first step in a similar way to that shown in Chart 8, the tri-substituted silyl group G is removed during the second step so as to obtain a compound of general formula (Iodp) (wherein $R^1$, $R^2$, $R^5$, and B are as defined above). The removal of the silyl group can be conducted in accordance with the method employed for obtaining the above compound of (Indp) shown in Chart 10.

In practice, a free base obtained from the above steps can be formed into a salt with a pharmacologically acceptable acid according to the following method: The obtained free base is dissolved or suspended in a solvent, precipitated as a solid or crystals by adding an acid, and then collected by filtration; and if precipitation does not occur by adding an acid, a less polar solvent is added or the solvent is replaced with a less polar solvent to achieve precipitation; or the solution is evaporated to dryness after forming a salt. If an organic solvent is left as the resultant of one of the above methods, the resultant may be rendered to an aqueous solution to be freeze-dried, followed by drying under reduced pressure. Solvents used for dissolving or suspending the base include: water; alcohols such as methanol, ethanol, and isopropyl alcohol; halocarbons such as dichloromethane and chloroform; ethers such as ether, THF, DME, and dioxane; esters such as ethyl acetate and methyl acetate; and mixtures thereof; with methanol, ethanol, isopropyl alcohol, ethyl acetate, chloroform, chloroform-methanol, water-methanol, and water-ethanol being preferable. Ether, ethyl acetate, and the like are preferably used to precipitate a solid. Although an equivalent amount of acid is desirable, 1 to 10 equivalents of acid may be used if the excess acid can be removed from the resulting salt by washing. Furthermore, the acid may be added as it is, or after being appropriately dissolved in one of the above solvents. For example, hydrochloric acid can be added as concentrated hydrochloric acid, a 1N aqueous solution, a saturated solution in methanol or a saturated solution in ethyl acetate; and tartaric acid can be added as a solid, an aqueous solution, or a methanol solution. In some cases, desirable results can be obtained by cooling in a water bath or an ice bath, since the temperature of the reaction system is occasionally raised by the heat of neutralization due to the salt formation.

It becomes apparent from both in vitro and in vivo pharmacological evaluations that the compound of general formula (I) incorporated in the present invention is effective in preventing death of cerebral neurocytes, as is shown in the following examples. As a result, the compound of the present invention can be utilized as a cerebral cytoprotective agent, indications of which are prevention and treatment of cerebrovascular disorder such as stroke and head trauma, disorder of cerebral neurocytes caused by cerebral ischemia, and aftereffects of cerebrovascular disorder such as dementia. In addition, because of the above effects, there is a possibility for utilizing the compound to prevent and treat cardiac ischemic diseases and circulation diseases, such as arterial sclerosis, myocardial infarction, arrhythmia, and angina pectoris. Furthermore, it has been found that the compound has strong analgesic and antitussive effects. Therefore, the compound of the present invention can be expected to be a useful analgesic and antitussive.

In practice, the compound is useful to the medicinal field as: a preventive and therapeutic agent for so-called stroke such as cerebral infarction (cerebral thrombosis and cerebral embolus), cerebral hemorrhage, subarachnoid hemorrhage, and transient ischemic attack (TIA); a therapeutic agent for cerebrovascular disorder due to head trauma; a preventive and therapeutic agent for cerebrovascular diseases caused by anoxia, hypoglycemia, cerebral palsy, and damage by active oxygen; a preventive and therapeutic agent for aftereffects of the above due to damaged cerebral neurocytes, such as dementia (disturbance of consciousness, motor paralysis, allophasis, sensory disorder, mental disorder, and memory disorder); a preventive and therapeutic agent for cerebral functional diseases such as senile dementia, Alzheimer-type dementia, and amnesia; a preventive and therapeutic agent for neuropathy such as epilepsy, depression, Parkinson's disease, and Huntington's chorea; an analgesic for postoperative pain, cancer pain and other broad-ranging general pain; and an antitussive for various kinds of respiratory diseases such as cold, acute bronchitis, chronic bronchitis, bronchiectasis, pneumonia, pulmonary silicosis and silicotuberculosis, lung cancer, upper respiratory tract inflammation (pharyngitis, laryngitis, and nasal catarrh), asthmatic bronchitis, bronchial asthma, infantile asthma, (chronic) pulmonary emphysema, pneumoconiosis, pulmonary fibrosis, pulmonary silicosis, pulmonary suppuration, pleurisy, tonsillitis, tussive urticaria, and pertussis, as well as suppression of caughing during bronchography and accompanying bronchial examination.

The cerebral cytoprotective agent, analgesic, and antitussive of the present invention may be applied to clinical use as a free base or a salt per se, and may be optionally mixed with an excipient such as a stabilizer, a buffer, a diluent, an isotonizing agent, or a preservative. Examples of the dosage form for oral administration are tablets, capsules, granules, powders, and syrups; those for parenteral administration are injections, suppositories, and liquid formulations; and those for local administration are ointments, creams, and cataplasms. It is desirable that the cerebral cytoprotective agent, analgesic, and antitussive of the present invention contain 1 to 90%, and in particular 30 to 70%, by weight of the above active ingredient. Although the dose is appropriately determined according to the symptoms, age, weight, the route of administration, and the like, the general daily dose for an adult is from 0.0001 mg to 1 g in the case of injections, and 0.001 mg to 10 g in the case of oral administration, in one to several parts as an active ingredient.

The present invention is illustrated in more detail with reference to the following examples, though the present invention is not limited to these examples.

[EXAMPLE 1]

Trans-2-cyclopropylmethyl-4a-(3-hydroxyphenyl)-6α-methylaminodecahydroisoquinoline 2

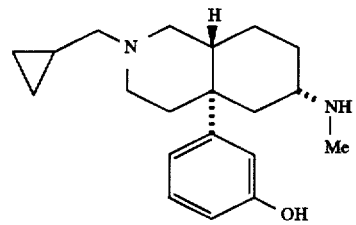

In 3 ml of methanol, 128.4 mg (0.429 mmol) of trans-2-cyclopropylmethyl-4a-(3-hydroxyphenyl)-6-oxodecahydroisoquinoline [Japanese Unexamined Patent Publication No. 5-155857] was dissolved, then 146.6 mg (2.17 mmol) of methylamine hydrochloride and 6.8 mg of platinum oxide were added thereto followed by stirring in a hydrogen atmosphere for 1 hour at room temperature and atmospheric pressure. The catalyst was removed by filtration using Celite, and after evaporating the filtrate, 5 ml of an aqueous saturated sodium hydrogencarbonate solution was added to the resulting residue followed by extraction with chloroform (3×5 ml). The resulting organic layers were combined, washed with an aqueous saturated sodium chloride solution, dried over anhydrous sodium sulfate, and evaporated to obtain 173.6 mg of a crude product of the title compound. The crude product was transferred to the next reaction step without further purification.

NMR (400 MHz, DMSO-d6) δ0.04–0.12 (2H, m), 0.44–0.54 (2H, m), 0.80–0.93 (2H, m), 1.22–1.28 (1H, m), 1.47–1.67 (3H, m), 1.73–2.34 (8H, m), 2.08 (3H, s), 2.50–2.60 (1H, m), 2.71–3.01 (4H, m), 6.38–6.45 (1H, m), 6.78 (1H, br s), 6.98–7.12 (2H, m). IR (KBr) ν3312, 2936, 1580, 1458, 756 cm$^{-1}$. Mass (EI) m/z 314 (M$^+$).

[EXAMPLE 2–3]

(4aS, 8aR)-trans-2-cyclopropylmethyl-4a-(3-hydroxyphenyl)-6α-methylaminodecahydroisoquinoline 3 and (4aR, 8aS)-trans-2-cyclopropylmethyl-4a-(3-hydroxyphenyl)-6α-methylaminodecahydroisoquinoline 4 were obtained according to the same procedure as Example 1, except that optically active (4aS, 8aR)-trans-2-cyclopropylmethyl-4a-(3-hydroxyphenyl)-6-oxodecahydroisoquinoline [Japanese Unexamined Patent Publication No. 5-155857] and (4aR, 8aS)-trans-2-cyclopropylmethyl-4a-(3-hydroxyphenyl)-6-oxodecahydroisoquinoline [Japanese Unexamined Patent Publication No. 5-155857] were employed instead of trans-2-cyclopropylmethyl-4a-(3-hydroxyphenyl)-6-oxodecahydroisoquinoline.

(4aS, 8aR)-trans-2-cyclopropylmethyl-4a-(3-hydroxyphenyl)-6α-methylaminodecahydroisoquinoline 3

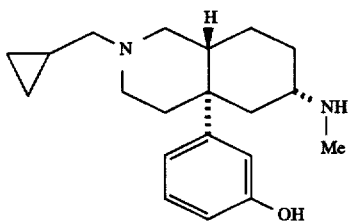

*NMR, IR, and Mass spectrum are the same as those of 2 described in Example 1.

(4aR, 8aS)-trans-2-cyclopropylmethyl-4a-(3-hydroxyphenyl)-6α-methylaminodecahydroisoquinoline 4

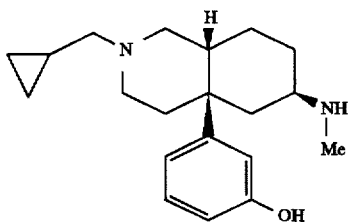

*NMR, IR, and Mass spectrum are the same as those of 2 described in Example 1.

[EXAMPLE 4]

(4aS, 8aR)-trans-2-cyclopropylmethyl-4a-(3-hydroxyphenyl)-6α-isobutylaminodecahydroisoquinoline 5 (77% yield after being purified by silica-gel chromatography) was obtained according to the same procedure as Example 1, except that optically active (4aS, 8aR)-trans-2-cyclopropylmethyl-4a-(3-hydroxyphenyl)-6-oxodecahydroisoquinoline [Japanese Unexamined Patent Publication No. 5-155857] was employed instead of trans-2-cyclopropylmethyl-4a-(3-hydroxyphenyl)-6-oxodecahydroisoquinoline and isobutylamine was used instead of methylamine hydrochloride.

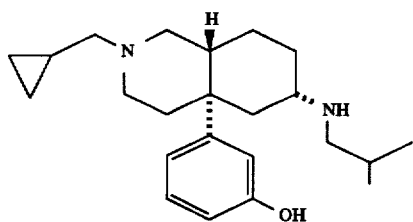

NMR (400 MHz, CDCl$_3$) δ0.00–0.10 (2H, m), 0.46 (2H, d, J=8.3 Hz), 0.51–0.58 (6H, m), 0.84 (1H, m), 1.00–3.00 (2H, br s), 1.30 (1H, m), 1.42–1.50 (1H, m), 1.50–1.64 (2H, m), 1.68–1.78 (2H, m), 1.94–2.07 (5H, m), 2.11–2.28 (3H, m), 2.48 (1H, d, J=14.2 Hz), 2.70–2.93 (4H, m), 6.54 (1H, dd, J=7.8, 2.0 Hz), 6.94 (1H, s), 7.05 (1H, d, J=7.8 Hz), 7.13 (1H, t, J=7.8 Hz). IR (liquid film) ν2922, 1580, 1487, 1450, 1270, 1243, 1089, 754 cm$^{-1}$. Mass (EI) m/z 356 (M$^+$)

[EXAMPLE 5]

Trans-2-cyclopropylmethyl-8a-hydroxy-4a-(3-hydroxyphenyl)-6α-methylaminodecahydroisoquinoline 6 (83% yield after being purified by silica-gel chromatography) was obtained according to the same procedure as Example 1, except that trans-2-cyclopropylmethyl-8a-hydroxy-4a-(3-hydroxyphenyl)-6-oxodecahydroisoquinoline [Japanese Unexamined Patent Publication No. 5-155857] was employed instead of trans-2-cyclopropylmethyl-4a-(3-hydroxyphenyl)-6-oxodecahydroisoquinoline.

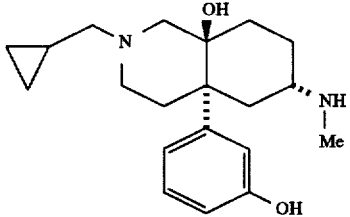

NMR (400 MHz, CDCl$_3$) δ0.01–0.08 (2H, m), 0.41–0.51 (2H, m), 0.78 (1H, m), 1.20–4.20 (2H, br s, OH), 1.48–1.55 (1H, m), 1.64–1.71 (1H, m), 1.76–1.91 (2H, m), 2.08 (3H, s), 2.09–2.19 (3H, m), 2.20 (2H, d, J=6.5 Hz), 2.29–2.43 (2H, m), 2.54–2.61 (1H, m), 2.66 (1H, d, J=10.7 Hz), 2.82 (1H, m), 3.09 (1H, d, J=10.7 Hz), 4.71 (1H, br s), 6.42 (1H, dd, J=7.8, 1.5 Hz), 6.76 (1H, s), 6.99 (1H, d, J=7.8 Hz), 7.06 (1H, t, J=7.8 Hz). IR (liquid film) ν3400, 2940, 1582, 1460, 1270, 1091, 1046, 934, 890, 783 cm Mass (EI) m/z 330 (M$^+$).

[EXAMPLE 6]

Trans-2-cyclopropylmethyl-8a-hydroxy-4a-(3-hydroxyphenyl)-6α-isobutylaminodecahydroisoquinoline 7 (94% yield after being purified by silica-gel chromatography) was obtained according to the same procedure as Example 1, except that trans-2-cyclopropylmethyl-8a-hydroxy-4a-(3-hydroxyphenyl)-6-oxodecahydroisoquinoline [Japanese Unexamined Patent Publication No. 5-155857] was employed instead of trans-2-cyclopropylmethyl-4a-(3-hydroxyphenyl)-6-oxodecahydroisoquinoline and isobutylamine was used instead of methyl amine hydrochloride.

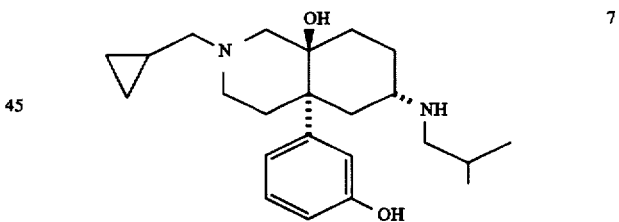

NMR (400 MHz, CDCl$_3$) δ0.04 (2H, m), 0.46 (2H, m), 0.59 (6H, dd, J=6.8, 13.2 Hz), 0.78 (1H, m), 1.41 (1H, m), 1.50 (1H, m), 1.69 (1H, m), 1.74–1.86 (2H, m), 1.92–3.60 (2H, br s), 2.05–2.18 (5H, m), 2.20 (2H, d, J=6.4 Hz), 2.26–2.33 (1H, m), 2.34–2.44 (1H, m), 2.57 (1H, m), 2.66 (1H, d, J=11.2 Hz), 2.89 (1H, m), 3.09 (1H, d, J=10.7 Hz), 4.30–5.70 (1H, m), 6.57 (1H, dd, J=1.5, 7.8 Hz), 6.85 (1H, s), 7.05 (1H, d, J=7.8 Hz), 7.12 (1H, t, J=7.8 Hz). IR (KBr) ν3400, 2934, 1580, 1458, 1270, 1087, 1046, 886, 781, 679 cm$^{-1}$ Mass (EI) m/z 372 (M$^+$).

[EXAMPLE 7]

Trans-2-cyclopropylmethyl-4a-(3-hydroxyphenyl)-6α-[N-methyl-(3-trifluoromethylcinnamamido)]decahydroisoquinoline 1 0.5 tartrate

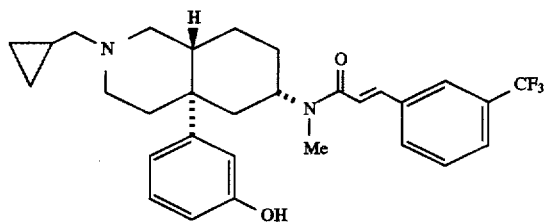

In 2.2 ml of chloroform, 173.6 mg (approximately 0.55 mmol) of trans-2-cyclopropylmethyl-4a-(3-hydroxyphenyl)-6α-methylaminodecahydroisoquinoline 2 obtained in Example 1 was dissolved and then 0.17 ml (1.22 mmol) of trimethylamine was added thereto followed by adding dropwise a solution of 258 mg (approximately 1.1 mmol) of 3-trifluoromethylcinnamoyl chloride (prepared by rendering commercially available 3-trifluoromethylcinnamic acid to an acid chloride according to a conventional method) in 1 ml of chloroform and stirring for 2 hours at room temperature. The reaction solution was concentrated and the resulting residue was dissolved in 4 ml of methanol followed by addition of 0.8 ml of a 2N aqueous sodium hydroxide solution and stirring for 1 hour at room temperature. The reaction solution was concentrated, mixed with 8 ml of water, and extracted with chloroform (3×5 ml). The resulting organic layers were combined, dried over anhydrous sodium sulfate, and evaporated to obtain 269 mg of a crude product. By purifying the crude product using silica-gel column chromatography (25 g of silica-gel; chloroform saturated with ammonia:methanol at 50:1), 215.1 mg of a free base of the title compound was obtained. The free base was dissolved in methanol, mixed with a solution of 31.4 mg of tartaric acid in methanol, concentrated, and reprecipitated by ethanol-ethyl acetate to give 191.3 mg of the title compound (76% yield, 2 steps from Example 1).

mp 140°–160° C. NMR (400 MHz, D2O) δ0.51 (m, 2H), 0.87 (m, 2H), 1.22 (m, 1H), 1.83–2.50 (m, 8H), 2.54 (br s, 3H), 2.68 (m, 1H), 2.94–3.22 (m, 3H), 3.53 3.92 (m, 3H), 4.53 (m, 1H), 4.58 (s, 1H), 6.50 (d, 1H, J=15.4 Hz), 6.83 (d, 1H, J=7.3 Hz), 7.08–7.34 (m, 3H), 7.43 (d, 1H, J=15.4 Hz), 7.62 (m, 1H), 7.68 (m, 1H), 7.79 (m, 1H), 7.84 (m, 1H). IR (KBr) v3486, 1649, 1599, 1491, 1444, 1338, 1260, 1199, 1166, 1116, 1071, 1035, 982, 880, 804 $cm^{-1}$. Mass (FAB) m/z 513 ((M+H)$^+$). Elemental Analysis as $C_{30}H_{35}F_3N_2O_2$.0.5 $C_4H_6O_6$.0.9 $H_2O$ Calcd.: C, 63.65; H, 6.64; F, 9.44; N, 4.64 Found: C, 63.61; H, 6.52; F, 9.60; N, 4.59

[EXAMPLE 8–9]

(4aS, 8aR)-trans-2-cyclopropylmethyl-4a-(3-hydroxyphenyl)-6α-[N-methyl-(3-trifluoromethylcinnamamido)]decahydroisoquinoline 8 0.5 tartrate (89% yield, 2 steps from Example 2) and (4aR, 8aS)-trans-2-cyclopropylmethyl-4a-(3-hydroxyphenyl)-6α-[N-methyl-(3-trifluoromethylcinnamamido)]decahydroisoquinoline 9 0.5 tartrate (87% yield, 2 steps from Example 3) were obtained according to the same procedure as Example 7, except that optically active (4aS, 8aR)-(trans-2-cyclopropylmethyl-4a-(3-hydroxyphenyl)-6α-methylaminodecahydroisoquinoline 3 and (4aR, 8aS)-trans-2cyclopropylmethyl-4a-(3-hydroxyphenyl)-6-oxodecahydroisoquinoline 4 were employed instead of trans-2-cyclopropylmethyl-4a-(3-hydroxyphenyl)-6α-methylaminodecahydroisoquinoline 2.

(4aS, 8aR)-trans-2-cyclopropylmethyl-4a-(3-hydroxyphenyl)-6α-[N-methyl-(3-trifluoromethylcinnamamide)]decahydroisoquinoline 8 0.5 tartrate

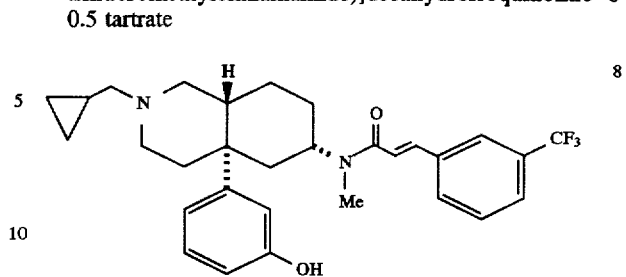

mp 140°–155 ° C. Elemental Analysis as $C_{30}H_{35}F_3N_2O_2$.0.5 $C_4H_6O_6$.0.4 $H_2O$ Calcd.: C, 64.61; H, 6.57; F, 9.58; N, 4.71 Found: C, 64.56; H, 6.54; F, 9.58; N, 4.70 *NMR, IR, and Mass spectrum are the same as those of 1.

(4aR, 8aS)-trans-2-cyclopropylmethyl-4a-(3-hydroxyphenyl)-6α-[N-methyl-(3-trifluoromethylcinnamamido)]decahydroisoquinoline 9 0.5 tartrate

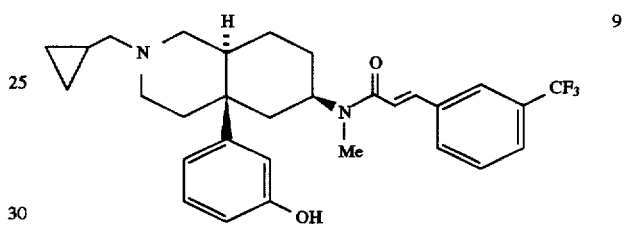

mp 140°–155° C. Elemental Analysis as $C_{30}H_{35}F_3N_2O_2$.0.5 $C_4HO_6$.0.4 $H_2O$ Calcd.: C, 64.61; H, 6.57; F, 9.58; N, 4.71. Found: C, 64.60; H, 6.56; F, 9.50; N, 4.70. *NMR, IR, and Mass spectrum are the same as those of 1 described in Example 7.

[EXAMPLE 10]

(4aS, 8aR)-trans-2-cyclopropylmethyl-4a-(3-hydroxyphenyl)-6α-[N-methyl-(6-phenylhexanoamido)]decahydroisoquinoline 10 1 tartrate (89% yield) was obtained according to the same procedure as Example 7, except that optically active (4aS, 8aR)-(trans-2-cyclopropylmethyl-4a-(3-hydroxyphenyl)-6α-methylaminodecahydroisoquinoline 3 was employed instead of trans-2-cyclopropylmethyl-4a-(3-hydroxyphenyl)-6α-methylaminodecahydroisoquinoline 2 and 6-phenylhexanoyl chloride was used instead of 3-trifluoromethylcinnamoyl chloride.

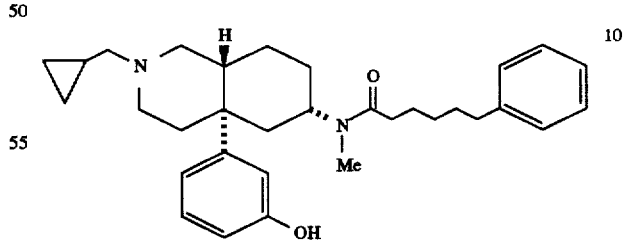

mp 85°–92° C. NMR (400 MHz, DMSO-d6) δ0.22–0.32 (2H, m), 0.51–0.60 (2H, m), 0.92–1.04 (1H, m), 1.17–1.32 (2H, m), 1.36–1.72 (7H, m), 1.73–2.08 (6H, m), 2.10–2.39 (6H, m), 2.51–2.60 (2H, m), 2.67–2.85 (2H, m), 2.80–5.50 (4H, br s), 3.05–3.42 (3H, m), 4.05 (2H, s), 4.09–4.16 (0.3H, m), 4.43–4.52 (0.7H, m), 6.56–6.63 (1H, m), 6.85–6.95 (2H, m), 7.07–7.22 (4H, m), 7.24–7.31 (2H, m), 9.31 (1H, br s). IR (KBr) v3420, 1730, 1605, 1454, 1410, 1409, 1267, 1129, 1077, 700 cm⁻¹. Mass (FAB) m/z 489 ((M+H)⁺). Elemental Analysis as $C_{32}H_{44}N_2O_2 \cdot C_4H_6O_6 \cdot H_2O$ Calcd.: C, 65.83; H, 7.98; N, 4.27. Found: C, 65.82; H, 7.75; N, 4.25.

[EXAMPLE 11]

(4aS, 8aR)-trans-2-cyclopropylmethyl-4a-(3-hydroxyphenyl)-6α-[N-isobutyl-(6-phenylhexanoamido)]decahydroisoquinoline 11 2 tartrate (60% yield) was obtained according to the same procedure as Example 7, except that optically active (4aS, 8aR)-trans-2-cyclopropylmethyl-4a-(3-hydroxyphenyl)-6α-isobutylaminodecahydroisoquinoline 5 was employed instead of trans-2-cyclopropylmethyl-4a-(3-hydroxyphenyl)-6α-methylaminodecahydroisoquinoline 2 and 6-phenylhexanoyl chloride was used instead of 3-trifluoromethylcinnamoyl chloride.

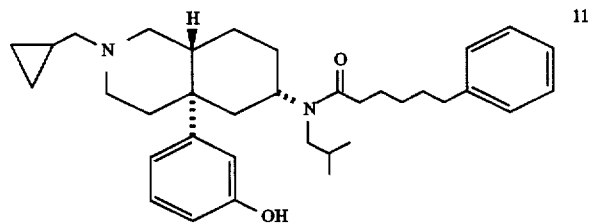

NMR (400 MHz, DMSO-d6) δ0.28 (2H, m), 0.50–0.59 (4H, m), 0.59–0.71 (4H, m), 0.80–5.50 (7H, br s), 1.00 (1H, m), 1.18–1.30 (2H, m), 1.35–1.65 (7H, m), 1.75–2.36 (12H, m), 2.52–2.58 (1H, m), 2.63–2.90 (4H, m), 3.20 (2H, m), 3.33–3.45 (1H, m), 4.15 (4H, s), 6.61 (1H, m), 6.84–6.93 (2H, m), 7.11–7.20 (4H, m), 7.25–7.30 (2H, m), 7.75–11.20 (2H, br s). IR (KBr) ν3370, 1738, 1603, 1440, 1410, 1309, 1265, 1135 cm⁻¹. Mass (FAB) m/z 531 ((M+H)⁺). Elemental Analysis as $C_{35}H_{50}N_2O_2 \cdot 2 \, C_4H_6O_6 \cdot 0.6 \, H_2O$ Calcd.: C, 61.35; H, 7.57; N, 3.33. Found: C, 61.28; H, 7.52; N, 3.53.

[EXAMPLE 12]

Trans-2-cyclopropylmethyl-8a-hydroxy-4a-(3-hydroxyphenyl)-6α-[N-methyl-(3-trifluoromethylcinnamamido)]decahydroisoquinoline 12 tartrate (89% yield) was obtained according to the same procedure as Example 7, except that trans-2-cyclopropylmethyl-8a-hydroxy-4a-(3-hydroxyphenyl)-6α-methylaminodecahydroisoquinoline 6 was employed instead of trans-2-cyclopropylmethyl-4a-(3-hydroxyphenyl)-6α-methylaminodecahydroisoquinoline 2.

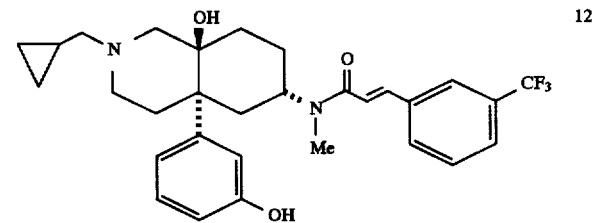

mp 109°–130° C. NMR (400 MHz, DMSO-d6) δ0.20–0.32 (2H, m), 0.48–0.61 (2H, m), 0.90–1.02 (1H, m), 1.32–1.70 (2H, m), 1.75–4.80 (6H, br s), 1.84–2.30 (4H, m), 2.25–2.40 (5H, m), 2.57–2.79 (2H, m), 2.89–3.00 (1H, m), 3.19–3.39 (2H, m), 3.99 (2H, s), 4.66 (0.4 H, br s), 5.07 (0.6 H, br s), 5.24 (1H, br s), 6.62 (1H, d, J=8.3 Hz), 6.92–7.01 (2H, m), 7.07–7.24 (2H, m), 7.48 (1H, d, J=15.6 Hz), 7.58–7.77 (2H, m), 7.95 (1H, d, J=7.3 Hz), 7.99–8.07 (1H, m). IR (KBr) ν3400, 1649, 1599, 1450, 1408, 1336, 1261, 1168, 1127, 1077 cm⁻¹. Mass (FAB) m/z 529 ((M+H)⁺). Elemental Analysis as $C_{30}H_{35}F_3N_2O_3 \cdot C_4H_6O_6 \cdot 0.7 \, H_2O$ Calcd.: C, 59.07; H, 6.18; F, 8.24; N, 4.05. Found: C, 59.22; H, 6.19; F, 7.92; N, 4.01.

[EXAMPLE 13–14]

Trans-2-cyclopropylmethyl-8a-hydroxy-4a-(3-hydroxyphenyl)-6α-[N-isobutyl-(6-phenylhexanoamido)]decahydroisoquinoline 13 0.6 tartrate (71% yield) and trans-2-cyclopropylmethyl-8a-hydroxy-4a-(3-hydroxyphenyl)-6α-[N-isobutyl-(3,4-dichlorophenylacetamido)]decahydroisoquinoline 14 0.5 tartrate (79% yield) were obtained according to the same procedure as Example 7, except that trans-2-cyclopropylmethyl-8a-hydroxy-4a(3-hydroxyphenyl)-6α-isobutylaminodecahydroisoquinoline 7 was employed instead of trans-2-cyclopropylmethyl-4a-(3-hydroxyphenyl)-6α-methylaminodecahydroisoquinoline 2 and 6-phenylhexanoyl chloride and 3,4-dichlorophenylacetyl chloride were used instead of 3-trifluoromethylcinnamoyl chloride. Trans-2-cyclopropylmethyl-8a-hydroxy-4a-(3-hydroxyphenyl)-6α-[N-isobutyl-(6-phenylhexanoamido)]decahydroisoquinoline 13 0.6 tartrate

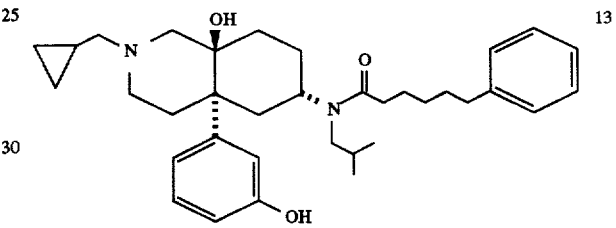

mp 118°–111° C. NMR (400 MHz, DMSO-d6) δ0.13–0.26 (2H, m), 0.43–0.70 (8H, m), 0.90 (1H, m), 1.25 (2H, m), 1.35 (1H, m), 1.40–1.70 (5H, m), 1.78–1.99 (4H, m), 2.05–2.40 (6H, m), 2.10–5.30 (3H, br s), 2.43–2.75 (6H, m), 2.78–2.92 (1H, m), 3.08 (1H, m), 3.15 (1H, m), 3.91 (1H, s), 4.34 (0.6H, br s), 4.72 (0.4H, br s), 6.55–6.62 (1H, m), 6.85–6.96 (2H, m), 7.05–7.22 (4H, m), 7.22–7.32 (2H, m), 8.30–10.20 (1H, br s). IR (KBr) ν3370, 2936, 1607, 1456, 1354, 1270, 1120, 1035, 700 cm⁻¹. Mass (FAB) m/z 547 ((M+H)⁺). Elemental Analysis as $C_{35}H_{50}N_2O_3 \cdot 0.6 \, C_4H_6O_6 \cdot 0.4 \, H_2O$ Calcd.: C, 69.75; H, 8.51; N, 4.35. Found: C, 69.72; H, 8.37; N, 4.71.

Trans-2-cyclopropylmethyl-8a-hydroxy-4a-(3-hydroxyphenyl)-6α-[N-isobutyl-(3,4-dichlorophenylacetamido)]decahydroisoquinoline 14 0.5 tartrate

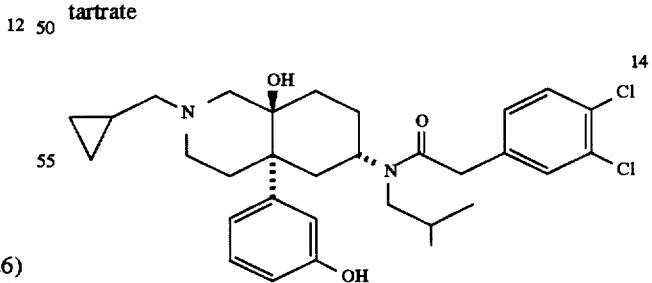

mp 139°–144° C. NMR (400 MHz, DMSO-d6) δ0.14–0.26 (2H, m), 0.45–0.58 (4H, m), 0.58–0.72 (4H, m), 0.90 (1H, m), 1.20–5.50 (3H, m), 1.23–1.76 (3H, m), 1.80–2.00 (4H, m), 2.08–2.39 (3H, m), 2.44–2.91 (5H, m), 3.03–3.24 (2H, m), 3.54–3.79 (2H, m), 3.92 (1H, s), 4.44 (0.7H, br s), 4.63–4.75 (0.3H, m), 6.59 (1H, d, J=8.8 Hz), 6.86–6.96 (2H, m), 7.07–7.26 (2H, m), 7.42–7.50 (1H, m), 7.50–7.60 (1H, m), 9.30 (1H, br s). IR (KBr) v3400, 2962, 1613, 1454, 1390, 1363, 1270, 1122, 1033, 880, 787, 719, 685 cm⁻¹. Mass (FAB) m/z 559 ((M+H)⁺). Elemental Analysis as $C_{31}H_{40}Cl_2N_2O_3 \cdot 0.5\ C_4H_6O_6 \cdot 0.9\ H_2O$ Calcd.: C, 60.96; H, 6.94; Cl, 10.89; N, 4.30. Found: C, 60.96; H, 6.72; Cl, 10.77; N, 4.30.

[EXAMPLE 15]

Trans-2-cyclopropylmethyl-8a-hydroxy-4a-(3-hydroxyphenyl)-6α-[N-isobutyl-(3-trifluoromethylcinnamamido)]decahydroisoquinoline 15 0.5 tartrate (76% yield) was obtained according to the same procedure as Example 7, except that trans-2-cyclopropylmethyl-8a-hydroxy-4a-(3-hydroxyphenyl)-6α-isobutylaminodecahydroisoquinoline 7 was employed instead of trans-2-cyclopropylmethyl-4a-(3-hydroxyphenyl)-6α-methylaminodecahydroisoquinoline 2.

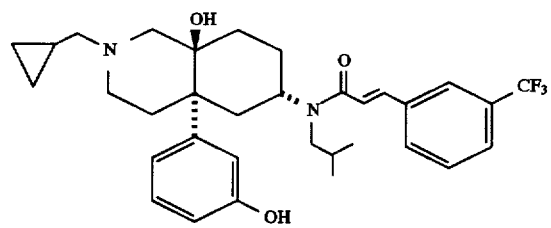

mp 137°–148° C. NMR (400 MHz, DMSO-d6) δ0.13–0.25 (2H, m), 0.44–0.57 (2H, m), 0.57–0.74 (6H, m), 0.90 (1H, m), 1.32–1.80 (3H, m), 1.82–2.03 (4H, m), 2.10–4.40 (2H, br s), 2.18–2.38 (3H, m), 2.42–3.25 (7H, m), 3.90 (1H, s), 4.40–5.62 (1H, br s), 4.58 (0.4H, br s), 4.83 (0.6H, br s), 6.61 (1H, m), 6.89–6.98 (2H, m), 7.07–7.16 (2H, m), 7.45 (1H, d, J=15.1 Hz), 7.60–7.74 (2H, m), 7.78–8.02 (2H, m), 8.54–10.06 (1H, br s). IR (KBr) v3400, 2966, 1649, 1599, 1444, 1336, 1168, 1127, 696 cm¹. Mass (FAB) m/z 571 ((M+H)⁺). Elemental Analysis as $C_{33}H_{41}F_3N_2O_3 \cdot 0.5\ C_4H_6O_6 \cdot 0.6\ H_2O$ Calcd.: C, 64.03; H, 6.94; F, 8.68; N, 4.27. Found: C, 63.98; H, 6.83; F, 8.71; N, 4.31.

[EXAMPLE 16]

Trans-4a-(3-t-butyldimethylsilyloxyphenyl)-2-cyclopropylmethyl-6-oxodecahydroisoquinoline 16

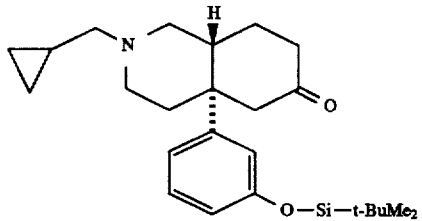

In 3.6 ml of anhydrous dimethylformaldehyde, 180 mg (0.601 mmol) of trans-2-cyclopropylmethyl-4a-(3-hydroxyphenyl)-6-oxodecahydroisoquinoline [Japanese Unexamined Patent Publication No. 5-155857] was dissolved, then 57 mg (0.837 mmol) of imidazole and 109 mg (0.723 mmol) of t-butyldimethylsilyl chloride were added thereto in that order at room temperature followed by stirring for 2 hours. After that, 81 mg (1.19 mmol) of imidazole and 90 mg (0.597 mmol) of t-butyldimethylsilyl chloride were added thereto followed by stirring for further 2 hours at room temperature. To the reaction solution, 10 ml of distilled water and 20 ml of diethyl ether were added for separation and then the aqueous layer was extracted with 15 ml of diethyl ether. The resulting organic layers were combined, dried over anhydrous sodium sulfate, and evaporated to obtain 269.8 mg of a crude product of the title compound. The crude product was transferred to the next reaction step without further purification.

Data of the crude product:

NMR (90 MHz, CDCl₃) δ–0.1–0.2(2H, m), 0.1 (6H, s), 0.3–0.6 (2H, m), 0.8 (1H, m), 0.9 (9H, m), 1.8–3.1 (15H, m), 6.6 (1H, dt, J=7.5 Hz, 1.5 Hz), 6.8–7.0 (2H, m), 7.0 (1H, t, J=7.5 Hz). IR (liquid film) v2934, 1715, 1601, 1582, 1489, 1473, 1253, 967 cm⁻¹. Mass (EI) m/z 413 (M⁺).

[EXAMPLE 17]

Trans-4a-(3-t-butyldimethylsilyloxyphenyl)-2-cyclopropylmethyl-6α-hydroxydecahydroisoquinoline 17

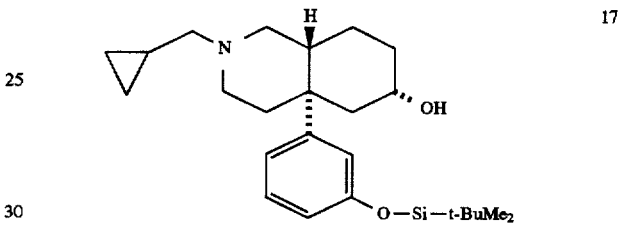

In 4 ml of methanol, 269.8 mg of crude trans-4a-(3-t-butyldimethylsilyloxyphenyl)-2-cyclopropylmethyl-6-oxodecahydroisoquinoline 16 obtained in Example 16 was dissolved, then 46 mg (1.22 mmol) of sodium borohydride was added thereto while cooling in a water bath followed by stirring for 1 hour at room temperature. To the reaction solution, 3 ml of distilled water, 10 ml of chloroform, and 3 ml of an aqueous saturated ammonium chloride solution were added; and then the aqueous layer was adjusted to approximate pH 8, separated, and extracted twice, each with 5 ml of chloroform. The thus-obtained organic layers were combined, dried over anhydrous sodium sulfate, and evaporated to obtain 276.7 mg of a crude product. The crude product was purified using silica-gel chromatography (25 g of silica-gel, hexane/ethyl acetate/10% ammonia in methanol =4/4/0.4) to obtain 198.2 mg (79% yield, 2 steps from Example 16) of the title compound. Furthermore, 57.1 mg (23% yield) of trans-4a-(3-t-butyldimethylsilyloxyphenyl)-2-cyclopropylmethyl-6β-hydroxydecahydroisoquinoline was obtained as a by-product.

Data of the title product:

NMR (90 MHz, CDCl₃) δ–0.1–0.2(2H, m), 0.2 (6H, s), 0.4–0.6 (2H, m), 0.9 (1H, m), 1.0 (9H, m), 1.4–3.0 (16H, m), 4.0 (1H, m), 6.6 (1H, m), 7.0–7.2 (3H, m). Mass (EI) m/z 415 (M⁺).

[EXAMPLE 18]

Trans-4a-(3-t-butyldimethylsilyloxyphenyl)-2-cyclopropylmethyl-6α-(methylsulfonyloxy)decahydroisoquinoline 18

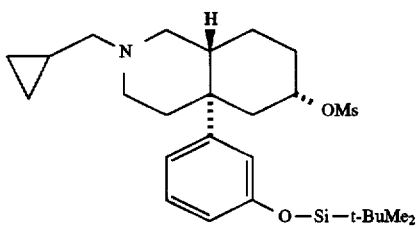

In 3 ml of pyridine, 198.2 mg (0.477 mmol) of trans-4a-(3-t-butyldimethylsilyloxyphenyl)-2-cyclopropylmethyl-6α-hydroxydecahydroisoquinoline 17 obtained in Example 17 was dissolved, then 0.048 ml (0.620 mmol) of methanesulfonyl chloride was added thereto under ice-cooled conditions followed by stirring for 2 hours at room temperature. To the reaction solution, 3 ml of distilled water, 10 ml of chloroform, and 3 ml of a saturated sodium hydrogencarbonate solution were added under ice-cooled conditions for separation, then the aqueous-layer was extracted twice, each with 6 ml of chloroform. The thus-obtained organic layers were combined, dried over anhydrous sodium sulfate, and evaporated to obtain 226.2 mg of a crude product of the title compound. The crude product was transferred to the next reaction step without further purification.

Data of the crude product:

NMR (90 MHz, CDCl$_3$) δ–0.1–0.1(2H, m), 0.2 (6H, s), 0.4–0.6 (2H, m), 0.8 (1H, m), 1.0 (9H, m), 1.4–3.0 (15H, m), 2.3 (3H, s), 5.1 (1H, m), 6.6 (1H, dt, J=7.0 Hz, 2.1 Hz), 7.0–7.2 (2H, m) IR (KBr) v2934, 1601, 1582, 1489, 1334, 1253, 1170, 967 cm$^{-1}$. Mass (EI) m/z 493 (M$^+$).

[EXAMPLE 19]

Trans-6β-azido-2-cyclopropylmethyl-4a-(3hydroxyphenyl)decahydroisoquinoline 19

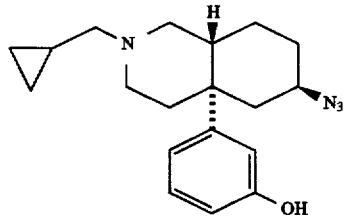

In 5.4 ml of dimethylformamide, 215.2 mg of crude trans-4a-(3-t-butyldimethylsilyloxyphenyl)-2-cyclopropylmethyl-6α-(methylsulfonyloxy)decahydroisoquinoline 18 obtained in Example 18 was dissolved, then 0.2 ml of distilled water and 43 mg (0.661 mmol) of sodium azide were added thereto followed by stirring for 2 hours at 90° C. To the reaction solution, 3 ml of distilled water, 10 ml of chloroform, and 3 ml of a saturated sodium hydrogencarbonate solution were added for separation, then the aqueous-layer was extracted twice, each with 8 ml of chloroform. The thus-obtained organic layers were combined, dried over anhydrous sodium sulfate, and evaporated to obtain 173 mg of crude trans-6β-azido-2-cyclopropylmethyl-4a-(3-t-butyldimethyloxyphenyl)decahydroisoquinoline.

The crude product was then dissolved in 1 ml of tetrahydrofuran, mixed with 0.5 ml of 1N hydrochloric acid, and stirred for 3 hours at room temperature. To the reaction solution, 8 ml of chloroform and 8 ml of a saturated sodium hydrogencarbonate solution were added for separation, then the aqueous-layer was extracted twice, each with 7 ml of chloroform. The thus-obtained organic layers were combined, dried over anhydrous sodium sulfate, and evaporated so that the resulting residue was purified using silica-gel chromatography (17 g of silica-gel; hexane/ethyl acetate/ 10% ammonia in methanol=4/4/0.4 –4/4/1.5) to obtain 181 mg of the title compound (a mixture with a compound produced by the elimination of the azide group).

NMR (90 MHz, CDCl$_3$) δ0.0–0.2(2H, m), 0.4–0.6 (2H, m), 0.8 (1H, m), 1.2–3.2 (16H, m), 6.6 (1H, m), 6.8–7.2 (3H, m), 8.2 (1H br s). IR (liquid film) v2934, 2096, 1582, 1458, 1251 cm$^{-1}$. Mass (EI) m/z 326 (M$^+$).

[EXAMPLE 20]

Trans-6β-amino-2-cyclopropylmethyl-4a-(3-hydroxyphenyl)decahydroisoquinoline 20

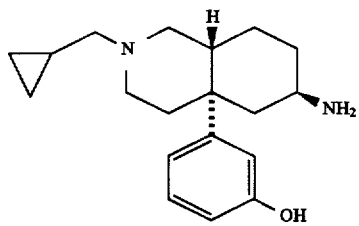

In 3.6 ml of methanol, 181 mg of trans-6β-azido-2-cyclopropylmethyl-4a-(3-hydroxyphenyl)decahydroisoquinoline 19 (containing the eliminated compound) was dissolved, and 36 mg of platinum oxide was added thereto, then the atmosphere of the system was replaced with hydrogen followed by stirring in a hydrogen atmosphere for 1 hour at room temperature and atmospheric pressure. The catalyst was removed by filtration using Celite and, after concentrating the filtrate, the filtrate was concentrated. The residue was dried using a vacuum pump to obtain 173 mg of a crude product of the title compound. The crude product was transferred to the next reaction step without further purification.

Data of the crude product:

Mass (EI) m/z 300 (M$^+$).

[EXAMPLE 21]

Trans-2-cyclopropylmethyl-4a-(3-hydroxyphenyl)-6β-(3,4-dichlorophenylacetamido)decahydroisoquinoline 21 hydrochloride

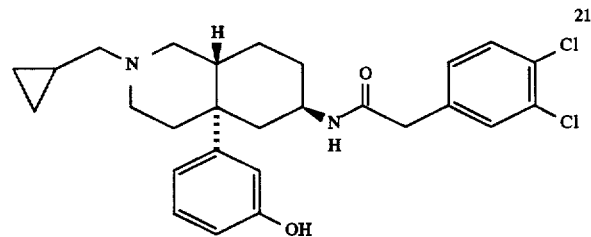

In 5.2 ml of methylene chloride, 173 mg of crude trans-6β-amino-2-cyclopropylmethyl-4a-(3-hydroxyphenyl) decahydroisoquinoline 20 obtained in Example 20 was dissolved, then 0.24 ml (1.72 mmol) of triethylamine and 0.19 ml (1.22 mmol) of 3,4-dichlorophenylacetyl chloride were added thereto in that order while cooling in an ice bath followed by stirring for 2 hours at room temperature. Separation was carried out by addition of 8 ml of distilled water and 6 ml of chloroform followed by two aqueous-layer extractions, each with 6 ml of chloroform. The thus-obtained organic layers were dried over anhydrous sodium sulfate and evaporated. The thus-obtained residue was dissolved in 4 ml of methanol and mixed with 80 mg (0.579 mmol) of potassium carbonate followed by stirring for 30 min. at room temperature. Separation was then carried out by addition of 10 ml of distilled water and 15 ml of chloroform followed by two aqueous-layer extractions, each with 8 ml of chloroform. The organic layers were combined, dried over anhydrous sodium sulfate and evaporated so that the resulting residue was purified using silica-gel chromatography (15 g of silica-gel; chloroform saturated with ammonia/methanol=20/1) to obtain 84 mg of a free base of the title compound (36% yield, 5 steps from 17). The free base was dissolved in 2 ml of methanol, a hydrogen chloride/methanol solution was added thereto until the pH thereof reached 4, and then the resultant was evaporated to dryness. The resulting residue was dissolved in 1 ml of methanol and mixed with an excess amount of ether to precipitate hydrochloride to obtain 80 mg (89% yield from the free base) of the title compound.

NMR (400 MHz, CD3OD: free base) δ0.37–0.43(2H, m), 0.68–0.74 (2H, m), 1.10 (1H, m), 1.43 (1H, m), 1.46 (1H, t, J=12.2 Hz), 1.74 (1H, m), 1.98–2.07 (2H, m), 2.12–2.26 (2H, m), 2.26–2.40 (2H, m), 2.53 (1H, m), 2.95 (2H, m), 3.39 (3H, s), 3.42 (1H, m), 3.54 (2H, m), 6.67 (1H, dd, J=8.2, 1.8 Hz), 6.94 (1H, m), 6.97 (1H, d, J=7.9 Hz), 7.14 (1H, dd, J=8.2, 2.1 Hz), 7.19 (1H, dd, J=8.2, 7.9 Hz), 7.39 (1H, d, J=1.8 Hz), 7.40 (1H, d, J=8.2 Hz). IR (KBr: free base) v3246, 2924, 1638, 1572, 1473, 1332, 1031 cm⁻¹. Mass (FAB) m/z 487 ((M+H)⁺). Elemental Analysis as $C_{27}H_{32}Cl_2N_2O_2 \cdot HCl0.3\ H_2O$ Calcd.: C, 61.27; H, 6.40; Cl, 20.09; N, 5.29. Found: C, 61.08; H, 6.45; Cl, 19.95; N, 5.34.

[EXAMPLES 22–23]

Trans-2-cyclopropylmethyl-4a-(3-hydroxyphenyl)-6β-benzamidodecahydroisoquinoline 22 methanesulfonate and trans-2-cyclopropylmethyl-4a-(3-hydroxyphenyl)-6β-(2-naphthoamido)decahydroisoquinoline 23 methanesulfonate were obtained according to the same procedure as Example 21, except that benzoyl chloride and 2-naphthoyl chloride were used instead of 3,4-dichlorophenylacetyl chloride.

Trans-2-cyclopropylmethyl-4a-(3-hydroxyphenyl)-6β-benzamidodecahydroisoquinoline 22 methanesulfonate

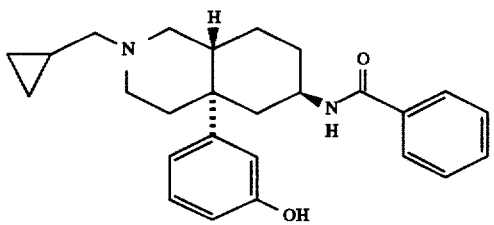

mp 158.5°–161° C. NMR (400 MHz, DMSO-d6) δ0.33–0.38(2H, m), 0.58–0.65(2H, m), 1.02(1H, m), 1.45 (1H, m), 1.53 (1H, t, J=12.2 Hz), 1.71(1H, m), 1.85(1H, m), 1.91–2.15(3H, m), 2.20–2.30(2H, m), 2.30(3H, s), 2.40(1H, m), 2.93–3.05(2H, m), 3.33–3.58(4H, m), 6.67(1H, d, J=8.5 Hz), 6.93(1H, s), 6.98(1H, d, J=7.3 Hz), 7.19(1H, t, J=7.9 Hz), 7.43(2H, t, J=7.9 Hz), 7.50(1H, t, J=7.3 Hz), 7.76(2H, d, J=7.3 Hz), 8.17(1H, d, J=7.9 Hz), 9.10(1H, br s), 9.37(1H, br s). IR (KBr) v3400, 1638, 1603, 1578, 1543, 1491, 1460, 1328, 1210, 1195, 1046, 785, 719, 561 cm⁻¹. Mass (FAB) m/z 405 ( (M+H)⁺).

Trans-2-cyclopropylmethyl-4a-(3-hydroxyphenyl)-6β-(2-naphthoamido)decahydroisoquinoline 23 methanesulfonate

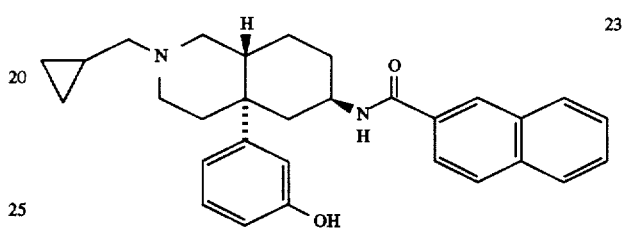

mp 150°–153° C. NMR (400 MHz, DMSO-d6) δ0.33–0.41(2H, m), 0.58–0.66(2H, m), 1.04(1H, m), 1.51 (1H, m), 1.60 (1H, t, J=12.5 Hz), 1.71(1H, m), 1.91(1H, m), 2.00–2.18(3H, m), 2.25 (1H, d, J=14.7 Hz), 2.33(3H, s), 2.33–2.45(2H, m), 2.94–3.05 (2H, m), 3.35–3.60(4H, m), 6.68(1H, d, J=7.7 Hz), 6.96(1H, s), 7.00(1H, d, J=8.1 Hz), 7.20(1H, t, J=8.1 Hz), 7.54–7.62(2H, m), 7.86(1H, d, J=8.4 Hz), 7.92–8.01(3H, m), 8.35–8.41(2H, m), 9.20 (1H, br s), 9.38(1H, br s). IR (KBr) v3250, 1638, 1626, 1543, 1460, 1325, 1210, 1195, 1044, 779 cm⁻¹. Mass (FAB) m/z 455 ((M+H)⁺). Elemental Analysis as $C_{30}H_{34}N_2O_2 \cdot CH_3SO_3H \cdot 0.17EtOAc \cdot 0.7\ H_2O$ Calcd.: C, 65.80; H, 7.10; N, 4.84; S, 5.54. Found: C, 65.80; H, 7.18; N, 4.84; S, 5.57.

[EXAMPLE 24]

Trans-2-(2-phenetyl)-4a-(3-hydroxyphenyl)-6β-(2-naphthoamido)decahydroisoquinoline 24 methanesulfonate was obtained according to the same procedure as Example 21, except that trans-2-(2-phenylethyl)-4a-(3-hydroxyphenyl)-6β-aminodecahydroisoquinoline was used instead of trans-2-cyclopropylmethyl-4a-(3-hydroxyphenyl)-6β-aminodecahydroisoquinoline and 2-naphthoyl chloride was used instead of 3,4-dichlorophenylacetyl chloride.

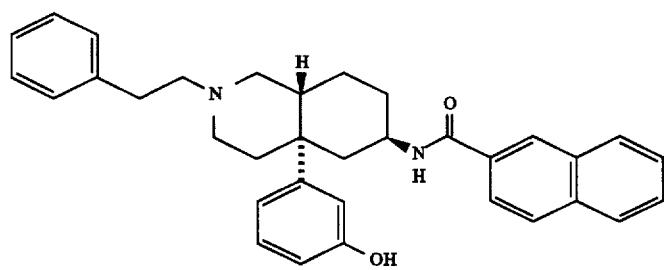

mp 242°–243° C. (salt-free form) NMR (400 MHz, DMSO-d6) δ1.50 (1H, m), 1.59 (1H, m), 1.74 (1H, m), 1.86 (1H, m), 2.00–2.08 (2H, m), 2.13 (1H, m), 2.23–2.48 (4H, m), 2.30 (3H, s), 2.50 (1H, m), 2.90–3.05 (2H, m), 3.26–3.33 (2H, m), 3.40 (1H, m), 3.50–3.67 (2H, m), 6.70 (1H, dd, J=8.8, 1.5 Hz), 6.96 (1H, br s), 7.00 (1H, d, J=8.3 Hz), 7.13–7.30 (4H, m), 7.30–7.39 (2H, m), 7.55–7.63 (2H, m), 7.86 (1H, dd, J=8.6, 1.7 Hz), 7.96 (1H, d, J=8.3 Hz), 8.01 (1H, m), 8.37 (1H, br s), 8.37 (1H, d, J=8.3 Hz) 9.32 (1H, br c), 9.40 (1H, br s). IR (KBr) ν3350, 1638, 1620, 1543, 1460, 1325, 1210, 1195, 1060, 1052, 783, 702 cm$^{-1}$. Mass (FAB) m/z 505 ( (M+H)$^{+}$).

[EXAMPLE 25]

Trans-2-cyclopropylmethyl-4a-(3-hydroxyphenyl)-6α-methylaminodecahydroisoquinoline 2

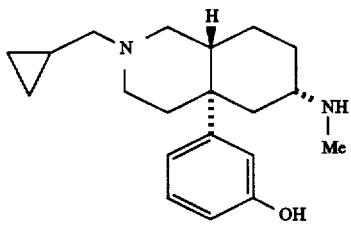

The title compound 2 described in Example 1 could be synthesized according to the following method:

In 3 ml of 1,2-dichloroethane, 0.10 g (0.334 mmol) of trans-2-cyclopropylmethyl-4a-(3-hydroxyphenyl)-6-oxodecahydroisoquinoline was dissolved, then 0.0756 ml (0.701 mmol) of a 40% methylamine/methanol solution and 156 mg (0.735 mmol) of sodium triacetoxyborohydride were added thereto followed by stirring for 2 hours at room temperature. To the reaction solution, 2 ml of an aqueous saturated sodium hydrogencarbonate solution and 4 ml of water were added followed by extraction with chloroform (2×8 ml). The resulting organic layers were combined, washed with an aqueous saturated sodium chloride solution, dried over anhydrous sodium sulfate, and evaporated to obtain 0.08 g of a crude product of the title compound. The crude product was transferred to the next reaction step without further purification.

*NMR, IR, and Mass spectrum are the same as those described in Example 1.

[EXAMPLE 26]

Trans-2-cyclopropylmethyl-4a-(3-hydroxyphenyl)-6α-[trans-β-(3-furyl)acrylamido]decahydroisoquinoline 25 1 tartrate

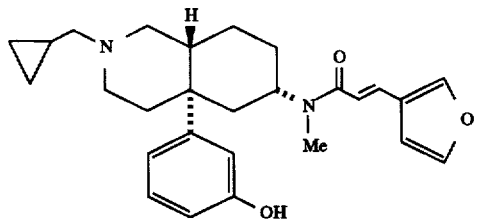

In a mixed solvent of 0.5 ml of THF and 0.5 ml of an aqueous solution of sodium carbonate (53.8 mg), 0.08 g (0.25 mmol) of the trans-2-cyclopropylmethyl-4a-(3-hydroxyphenyl)-6α-methylaminodecahydroisoquinoline 2 obtained in Example 25 was dissolved and a solution of 49.7 mg (0.318 mmol) of trans-β-(3-furyl)acryloyl chloride (prepared by rendering commercially available trans-β-(3-furan)acrylic acid to an acid chloride according to a conventional method) in 0.2 ml of THF was added dropwise therein followed by stirring for 3.5 hours at room temperature while adding another 8 mg of trans-β-(3-furyl)acryloyl chloride twice. To the reaction solution, 0.2 ml of methanol and 0.2 ml of an aqueous solution of sodium hydroxide (40.6 mg) were added followed by stirring for 20 min. at room temperature. Water and THF were added to the reaction solution followed by extraction with ethyl acetate. The resulting organic layers were combined, washed with an aqueous sodium hydrogencarbonate solution, dried over anhydrous sodium sulfate, and evaporated to obtain 0.21 g of a crude product. The crude product obtained as a solid was suspended in ethyl acetate and then in water for washing and purification to give 67.0 mg (61% yield) of a free base of the title compound. The free base was dissolved in chloroform-methanol, concentrated after being mixed with 11.6 mg of tartaric acid, and crystallized by ethyl acetate to give 64.8 mg of the title product.

mp 127°–129° C. NMR (500 MHz, DMSO-d6) δ0.24 (2H, m), 0.49–0.65 (2H, m), 0.92–1.01 (1H, m), 1.41–1.49 (1H, m), 1.63–2.80 (15H, m), 2.85–4.73 (7.5H, m), 4.72 (2H, s), 6.56–6.61 (2H, m), 6.83–6.97 (3H, m), 7.11 (1H, t, J=7.3 Hz), 7.34 (1H, br s), 7.70 (1H, s), 8.00 (1H, s), 8.63–9.80 (0.5H, br s). IR (KBr) ν3316, 1719, 1651, 1582 cm$^{-1}$. Mass (EI) (salt-free form) m/z 434 (M$^{+}$). Elemental Analysis as $C_{27}H_{34}N_2O_2 \cdot 1.1\ C_4H_6O_6 \cdot 0.2EtOAc \cdot 0.9\ H_2O$ Calcd.: C, 61.05; H, 7.00; N, 4.42. Found: C, 60.93; H, 7.16; N, 4.61.

[EXAMPLE 27]

Cultured-Neurocyte Protective Effect against Glutamic Acid Toxicity

It is known that delayed cerebral-neuronal death is induced if blood flow to the brain is transiently stopped by transient ischemia, anoxia, hypoglycemia, or trauma [T. Kirino, Brain Research, 239, 57 (1982).]. The excitatory toxicity of excitatory neurotransmitters, such as glutamic acid, which is excessively released when associated with ischemia is considered as the cause of the neurocyte damage [S. M. Rotherman and J. W. Olney, Trends in Neuroscience, 10, 299 (1987).]. A compound which protects neurocytes from the cytotoxicity of glutamic acid will be promising as a preventive and therapeutic agent for cerebral ischemic diseases, cerebral neurocyte disorder, and dementia. The following method is employed as an in vitro evaluation system of the protective effect.

Under sterilized conditions, fetuses were taken from female Wistar rats 18 to 19 day-pregnant and the brains thereof were obtained by opening their cranial portions. The brains were placed in an ice-cold L-15 medium to microscopically separate the cerebral cortexes. After being cut into small pieces, the cerebral cortexes of approximately 30 rats were suspended in a mixture of 10 ml of a 0.25% trypsin solution and 0.2 ml of a 0.01% DNase solution to be cultured at 37° C. for 30 min. Then, immediately after addition of 2 ml of serum, the resultant was centrifuged at 1,200 rpm for 2 min. to separate a sediment. To the sediment, 7 ml of a DF medium (prepared by addition of 20 nM of transferrin, 5 μg/ml of insulin, 20 nM of progesterone, 60 nM of selenite, 50 U/ml of penicillin, and 50 U/ml of streptomycin to an equivalent admixture of Dulbecco modified Eagle medium and F-12 medium) was added to prepare a cell suspension which was pipetted 20 times using a 10 ml plastic pipette followed by filtration using a nylon mesh (pore size of 43

μm) to obtain isolated cells. The resulting isolated cells were diluted to 6.0×10⁵ cells/ml with the DF medium, inoculated in a polylysine-precoated culture plate having 48 wells at 500 μl per well, and cultured at 37° C. in the presence of 5% $CO_2$ for 1 day. The medium was changed with fresh DF medium on the second day, and 10 μl of a 0.5M glutamic acid solution in distilled water is added to each of the wells (the final concentration of the glutamic acid was 10 mM), and the cells were cultured for further 24 hours at 37° C. in the presence of 5% $CO_2$. Each of the subject compounds was dissolved in distilled water, 10% or 100% DMSO, or 10% methanol and then a 5 μl aliquot was added to each well immediately before addition of glutamic acid. The enzymatic activity of lactate dehydrogenase (LDH) which leaked into the medium from the damaged cells was measured as an index of the neurocyte damage. With respect to each of the subject compounds, LDH leakage at the respective concentrations was measured and a dose-response curve was obtained by a modified Cochran-Armitige method to obtain the 50% effective dose ($ED_{50}$) of each subject compound. The results are shown in Table 1.

TABLE 1

Cultured Neurocyte Protective Effect against Glutamic Acid Toxicity

| Compounds | $ED_{50}$ (μM) | Compounds | $ED_{50}$ (μM) |
|---|---|---|---|
| 1 | 0.34 | 12 | 0.48 |
| 8 | 0.013 | 13 | 3.0 |
| 9 | 0.52 | 14 | 1.10 |
| 10 | 0.043 | 21 | 12.56 |
| 11 | 60.89 | 23 | 0.092 |

As a result, it became apparent that the compounds of the invention protected neurocytes from the cytotoxicity of glutamic acid.

[EXAMPLE 28]

Infarction Suppression Effect in Rat Middle Cerebral Artery Occlusion Model

Remarkable cerebral edema accompanied with severe cerebrovascular lesions appears in the acute stage of human cerebral infarction. It is well known that the cerebral infarction becomes significantly more severe if blood flow restarts in the acute stage of cerebral infarction. Corresponding to development of the lesion from the infarction area to surrounding tissues, the patient's life is seriously affected besides motor and mental functional loss in the conditions of the acute stage of cerebral infarction. A middle cerebral artery occlusion (MCAO; Middle Cerebral Artery Occlusion) model in Wistar rats using emboli with threads is well known as an experimental cerebral ischemia model in which clinical potency of a medicine can be accurately evaluated conforming to clinical conditions of human cerebral infarction [J. Koizumi, Japan Journal of Stroke, 8, 1 (1986)]. This MCAO model was employed as an in vivo evaluation system for evaluating the suppression effect of the compounds of the present invention on infarction development and was conducted according to the following method:

Under 1.0% halothane anesthesia induced by ether, the cervical region of each 10-week old rat was excised at center to expose the furcation of the right carotid while paying attention not to damage the vagus nerve. Centering around the furcation of the right carotid, the common carotid and the external carotid were separated from the surrounding tissues, each of them was ligated with 6-0 floss (Eto K.K.), and another floss was wound around the origin of the internal carotid so as to ligate and fix after inserting the embolus into the carotid. The common carotid was then incised to insert the ebolus toward the internal carotid to approximately 15 to 16 mm, and the proximal terminal of a nylon thread of the embolus was ligated and fixed to the internal carotid with the above mentioned floss. Due to the above procedure, the tip of the embolus exceeded the furcation of the middle cerebral artery, entered into the anterior cerebral artery to approximately 1 to 2 mm, and the entrance of the middle cerebral artery was occluded by the embolus body (made of a resin) for 2 hours. To reopen, the embolus with a thread was pulled away so as to restart the blood flow to the middle cerebral artery. Each of the subject compounds was intraperitoneally administered 1 hour before occlusion and 1 hour after reopening. Four days after the occlusion-reopening, each rat was systematically perfused with a saline from the heart and the brain was removed. After cooling each of the obtained brains with iced-water for 5 min., 7 coronary slices, taken at 2.0 mm intervals, of the cerebrum were prepared. Each slice was stained with TTC (triphenyltetrazolium chloride) and fixed with a neutral 5% formalin buffer solution, then the infarction area of the right cerebral hemisphere was measured by an image analyzer (Olympus) so as to evaluate the infraction expressed as a volume (mm3). The resulting infraction volume was compared with that of a control group to calculate the infarction suppression ratio. The results are shown in Table 2.

TABLE 2

Infarction Suppression Ratio in Rat MCAo Model

| | Infarction suppression ratio (%) Dose (mg/kg) | | |
|---|---|---|---|
| Compounds | 0.03 | 0.3 | 3 |
| 1 | 32 | 13 | 23 |
| 8 | 26 | 43 | 32 |
| 9 | | 28 | 7 |
| 10 | 19 | 21 | 7 |
| 11 | 5 | | 33 |
| 12 | | 64 | 48 |
| 23 | | 23 | |

As a result, it became apparent that, by protecting the cerebral neurocytes from various types of damage associated with the onset of cerebral ischemia, the compounds of the present invention suppressed the development of infarction and prevented the pathological conditions of cerebral infarction from worsening.

[EXAMPLE 29]

Analgesic Activity Test by Acetic Acid-Induced Writhing Method

For this experiment, 5-week old ddY mice were employed. A 0.6% aqueous acetic acid solution was intraperitoneally administered to each of the mice at 0.1 ml/10 g body weight to evaluate the analgesic activity by employing the number of writhing reactions occurring over a 10 min.-period starting from 10 min. after administration as an index. Each of the subject compounds was subcutaneously administered to the back of each mouse 15 min. before the acetic acid administration. The results are shown in Table 3.

TABLE 3

Analgesic Activity by Acetic Acid-Induced Writhing Method

| Compounds | Ed$_{50}$ (mg/kg) | Compounds | ED$_{50}$ (mg/kg) |
|---|---|---|---|
| 1 | 3.85 | 12 | 1.49 |
| 8 | 0.42 | 14 | 5.78 |
| 9 | 3.11 | 24 | 1.70 |
| 10 | 5.00 | 25 | 0.83 |

As a result, it became apparent that the compounds of the present invention had strong analgesic activity.

[EXAMPLE 30]

Antitussive Effect Evaluation Using Capsaicin Induced Cough Model in Rat

<Cough Induction>

Coughing was induced such that capsaicin (60 μM) which had been rendered as aerosol using an ultrasonic nebulizer was sent to the cap covering the head of the rat through a silicone tube by an artificial respirator to be inhaled by the rat. The respirator sent 10 ml of air per time at a rate of 70 times per min.

<Experimental Schedule>

Capsaicin was inhaled for 5 min. at 270 min. before administering a medicine, during which period cough induction was confirmed. Thirty min. after administering a test drug rats inhaled capsaicin for 5 min. to measure the number of coughs induced during this period. The antitussive effect was evaluated using the ratio of suppression to the number of coughs before applying a drug, which ratio was obtained from the number of coughs before and after applying a drug. Capsaicin was dissolved in a saline. Each of the test drugs was dissolved in 10% DMSO water and intraperitoneally applied. The effect of the drugs were expressed such that the dose exhibiting a 50% cough suppression ratio was indicated as the ED$_{50}$ value. The results are shown in Table 4.

TABLE 4

Antitussive Effect in Capsaicin Induced Cough Model in Rat

| Compounds | ED$_{50}$ (μg/kg) |
|---|---|
| 8 | 5.39 |
| 12 | 6.07 |

As a result, it became apparent that the compounds of the present invention had strong antitussive activity.

Industrial Availability

As the results of in vitro and in vivo pharmacological evaluations, it was found that the compounds of the present invention had excellent preventive effects on ischemic death of cerebral neurocytes, suppression effects on development of cerebral infarction, and strong cerebral cytoprotective effects. It also became apparent that the compounds of the present invention had strong analgesic and antitussive activities. From the above, it became apparent that the compounds of the present invention can be expected to be useful cerebral cytoprotective agent aimed at preventing and treating cerebrovascular disorder, ischemic cerebral disorder, cerebral neurocyte disorder, and dementia, an analgesic, and an antitussive in the medicinal field.

What is claimed is:

1. A 4a-aryldecahydroisoquinoline compound of formula (I) or a pharmacologically acceptable acid addition salt thereof:

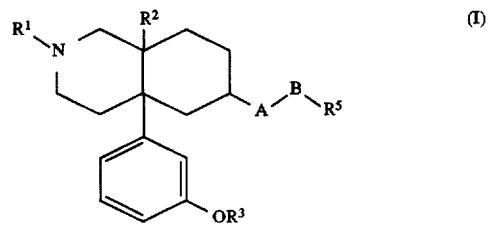

wherein $R^1$ is either hydrogen, alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 2 to 7 carbon atoms, furan-2-ylalkyl having 1 to 5 carbon atoms, or thiophene-2-ylalkyl having 1 to 5 carbon atoms;

$R^2$ is either hydrogen, hydroxy, alkanoyloxy having 1 to 5 carbon atoms, or alkoxy having 1 to 5 carbon atoms;

$R^3$ is either hydrogen, alkyl having 1 to 5 carbon atoms, alkanoyl having 1 to 5 carbon atoms, or aralkyl having 7 to 13 carbon atoms;

A is either —XC(=Y)—, —XC(=Y)Z—, —X— or —OC(OR$^4$)R$^4$— (wherein X is NR$^4$ or S, and Y and Z are each independently NR$^4$, S or O);

$R^4$ is either hydrogen, straight or branched alkyl having 1 to 14 carbon atoms (which may be substituted by at least one substituent selected from the group consisting of alkoxy having 1 to 5 carbon atoms, alkanoyloxy having 1 to 5 carbon atoms, fluoro, chloro, bromo, iodo, nitro and cyano), cycloalkylalkyl having 4 to 15 carbon atoms (which may be substituted by at least one substituent selected from the group consisting of alkyl having 1 to 5 carbon atoms, aryl having 6 to 12 carbon atoms, alkoxy having 1 to 5 carbon atoms, alkanoyloxy having 1 to 5 carbon atoms, fluoro, chloro, bromo, iodo, nitro, cyano and trifluoromethyl), aralkyl having 7 to 15 carbon atoms (which may be substituted by at least one substituent selected from the group consisting of alkyl having 1 to 5 carbon atoms, aryl having 6 to 12 carbon atoms, alkoxy having 1 to 5 carbon atoms, alkanoyloxy having 1 to 5 carbon atoms, fluoro, chloro, bromo, iodo, nitro, cyano, trifluoromethyl and trifluoromethoxy), or aryl having 6 to 12 carbon atoms (which may be substituted by at least one substituent selected from the group consisting of alkyl having 1 to 5 carbon atoms, aryl having 6 to 12 carbon atoms, alkoxy having 1 to 5 carbon atoms, alkanoyloxy having 1 to 5 carbon atoms, fluoro, chloro, bromo, iodo, nitro, cyano, trifluoromethyl and trifluoromethoxy), and R may be the same or different;

B is a valence bond, a straight acyclic hydrocarbon chain having 1 to 14 carbon atoms or a branched acyclic hydrocarbon chain having 3 to 14 carbon atoms (wherein (i) the hydrocarbon chains may have 1 to 3 unsaturated bonds, (ii) 1 to 3 methylene groups that are not positioned adjacent to each other and that are not directly linked with A may be replaced by —(C=O)—, —S—, —O— and/ or —NH—, and (iii) the hydrocarbon chains may be substituted by at least one substituent selected from the group consisting of alkoxy having 1 to 5 carbon atoms, alkanoyloxy having 1 to 5 carbon atoms , hydroxy, fluoro, chloro, bromo, iodo, amino, nitro, cyano, and phenoxy);

$R^5$ is hydrogen or an organic group including saturated or unsaturated monocyclic hydrocarbon having 3 to 8 carbon atoms, saturated or unsaturated fused polycyclic hydrocarbon having 8 to 18 carbon atoms, aromatic hydrocarbon having 6 to 18 carbon atoms, a saturated or unsaturated hetero monocyclic hydrocarbon compound having 3 to 7 carbon atoms, a saturated or unsaturated hetero fused polycyclic hydrocarbon compound having 5 to 17 carbon atoms or an aromatic hetero hydrocarbon compound having 3 to 17 carbon atoms (wherein (i) the hetero atoms are independently selected from the group consisting of nitrogen, oxygen and sulfur atoms, and (ii) said organic group may be substituted by at least one substituent selected from the group consisting of alkyl having 1 to 5 carbon atoms, alkoxy having 1 to 5 carbon atoms, alkanoyloxy having 1 to 5 carbon atoms, hydroxy, fluoro, chloro, bromo, iodo, amino, nitro, cyano, isothiocyanato, trifluoromethyl, trifluoromethoxy, and methylenedioxy); and said formula (I) includes (+), (−) and (±) isomers.

2. A 4a-aryldecahydroisoquinoline compound of formula (I) or a pharmacologically acceptable acid addition salt thereof as set forth in claim 1, wherein X is $NR^4$.

3. A 4a-aryldecahydroisoquinoline compound of formula (I) or a pharmacologically acceptable acid addition salt thereof as set forth in claim 1, wherein A is either $-NR^4C(=Y)-$, $-NR^4C(=Y)Z-$, $-NR^4-$, or $-NR^4SO_2-$.

4. A 4a-aryldecahydroisoquinoline compound of formula (I) or a pharmacologically acceptable acid addition salt thereof as set forth in claim 3, wherein A is either $-NR^4C(=O)-$, $-NR^4C(=O)O-$, $-NR^4C(=O)NR^4-$, $-NR^4C(=S)NR^4-$, $-NR^4-$, or $-NR^4SO_2-$.

5. A 4a-aryldecahydroisoquinoline compound of formula (I) or a pharmacologically acceptable acid addition salt thereof as set forth in claim 3, wherein A is either $-NR^4C(=O)-$ or $-NR^4C(=O)O-$.

6. A 4a-aryldecahydroisoquinoline compound of formula (I) or a pharmacologically acceptable acid addition salt thereof as set forth in claim 1, wherein $R^5$ is hydrogen or an organic group including cycloalkyl having 3 to 8 carbon atoms, cycloalkenyl having 3 to 8 carbon atoms, fused bicycloalkyl having 8 to 14 carbon atoms, fused bicycloalkenyl having 8 to 14 carbon atoms and 1 to 3 unsaturated bonds, aryl having 6 to 18 carbon atoms, hetero cycloalkyl having 3 to 7 carbon atoms and 1 or 2 hetero atoms, hetero cycloalkenyl having 3 to 7 carbon atoms, 1 or 2 hetero atoms, and 1 unsaturated bond, hetero fused bicycloalkyl having 6 to 13 carbon atoms and 1 or 2 hetero atoms, hetero fused bicycloalkenyl having 6 to 13 carbon atoms, 1 or 2 hetero atoms, and 1 to 3 unsaturated bonds, and hetero aryl having 3 to 13 carbon atoms and 1 to 3 hetero atoms (wherein said organic group may be substituted by at least one substituent selected from the group consisting of alkyl having 1 to 5 carbon atoms, alkoxy having 1 to 5 carbon atoms, alkanoyloxy having 1 to 5 carbon atoms, hydroxy, fluoro, chloro, bromo, iodo, amino, nitro, cyano, isothiocyanato, trifluoromethyl, trifluoromethoxy, and methylenedioxy).

7. A 4a-aryldecahydroisoquinoline compound of formula (I) or a pharmacologically acceptable acid addition salt thereof as set forth in claim 6, wherein R is hydrogen or an organic group including cycloalkyl having 3 to 8 carbon atoms, cycloalkenyl having 3 to 8 carbon atoms, aryl having 6 to 18 carbon atoms, hetero cycloalkyl having 4 to 7 carbon atoms and 1 hetero atom, hetero cycloalkenyl having 4 to 7 carbon atoms and 1 hetero atom, and hetero aryl having 3 to 13 carbon atoms and 1 to 3 hetero atoms (wherein said organic group may be substituted by at least one substituent selected from the group consisting of alkyl having 1 to 5 carbon atoms, alkoxy having 1 to 5 carbon atoms, alkanoyloxy having 1 to 5 carbon atoms, hydroxy, fluoro, chloro, bromo, iodo, amino, nitro, cyano, isothiocyanato, trifluoromethyl, trifluoromethoxy, and methylenedioxy).

8. A 4a-aryldecahydroisoquinoline compound of formula (I) or a pharmacologically acceptable acid addition salt thereof as set forth in claim 6, wherein $R^5$ is hydrogen or an organic group including cycloalkyl having 3 to 8 carbon atoms, aryl having 6 to 18 carbon atoms, and hetero aryl having 3 to 13 carbon atoms and 1 to 3 hetero atoms (wherein said organic group may be substituted by at least one substituent selected from the group consisting of alkyl having 1 to 5 carbon atoms, alkoxy having 1 to 5 carbon atoms, alkanoyloxy having 1 to 5 carbon atoms, hydroxy, fluoro, chloro, bromo, iodo, amino, nitro, cyano, isothiocyanato, trifluoromethyl, trifluoromethoxy, and methylenedioxy).

9. A 4a-aryldecahydroisoquinoline compound of formula (I) or a pharmacologically acceptable acid addition salt thereof as set forth in claim 6, wherein $R^5$ is hydrogen or an organic including cycloalkyl having 3 to 8 carbon atoms, phenyl, naphthyl, pyrrolyl, furyl, thienyl, pyridyl, quinolyl, isoquinolyl, indolyl, benzofuranyl, and benzothienyl (wherein said organic group may be substituted by at least one substituent selected from the group consisting of alkyl having 1 to 5 carbon atoms, alkoxy having 1 to 5 carbon atoms, alkanoyloxy having 1 to 5 carbon atoms, hydroxy, fluoro, chloro, bromo, iodo, amino, nitro, cyano, isothiocyanato, trifluoromethyl, trifluoromethoxy, and methylenedioxy).

10. A pharmaceutical composition comprising an effective dose of a 4a-aryldecahydroisoquinoline compound of formula (I) or a pharmacologically acceptable acid addition salt thereof as set forth in claim 1 in a pharmacologically acceptable carrier.

11. A method of treating a condition in a patient that is susceptible to treatment with a cerebral neurocyte protective agent, the method comprising the step of administering to the patient having said condition a pharmacologically effective amount of a 4a-aryldecahydroisoquinoline compound of formula (I) or a pharmacologically acceptable acid addition salt thereof as set forth in claim 1 as an active ingredient.

12. A method of treating a condition in a patient that is susceptible to treatment with an analgesic, the method comprising the step of administering to the patient having said condition a pharmacologically effective amount of a 4a-aryldecahydroisoquinoline compound of formula (I) or a pharmacologically acceptable acid addition salt thereof as set forth in claim 1 as an active ingredient.

13. A method of treating a condition in a patient that is susceptible to treatment with an antitussive, the method comprising the step of administering to the patient having said condition a pharmacologically effective amount of a 4a-aryldecahydroisoquinoline compound of formula (I) or a pharmacologically acceptable acid addition salt thereof as set forth in claim 1 as an active ingredient.

* * * * *